(12) United States Patent
Novak et al.

(10) Patent No.: US 11,319,363 B2
(45) Date of Patent: *May 3, 2022

(54) HUMANIZED TAU ANTIBODIES IN ALZHEIMER'S DISEASE

(71) Applicant: AXON NEUROSCIENCE SE, Larnaka (CY)

(72) Inventors: Michal Novak, Bratislava (SK); Eva Kontsekova, Senec (SK); Branislav Kovacech, Bratislava (SK); Rostislav Skrabana, Bratislava (SK)

(73) Assignee: AXON NEUROSCIENCE SE, Larnaka (CY)

( * ) Notice: Subject to any disclaimer, the term of this patent is extended or adjusted under 35 U.S.C. 154(b) by 10 days.

This patent is subject to a terminal disclaimer.

(21) Appl. No.: 16/926,062

(22) Filed: Jul. 10, 2020

(65) Prior Publication Data
US 2021/0009666 A1    Jan. 14, 2021

Related U.S. Application Data

(63) Continuation of application No. 16/181,088, filed on Nov. 5, 2018, now Pat. No. 10,745,469, which is a continuation of application No. 15/528,333, filed as application No. PCT/IB2015/002610 on Nov. 18, 2015, now Pat. No. 10,160,799.

(60) Provisional application No. 62/081,809, filed on Nov. 19, 2014.

(51) Int. Cl.
*C07K 16/18* (2006.01)
*G01N 33/68* (2006.01)
*A61P 25/28* (2006.01)

(52) U.S. Cl.
CPC ............ *C07K 16/18* (2013.01); *A61P 25/28* (2018.01); *G01N 33/6896* (2013.01); *C07K 2317/24* (2013.01); *C07K 2317/31* (2013.01); *C07K 2317/34* (2013.01); *C07K 2317/515* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01); *G01N 2800/2821* (2013.01); *G01N 2800/50* (2013.01); *G01N 2800/7047* (2013.01)

(58) Field of Classification Search
None
See application file for complete search history.

(56) References Cited

U.S. PATENT DOCUMENTS

| | | | |
|---|---|---|---|
| 9,518,101 B2 | 12/2016 | Novak et al. | |
| 9,828,421 B2 | 11/2017 | Novak et al. | |
| 9,845,352 B2 | 12/2017 | Novak et al. | |
| 2015/0050215 A1 | 2/2015 | Novak et al. | |
| 2017/0145082 A1 | 5/2017 | Novak et al. | |
| 2017/0260263 A1 | 9/2017 | Novak et al. | |

FOREIGN PATENT DOCUMENTS

| | | |
|---|---|---|
| WO | WO 2012/049570 A1 | 4/2012 |
| WO | WO 2013/041962 A1 | 3/2013 |
| WO | WO 2013/151762 A1 | 10/2013 |
| WO | WO 2014/100600 A2 | 6/2014 |

OTHER PUBLICATIONS

Anonymous, "Antibody Engineering—MRC Technology," Retrieved from URL: http://www.antibodyengineering.co.uk/, 2 pages (2016).
Anonymous, "Axon Neuroscience SE," Retrieved from URL: http://www.axon-neuroscience.eu/docs/axon-neuroscience.pdf, 4 pages (2015).
Anonymous, "MRC Technology Announces Humanization of Anti-Tau Monoclonal Antibody for Alzheimer's Disease Therapy," Retrieved from URL: http://www.mrctechnology.org/mrc-technology-announces-humanization-anti-tau-mono-clonal-antibody-alzheimers-disease-therapy, 2 pages (2014).
Anonymous, "Our Process—Antibody Engineering—MRC Technology," Retrieved from URL: http://www.antibodyengineering.co.uk/our-process, 2 pages (2016).
Chen et al., "Enhancement and destruction of antibody function by somatic mutation: unequal occurrence is controlled by V gene combinatorial associations," EMBO Journal, 14(12):2784-2794 (1995).
Foote et al., "Antibody Framework Residues Affecting the Conformation of the Hypervariable Loops," Journal of Molecular Biology, 224(2):487-499 (1992).
Ghezzi et al., "Disease-modifying drugs in Alzheimer's disease," (2013) Drug Design, Development and Therapy, 7:1471-1479.
Hwang et al., "Use of human germline genes in a CDR homology-based approach to antibody humanization," Methods, 36: 35-42 (2005).
International Patent Application No. PCT/IB2015/002610, filed Nov. 18, 2015, by Axon Neuroscience SE, International Search Report and Written Opinion, dated Apr. 15, 2016.
Ji et al., "Hepatitis B core VLP-based mis-disordered tau vaccine elicits strong immune response and alleviates cognitive deficits and neuropathology progression in Tau. P301S mouse model of Alzheimer's disease and frontotemporal dementia," Alzheimer's Research & Therapy (2018) 10:55.
Kontsekova et al., "Identification of structural determinants on tau protein essential for its pathological function: novel therapeutic target for tau immunotherapy in Alzheimer's disease," Alzheimer's Research & Therapy, 6(45): 16 pages (2014).
Kussie et al., "A Single Engineered Amino Acid Substitution Changes Antibody Fine Specificity," J Immunology, 152(1):146-152 (1994).

(Continued)

*Primary Examiner* — Adam Weidner
(74) *Attorney, Agent, or Firm* — Finnegan, Henderson, Farabow, Garrett & Dunner, LLP

(57) ABSTRACT

The present invention is in the fields of biochemistry, molecular biology, and Alzheimer's disease diagnosis, prevention, and treatment. Provided herein are humanized antibodies against human tau that are capable of discriminating between normal (healthy) and pathological (disease-associated) tau.

27 Claims, 64 Drawing Sheets

Specification includes a Sequence Listing.

(56) References Cited

OTHER PUBLICATIONS

Lockard et al., "Efficacy and Toxicity of the Solvent Polyethylene Glycol 400 in Monkey Model," Epilepsia, 20:77-84, 1979.
Reitz et al., "Toward precision medicine in Alzheimer's disease," Annals of Translational Medicine, 4(6):107 (2016).
Rouet et al., "Stability Engineering of the Human Antibody Repertoire," FEBS Letters, 588:269-277 (2014).
Safdari et al., "Antibody humanization methods—a review and update", Biotechnology and Genetic Engineering Reviews, 29(2): 175-186 (2013).
Salomone et al., "New pharmacological strategies for treatment of Alzheimer's disease: focus on disease modifying drugs," (2012) British Journal of Clinical Pharmacology, 73(4):504-517.
Vaidos et al., "Comprehensive Functional Maps of the Antigen-binding Site of an Anti-ErbB2 Antibody Obtained with Shotgun Scanning Mutagenesis," J. Mol. Biol., 320:415-428, 2002.
Wykes, S, "5 Questions: Frank Longo on Alzheimer's, new neuroscience center," News Center, Stanford University, Retrieved from URL: https://med.stanford.edu/news/all-news/2016/02/frank-longo-on-alzheimers-new-neuroscience-center.html, 3 pages (2016).

DC8E8_VK
Closest V-REGIONs (evaluated from the V-REGION first nucleotide to the 2$^{nd}$-Cys codon plus 15 nt of the CDR3-IMGT)

```
                                  Score     Identity
Y15982 Musmus IGKV8-21*01 F       1453      98.99% (294/297 nt)
L17135 Musmus IGKV8-28*02 F       1264      91.92% (273/297 nt)
Y15980 Musmus IGKV8-19*01 F       1255      91.58% (272/297 nt)
AJ235948 Musmus IGKV8-30*01 F     1255      91.25% (271/297 nt)
AJ235947 Musmus IGKV8-28*01 F     1228      90.57% (269/297 nt)

10        20        30        40        50        60        70        80        90       100
                  +---------+---------+---------+---------+---------+---------+---------+---------+---------+
Y15982.seq  DIVMSQSPSSLAVSAGEKVTMSCkssqsllnsrtrknylaWYQQKPGQSPKLLIYwastresGVPDRFTGSGSGTDFTLTISSVQAEDLAVYYCkqsynlp
DC8E8_VKc   ........................................................................................fy.r
                                                                                                    ......
```

Fig.6

DC8E8_VH
Closest V-REGIONs (evaluated from the V-REGION first nucleotide to the 2$^{nd}$-Cys codon)

```
                              Score    Identity
AC160990 Musmus IGHV1-81*01 F  1237    92.36%  (266/288 nt)
AC160473 Musmus IGHV1-77*01 F  1219    91.67%  (264/288 nt)
AC160990 Musmus IGHV1-83*01 P  1210    91.32%  (263/288 nt)
AC160473 Musmus IGHV1-75*01 F  1192    90.62%  (261/288 nt)
X02064  Musmus IGHV1-54*02 F   1174    89.93%  (259/288 nt)

10         20         30         40         50         60         70         80         90
                  +----+----+----+----+----+----+----+----+----+----+----+----+----+----+----+----+----+----+
AC160990.seq  QVQLQQSGAELARPGASVKLSCKASGYTFTSygisWVKQRTGQGLEWIGeiyprsgntyynekfkgKATLTADKSSTAYMELRSLTSEDSAVYFCAR
DC8E8_VHc     .......P..VK..T...MP......I.d.v...........f...s................N....Q.S.V..
```

Fig. 8

| Kabat Number | |
|---|---|
| DC8E8_Heavy | QVQLQQSGPELVKPGTSVKMPCKASGYIFTxxxxxxisWVKQRTGQGLxWxIGeifpgstvyneKKgKATLTAxKxNTAYMQLSSVTSERSAVYFCARdyygtsfamdyWGQGTSVTVSS |
| M65092 | QVQLVQSGAEVKKPGSSVRVSCKASGGTFSsyaisWVRQAPGQGLEWMGgdipifgtanyaqktqgRVxTTADKSTSTAYMELSSLRSEDTAVYYCARgstvtgdfdyWGQGTLVTVSS |
| RHA | QVQLVQSGAEVKKPGSSVKVSCKASGGTFSdyvxxxRQAPGQGLEWMGeifpsgstvyneKKgRVTITADKSTSTAYMELSSLRSEDTAVYYCARdyygtsfamdyWGQGTLVTVSS |
| RHB | QVQLVQSGPEVKKPGSSVRVPCKASGYIFTdyv1sWVRQAPGQGLEWIGeifpsgstvyneKKgKATLTADKSTSTAYMELSSLRSEDTAVYFCARdyygtsfamdyWGQGTLVTVSS |
| RHC | QVQLVQSGPEVKKPGSSVRVPCKASGGTFSdyvisWVRQAPGQGLEWIGeifpsgstvyneKKgKATLTADKSTSTAYMELSSLRSEDTAVYFCARdyygtsfamdyWGQGTLVTVSS |
| RHD | QVQLVQSGAEVKKPGSSVRVSCKASGYIFSdyvisWVRQAPGQGLEWMGeifpsgstvyneKKgRVTITADKSTSTAYMELSSLRSEDTAVYYCARdyygtsfamdyWGQGTLVTVSS |
| RHE | QVQLVQSGAEVKKPGSSVKVSCKASGGTFSdyxxxxxxxWVRQAPGQGLEWMGeifpsgstvyneKKgRVTITADKSTSTAYMELSSLRSEDTAVYYCARdyygtsfamdyWGQGTLVTVSS |
| RHF | QVQLVQSGAEVKxxxxVKPGSSVRVSCKASGGTFSdxxxxxxxxisWVRQAPGxxxLExxxxxxxxxxxfpsgstvyneKKgRVTITADKSTSTAYMELSSLRSEDTAVYYCARdyygtsfamdyWGQGTLVTVSS |
| RHG | QVQLVQSGAEVKKPGSSVKVSCKASGGTFSdyvisWVRQAPGxxxLExxxMGeifpsgstvyneKKgRVTITADKSTSTAYMELSSLRSEDTAVYYCARdyygtsfamdyWGQGTLVTVSS |
| RHH | QVQLVQSGAEVKKPGSSVKVSCKASGGTFSdyvisWVRQAPGQGLEWIGeifpsgstvyneKKgRVTITADKSTSTAYMELSSLRSEDTAVYYCARdyygtsfamdyWGQGTLVTVSS |
| RHI | QVQLVQSGAEVKKPGSSVKVSCKASGGTFSdyvisWVRQAPGQGLEWMGeifpsgstvyneKKgKVTITADKSTSTAYMELSSLRSEDTAVYYCARdyygtsfamdyWGQGTLVTVSS |
| RHJ | QVQLVQSGAEVKKPGSSVKVSCKASGGTFSdyvisWVRQAPGQGLEWxxxxeifpsgstvyneKKgRATITADKSTSTAYMELSSLRSEDTAVYYCARdyygtsfamdyWGQGTLVTVSS |
| RHK | QVQLVQSGAEVKLPGSSVKVSCKASGGTFSdyvisWVRQAPGQGLExxxMGeifpsgstvyneKKgRVTITADKSTSTAYMELSSLRSEDTAVYYCARdyygtsfamdyWGQGTLVTVSS |
| RHL | QVQLVQSGAEVKKPGSSVKVSCKASGGTFSdyvisWVRQAPGxxxLExxxMGeifpsgstvyneKKgRVTITADKSTSTAYMELSxxxxxxxTAVYFCARdyygtsfamdyWGQGTLVTVSS |
| RHM | QVQLVQSGAEVKKPGSSVKVSCKASGYIFSdyvisWVRQAPGQGLEWMGeifpsgstvyneKKgRVTITADKSTSTAYMELSSLRSEDTAVYYCARdyygtsfamdyWGQGTLVTVSS |

Fig. 9

| Kabat Number | |
|---|---|
| DC8E8_Kappa | ****** ............... * .............. **** **** ***** ************ ** |
| X72449 | DIVMTQSPLSLPVTPGEPASISCrssqslihs...ngynylaWYLQKPGQSPQLLIYlgsnrasGVPDRFTGSGSGTDFTLKISRVEAEDVGVYYCmqalqtvrtFGQGTKVEIK |
| RKA | DIVMTQSPLSLPVTPGEPASISCkssqslinsrtrknylaWYLQKPGQSPQLLIYwastresGVPDRFTGSGSGTDFTLKISRVEAEDVGVYYCkqsfylrtFGQGTKVEIK |
| RKB | DIVMSQSPLSLPVTPGEPASISCkssqslinsrtrknylaWYLQKPGQSPQLLIYwastresGVPLRFTGSGSGTDFTLKISRVHAEDVGVYYCkqsfylrtFGQGTKVEIK |

| Name | Chain Composition | | EC50 (µg/ml) |
|---|---|---|---|
| cDC8E8 | VH | VK | 0.0199 |
| AX001 | RHA | RKA | 0.1951 |
| AX002 | RHB | RKA | 0.0271 |
| AX003 | RHC | RKA | 0.3083 |
| AX004 | RHD | RKA | 0.0285 |
| AX005 | RHE | RKA | 0.0356 |
| AX006 | RHF | RKA | 0.1015 |
| AX007 | RHG | RKA | 0.8311 |
| AX008 | RHH | RKA | 0.1286 |
| AX009 | RHI | RKA | 0.6491 |
| AX010 | RHJ | RKA | 0.3471 |
| AX011 | RHK | RKA | 0.4510 |
| AX012 | RHL | RKA | 0.1945 |

| Name | Chain Composition | | EC50 (µg/ml) |
|---|---|---|---|
| cDC8E8 | VH | VK | 0.0199 |
| AX025 | RHA | Vk | 0.1024 |
| AX026 | RHB | Vk | 0.0310 |
| AX027 | RHC | Vk | 0.1156 |
| AX028 | RHD | Vk | 0.0234 |
| AX029 | RHE | Vk | 0.0283 |
| AX030 | RHF | Vk | 0.0652 |
| AX031 | RHG | Vk | 0.4299 |
| AX032 | RHH | Vk | 0.1126 |
| AX033 | RHI | Vk | 0.2599 |
| AX034 | RHJ | Vk | 0.1556 |
| AX035 | RHK | Vk | 0.6510 |
| AX036 | RHL | Vk | 0.1463 |

| Name | Chain Composition | | EC50 (µg/ml) |
|---|---|---|---|
| cDC8E8 | VH | VK | 0.0338 |
| AX004 | RHD | RKA | 0.0322 |
| AX005 | RHE | RKA | 0.1074 |
| AX016 | RHD | RKB | 0.0615 |
| AX017 | RHE | RKB | 0.1265 |
| AX037 | RHM | RKA | 0.0346 |
| AX038 | RHM | RKB | 0.0352 |

| | AX004 | AX005 | AX016 | AX017 | cDC8E8 | mDC8E8 |
|---|---|---|---|---|---|---|
| Tm (rounded) | 70 | 70 | 70 | 69 | 70 | 73 |
| Maximum | 4300.9046 | 3135.43837 | 4187.99894 | 4529.31902 | 4857.25689 | 6791.01988 |
| Minimum | -1193.26152 | -725.47317 | -936.2542 | -28.01788 | -1098.6411 | -25.13077 |
| Max - Min | 5494.16612 | 3860.91154 | 5124.25314 | 4557.3369 | 5955.89801 | 6816.15065 |
| Slope | 4.414670596 | 3.678766181 | 3.965288376 | 3.348855489 | 3.62506314 | 2.02029628 |

| KD (M) | Rmax (RU) | offset (RU) | Chi² (RU²) |
|---|---|---|---|
| 1.649x10⁻⁸ | 43.96 | 1.011 | 0.292 |

Fig.22
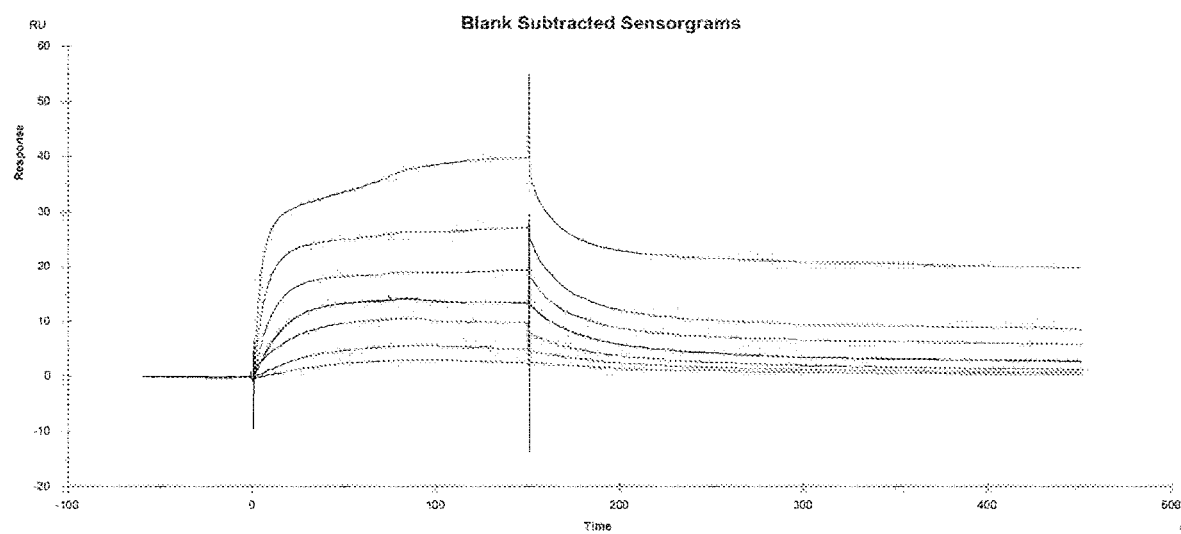
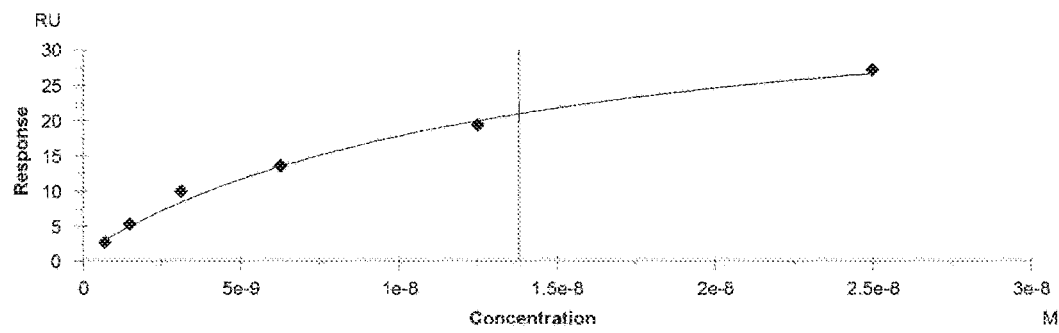
| KD (M) | Rmax (RU) | offset (RU) | Chi² (RU²) |
|---|---|---|---|
| 1.381x10⁻⁸ | 39.68 | 1.130 | 0.685 |

Fig.23

|  | KD (M) | Rmax (RU) | offset (RU) | Chi² (RU²) |
|---|---|---|---|---|
| mDC8E8 | $1.040 \times 10^{-8}$ | 92.43 | 10.61 | 8.39 |
| cDC8E8 | $1.037 \times 10^{-8}$ | 28.56 | 2.921 | 0.226 |
| AX004 | $1.473 \times 10^{-8}$ | 43.02 | 3.320 | 0.668 |
| AX005 | $1.649 \times 10^{-8}$ | 43.96 | 1.011 | 0.292 |
| AX016 | $9.386 \times 10^{-9}$ | 35.18 | 3.184 | 0.987 |
| AX017 | $1.381 \times 10^{-8}$ | 39.68 | 1.130 | 0.685 |

| Time (min) | Concentration(mg/ml) | | | |
|---|---|---|---|---|
| | AX004 | AX005 | AX016 | AX017 |
| 0 | 1.248 | 0.935 | 1.281 | 0.961 |
| 15 | 0.900 | 0.906 | 1.252 | 0.969 |
| 30 | 3.175 | 22.156 | 8.643 | 23.296 |
| 45 | 41.455 | 40.965 | 36.767 | 34.497 |
| 60 | 41.204 | 40.906 | 41.856 | 35.545 |
| 75 | 41.447 | ND | 41.864 | 32.385 |

|  | AX004 | AX016 | AX017 |
|---|---|---|---|
| $EC_{50}$ | 0.03287 | 0.005483 | 0.02067 |

| Sample | Sample Concentration (mg/ml) | Mw (kDa) | Polydispersity (< 1.05 is acceptable) | Mass fraction (%) |
|---|---|---|---|---|
| Ax004_freeze_thaw | 1.25 | 160.0 (± 0.3 %) | 1.033 (± 0.5 %) | > 99.5 |
| Ax005_freeze_thaw | 0.94 | 159.9 (± 0.3 %) | 1.037 (± 0.4 %) | > 99.5 |
| Ax016_freeze_thaw | 1.28 | 157.6 (± 0.3 %) | 1.039 (± 0.5 %) | > 99.5 |
| Ax017_freeze_thaw | 0.96 | 155.8 (± 0.3 %) | 1.037 (± 0.4 %) | > 99.5 |

|  | Mw (kDa) | Polydispersity (Mw/Mn) | Mass Fraction (%) |
|---|---|---|---|
| AX004 RT 20d | 146.7 ±0.4 | 1.014 ±0.004 | 100.0 |
| AX004 37°C 20d | 143.4 ±0.4 | 1.026 ±0.004 | 99.7 |
| AX004 50°C 20d | 152.4 ±2.4 | 1.023 ±0.026 | 99.4 |

| | Mw (kDa) | Polydispersity (Mw/Mn) | Mass Fraction (%) |
|---|---|---|---|
| AX005 RT 20d | 145.0 ±0.4 | 1.013 ±0.005 | 100.0 |
| AX005 37°C 20d | 143.6 ±0.4 | 1.016 ±0.004 | 99.9 |
| AX005 50°C 20d | 146.3 ±0.3 | 1.009 ±0.003 | 99.4 |

|  | Mw (kDa) | Polydispersity (Mw/Mn) | Mass Fraction (%) |
|---|---|---|---|
| AX016 RT 20d | 144.0 ±0.4 | 1.018 ±0.004 | 99.9 |
| AX016 37°C 20d | N/A | N/A | N/A |
| AX016 50°C 20d | 145.6 ±0.3 | 1.012 ±0.004 | 99.3 |

| | Mw (kDa) | Polydispersity (Mw/Mn) | Mass Fraction (%) |
|---|---|---|---|
| AX017 RT 20d | 143.3 ±0.4 | 1.017 ±0.004 | 100.0 |
| AX017 37°C 20d | 143.2 ±0.3 | 1.016 ±0.004 | 99.9 |
| AX017 50°C 20d | 146.1 ±0.4 | 1.009 ±0.004 | 99.2 |

Fig.29C

| EC50 (ng/ml) Ab | Chimeric DC8E8 | Mouse DC8E8 |
|---|---|---|
| Tau 151-391/4R | 10.1 | 15.7 |
| Tau 2N4R | 52.7 | 52.4 |

| $K_A$ (M$^{-1}$) Ab | Chimeric DC8E8 | Mouse DC8E8 |
|---|---|---|
| Tau 151-391/4R | 4.2E+08 | 1.9E+08 |
| Tau 2N4R | 4.4E+07 | 3.9E+07 |

| EC50 (ng/ml) Antibodies | Chimeric DC8E8 | Mouse DC8E8 |
|---|---|---|
| Tau peptide 256-285 | 21.2 | 43.33 |
| Tau peptide 282-311 | 7.31 | 11.76 |
| Tau peptide 314-342 | 17.28 | 38.97 |
| Tau peptide 352-380 | 86.96 | 212.8 |

Fig.33F

| EC50 (ng/ml) Humanized Ab/IgG4 | AX004 | AX005 | AX016 | AX017 | Chimeric DC8E8 |
|---|---|---|---|---|---|
| Tau 151-391/4R | 25.19 | 33.69 | 23.91 | 33.96 | 24.6 |
| Tau 2N4R | 93.32 | 184.1 | 97.67 | 215.4 | 109 |

| EC50 (ng/ml) | | | | |
|---|---|---|---|---|
| Humanized Ab/IgG1 | AX004 | AX005 | AX016 | AX017 |
| Tau 151-391/4R | 14.68 | 20.55 | 13.71 | 19.36 |
| Tau 2N4R | 53.15 | 134.5 | 51.35 | 91.13 |

Fig.36F

| EC50 (ng/ml) | | | | | |
|---|---|---|---|---|---|
| Humanized Ab/IgG4 | AX004 | AX005 | AX016 | AX017 | Chimeric DC8E8 |
| Tau peptide 256-285 | 13.18 | 75.27 | 13.95 | 72.47 | 29.72 |
| Tau peptide 282-311 | 6.7 | 8.982 | 7.558 | 9.014 | 8.52 |
| Tau peptide 314-342 | 13.03 | 74.47 | 15.27 | 72.57 | 26.47 |
| Tau peptide 352-380 | 81.37 | 397.2 | 85.01 | 385.3 | 81.44 |

| EC50 (ng/ml) | | | | |
| --- | --- | --- | --- | --- |
| Humanized Ab/IgG1 | AX004 | AX005 | AX016 | AX017 |
| Tau peptide 256-285 | 12.06 | 58.25 | 11.7 | 97.95 |
| Tau peptide 282-311 | 5.981 | 6.801 | 6.474 | 7.664 |
| Tau peptide 314-342 | 11.8 | 56.22 | 12.16 | 95.95 |
| Tau peptide 352-380 | 58.72 | 578.7 | 56.63 | 882.7 |

Fig. 39A
Fig. 39B
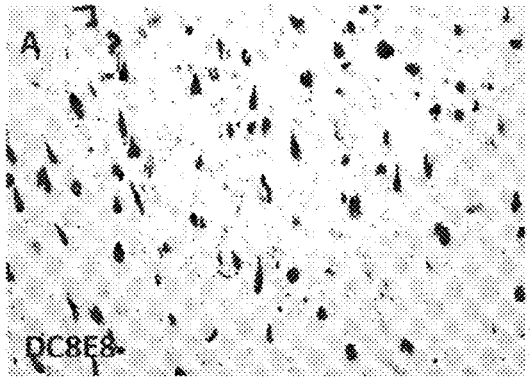
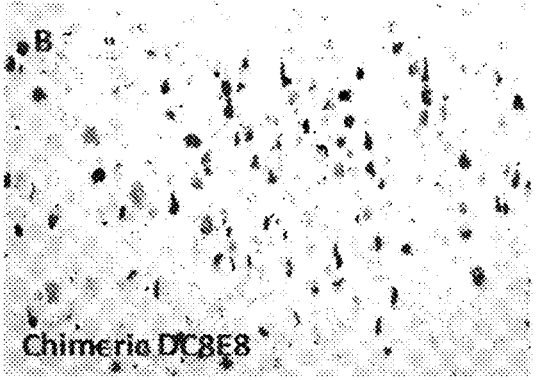
Fig. 39C
Fig. 39D
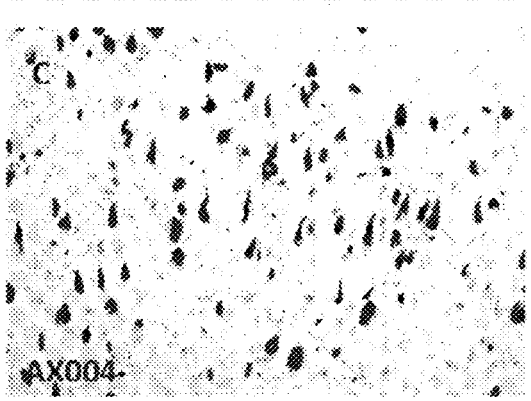
Fig. 39E
Fig. 39F

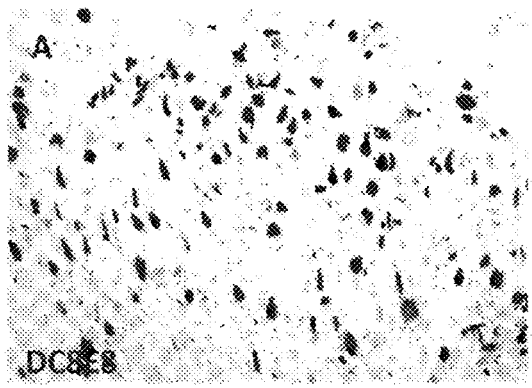
Fig. 40A DC8E8
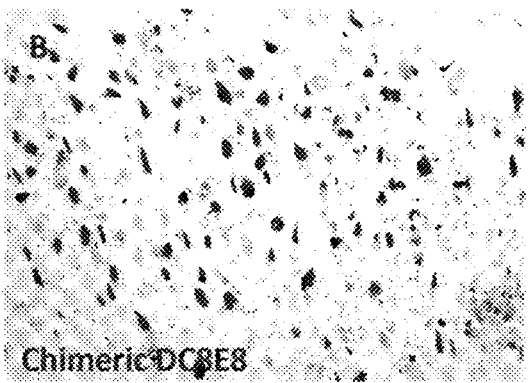
Fig. 40B Chimeric DC8E8
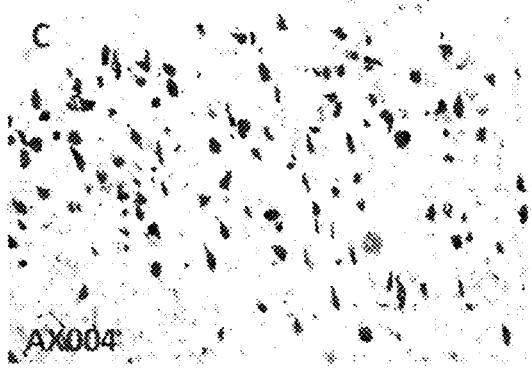
Fig. 40C AX004
Fig. 40D AX005
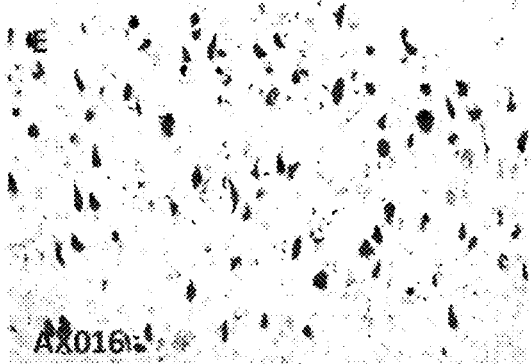
Fig. 40E AX016
Fig. 40F AX017

Fig. 41A  DC8E8
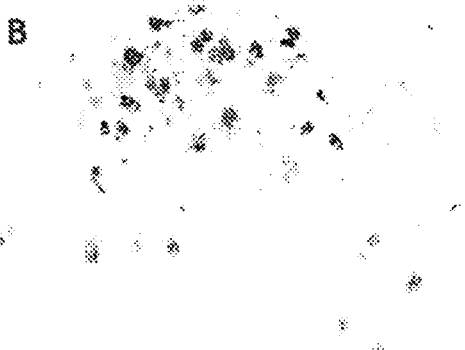
Fig. 41B  Chimeric DC8E8
Fig. 41C  AX004
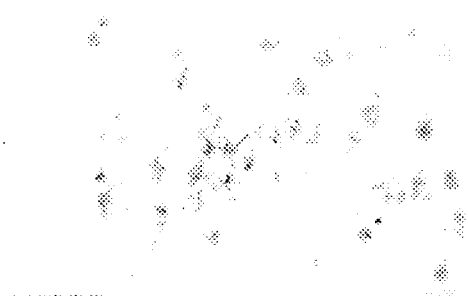
Fig. 41D  AX005
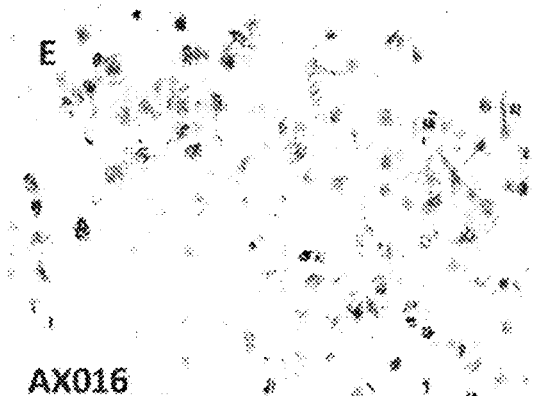
Fig. 41E  AX016
Fig. 41F  AX017

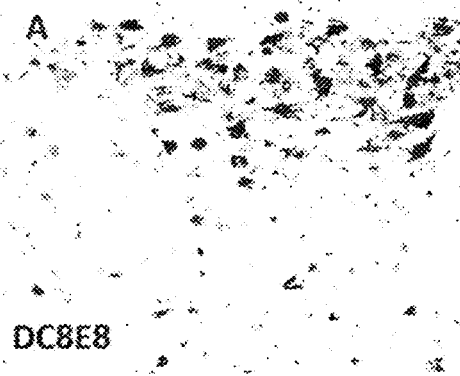
Fig. 42A
Fig. 42B
Fig. 42C
Fig. 42E
Fig. 42D
Fig. 42F

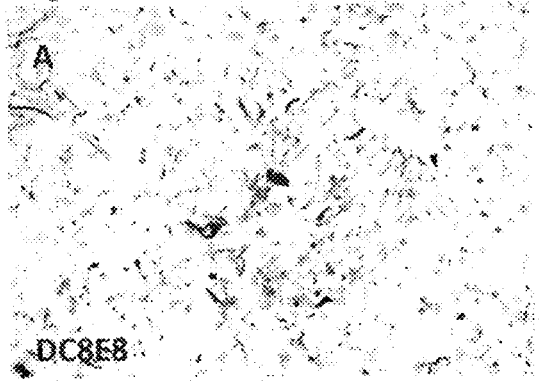
Fig. 43A
Fig. 43B
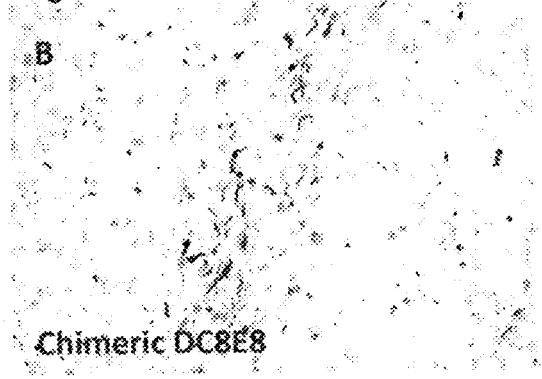
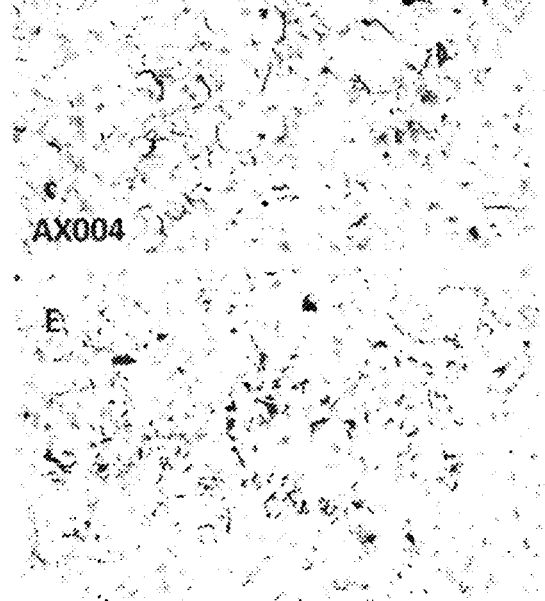
Fig. 43C
Fig. 43E
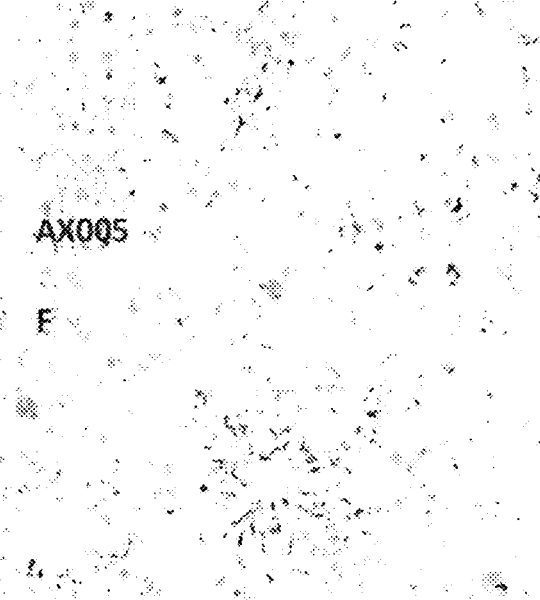
Fig. 43D
Fig. 43F

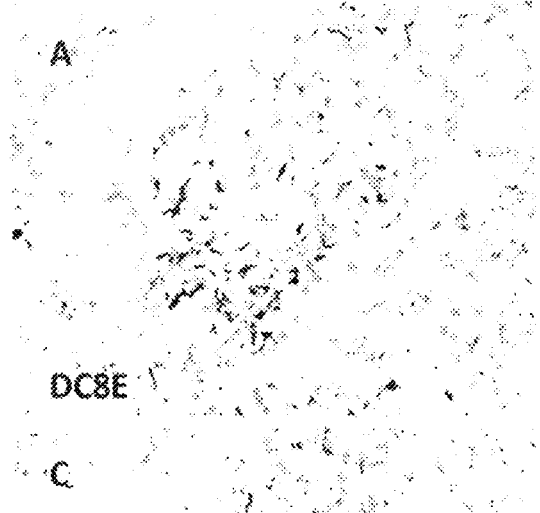
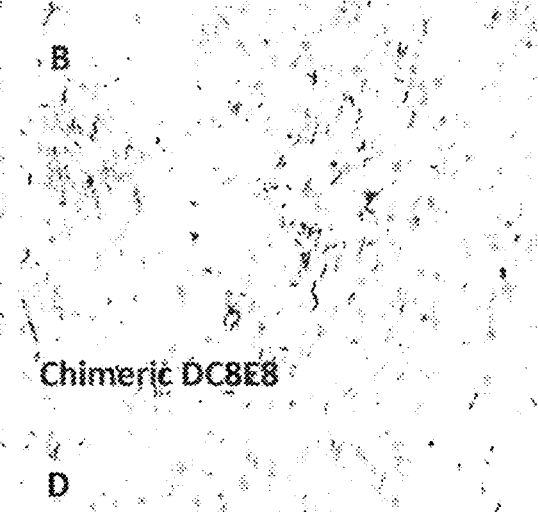
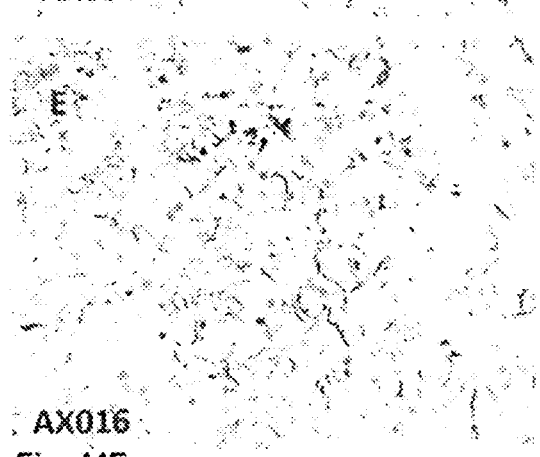
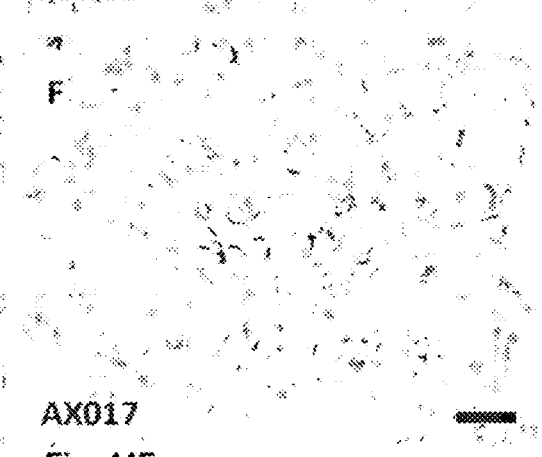
Fig. 44A Fig. 44B Fig. 44C Fig. 44D Fig. 44E Fig. 44F

Fig. 45A  DC8E8
Fig. 45B  Chimeric DC8E8
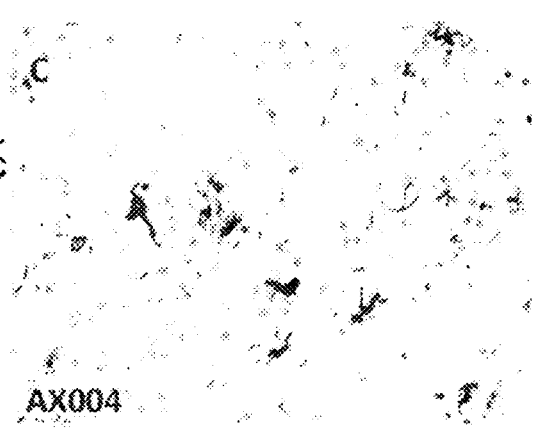
Fig. 45C  AX004
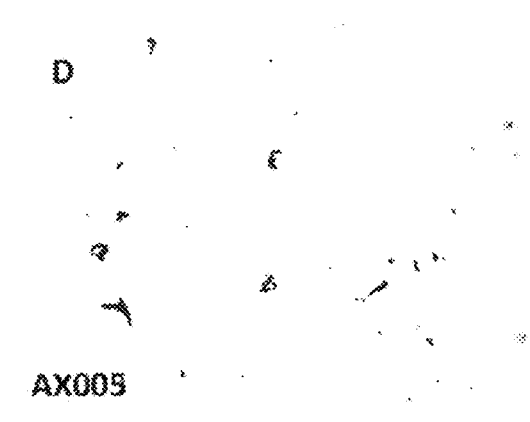
Fig. 45D  AX005
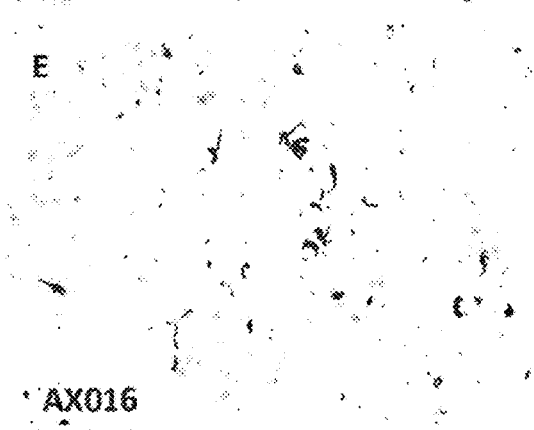
Fig. 45E  AX016
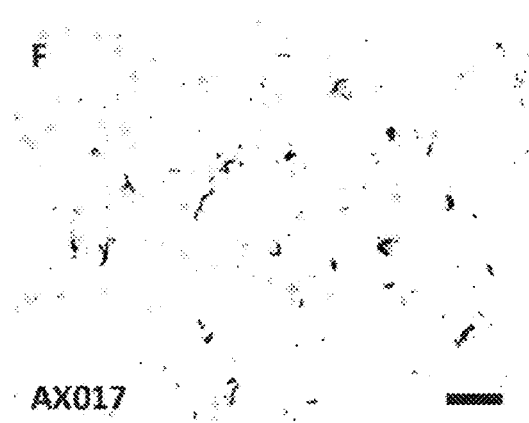
Fig. 45F  AX017

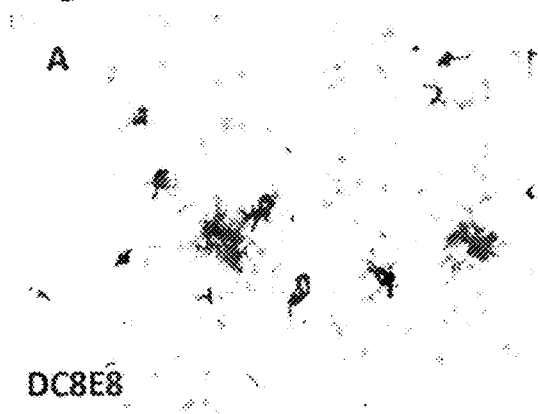
Fig. 46A DC8E8
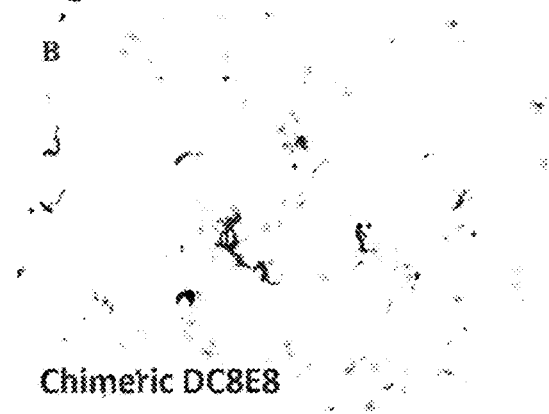
Fig. 46B Chimeric DC8E8
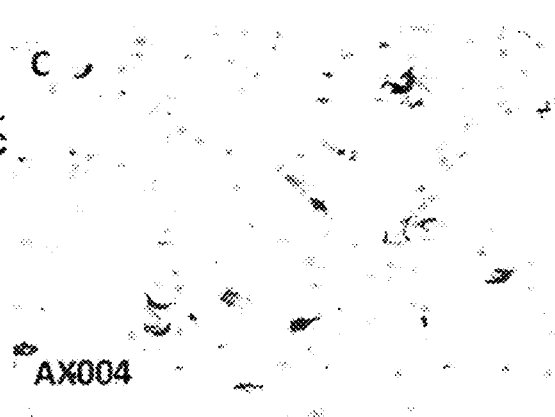
Fig. 46C AX004
Fig. 46D AX005
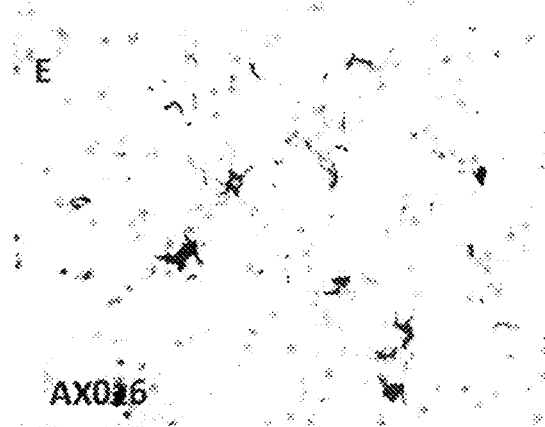
Fig. 46E AX016
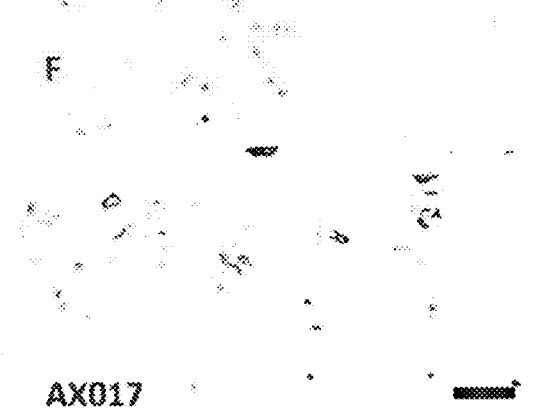
Fig. 46F AX017

```
                              SEQUENCE LISTING

<160> NUMBER OF SEQ ID NOS: 177

<210> SEQ ID NO 1
   <211> LENGTH: 5
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 1

Asp Tyr Val Ile Ser
   1               5

<210> SEQ ID NO 2
   <211> LENGTH: 17
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 2

Glu Ile Phe Pro Arg Ser Gly Ser Thr Tyr Tyr Asn Glu Lys Phe Lys
   1               5                   10                  15

Gly

<210> SEQ ID NO 3
   <211> LENGTH: 11
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 3

Asp Tyr Tyr Gly Thr Ser Phe Ala Met Asp Tyr
   1               5                   10

<210> SEQ ID NO 4
   <211> LENGTH: 17
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 4

Lys Ser Ser Gln Ser Leu Leu Asn Ser Arg Thr Arg Lys Asn Tyr Leu
   1               5                   10                  15

Ala
```

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gln Ser Phe Tyr Leu Arg Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
            20                  25                  30

Val Ile Ser Trp Val Lys Gln Arg Thr Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Ser Val Thr Val Ser Ser
        115                 120

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

```
Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Tyr Leu Arg Thr Phe Gly Gly Gly Thr Lys Leu Asp Ile Lys
            100                 105                 110

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
                20                  25                  30

Val Ile Ser Trp Val Lys Gln Arg Thr Gly Gln Gly Leu Glu Trp Ile
            35                  40                  45

Gly Glu Ile Phe Pro Arg Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Ser Val Thr Val Ser Ser
        115                 120

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95
```

```
Ser Phe Tyr Leu Arg Thr Phe Gly Gly Gly Thr Lys Leu Asp Ile Lys
            100                 105                 110
```

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
            20                  25                  30

Val Ile Ser Trp Val Lys Gln Arg Thr Gly Gln Gly Leu Glu Trp Ile
        35                  40                  45

Gly Glu Ile Phe Pro Arg Ser Gly Ser Thr Tyr Tyr Asn Glu Lys Phe
50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Ser Val Thr Val Ser Ser
        115                 120
```

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Tyr Leu Arg Thr Phe Gly Gly Gly Thr Lys Leu Asp Ile Lys
            100                 105                 110
```

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Pro Glu Val Lys Lys Pro Gly Ser
1               5                   10                  15

Ser Val Lys Val Pro Cys Lys Ala Ser Gly Tyr Ile Phe Thr Asp Tyr
            20                  25                  30

Val Ile Ser Trp Val Lys Gln Ala Pro Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Pro Glu Val Lys Lys Pro Gly Ser
1               5                   10                  15

Ser Val Lys Val Pro Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
                35                  40                  45

Gly Glu Ile Phe Pro Arg Ser Gly Ser Thr Tyr Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Tyr Gly Thr Ser Phe Ala Met Asp Tyr Trp Gly Gln
                100                 105                 110

Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Tyr
                20                  25                  30

Val Ile Ser Trp Val Arg Gln Ala Pro Gly Gln Gly Leu Glu Trp Met
                35                  40                  45

Gly Glu Ile Phe Pro Arg Ser Gly Ser Thr Tyr Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Tyr Gly Thr Ser Phe Ala Met Asp Tyr Trp Gly Gln
                100                 105                 110

Gly Thr Leu Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ile Phe Ser Asp Tyr
                20                  25                  30

Val Ile Ser Trp Val Arg Gln Ala Pro Gly Gln Gly Leu Glu Trp Met
                35                  40                  45

Gly Glu Ile Phe Pro Arg Ser Gly Ser Thr Tyr Tyr Asn Glu Lys Phe
 50                  55                  60

Lys Gly Arg Val Thr Ile Thr Ala Asp Lys Ser Thr Ser Thr Ala Tyr
 65                  70                  75                  80

```
Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120
```

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120
```

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Lys Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120
```

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met

```
                35                  40                  45
Gly Glu Ile Phe Pro Arg Ser Gly Ser Thr Tyr Tyr Asn Glu Lys Phe
         50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Asp Tyr Tyr Gly Thr Ser Phe Ala Met Asp Tyr Trp Gly Gln
            100                 105                 110
Gly Thr Leu Val Thr Val Ser Ser
            115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Ile Phe Ser Asp Tyr
                 20                  25                  30
Val Ile Ser Trp Val Arg Gln Ala Pro Gly Gln Gly Leu Glu Trp Met
             35                  40                  45
Gly Glu Ile Phe Pro Arg Ser Gly Ser Thr Tyr Tyr Asn Glu Lys Phe
         50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Tyr Tyr Gly Thr Ser Phe Ala Met Asp Tyr Trp Gly Gln
            100                 105                 110
Gly Thr Leu Val Thr Val Ser Ser
            115                 120

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Met Thr Gln Ser Pro Leu Ser Leu Pro Val Thr Pro Gly
 1               5                  10                  15
Glu Pro Ala Ser Ile Ser Cys Lys Ser Ser Gln Ser Leu Leu Asn Ser
                 20                  25                  30
Arg Thr Arg Lys Asn Tyr Leu Ala Trp Tyr Leu Gln Lys Pro Gly Gln
             35                  40                  45
Ser Pro Gln Leu Leu Ile Tyr Trp Ala Ser Thr Arg Glu Ser Gly Val
         50                  55                  60
Pro Asp Arg Phe Thr Gly Ser Gly Ser Gly Thr Asp Phe Thr Leu Lys
 65                  70                  75                  80
Ile Ser Arg Val Glu Ala Glu Asp Val Gly Val Tyr Tyr Cys Lys Gln
```

```
                    85                  90                  95
Ser Phe Tyr Leu Arg Thr Phe Gly Gln Gly Thr Lys Val Glu Ile Lys
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Ser Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Arg Thr Arg Lys Asn Tyr Leu Ala Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Phe Tyr Leu Arg Thr Phe Gly Gln Gly Thr Lys Val Glu Ile Lys
            100                 105                 110

<210> SEQ ID NO 28
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                    165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 29
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Pro Glu Val Lys Lys Pro Gly Ser
1               5                   10                  15

Ser Val Lys Val Pro Cys Lys Ala Ser Gly Tyr Ile Phe Thr Asp Tyr
            20                  25                  30

Val Ile Ser Trp Val Lys Gln Ala Pro Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60
```

-continued

Lys Gly Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
             85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 30
<211> LENGTH: 450
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 30

```
Gln Val Gln Leu Val Gln Ser Gly Pro Glu Val Lys Lys Pro Gly Ser
1               5                   10                  15

Ser Val Lys Val Pro Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
                20                  25                  30

Val Ile Ser Trp Val Arg Gln Ala Pro Gly Gln Gly Leu Glu Trp Met
            35                  40                  45

Gly Glu Ile Phe Pro Arg Ser Gly Ser Thr Tyr Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 32
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180                 185                 190
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 33
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                 85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 34
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Lys Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 36
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
                195                 200                 205
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 37
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 38
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

-continued

```
Gln Val Gln Leu Val Gln Ser Gly Ala Glu Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
            35                  40                  45

Gly Glu Ile Phe Pro Arg Ser Gly Ser Thr Tyr Tyr Asn Glu Lys Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 39
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 40
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 41
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
                20                  25                  30

Val Ile Ser Trp Val Lys Gln Arg Thr Gly Gln Gly Leu Glu Trp Ile
            35                  40                  45

Gly Glu Ile Phe Pro Arg Ser Gly Ser Thr Tyr Tyr Asn Glu Lys Phe
        50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95

Ala Arg Asp Tyr Tyr Gly Thr Ser Phe Ala Met Asp Tyr Trp Gly Gln
            100                 105                 110
```

Gly Thr Ser Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 42
<211> LENGTH: 444
<212> TYPE: PRT
<213> ORGANISM: Mus musculus

<400> SEQUENCE: 42

Gln Val Gln Leu Gln Gln Ser Gly Pro Glu Leu Val Lys Pro Gly Thr
1               5                   10                  15
Ser Val Lys Met Pro Cys Lys Ala Ser Gly Tyr Ile Phe Thr Asp Tyr
            20                  25                  30

```
Val Ile Ser Trp Val Lys Gln Arg Thr Gly Gln Gly Leu Glu Trp Ile
         35                  40                  45
Gly Glu Ile Phe Pro Arg Ser Gly Ser Thr Tyr Tyr Asn Glu Lys Phe
     50                  55                  60
Lys Gly Lys Ala Thr Leu Thr Ala Asp Lys Ser Ser Asn Thr Ala Tyr
 65                  70                  75                  80
Met Gln Leu Ser Ser Val Thr Ser Glu Asp Ser Ala Val Tyr Phe Cys
                 85                  90                  95
Ala Arg Asp Tyr Tyr Gly Thr Ser Phe Ala Met Asp Tyr Trp Gly Gln
                100                 105                 110
Gly Thr Ser Val Thr Val Ser Ser Ala Lys Thr Thr Pro Pro Ser Val
            115                 120                 125
Tyr Pro Leu Ala Pro Gly Ser Ala Ala Gln Thr Asn Ser Met Val Thr
        130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Ser Val Thr Val Pro Ser
            180                 185                 190
Ser Thr Trp Pro Ser Gln Thr Val Thr Cys Asn Val Ala His Pro Ala
        195                 200                 205
Ser Ser Thr Lys Val Asp Lys Lys Ile Val Pro Arg Asp Cys Gly Cys
210                 215                 220
Lys Pro Cys Ile Cys Thr Val Pro Glu Val Ser Ser Val Phe Ile Phe
225                 230                 235                 240
Pro Pro Lys Pro Lys Asp Val Leu Thr Ile Thr Leu Thr Pro Lys Val
                245                 250                 255
Thr Cys Val Val Val Asp Ile Ser Lys Asp Asp Pro Glu Val Gln Phe
            260                 265                 270
Ser Trp Phe Val Asp Asp Val Glu Val His Thr Ala Gln Thr Lys Pro
        275                 280                 285
Arg Glu Glu Gln Ile Asn Ser Thr Phe Arg Ser Val Ser Glu Leu Pro
290                 295                 300
Ile Met His Gln Asp Trp Leu Asn Gly Lys Glu Phe Lys Cys Arg Val
305                 310                 315                 320
Asn Ser Ala Ala Phe Pro Ala Pro Ile Glu Lys Thr Ile Ser Lys Thr
                325                 330                 335
Lys Gly Arg Pro Lys Ala Pro Gln Val Tyr Thr Ile Pro Pro Pro Lys
            340                 345                 350
Glu Gln Met Ala Lys Asp Lys Val Ser Leu Thr Cys Met Ile Thr Asn
        355                 360                 365
Phe Phe Pro Glu Asp Ile Thr Val Glu Trp Gln Trp Asn Gly Gln Pro
370                 375                 380
Ala Glu Asn Tyr Lys Asn Thr Gln Pro Ile Met Asp Thr Asp Gly Ser
385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
            420                 425                 430
His Thr Glu Lys Ser Leu Ser His Ser Pro Gly Lys
        435                 440
```

<210> SEQ ID NO 43
<211> LENGTH: 447
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 44
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Pro Glu Val Lys Lys Pro Gly Ser
1               5                   10                  15

Ser Val Lys Val Pro Cys Lys Ala Ser Gly Tyr Ile Phe Thr Asp Tyr
                20                  25                  30

Val Ile Ser Trp Val Lys Gln Ala Pro Gly Gln Gly Leu Glu Trp Ile
            35                  40                  45

Gly Glu Ile Phe Pro Arg Ser Gly Ser Thr Tyr Tyr Asn Glu Lys Phe
50                  55                  60

Lys Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Tyr Tyr Gly Thr Ser Phe Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
```

```
                275                 280                 285
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 45
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Pro Glu Val Lys Lys Pro Gly Ser
1               5                   10                  15

Ser Val Lys Val Pro Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 46
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 47
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asp Tyr

```
            20                  25                  30
Val Ile Ser Trp Val Arg Gln Ala Pro Gly Gln Gly Leu Glu Trp Met
            35                  40                  45
Gly Glu Ile Phe Pro Arg Ser Gly Ser Thr Tyr Tyr Asn Glu Lys Phe
            50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
            85                  90                  95
Ala Arg Asp Tyr Tyr Gly Thr Ser Phe Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
            210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
            405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
            435                 440                 445
```

<210> SEQ ID NO 48
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu

```
              355                 360                 365
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 49
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Lys Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 50
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Ile
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 51
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
```

Gly Thr Leu Val Thr Val Ser Ser Ala Ser Thr Lys Gly Pro Ser Val
            100                 105                 110

Phe Pro Leu Ala Pro Cys Ser Arg Ser Thr Ser Glu Ser Thr Ala Ala
        115                 120                 125

Leu Gly Cys Leu Val Lys Asp Tyr Phe Pro Glu Pro Val Thr Val Ser
    130                 135                 140

Trp Asn Ser Gly Ala Leu Thr Ser Gly Val His Thr Phe Pro Ala Val
145                 150                 155                 160

Leu Gln Ser Ser Gly Leu Tyr Ser Leu Ser Ser Val Val Thr Val Pro
                165                 170                 175

Ser Ser Ser Leu Gly Thr Lys Thr Tyr Thr Cys Asn Val Asp His Lys
            180                 185                 190

Pro Ser Asn Thr Lys Val Asp Lys Arg Val Glu Ser Lys Tyr Gly Pro
        195                 200                 205

Pro Cys Pro Pro Cys Pro Ala Pro Glu Phe Leu Gly Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser Gln Glu Asp Pro Glu
                245                 250                 255

Val Gln Phe Asn Trp Tyr Val Asp Gly Val Glu Val His Asn Ala Lys
            260                 265                 270

Thr Lys Pro Arg Glu Glu Gln Phe Asn Ser Thr Tyr Arg Val Val Ser
        275                 280                 285

Val Leu Thr Val Leu His Gln Asp Trp Leu Asn Gly Lys Glu Tyr Lys
    290                 295                 300

Cys Lys Val Ser Asn Lys Gly Leu Pro Ser Ser Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Gln Glu Glu Met Thr Lys Asn Gln Val Ser Leu Thr Cys Leu
            340                 345                 350

Val Lys Gly Phe Tyr Pro Ser Asp Ile Ala Val Glu Trp Glu Ser Asn
        355                 360                 365

Gly Gln Pro Glu Asn Asn Tyr Lys Thr Thr Pro Pro Val Leu Asp Ser
    370                 375                 380

Asp Gly Ser Phe Phe Leu Tyr Ser Arg Leu Thr Val Asp Lys Ser Arg
385                 390                 395                 400

Trp Gln Glu Gly Asn Val Phe Ser Cys Ser Val Met His Glu Ala Leu
                405                 410                 415

His Asn His Tyr Thr Gln Lys Ser Leu Ser Leu Ser Leu Gly Lys
            420                 425                 430

435                 440                 445

<210> SEQ ID NO 52
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ser
1               5                   10                  15

-continued

Ser Val Lys Val Ser Cys Lys Ala Ser Gly Thr Phe Ser Asp Tyr
            20                  25                  30

Val Ile Ser Trp Val Arg Gln Ala Pro Gly Gln Gly Leu Glu Trp Met
         35                  40                  45

Gly Glu Ile Phe Pro Arg Ser Gly Ser Thr Tyr Tyr Asn Glu Lys Phe
     50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Asp Tyr Tyr Gly Thr Ser Phe Ala Met Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
             180                 185                 190

Ser Ser Ser Leu Gly Thr Lys Thr Tyr Thr Cys Asn Val Asp His Lys
         195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
             245                 250                 255

Pro Glu Val Thr Cys Val Val Val Asp Val Ser Gln Glu Asp Pro Glu
         260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
             325                 330                 335

Ser Lys Ala Lys Gly Gln Pro Arg Glu Pro Gln Val Tyr Thr Leu Pro
             340                 345                 350

Pro Ser Gln Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
             405                 410                 415

Trp Gln Glu Gly Asn Val Phe Ser Cys Ser Val Met His Glu Ala Leu
             420                 425                 430

His Asn His Tyr Thr Gln Lys Ser Leu Ser Leu Ser Leu Gly Lys

<210> SEQ ID NO 53
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Gln Val Gln Leu Val Gln Ser Gly Ala Glu Val Lys Pro Gly Ser
1               5                   10                  15

Ser Val Lys Val Ser Cys Lys Ala Ser Gly Thr Phe Ser Asp Tyr
                20                  25                  30

Val Ile Ser Trp Val Arg Gln Ala Pro Gly Gln Gly Leu Glu Trp Met
            35                  40                  45

Gly Glu Ile Phe Pro Arg Ser Gly Ser Thr Tyr Tyr Asn Glu Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 54
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445
```

<210> SEQ ID NO 55
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ser Asp Tyr
            20                  25                  30

Val Ile Ser Trp Val Arg Gln Ala Pro Gly Gln Gly Leu Glu Trp Met
        35                  40                  45

Gly Glu Ile Phe Pro Arg Ser Gly Ser Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Thr Ser Phe Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180             185                 190
Ser Ser Ser Leu Gly Thr Lys Thr Tyr Thr Cys Asn Val Asp His Lys
            195                 200             205

Pro Ser Asn Thr Lys Val Asp Lys Arg Val Glu Ser Lys Tyr Gly Pro
        210                 215             220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 56
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Gln Ser Gly Pro Glu Leu Val Lys Pro Gly Thr
1               5                   10                  15

Ser Val Lys Met Pro Cys Lys Ala Ser Gly Tyr Ile Phe Thr Asp Tyr
            20                  25                  30

Val Ile Ser Trp Val Lys Gln Arg Thr Gly Gln Gly Leu Glu Trp Ile
        35                  40                  45

Gly Glu Ile Phe Pro Arg Ser Gly Ser Thr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Val Thr Ser Glu Asp Ser Ala Val Tyr Phe Cys
                85                  90                  95
```

```
Ala Arg Asp Tyr Tyr Gly Thr Ser Phe Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 57
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Ser Pro Leu Ser Leu Pro Val Thr Pro Gly
1               5                   10                  15
```

Glu Pro Ala Ser Ile Ser Cys Lys Ser Ser Gln Ser Leu Leu Asn Ser
                20                  25                  30

Arg Thr Arg Lys Asn Tyr Leu Ala Trp Tyr Leu Gln Lys Pro Gly Gln
            35                  40                  45

Ser Pro Gln Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Phe Tyr Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 58
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Ser Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
                20                  25                  30

Arg Thr Arg Lys Asn Tyr Leu Ala Trp Tyr Leu Gln Lys Pro Gly Gln
            35                  40                  45

Ser Pro Gln Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Phe Tyr Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln

```
                145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 59
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Tyr Leu Arg Thr Phe Gly Gly Gly Thr Lys Leu Asp Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 60
<211> LENGTH: 120
<212> TYPE: PRT
<213> ORGANISM: Mus musculus

<400> SEQUENCE: 60

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
```

```
                    20                  25                  30

Val Ser Ala Gly Glu Lys Val Thr Met Ser Cys Lys Ser Gln Ser
                35                  40                  45

Leu Leu Asn Ser Arg Thr Arg Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu
            115                 120

<210> SEQ ID NO 61
<211> LENGTH: 101
<212> TYPE: PRT
<213> ORGANISM: Mus musculus

<400> SEQUENCE: 61

Asp Ile Val Met Thr Gln Ser Pro Ser Ser Leu Ser Val Ser Ala Gly
1               5                   10                  15

Asp Lys Val Thr Met Ser Cys Lys Ser Gln Ser Leu Leu Asn Ser
                20                  25                  30

Arg Asn Gln Lys Asn Tyr Leu Ala Trp Tyr Gln Gln Lys Pro Trp Gln
            35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro
            100

<210> SEQ ID NO 62
<211> LENGTH: 121
<212> TYPE: PRT
<213> ORGANISM: Mus musculus

<400> SEQUENCE: 62

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro
```

```
                 115                 120

<210> SEQ ID NO 63
<211> LENGTH: 121
<212> TYPE: PRT
<213> ORGANISM: Mus musculus

<400> SEQUENCE: 63

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Leu Ala
                20                  25                  30

Val Ser Val Gly Glu Lys Val Thr Met Ser Cys Lys Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro
        115                 120

<210> SEQ ID NO 64
<211> LENGTH: 121
<212> TYPE: PRT
<213> ORGANISM: Mus musculus

<400> SEQUENCE: 64

Met Glu Ser Gln Thr Gln Val Leu Ile Ser Leu Leu Phe Trp Val Ser
1               5                   10                  15

Gly Thr Cys Gly Asp Ile Val Met Thr Gln Ser Pro Ser Ser Leu Ser
                20                  25                  30

Val Ser Ala Gly Glu Lys Val Thr Met Ser Cys Lys Ser Ser Gln Ser
            35                  40                  45

Leu Leu Asn Ser Gly Asn Gln Lys Asn Tyr Leu Ala Trp Tyr Gln Gln
        50                  55                  60

Lys Pro Gly Gln Pro Pro Lys Leu Leu Ile Tyr Gly Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp His Ser Tyr Pro
        115                 120

<210> SEQ ID NO 65
<211> LENGTH: 126
<212> TYPE: PRT
<213> ORGANISM: Homo sapiens

<400> SEQUENCE: 65

Gln Leu Leu Gly Leu Leu Met Leu Trp Val Ser Gly Ser Ser Gly Asp
1               5                   10                  15

Ile Val Met Thr Gln Ser Pro Leu Ser Leu Pro Val Thr Pro Gly Glu
                20                  25                  30
```

```
Pro Ala Ser Ile Ser Cys Arg Ser Ser Gln Ser Leu His Ile Asn
            35                  40                  45

Gly Tyr Asn Tyr Leu Asp Trp Tyr Leu Gln Lys Pro Gly Gln Ser Pro
 50                  55                  60

Gln Leu Leu Ile Tyr Leu Gly Ser Asn Arg Ala Ser Gly Val Pro Asp
 65                  70                  75                  80

Arg Phe Thr Gly Ser Gly Ser Gly Thr Asp Phe Thr Leu Lys Ile Ser
                 85                  90                  95

Arg Val Glu Ala Glu Asp Val Gly Val Tyr Tyr Cys Met Gln Ala Leu
                100                 105                 110

Gln Pro Trp Thr Phe Gly Gln Gly Thr Lys Val Glu Ile Lys
                115                 120                 125

<210> SEQ ID NO 66
<211> LENGTH: 98
<212> TYPE: PRT
<213> ORGANISM: Mus musculus

<400> SEQUENCE: 66

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
                20                  25                  30

Gly Ile Ser Trp Val Lys Gln Arg Thr Gly Gln Gly Leu Glu Trp Ile
                35                  40                  45

Gly Glu Ile Tyr Pro Arg Ser Gly Asn Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Glu Leu Arg Ser Leu Thr Ser Glu Asp Ser Ala Val Tyr Phe Cys
                 85                  90                  95

Ala Arg

<210> SEQ ID NO 67
<211> LENGTH: 98
<212> TYPE: PRT
<213> ORGANISM: Mus musculus

<400> SEQUENCE: 67

Gln Val Gln Leu Lys Gln Ser Gly Ala Glu Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Ile Asn Trp Val Lys Gln Arg Pro Gly Gln Gly Leu Glu Trp Ile
                35                  40                  45

Gly Lys Ile Gly Pro Gly Ser Gly Ser Thr Tyr Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg

<210> SEQ ID NO 68
<211> LENGTH: 97
<212> TYPE: PRT
```

```
<213> ORGANISM: Mus musculus

<400> SEQUENCE: 68

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Asp Tyr Tyr
            20                  25                  30

Met His Trp Val Lys Gln Lys Pro Gly Lys Gly Leu Glu Trp Ile Gly
        35                  40                  45

Glu Ile Tyr Pro Gly Ser Gly Asn Thr Tyr Tyr Asn Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg

<210> SEQ ID NO 69
<211> LENGTH: 98
<212> TYPE: PRT
<213> ORGANISM: Mus musculus

<400> SEQUENCE: 69

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Tyr Asn Glu Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg

<210> SEQ ID NO 70
<211> LENGTH: 98
<212> TYPE: PRT
<213> ORGANISM: Mus musculus

<400> SEQUENCE: 70

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg
```

<210> SEQ ID NO 71
<211> LENGTH: 139
<212> TYPE: PRT
<213> ORGANISM: Homo sapiens

<400> SEQUENCE: 71

Met Asp Trp Thr Trp Arg Phe Leu Phe Val Val Ala Ala Val Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Ser Thr Val Thr Gly Asp Phe Asp Tyr
        115                 120                 125

Trp Gly Gln Gly Thr Leu Val Thr Val Ser Ser
    130                 135

<210> SEQ ID NO 72
<211> LENGTH: 764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
ggctgctttg catagacgcc tccagcctag cccagctgct cagaatttat aaaccagtat      60
gaactgagaa gcatcagaca ggcagtggga gcaagatgga ttcacaggcc caggttctta     120
tattgctgct gctatgggta tctggtgaga aatttaaaag tattatcatt tcagagttaa     180
acctttttat ataaggaatt tataatatgt gcaagtgtgt aatatttctt ccataataac     240
tctctgacaa tatgaaatta caaagacctt tgacaaattt caactgttat aataatctat     300
acttgtgtat gtatgcatgt tcactttcta cttatttcag gtacctgtgg ggacattgtg     360
atgtcacagt ctccatcctc cctggctgtg tcagcaggag agaaggtcac tatgagctgc     420
aaatccagtc agagtctgct aacagtaga acccgaaaga actacttggc ttggtaccag     480
cagaaaccag ggcagtctcc taaactgctg atctactggg catccactag ggaatctggg     540
gtccctgatc gcttcacagg cagtggatct gggacagatt tcactctcac catcagcagt     600
gtgcaggctg aagacctggc agtttattac tgcaagcaat cttataatct tcccacagtg     660
cttcagtctc ctacacaaac ctcctttaga gtttcaccag ctgcctgcat aacacacagc     720
catgggtctg cacacttcct ctttctacaa gagagccagc atgc                      764

<210> SEQ ID NO 73
<211> LENGTH: 302
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 73

| gacattgtga tgacacagtc tccatcctcc ctgagtgtgt cagcaggaga taaggtcact | 60 |
| atgagctgca agtccagtca gagtctgtta aacagtagaa accaaaagaa ctacttggcc | 120 |
| tggtaccagc agaaaccatg gcagcctcct aaactgctga tctacggggc atccactagg | 180 |
| gaatctgggg tccctgatcg cttcacaggc agtggatctg gaacagattt cactctcacc | 240 |
| atcagcagtg tgcaggctga agacctggca gtttattact gtcagaatga ttatagttat | 300 |
| cc | 302 |

<210> SEQ ID NO 74
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

| tttctgtcag ctttgcatgg gttcctccag cccagcccac cttctcagaa tttataaacc | 60 |
| aggcctttgc attgtgactg atctacatct gaaaggcagg tggagcaaga tggaatcaca | 120 |
| gactcaggtc ctcatgtccc tgctgttctg ggtatctggt aagaaattta agtattaaa | 180 |
| acctttttcaa agtttcatct ttgtaataag caatttataa tatatgccag tatatagtat | 240 |
| ttcttacaca ataatgtttg atattatgac attttaagga catttaaatg acaaattaca | 300 |
| actgtaatta taatacatat atattagtgt agctatgcat tttcactgtc tattcattat | 360 |
| ttcaggtacc tgtggggaca ttgtgatgac acagtctcca tcctccctga ctgtgacagc | 420 |
| aggagagaag gtcactatga gctgcaagtc cagtcagagt ctgttaaaca gtggaaatca | 480 |
| aaagaactac ttgacctggt accagcagaa accaggcag cctcctaaac tgttgatcta | 540 |
| ctgggcatcc actagggaat ctggggtccc tgatcgcttc acaggcagtg gatctggaac | 600 |
| agatttcact ctcaccatca gcagtgtgca ggctgaagac ctggcagttt attactgtca | 660 |
| gaatgattat agttatcctc ccacagtgct tcagcctcct acacaaacct ccttaagagt | 720 |

<210> SEQ ID NO 75
<211> LENGTH: 856
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

| agtgatccct cttgctctct gtgatggcat ttttgttgat tgacaccatc cactctcaca | 60 |
| cacactgccc aggcatttgc ttttgtattt gctggctgct ttgcatagac ccctccagcc | 120 |
| taacccagct gctcagaatt tataaaccag tatgaactga gcagcatcag acaggcaggg | 180 |
| gaagcaagat ggattcacag gcccaggttc ttatgttact gctgctatgg gtatctggtg | 240 |
| agaaatttaa agtattatc atttcagagt tacacctttt tatataagaa atttatacta | 300 |
| tgtgcaagtg tgtaatatta cttccataat aactctgaca atatgacatt acaaagacct | 360 |
| ttgacaaatt tcaactgtta taataatcta tttgtgtatg tattcatgtt cactttctac | 420 |
| ttatttcagg tacctgtggg gacattgtga tgtcacagtc tccatcctcc ctagctgtgt | 480 |

```
cagttggaga gaaggttact atgagctgca agtccagtca gagccttta tatagtagca      540 atcaaaagaa ctacttggcc tggtaccagc agaaaccagg gcagtctcct aaactgctga      600
tttactgggc atccactagg gaatctgggg tccctgatcg cttcacaggc agtggatctg      660
ggacagattt cactctcacc atcagcagtg tgaaggctga agacctggca gtttattact      720
gtcagcaata ttatagctat cctcccacag tgcttcagcc tcctacacaa acctccttga      780
gaatttcacc agctgcctgc ataacacaca gtccttggtc tgaacacttc ctctttcttc      840
atgaaagcca gcatgc                                                      856

<210> SEQ ID NO 76
<211> LENGTH: 707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
ctgtcagctt tgcatgggtt cctccagccc agcccagctg ctcagaattt ataaaccagg       60
cctttgcatt gtgactgatc tacatctgaa aggcaggtgg agcaagatgg aatcacagac      120
tcaggtcctc atctccttgc tgttctgggt atctggtaag aaatttaaag tagtaaaacc      180
ttttcaaagt ttcatctttg taataagcaa tttacaatat atgccagtgt atagtatttc      240
ttacacaatg atgttttgat attatgacat tttaaggaca tttaaatgac aaattacaac      300
tgttgttata atatatatta gtgtagatat gcattttcac tgtctattca ttatttcagg      360
tacctgtggg gacattgtga tgacacagtc tccatcctcc ctgagtgtgt cagcaggaga      420
gaaggtcact atgagctgca agtccagtca gagtctgtta acagtggaa atcaaaagaa      480 ctacttggcc tggtaccagc agaaaccagg gcagcctcct aaactgttga tctacggggc      540
atccactagg gaatctgggg tccctgatcg cttcacaggc agtggatctg gaaccgattt      600
cactcttacc atcagcagtg tgcaggctga agacctggca gtttattact gtcagaatga      660
tcatagttat cctcccacag tgcttcagcc tcctacacaa acctcct                    707

<210> SEQ ID NO 77
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
ctcagctcct ggggctgcta atgctctggg tctctggatc cagtggggat attgtgatga       60
ctcagtctcc actctccctg cccgtcaccc ctggagagcc ggcctccatc tcctgcaggt      120
ctagtcagag cctcctgcat attaatggat acaactattt ggattggtac ctgcagaagc      180
cagggcagtc tccacagctc ctgatctatt tgggttctaa tcgggcctcc ggggtccctg      240
acaggttcac tggcagtgga tcaggcacag attttacact gaaaatcagc agagtggagg      300
ctgaggatgt tggggtttat tactgcatgc aagctctaca accgtggacg ttcggccaag      360
ggaccaaggt ggaaatcaaa                                                  380

<210> SEQ ID NO 78
<211> LENGTH: 294
<212> TYPE: DNA
<213> ORGANISM: Mus musculus
```

<400> SEQUENCE: 78

```
caggttcagc tgcagcagtc tggagctgag ctggcgaggc tggggcttc agtgaagctg    60
tcctgcaagg cttctggcta caccttcaca agctatggta taagctgggt gaagcagaga   120
actggacagg gccttgagtg gattggagag atttatccta gaagtggtaa tacttactac   180
aatgagaagt tcaagggcaa ggccacactg actgcagaca aatcctccag cacagcgtac   240
atggagctcc gcagcctgac atctgaggac tctgcggtct atttctgtgc aaga          294
```

<210> SEQ ID NO 79
<211> LENGTH: 294
<212> TYPE: DNA
<213> ORGANISM: Mus musculus

<400> SEQUENCE: 79

```
caggtccagc tgaagcagtc tggagctgag ctggtgaagc ctggggcttc agtgaagata    60
tcctgcaagg cttctggcta caccttcact gactactata taaactgggt gaagcagagg   120
cctggacagg gccttgagtg gattggaaag attggtcctg gaagtggtag tacttactac   180
aatgagaagt tcaagggcaa ggccacactg actgcagaca aatcctccag cacagcctac   240
atgcagctca gcagcctgac atctgaggac tctgcagtct atttctgtgc aaga          294
```

<210> SEQ ID NO 80
<211> LENGTH: 294
<212> TYPE: DNA
<213> ORGANISM: Mus musculus

<400> SEQUENCE: 80

```
taggtccagc tgcagcagtc tggacctgag ctggtaaagc ctggggcttc agtgaagatg    60
tcctgcaagg cttctggata cacattcact gactactaca tgcactgggt gaagcagaag   120
cctgggaagg gccttgagtg gattggagag atttatcctg gaagtggtaa tacttactac   180
aatgagaagt tcaagggcaa ggccacactg actgcagaca catcctccag cacagcctac   240
atgcagctca gcagcctgac atctgaggac tctgcagtct atttctgtgc aaga          294
```

<210> SEQ ID NO 81
<211> LENGTH: 294
<212> TYPE: DNA
<213> ORGANISM: Mus musculus

<400> SEQUENCE: 81

```
caggtccagc tacagcagtc tggacctgag ctggtgaagc ctggggcttc agtgaagata    60
tcctgcaagg cttctggcta caccttcact gactactata taaactgggt gaagcagagg   120
cctggacagg gacttgagtg gattggatgg atttttcctg gaagtggtag tacttactac   180
aatgagaagt tcaagggcaa ggccacactt actgtagaca aatcctccag cacagcctac   240
atgttgctca gcagcctgac ctctgaggac tctgcggtct atttctgtgc aaga          294
```

<210> SEQ ID NO 82
<211> LENGTH: 294
<212> TYPE: DNA
<213> ORGANISM: Mus musculus

<400> SEQUENCE: 82

```
caggtccagc tgcagcagtc tggagctgag ctggtaaggc ctgggacttc agtgaaggtg    60
tcctgcaagg cttctggata cgccttcact aattacttga tagagtgggt aaagcagagg   120
```

```
cctggacagg gccttgagtg gattggagtg attaatcctg gaagtggtgg tactaactac      180
aatgagaagt tcaagggcaa ggcaacactg actgcagaca atcctccaa cacagcctac       240 atgcagctca gcagcctgac atctgaggac tctgcggtct atttctgtgc aaga            294
```

<210> SEQ ID NO 83
<211> LENGTH: 513
<212> TYPE: DNA
<213> ORGANISM: Homo sapiens

<400> SEQUENCE: 83

```
gttcctcacc atggactgga cctggaggtt cctctttgtg gtggcagcag ttacaggtaa      60
ggggcttcct agtcctaagg ctgaggaagg gatcctggtt tagttaaaga ggattttatt     120 caccctgtg tcctctccac aggtgtccag tcccaggtgc agctggtgca gtctggggct      180
gaggtgaaga agcctgggtc ctcggtgaag gtctcctgca aggcttctgg aggcaccttc    240
agcagctatg ctatcagctg ggtgcgacag gcccctggac aagggcttga gtggatggga     300
gggatcatcc ctatctttgg tacagcaaac tacgcacaga agttccaggg cagagtcacg     360
attaccgcgg acaaatccac gagcacagcc tacatggagc tgagcagcct gagatctgag     420
gacacggccg tgtattactg tgcgagaggg agtacggtga ctacgggaga ttttgactac    480
tggggccagg gaaccctggt caccgtctcc tca                                   513
```

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

```
gattacgtga tctct                                                        15
```

<210> SEQ ID NO 85
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

```
gaaattttcc ccagatccgg atctacttac tataacgaga agtttaaagg c                51
```

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86

```
gattactatg ggacaagttt tgccatggac tat                                   33
```

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aagtcttcac agagcctgct gaactcccgg accagaaaga attacctggc a    51

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgggcatcaa caagggagag c    21

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aaacagagct tctatctgcg aact    24

<210> SEQ ID NO 90
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 90

```
cag gtc caa ttg cag cag tct gga cct gag ctg gtg aag cct ggg act      48
Gln Val Gln Leu Gln Gln Ser Gly Pro Glu Leu Val Lys Pro Gly Thr
1               5                   10                  15 tca gtg aag atg ccc tgt aag gct tct gga tac ata ttc act gac tat      96
Ser Val Lys Met Pro Cys Lys Ala Ser Gly Tyr Ile Phe Thr Asp Tyr
            20                  25                  30 gtc ata agc tgg gtg aag cag aga act gga cag ggc ctt gag tgg att     144
Val Ile Ser Trp Val Lys Gln Arg Thr Gly Gln Gly Leu Glu Trp Ile
        35                  40                  45 gga gag att ttt cct aga agt ggt agt act tac tac aat gag aag ttc     192
Gly Glu Ile Phe Pro Arg Ser Gly Ser Thr Tyr Tyr Asn Glu Lys Phe
    50                  55                  60 aag ggc aag gcc aca ctg act gca gac aaa tcc tcc aac aca gcc tac     240
Lys Gly Lys Ala Thr Leu Thr Ala Asp Lys Ser Ser Asn Thr Ala Tyr
65                  70                  75                  80 atg cag ctc agc agc gtg aca tct gag gac tct gcg gtc tat ttc tgt     288
Met Gln Leu Ser Ser Val Thr Ser Glu Asp Ser Ala Val Tyr Phe Cys
                85                  90                  95 gca aga gat tac tac ggt act tca ttt gct atg gac tac tgg ggt caa     336
Ala Arg Asp Tyr Tyr Gly Thr Ser Phe Ala Met Asp Tyr Trp Gly Gln
            100                 105                 110 gga acc tca gtc acc gtc tcc tca                                     360
Gly Thr Ser Val Thr Val Ser Ser
        115                 120
```

<210> SEQ ID NO 91

```
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 91 gac att gtg atg tca cag tct cca tcc tcc ctg gct gtg tca gca gga    48
Asp Ile Val Met Ser Gln Ser Pro Ser Ser Leu Ala Val Ser Ala Gly
1               5                  10                  15 gag aag gtc act atg agc tgc aaa tcc agt cag agt ctg ctc aac agt    96
Glu Lys Val Thr Met Ser Cys Lys Ser Ser Gln Ser Leu Leu Asn Ser
            20                  25                  30 aga acc cga aag aac tac ctg gct tgg tac cag cag aaa cca ggg cag   144
Arg Thr Arg Lys Asn Tyr Leu Ala Trp Tyr Gln Gln Lys Pro Gly Gln
        35                  40                  45 tct cct aaa ctg ctg atc tac tgg gca tcc act agg gaa tct ggg gtc   192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc   240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgc aag caa   288
Ile Ser Ser Val Gln Ala Glu Asp Leu Ala Val Tyr Tyr Cys Lys Gln
                85                  90                  95 tct ttt tat ctt cgg acg ttc ggt gga ggc acc aag ctg gac atc aaa   336
Ser Phe Tyr Leu Arg Thr Phe Gly Gly Gly Thr Lys Leu Asp Ile Lys
            100                 105                 110

<210> SEQ ID NO 92
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
caggtccagc tgcagcagag cggccccgaa ctggtcaaac ccggaacctc cgtgaagatg     60
ccttgtaaag cctcaggata cattttcacc gattacgtga tctcttgggt caaacagcga    120
acaggacagg gactggagtg gatcggggaa attttcccca gatccggatc tacttactat    180
aacgagaagt taaaggcaa ggccaccctg acagctgaca gagctccaa tacagcttac     240 atgcagctgt ctagtgtgac tagtgaagac tcagcagtct atttctgcgc cagggattac    300
tatgggacaa gttttgccat ggactattgg ggacagggca cttccgtgac cgtctcaagc    360

<210> SEQ ID NO 93
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gatattgtca tgtcacagtc accttcatcc ctggcagtca gcgccggaga aaaagtcact     60
atgtcttgta agtcttcaca gagcctgctg aactcccgga ccagaaagaa ttacctggca    120
tggtatcagc agaagcccgg ccagtctcct aaactgctga tctactgggc atcaacaagg    180
```

```
gagagcggag tgccagaccg cttcacaggc tctgggagtg gaactgattt taccctgaca    240
attagctccg tgcaggccga agacctggct gtctactatt gcaaacagag cttctatctg    300
cgaacttttg gcgggggaac caagctggat atcaaa                              336
```

```
<210> SEQ ID NO 94
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
caggtccagc tgcagcagag cggccccgaa ctggtcaaac ccggaacctc cgtgaagatg    60
ccttgtaaag cctcaggata catttttcacc gattacgtga tctcttgggt caaacagcga   120
acaggacagg gactggagtg gatcggggaa attttcccca gatccggatc tacttactat    180
aacgagaagt ttaaaggcaa ggccaccctg acagctgaca agagctccaa tacagcttac    240
atgcagctgt ctagtgtgac tagtgaagac tcagcagtct atttctgcgc cagggattac    300
tatgggacaa gttttgccat ggactattgg ggacagggca cttccgtgac cgtctcaagc    360
```

```
<210> SEQ ID NO 95
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gatattgtca tgtcacagtc accttcatcc ctggcagtca gcgccggaga aaaagtcact    60
atgtcttgta agtcttcaca gagcctgctg aactcccgga ccagaaagaa ttacctggca   120
tggtatcagc agaagcccgg ccagtctcct aaactgctga tctactgggc atcaacaagg   180
gagagcggag tgccagaccg cttcacaggc tctgggagtg gaactgattt taccctgaca    240
attagctccg tgcaggccga agacctggct gtctactatt gcaaacagag cttctatctg    300
cgaacttttg gcgggggaac caagctggat atcaaa                              336
```

```
<210> SEQ ID NO 96
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
caggtccagc tggtccagag cggagcagaa gtgaagaaac ccggaagtag cgtgaaggtg    60
tcatgcaagg caagcggcgg aacatttagt gattacgtga tctcctgggt ccgacaggct   120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
```

```
<210> SEQ ID NO 97
<211> LENGTH: 360
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
caggtccagc tggtgcagtc aggccccgaa gtgaagaagc ccggaagtag tgtcaaggtc     60
ccatgtaaag catcagggta tatttttact gattacgtga tcagctgggt caaacaggca    120
ccaggacagg gactggagtg gatcggggaa attttcccta gatcaggaag cacatactat    180
aacgagaagt ttaaaggcaa ggccaccctg acagctgaca agtccacttc taccgcttac    240
atggagctga gctccctgcg gagtgaagac accgcagtgt atttctgcgc cagagattac    300
tatgggacat cctttgcaat ggactattgg ggacagggca cactggtgac tgtctctagt    360

<210> SEQ ID NO 98
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggtccagc tggtccagag cggacccgaa gtgaagaaac ccggaagtag cgtgaaggtg     60
ccatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 99
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
caggtccagc tggtccagag cggagcagaa gtgaagaaac ccggaagtag cgtgaaggtg     60
tcatgcaagg caagcgggta tacatttagt gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 100
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
caggtccagc tggtccagag cggagcagaa gtgaagaaac ccggaagtag cgtgaaggtg     60
```

```
tcatgcaagg caagcggcgg aattttagt gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 101
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
caggtccagc tggtccagag cggagcagaa gtgaagaaac ccggaagtag cgtgaaggtg     60
tcatgcaagg caagcggcgg aacatttact gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 102
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
caggtccagc tggtccagag cggagcagaa gtgaagaaac ccggaagtag cgtgaaggtg     60
tcatgcaagg caagcggcgg aacatttagt gattacgtga tctcctgggt caaacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 103
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatcggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
```

<210> SEQ ID NO 104
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggcaa ggtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 105
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggccg cgccaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 106
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggccg cgtgaccctg acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360

<210> SEQ ID NO 107
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
caggtccagc tggtccagag cggagcagaa gtgaagaaac ccggaagtag cgtgaaggtg      60
tcatgcaagg caagcggcgg aacatttagt gattacgtga tctcctgggt ccgacaggct     120
ccaggacagg gactggagtg gatgggggaa attttcccta gatcaggaag cacctactat     180
aacgagaagt ttaaaggccg cgtgaccatc acagcagaca agtccacttc taccgcctac     240
atggagctga gctccctgcg gagcgaagac accgccgtct atttctgcgc tagagattac     300
tatgggacat ctttcgccat ggactattgg ggacagggca cactggtgac tgtctctagt     360
```

<210> SEQ ID NO 108
<211> LENGTH: 360
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 108

```
caggtccagc tggtccagag cggagcagaa gtgaagaaac ccggaagtag cgtgaaggtg      60
tcatgcaagg caagcgggta tatttttagt gattacgtga tctcctgggt ccgacaggct     120
ccaggacagg gactggagtg gatgggggaa attttcccta gatcaggaag cacctactat     180
aacgagaagt ttaaaggccg cgtgaccatc acagcagaca agtccacttc taccgcctac     240
atggagctga gctccctgcg gagcgaagac accgccgtct actattgcgc tagagattac     300
tatgggacat ctttcgccat ggactattgg ggacagggca cactggtgac tgtctctagt     360
```

<210> SEQ ID NO 109
<211> LENGTH: 336
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 109

```
gacatcgtga tgacacagtc cccactgtct ctgcccgtca ctcctgggga gccagcatct      60
attagttgca agagctccca gagtctgctg aactcacgga ccagaaagaa ttacctggcc     120
tggtatctgc agaaacccgg acagagccct cagctgctga tctactgggc tagcaccagg     180
gaatccggag tgccagaccg cttcacagga tcaggaagcg gaaccgattt tacactgaag     240
atcagccggg tggaggccga agatgtgggc gtctactatt gtaaacagtc cttctatctg     300
agaacttttg gccaggggac caaggtggag atcaaa                                336
```

<210> SEQ ID NO 110
<211> LENGTH: 336
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 110

```
gacatcgtga tgtctcagag tccactgtct ctgccagtca ccctggaga gccagcatca      60 attagctgca agagctccca gagtctgctg aactcacgga caagaaagaa ttacctggcc     120
tggtatctgc agaaacccgg acagagccct cagctgctga tctactgggc tagcacaagg     180
gaatccggag tgccagaccg cttcactgga tccggatctg gaaccgattt tacactgaag     240
atcagccggg tggaggccga agatgtgggc gtctactatt gtaaacagag tttctatctg     300
``` agaactttg gccaggggac caaggtggag atcaaa 336

<210> SEQ ID NO 111
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat cttcgccat ggactattgg ggacagggca cactggtgac tgtctctagt    360
gcctccacca agggcccttc cgtgttccct ctggcccctt cctccaagtc cacctccggc    420
ggcaccgccg ctctgggctg cctggtgaag gactacttcc ctgagcctgt gaccgtgtcc    480
tggaactctg gcgccctgac cagcggcgtg cacaccttcc ctgccgtgct gcagtcctcc    540
ggcctgtact ccctgtcctc cgtggtgacc gtgccttcct cctccctggg cacccagacc    600
tacatctgca acgtgaacca caagccttcc aacaccaagg tggacaagaa ggtggagcct    660
aagtcctgcg acaagaccca cacgtgccct ccatgcccag ctcccgagct gctgggcgga    720
ccaagcgtgt ttctgttccc tcctaagcct aaggacaccc tgatgatctc ccggacccct    780
gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg gccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                   1350

<210> SEQ ID NO 112
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
caggtccagc tggtgcagtc aggccccgaa gtgaagaagc ccggaagtag tgtcaaggtc     60
ccatgtaaag catcagggta tattttact gattacgtga tcagctgggt caaacaggca    120
ccaggacagg gactggagtg gatcggggaa attttcccta gatcaggaag cacatactat    180
aacgagaagt ttaaaggcaa ggccaccctg acagctgaca agtccacttc taccgcttac    240

| | |
|---|---|
| atggagctga gctccctgcg gagtgaagac accgcagtgt atttctgcgc cagagattac | 300 |
| tatgggacat cctttgcaat ggactattgg ggacagggca cactggtgac tgtctctagt | 360 |
| gcctccacca agggcccttc cgtgttccct ctggcccctt cctccaagtc cacctccggc | 420 |
| ggcaccgccg ctctgggctg cctggtgaag gactacttcc ctgagcctgt gaccgtgtcc | 480 |
| tggaactctg gcgccctgac cagcggcgtg cacaccttcc ctgccgtgct gcagtcctcc | 540 |
| ggcctgtact ccctgtcctc cgtggtgacc gtgccttcct cctccctggg cacccagacc | 600 |
| tacatctgca acgtgaacca caagccttcc aacaccaagg tggacaagaa ggtggagcct | 660 |
| aagtcctgcg acaagaccca cgtgccctcc catgcccag ctcccgagct gctgggcgga | 720 |
| ccaagcgtgt ttctgttccc tcctaagcct aaggacaccc tgatgatctc ccggacccct | 780 |
| gaggtgacgt gcgtggtggt ggacgtgtcc cacgaggacc cagaggtgaa gttcaattgg | 840 |
| tacgtggacg gcgtggaggt gcacaacgcc aagaccaagc ctcgggagga acagtacaac | 900 |
| tccacctacc gggtggtgtc tgtgctgacc gtgctgcacc aggactggct gaacggcaag | 960 |
| gaatacaagt gcaaagtctc caacaaggcc ctgcctgccc ccatcgaaaa gaccatctcc | 1020 |
| aaggccaagg gccagcctcg cgagcctcag gtgtacaccc tgcctccaag cagggaggaa | 1080 |
| atgaccaaga accaggtgtc cctgacctgt ctggtgaagg gcttctaccc ttccgatatc | 1140 |
| gccgtggagt gggagtccaa cggccagcct gagaacaact acaagaccac ccctcctgtg | 1200 |
| ctggactccg acggctcctt cttcctgtac tccaagctga ccgtggacaa gtcccggtgg | 1260 |
| cagcagggca acgtgttctc ctgctccgtg atgcacgagg ccctgcacaa ccactacacc | 1320 |
| cagaagagcc tctccctgtc cccgggtaaa | 1350 |

<210> SEQ ID NO 113
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

| | |
|---|---|
| caggtccagc tggtccagag cggacccgaa gtgaagaaac ccggaagtag cgtgaaggtg | 60 |
| ccatgcaagg caagcggcgg aacatttagt gattacgtga tctcctgggt ccgacaggct | 120 |
| ccaggacagg gactggagtg gatgggggaa attttcccta gatcaggaag cacctactat | 180 |
| aacgagaagt ttaaaggccg cgtgaccatc acagcagaca gtccacttc taccgcctac | 240 |
| atggagctga gctccctgcg gagcgaagac accgccgtct actattgcgc tagagattac | 300 |
| tatgggacat ctttcgccat ggactattgg ggacagggca cactggtgac tgtctctagt | 360 |
| gcctccacca agggcccttc cgtgttccct ctggcccctt cctccaagtc cacctccggc | 420 |
| ggcaccgccg ctctgggctg cctggtgaag gactacttcc ctgagcctgt gaccgtgtcc | 480 |
| tggaactctg gcgccctgac cagcggcgtg cacaccttcc ctgccgtgct gcagtcctcc | 540 |
| ggcctgtact ccctgtcctc cgtggtgacc gtgccttcct cctccctggg cacccagacc | 600 |
| tacatctgca acgtgaacca caagccttcc aacaccaagg tggacaagaa ggtggagcct | 660 |
| aagtcctgcg acaagaccca cgtgccctcc catgcccag ctcccgagct gctgggcgga | 720 |
| ccaagcgtgt ttctgttccc tcctaagcct aaggacaccc tgatgatctc ccggacccct | 780 |
| gaggtgacgt gcgtggtggt ggacgtgtcc cacgaggacc cagaggtgaa gttcaattgg | 840 |
| tacgtggacg gcgtggaggt gcacaacgcc aagaccaagc ctcgggagga acagtacaac | 900 |

```
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg ccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                    1350
```

<210> SEQ ID NO 114
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

```
caggtccagc tggtccagag cggagcagaa gtgaagaaac ccggaagtag cgtgaaggtg     60
tcatgcaagg caagcgggta tacatttagt gattacgtga tctcctgggt ccgacaggct    120
ccaggacagg gactgagtg gatgggggaa atttttccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccttc cgtgttccct ctggccccct tctccaagtc cacctccggc    420
ggcaccgccg ctctgggctg cctggtgaag gactacttcc ctgagcctgt gaccgtgtcc    480
tggaactctg gcgccctgac cagcggcgtg cacaccttcc ctgccgtgct gcagtcctcc    540
ggcctgtact ccctgtcctc cgtggtgacc gtgccttcct cctccctggg cacccagacc    600
tacatctgca acgtgaacca caagccttcc aacaccaagg tggacaagaa ggtgagcct    660 aagtcctgcg acaagaccca cacgtgccct ccatgcccag ctcccgagct gctgggcgga    720
ccaagcgtgt ttctgttccc tcctaagcct aaggacaccc tgatgatctc ccggacccct    780
gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg ccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                    1350
```

<210> SEQ ID NO 115
<211> LENGTH: 1350
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 115

```
caggtccagc tggtccagag cggagcagaa gtgaagaaac ccggaagtag cgtgaaggtg      60
tcatgcaagg caagcggcgg aattttagt gattacgtga tctcctgggt ccgacaggct      120
ccaggacagg gactggagtg gatggggaa attttcccta gatcaggaag cacctactat      180
aacgagaagt ttaaaggccg cgtgaccatc acagcagaca agtccacttc taccgcctac      240
atggagctga gctccctgcg gagcgaagac accgccgtct actattgcgc tagagattac      300
tatgggacat ctttcgccat ggactattgg ggacagggca cactggtgac tgtctctagt      360
gcctccacca agggccttc cgtgttccct ctggccctt cctccaagtc cacctccggc      420
ggcaccgccg ctctgggctg cctggtgaag gactacttcc ctgagcctgt gaccgtgtcc      480
tggaactctg gcgccctgac cagcggcgtg cacaccttcc ctgccgtgct gcagtcctcc      540
ggcctgtact ccctgtcctc cgtggtgacc gtgccttcct cctccctggg cacccagacc      600
tacatctgca acgtgaacca caagccttcc aacaccaagg tggacaagaa ggtggagcct      660
aagtcctgcg acaagaccca cacgtgccct ccatgcccag ctcccgagct gctgggcgga      720
ccaagcgtgt ttctgttccc tcctaagcct aaggacaccc tgatgatctc ccggacccct      780
gaggtgacgt gcgtggtggt ggacgtgtcc cacgaggacc cagaggtgaa gttcaattgg      840
tacgtggacg gcgtggaggt gcacaacgcc aagaccaagc ctcgggagga acagtacaac      900
tccacctacc gggtggtgtc tgtgctgacc gtgctgcacc aggactggct gaacggcaag      960
gaatacaagt gcaaagtctc caacaaggcc ctgcctgccc ccatcgaaaa gaccatctcc     1020
aaggccaagg gccagcctcg cgagcctcag gtgtacaccc tgcctccaag cagggaggaa     1080
atgaccaaga accaggtgtc cctgacctgt ctggtgaagg gcttctaccc ttccgatatc     1140
gccgtggagt gggagtccaa cggccagcct gagaacaact acaagaccac ccctcctgtg     1200
ctggactccg acggctcctt cttcctgtac tccaagctga ccgtggacaa gtcccggtgg     1260
cagcagggca acgtgttctc ctgctccgtg atgcacgagg ccctgcacaa ccactacacc     1320
cagaagagcc tctccctgtc cccgggtaaa                                     1350
```

<210> SEQ ID NO 116
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
caggtccagc tggtccagag cggagcagaa gtgaagaaac ccggaagtag cgtgaaggtg      60
tcatgcaagg caagcggcgg aacatttact gattacgtga tctcctgggt ccgacaggct     120
ccaggacagg gactggagtg gatggggaa attttcccta gatcaggaag cacctactat      180
aacgagaagt ttaaaggccg cgtgaccatc acagcagaca agtccacttc taccgcctac      240
atggagctga gctccctgcg gagcgaagac accgccgtct actattgcgc tagagattac      300
tatgggacat ctttcgccat ggactattgg ggacagggca cactggtgac tgtctctagt      360
gcctccacca agggccttc cgtgttccct ctggccctt cctccaagtc cacctccggc      420
ggcaccgccg ctctgggctg cctggtgaag gactacttcc ctgagcctgt gaccgtgtcc      480
tggaactctg gcgccctgac cagcggcgtg cacaccttcc ctgccgtgct gcagtcctcc      540
```

```
ggcctgtact ccctgtcctc cgtggtgacc gtgccttcct cctccctggg cacccagacc    600
tacatctgca acgtgaacca caagccttcc aacaccaagg tggacaagaa ggtggagcct    660
aagtcctgcg acaagaccca cacgtgccct ccatgcccag ctcccgagct gctgggcgga    720
ccaagcgtgt ttctgttccc tcctaagcct aaggacaccc tgatgatctc ccggaccect    780 gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg gccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                    1350
```

<210> SEQ ID NO 117
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
caggtccagc tggtccagag cggagcagaa gtgaagaaac ccggaagtag cgtgaaggtg     60
tcatgcaagg caagcggcgg aacatttagt gattacgtga tctcctgggt caaacaggct    120
ccaggacagg gactggagtg gatgggggaa attttcccta gatcaggaag cacctactat    180
aacgagaagt ttaaaggccg cgtgaccatc acagcagaca gtccacttc taccgcctac    240 atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccttc cgtgttccct ctggcccctt cctccaagtc cacctccggc    420
ggcaccgccg ctctgggctg cctggtgaag gactacttcc ctgagcctgt gaccgtgtcc    480
tggaactctg gcgccctgac cagcggcgtg cacaccttcc ctgccgtgct gcagtcctcc    540
ggcctgtact ccctgtcctc cgtggtgacc gtgccttcct cctccctggg cacccagacc    600
tacatctgca acgtgaacca caagccttcc aacaccaagg tggacaagaa ggtggagcct    660
aagtcctgcg acaagaccca cacgtgccct ccatgcccag ctcccgagct gctgggcgga    720
ccaagcgtgt ttctgttccc tcctaagcct aaggacaccc tgatgatctc ccggaccect    780 gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg gccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
```

```
ctggactccg acggctcctt cttcctgtac tccaagctga ccgtggacaa gtcccggtgg    1260
cagcagggca acgtgttctc ctgctccgtg atgcacgagg ccctgcacaa ccactacacc    1320
cagaagagcc tctccctgtc cccgggtaaa                                      1350
```

<210> SEQ ID NO 118
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
caggtccagc tggtccagag cggagcagaa gtgaagaaac ccggaagtag cgtgaaggtg      60
tcatgcaagg caagcggcgg aacatttagt gattacgtga tctcctgggt ccgacaggct    120
ccaggacagg gactggagtg gatcggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccttc cgtgttccct ctggccccct tctccaagtc cacctccggc    420
ggcaccgccg ctctgggctg cctggtgaag gactacttcc ctgagcctgt gaccgtgtcc    480
tggaactctg gcgccctgac cagcggcgtg cacaccttcc ctgccgtgct gcagtcctcc    540
ggcctgtact ccctgtcctc cgtggtgacc gtgccttcct cctccctggg cacccagacc    600
tacatctgca acgtgaacca caagccttcc aacaccaagg tggacaagaa ggtggagcct    660
aagtcctgcg acaagaccca cacgtgccct ccatgcccag ctcccgagct gctgggcgga    720
ccaagcgtgt ttctgttccc tcctaagcct aaggacaccc tgatgatctc ccggacccct    780
gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg gccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                     1350
```

<210> SEQ ID NO 119
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
caggtccagc tggtccagag cggagcagaa gtgaagaaac ccggaagtag cgtgaaggtg      60
tcatgcaagg caagcggcgg aacatttagt gattacgtga tctcctgggt ccgacaggct    120
```

| | |
|---|---|
| ccaggacagg gactggagtg gatggggaa attttcccta gatcaggaag cacctactat | 180 |
| aacgagaagt ttaaaggcaa ggtgaccatc acagcagaca agtccacttc taccgcctac | 240 |
| atggagctga gctccctgcg gagcgaagac accgccgtct actattgcgc tagagattac | 300 |
| tatgggacat ctttcgccat ggactattgg ggacagggca cactggtgac tgtctctagt | 360 |
| gcctccacca agggcccttc cgtgttccct ctggcccctt cctccaagtc cacctccggc | 420 |
| ggcaccgccg ctctgggctg cctggtgaag gactacttcc ctgagcctgt gaccgtgtcc | 480 |
| tggaactctg gcgccctgac cagcggcgtg cacaccttcc ctgccgtgct gcagtcctcc | 540 |
| ggcctgtact ccctgtcctc cgtggtgacc gtgccttcct cctccctggg cacccagacc | 600 |
| tacatctgca acgtgaacca caagccttcc aacaccaagg tggacaagaa ggtggagcct | 660 |
| aagtcctgcg acaagaccca cacgtgccct ccatgcccag ctcccgagct gctgggcgga | 720 |
| ccaagcgtgt ttctgttccc tcctaagcct aaggacaccc tgatgatctc ccggacccct | 780 |
| gaggtgacgt gcgtggtggt ggacgtgtcc cacgaggacc cagaggtgaa gttcaattgg | 840 |
| tacgtggacg gcgtggaggt gcacaacgcc aagaccaagc ctcgggagga acagtacaac | 900 |
| tccacctacc gggtggtgtc tgtgctgacc gtgctgcacc aggactggct gaacggcaag | 960 |
| gaatacaagt gcaaagtctc caacaaggcc ctgcctgccc ccatcgaaaa gaccatctcc | 1020 |
| aaggccaagg gccagcctcg cgagcctcag gtgtacaccc tgcctccaag caggaggaa | 1080 |
| atgaccaaga accaggtgtc cctgacctgt ctggtgaagg gcttctaccc ttccgatatc | 1140 |
| gccgtggagt gggagtccaa cggccagcct gagaacaact acaagaccac ccctcctgtg | 1200 |
| ctggactccg acggctcctt cttcctgtac tccaagctga ccgtggacaa gtcccggtgg | 1260 |
| cagcagggca acgtgttctc ctgctccgtg atgcacgagg ccctgcacaa ccactacacc | 1320 |
| cagaagagcc tctccctgtc cccgggtaaa | 1350 |

<210> SEQ ID NO 120
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

| | |
|---|---|
| caggtccagc tggtccagag cggagcagaa gtgaagaaac cggaagtag cgtgaaggtg | 60 |
| tcatgcaagg caagcggcgg aacatttagt gattacgtga tctcctgggt ccgacaggct | 120 |
| ccaggacagg gactggagtg gatggggaa attttcccta gatcaggaag cacctactat | 180 |
| aacgagaagt ttaaaggccg cgccaccatc acagcagaca agtccacttc taccgcctac | 240 |
| atggagctga gctccctgcg gagcgaagac accgccgtct actattgcgc tagagattac | 300 |
| tatgggacat ctttcgccat ggactattgg ggacagggca cactggtgac tgtctctagt | 360 |
| gcctccacca agggcccttc cgtgttccct ctggcccctt cctccaagtc cacctccggc | 420 |
| ggcaccgccg ctctgggctg cctggtgaag gactacttcc ctgagcctgt gaccgtgtcc | 480 |
| tggaactctg gcgccctgac cagcggcgtg cacaccttcc ctgccgtgct gcagtcctcc | 540 |
| ggcctgtact ccctgtcctc cgtggtgacc gtgccttcct cctccctggg cacccagacc | 600 |
| tacatctgca acgtgaacca caagccttcc aacaccaagg tggacaagaa ggtggagcct | 660 |
| aagtcctgcg acaagaccca cacgtgccct ccatgcccag ctcccgagct gctgggcgga | 720 |
| ccaagcgtgt ttctgttccc tcctaagcct aaggacaccc tgatgatctc ccggacccct | 780 |

| | |
|---|---|
| gaggtgacgt gcgtggtggt ggacgtgtcc cacgaggacc cagaggtgaa gttcaattgg | 840 |
| tacgtggacg gcgtggaggt gcacaacgcc aagaccaagc ctcggga gga acagtacaac | 900 |
| tccacctacc gggtggtgtc tgtgctgacc gtgctgcacc aggactggct gaacggcaag | 960 |
| gaatacaagt gcaaagtctc caacaaggcc ctgcctgccc ccatcgaaaa gaccatctcc | 1020 |
| aaggccaagg gccagcctcg cgagcctcag gtgtacaccc tgcctccaag cagggaggaa | 1080 |
| atgaccaaga accaggtgtc cctgacctgt ctggtgaagg gcttctaccc ttccgatatc | 1140 |
| gccgtggagt gggagtccaa cggccagcct gagaacaact acaagaccac cctcctgtg | 1200 |
| ctggactccg acggctcctt cttcctgtac tccaagctga ccgtggacaa gtccggtgg | 1260 |
| cagcagggca acgtgttctc ctgctccgtg atgcacgagg ccctgcacaa ccactacacc | 1320 |
| cagaagagcc tctccctgtc cccgggtaaa | 1350 |

<210> SEQ ID NO 121
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121

| | |
|---|---|
| caggtccagc tggtccagag cggagcagaa gtgaagaaac ccggaagtag cgtgaaggtg | 60 |
| tcatgcaagg caagcggcgg aacatttagt gattacgtga tctcctgggt ccgacaggct | 120 |
| ccaggacagg gactggagtg gatgggggaa attttcccta gatcaggaag cacctactat | 180 |
| aacgagaagt ttaaaggccg cgtgaccctg acagcagaca agtccacttc taccgcctac | 240 |
| atggagctga gctccctgcg gagcgaagac accgccgtct actattgcgc tagagattac | 300 |
| tatgggacat ctttcgccat ggactattgg ggacagggca cactggtgac tgtctctagt | 360 |
| gcctccacca agggcccttc cgtgttccct ctggcccctt cctccaagtc cacctccggc | 420 |
| ggcaccgccg ctctgggctg cctggtgaag gactacttcc ctgagcctgt gaccgtgtcc | 480 |
| tggaactctg gcgccctgac cagcggcgtg cacaccttcc ctgccgtgct gcagtcctcc | 540 |
| ggcctgtact ccctgtcctc cgtggtgacc gtgccttcct cctccctggg cacccagacc | 600 |
| tacatctgca acgtgaacca caagccttcc aacaccaagg tggacaagaa ggtggagcct | 660 |
| aagtcctgcg acaagaccca cacgtgccct ccatgcccag ctcccgagct gctgggcgga | 720 |
| ccaagcgtgt ttctgttccc tcctaagcct aaggacaccc tgatgatctc ccggacccct | 780 |
| gaggtgacgt gcgtggtggt ggacgtgtcc cacgaggacc cagaggtgaa gttcaattgg | 840 |
| tacgtggacg gcgtggaggt gcacaacgcc aagaccaagc ctcggga gga acagtacaac | 900 |
| tccacctacc gggtggtgtc tgtgctgacc gtgctgcacc aggactggct gaacggcaag | 960 |
| gaatacaagt gcaaagtctc caacaaggcc ctgcctgccc ccatcgaaaa gaccatctcc | 1020 |
| aaggccaagg gccagcctcg cgagcctcag gtgtacaccc tgcctccaag cagggaggaa | 1080 |
| atgaccaaga accaggtgtc cctgacctgt ctggtgaagg gcttctaccc ttccgatatc | 1140 |
| gccgtggagt gggagtccaa cggccagcct gagaacaact acaagaccac cctcctgtg | 1200 |
| ctggactccg acggctcctt cttcctgtac tccaagctga ccgtggacaa gtccggtgg | 1260 |
| cagcagggca acgtgttctc ctgctccgtg atgcacgagg ccctgcacaa ccactacacc | 1320 |
| cagaagagcc tctccctgtc cccgggtaaa | 1350 |

<210> SEQ ID NO 122

```
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
caggtccagc tggtccagag cggagcagaa gtgaagaaac ccggaagtag cgtgaaggtg      60
tcatgcaagg caagcggcgg aacatttagt gattacgtga tctcctgggt ccgacaggct     120
ccaggacagg gactggagtg gatgggggaa attttcccta gatcaggaag cacctactat     180
aacgagaagt ttaaaggccg cgtgaccatc acagcagaca gtccacttc taccgcctac      240 atggagctga gctccctgcg gagcgaagac accgccgtct atttctgcgc tagagattac     300
tatgggacat ctttcgccat ggactattgg ggacagggca cactggtgac tgtctctagt     360
gcctccacca agggcccttc cgtgttccct ctggccccctt cctccaagtc cacctccggc    420
ggcaccgccg ctctgggctg cctggtgaag gactacttcc ctgagcctgt gaccgtgtcc     480
tggaactctg gcgccctgac cagcggcgtg cacaccttcc ctgccgtgct gcagtcctcc     540
ggcctgtact ccctgtcctc cgtggtgacc gtgccttcct cctccctggg cacccagacc     600
tacatctgca acgtgaacca caagccttcc aacaccaagg tggacaagaa ggtggagcct     660
aagtcctgcg acaagaccca cacgtgccct ccatgcccag ctcccgagct gctgggcgga     720
ccaagcgtgt ttctgttccc tcctaagcct aaggacaccc tgatgatctc ccggaccct      780 gaggtgacgt gcgtggtggt ggacgtgtcc cacgaggacc cagaggtgaa gttcaattgg     840
tacgtggacg gcgtggaggt gcacaacgcc aagaccaagc ctcgggagga acagtacaac     900
tccacctacc gggtggtgtc tgtgctgacc gtgctgcacc aggactggct gaacggcaag     960
gaatacaagt gcaaagtctc caacaaggcc ctgcctgccc ccatcgaaaa gaccatctcc    1020
aaggccaagg gccagcctcg cgagcctcag gtgtacaccc tgcctccaag cagggaggaa    1080
atgaccaaga accaggtgtc cctgacctgt ctggtgaagg gcttctaccc ttccgatatc    1140
gccgtggagt gggagtccaa cggccagcct gagaacaact acaagaccac ccctcctgtg    1200
ctggactccg acggctcctt cttcctgtac tccaagctga ccgtggacaa gtcccggtgg    1260
cagcagggca acgtgttctc ctgctccgtg atgcacgagg ccctgcacaa ccactacacc    1320
cagaagagcc tctccctgtc cccgggtaaa                                     1350

<210> SEQ ID NO 123
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
caggtccagc tggtccagag cggagcagaa gtgaagaaac ccggaagtag cgtgaaggtg      60
tcatgcaagg caagcgggta tatttttagt gattacgtga tctcctgggt ccgacaggct     120
ccaggacagg gactggagtg gatgggggaa attttcccta gatcaggaag cacctactat     180
aacgagaagt ttaaaggccg cgtgaccatc acagcagaca gtccacttc taccgcctac      240 atggagctga gctccctgcg gagcgaagac accgccgtct actattgcgc tagagattac     300
tatgggacat ctttcgccat ggactattgg ggacagggca cactggtgac tgtctctagt     360
gcctccacca agggcccttc cgtgttccct ctggccccctt cctccaagtc cacctccggc    420
```

```
ggcaccgccg ctctgggctg cctggtgaag gactacttcc ctgagcctgt gaccgtgtcc      480
tggaactctg gcgccctgac cagcggcgtg cacaccttcc ctgccgtgct gcagtcctcc      540
ggcctgtact ccctgtcctc cgtggtgacc gtgccttcct cctccctggg cacccagacc      600
tacatctgca acgtgaacca caagccttcc aacaccaagg tggacaagaa ggtggagcct      660
aagtcctgcg acaagaccca cacgtgccct ccatgcccag ctcccgagct gctgggcgga      720
ccaagcgtgt ttctgttccc tcctaagcct aaggacaccc tgatgatctc ccggacccct      780
gaggtgacgt gcgtggtggt ggacgtgtcc cacgaggacc cagaggtgaa gttcaattgg      840
tacgtggacg gcgtggaggt gcacaacgcc aagaccaagc ctcgggagga acagtacaac      900
tccacctacc gggtggtgtc tgtgctgacc gtgctgcacc aggactggct gaacggcaag      960
gaatacaagt gcaaagtctc caacaaggcc ctgcctgccc ccatcgaaaa gaccatctcc     1020
aaggccaagg gccagcctcg cgagcctcag gtgtacaccc tgcctccaag cagggaggaa     1080
atgaccaaga accaggtgtc cctgacctgt ctggtgaagg gcttctaccc ttccgatatc     1140
gccgtggagt gggagtccaa cggccagcct gagaacaact acaagaccac ccctcctgtg     1200
ctggactccg acggctcctt cttcctgtac tccaagctga ccgtggacaa gtcccggtgg     1260
cagcagggca acgtgttctc ctgctccgtg atgcacgagg ccctgcacaa ccactacacc     1320
cagaagagcc tctccctgtc cccgggtaaa                                      1350
```

<210> SEQ ID NO 124
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
caggtccagc tgcagcagag cggccccgaa ctggtcaaac ccggaacctc cgtgaagatg       60
ccttgtaaag cctcaggata cattttcacc gattacgtga tctcttgggt caaacagcga      120
acaggacagg gactggagtg gatcggggaa attttcccca gatccggatc tacttactat      180
aacgagaagt ttaaaggcaa ggccaccctg acagctgaca gagctccaa tacagcttac      240 atgcagctgt ctagtgtgac tagtgaagac tcagcagtct atttctgcgc cagggattac      300
tatgggacaa gttttgccat ggactattgg ggacagggca cttccgtgac cgtctcaagc      360
gcctccacca agggcccttc cgtgttccct ctggccccct cctccaagtc cacctccggc      420
ggcaccgccg ctctgggctg cctggtgaag gactacttcc ctgagcctgt gaccgtgtcc      480
tggaactctg gcgccctgac cagcggcgtg cacaccttcc ctgccgtgct gcagtcctcc      540
ggcctgtact ccctgtcctc cgtggtgacc gtgccttcct cctccctggg cacccagacc      600
tacatctgca acgtgaacca caagccttcc aacaccaagg tggacaagaa ggtggagcct      660
aagtcctgcg acaagaccca cacgtgccct ccatgcccag ctcccgagct gctgggcgga      720
ccaagcgtgt ttctgttccc tcctaagcct aaggacaccc tgatgatctc ccggacccct      780
gaggtgacgt gcgtggtggt ggacgtgtcc cacgaggacc cagaggtgaa gttcaattgg      840
tacgtggacg gcgtggaggt gcacaacgcc aagaccaagc ctcgggagga acagtacaac      900
tccacctacc gggtggtgtc tgtgctgacc gtgctgcacc aggactggct gaacggcaag      960
gaatacaagt gcaaagtctc caacaaggcc ctgcctgccc ccatcgaaaa gaccatctcc     1020
aaggccaagg gccagcctcg cgagcctcag gtgtacaccc tgcctccaag cagggaggaa     1080
```

| | |
|---|---:|
| atgaccaaga accaggtgtc cctgacctgt ctggtgaagg gcttctaccc ttccgatatc | 1140 |
| gccgtggagt gggagtccaa cggccagcct gagaacaact acaagaccac ccctcctgtg | 1200 |
| ctggactccg acggctcctt cttcctgtac tccaagctga ccgtggacaa gtcccggtgg | 1260 |
| cagcagggca acgtgttctc ctgctccgtg atgcacgagg ccctgcacaa ccactacacc | 1320 |
| cagaagagcc tctccctgtc cccgggtaaa | 1350 |

<210> SEQ ID NO 125
<211> LENGTH: 1332
<212> TYPE: DNA
<213> ORGANISM: Mus musculus

<400> SEQUENCE: 125

| | |
|---|---:|
| caggtccaat tgcagcagtc tggacctgag ctggtgaagc ctgggacttc agtgaagatg | 60 |
| ccctgtaagg cttctggata catattcact gactatgtca taagctgggt gaagcagaga | 120 |
| actggacagg gccttgagtg gattggagag attttttccta gaagtggtag tacttactac | 180 |
| aatgagaagt tcaagggcaa ggccacactg actgcagaca atcctccaa cacagcctac | 240 |
| atgcagctca gcagcgtgac atctgaggac tctgcggtct atttctgtgc aagagattac | 300 |
| tacggtactt catttgctat ggactactgg ggtcaaggaa cctcagtcac cgtctcctca | 360 |
| gccaaaacga cacccccatc tgtctatcca ctggcccctg gatctgctgc ccaaactaac | 420 |
| tccatggtga ccctgggatg cctggtcaag ggctatttcc ctgagccagt gacagtgacc | 480 |
| tggaactctg gatccctgtc cagcggtgtg cacaccttcc cagctgtcct gcagtctgac | 540 |
| ctctacactc tgagcagctc agtgactgtc ccctccagca cctggcccag ccagaccgtc | 600 |
| acctgcaacg ttgcccaccc ggccagcagc accaaggtgg acaagaaaat tgtgcccagg | 660 |
| gattgtggtt gtaagccttg catatgtaca gtcccagaag tatcatctgt cttcatcttc | 720 |
| cccccaaagc ccaaggatgt gctcaccatt actctgactc ctaaggtcac gtgtgttgtg | 780 |
| gtagacatca gcaaggatga tcccgaggtc cagttcagct ggtttgtaga tgatgtggag | 840 |
| gtgcacacag ctcagacgaa accccgggag gagcagatca acagcacttt ccgttcagtc | 900 |
| agtgaacttc ccatcatgca ccaggactgg ctcaatggca aggagttcaa atgcagggtc | 960 |
| aacagtgcag cttttcctgc ccccatcgag aaaaccatct ccaaaaccaa aggcagaccg | 1020 |
| aaggctccac aggtgtacac cattccacct cccaaggagc agatggccaa ggataaagtc | 1080 |
| agtctgacct gcatgataac aaacttcttc cctgaagaca ttactgtgga gtggcagtgg | 1140 |
| aatgggcagc cagcggagaa ctacaagaac actcagccca tcatggacac agatggctct | 1200 |
| tacttcgtct acagcaagct caatgtgcag aagagcaact gggaggcagg aaatactttc | 1260 |
| acctgctctg tgttacatga gggcctgcac aaccaccata tgagaagag cctctcccac | 1320 |
| tctcctggta aa | 1332 |

<210> SEQ ID NO 126
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

| | |
|---|---:|
| caggtccagc tgcagcagag cggccccgaa ctggtcaaac ccggaacctc cgtgaagatg | 60 |
| ccttgtaaag cctcaggata catttttcacc gattacgtga tctcttgggt caaacagcga | 120 |

```
acaggacagg gactggagtg gatcggggaa attttcccca gatccggatc tacttactat    180
aacgagaagt ttaaaggcaa ggccaccctg acagctgaca agagctccaa tacagcttac    240
atgcagctgt ctagtgtgac tagtgaagac tcagcagtct atttctgcgc cagggattac    300
tatgggacaa gttttgccat ggactattgg ggacagggca cttccgtgac cgtctcaagc    360
gcctccacca agggcccttc cgtgttccct ctggccccct cctccaagtc cacctccggc    420
ggcaccgccg ctctgggctg cctggtgaag gactacttcc ctgagcctgt gaccgtgtcc    480
tggaactctg gcgccctgac cagcggcgtg cacaccttcc ctgccgtgct gcagtcctcc    540
ggcctgtact ccctgtcctc cgtggtgacc gtgccttcct cctccctggg cacccagacc    600
tacatctgca acgtgaacca caagccttcc aacaccaagg tggacaagaa ggtggagcct    660
aagtcctgcg acaagaccca cacgtgccct ccatgcccag ctcccgagct gctgggcgga    720
ccaagcgtgt ttctgttccc tcctaagcct aaggacaccc tgatgatctc ccggacccct    780
gaggtgacgt gcgtggtggt ggacgtgtcc cacgaggacc cagaggtgaa gttcaattgg    840
tacgtggacg gcgtggaggt gcacaacgcc aagaccaagc ctcgggagga acagtacaac    900
tccacctacc gggtggtgtc tgtgctgacc gtgctgcacc aggactggct gaacggcaag    960
gaatacaagt gcaaagtctc caacaaggcc ctgcctgccc ccatcgaaaa gaccatctcc   1020
aaggccaagg gccagcctcg cgagcctcag gtgtacaccc tgcctccaag cagggaggaa   1080
atgaccaaga accaggtgtc cctgacctgt ctggtgaagg gcttctaccc ttccgatatc   1140
gccgtggagt gggagtccaa cggccagcct gagaacaact acaagaccac ccctcctgtg   1200
ctggactccg acggctcctt cttcctgtac tccaagctga ccgtggacaa gtcccggtgg   1260
cagcagggca acgtgttctc ctgctccgtg atgcacgagg ccctgcacaa ccactacacc   1320
cagaagagcc tctccctgtc cccgggtaaa                                   1350

<210> SEQ ID NO 127
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc cccatgccca accatgccca gcacctgagt tcctgggggg accatcagtc    720
ttcctgttcc ccccaaaacc caaggacact ctcatgatct cccggacccc tgaggtcacg    780
```

```
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcagatg gcaggagggg   1260
aatgtcttct catgctccgt gatgcatgag gctctgcaca accactacac acagaagagc   1320 ctctcccctgt ctctgggtaa a                                            1341
```

<210> SEQ ID NO 128
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
caggtccagc tggtgcagtc aggccccgaa gtgaagaagc ccggaagtag tgtcaaggtc     60
ccatgtaaag catcagggta tatttttact gattacgtga tcagctgggt caaacaggca    120
ccaggacagg gactggagtg gatcggggaa attttcccta gatcaggaag cacatactat    180
aacgagaagt ttaaaggcaa ggccaccctg acagctgaca agtccacttc taccgcttac    240
atggagctga gctccctgcg gagtgaagac accgcagtgt atttctgcgc cagagattac    300
tatgggacat cctttgcaat ggactattgg ggacagggca cactggtgac tgtctctagt    360
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcagatg gcaggagggg   1260
aatgtcttct catgctccgt gatgcatgag gctctgcaca accactacac acagaagagc   1320 ctctcccctgt ctctgggtaa a                                            1341
```

<210> SEQ ID NO 129
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
caggtccagc tggtccagag cggacccgaa gtgaagaaac ccggaagtag cgtgaaggtg      60
ccatgcaagg caagcggcgg aacatttagt gattacgtga tctcctgggt ccgacaggct     120
ccaggacagg gactggagtg gatggggaa attttcccta gatcaggaag cacctactat     180
aacgagaagt ttaaaggccg cgtgaccatc acagcagaca agtccacttc taccgcctac     240
atggagctga gctccctgcg gagcgaagac accgccgtct actattgcgc tagagattac     300
tatgggacat ctttcgccat ggactattgg ggacagggca cactggtgac tgtctctagt     360
gcctccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacgtgca acgtagatca caagcccagc aacaccaagg tggacaagag agttgagtcc     660
aaatatggtc ccccatgccc accatgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacgtg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcagatg gcaggagggg    1260
aatgtcttct catgctccgt gatgcatgag gctctgcaca accactacac acagaagagc    1320
ctctcctgt ctctgggtaa a                                               1341
```

<210> SEQ ID NO 130
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
caggtccagc tggtccagag cggagcagaa gtgaagaaac ccggaagtag cgtgaaggtg      60
tcatgcaagg caagcgggta tacatttagt gattacgtga tctcctgggt ccgacaggct     120
ccaggacagg gactggagtg gatggggaa attttcccta gatcaggaag cacctactat     180
aacgagaagt ttaaaggccg cgtgaccatc acagcagaca agtccacttc taccgcctac     240
atggagctga gctccctgcg gagcgaagac accgccgtct actattgcgc tagagattac     300
tatgggacat ctttcgccat ggactattgg ggacagggca cactggtgac tgtctctagt     360
```

```
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc cccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcagatg gcaggagggg   1260
aatgtcttct catgctccgt gatgcatgag gctctgcaca accactacac acagaagagc   1320 ctctcccctgt ctctgggtaa a                                            1341
```

<210> SEQ ID NO 131
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
caggtccagc tggtccagag cggagcagaa gtgaagaaac ccggaagtag cgtgaaggtg     60
tcatgcaagg caagcggcgg aatttttagt gattacgtga tctcctgggt ccgacaggct    120
ccaggacagg gactggagtg gatggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc cccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
```

```
gggcagcccc gagagccaca ggtgtacacc ctgcccccat cccaggagga gatgaccaag    1080
aaccaggtca gcctgacgtg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcagatg gcaggagggg    1260
aatgtcttct catgctccgt gatgcatgag gctctgcaca accactacac acagaagagc    1320 ctctcccctgt ctctgggtaa a                                             1341
```

<210> SEQ ID NO 132
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
caggtccagc tggtccagag cggagcagaa gtgaagaaac ccggaagtag cgtgaaggtg     60
tcatgcaagg caagcggcgg aacatttact gattacgtga tctcctgggt ccgacaggct    120
ccaggacagg gactggagtg gatgggggaa attttcccta gatcaggaag cacctactat    180
aacgagaagt ttaaaggccg cgtgaccatc acagcagaca agtccacttc taccgcctac    240
atggagctga gctccctgcg gagcgaagac accgccgtct actattgcgc tagagattac    300
tatgggacat ctttcgccat ggactattgg ggacagggca cactggtgac tgtctctagt    360
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga gatgaccaag   1080
aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcagatg gcaggagggg   1260
aatgtcttct catgctccgt gatgcatgag gctctgcaca accactacac acagaagagc   1320 ctctcccctgt ctctgggtaa a                                            1341
```

<210> SEQ ID NO 133
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
caggtccagc tggtccagag cggagcagaa gtgaagaaac ccggaagtag cgtgaaggtg    60
tcatgcaagg caagcggcgg aacatttagt gattacgtga tctcctgggt caaacaggct   120
ccaggacagg gactggagtg gatgggggaa attttcccta gatcaggaag cacctactat   180
aacgagaagt ttaaaggccg cgtgaccatc acagcagaca agtccacttc taccgcctac   240
atggagctga gctccctgcg gagcgaagac accgccgtct actattgcgc tagagattac   300
tatgggacat ctttcgccat ggactattgg ggacagggca cactggtgac tgtctctagt   360
gcctccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacgtgca acgtagatca caagcccagc aacaccaagg tggacaagag agttgagtcc   660
aaatatggtc ccccatgccc accatgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtct ccaacaaagg cctcccgtcc tccatcgaga aaaccatctc caaagccaaa  1020
gggcagcccc gagagccaca ggtgtacacc ctgcccccat cccaggagga tgaccaag   1080
aaccaggtca gcctgacgtg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcagatg gcaggagggg  1260
aatgtcttct catgctccgt gatgcatgag gctctgcaca accactacac acagaagagc  1320
ctctccctgt ctctgggtaa a                                             1341
```

<210> SEQ ID NO 134
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
caggtccagc tggtccagag cggagcagaa gtgaagaaac ccggaagtag cgtgaaggtg    60
tcatgcaagg caagcggcgg aacatttagt gattacgtga tctcctgggt ccgacaggct   120
ccaggacagg gactggagtg gatcggggaa attttcccta gatcaggaag cacctactat   180
aacgagaagt ttaaaggccg cgtgaccatc acagcagaca gtccacttc taccgcctac   240
atggagctga gctccctgcg gagcgaagac accgccgtct actattgcgc tagagattac   300
tatgggacat ctttcgccat ggactattgg ggacagggca cactggtgac tgtctctagt   360
gcctccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacgtgca acgtagatca caagcccagc aacaccaagg tggacaagag agttgagtcc   660
```

```
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca gagcagatg gcaggagggg    1260 aatgtcttct catgctccgt gatgcatgag gctctgcaca accactacac acagaagagc   1320 ctctcccctgt ctctgggtaa a                                            1341
```

<210> SEQ ID NO 135
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
caggtccagc tggtccagag cggagcagaa gtgaagaaac ccggaagtag cgtgaaggtg     60
tcatgcaagg caagcggcgg aacatttagt gattacgtga tctcctgggt ccgacaggct    120
ccaggacagg gactggagtg gatgggggaa attttcccta gatcaggaag cacctactat    180
aacgagaagt ttaaaggcaa ggtgaccatc acagcagaca agtccacttc taccgcctac    240
atggagctga gctccctgcg gagcgaagac accgccgtct actattgcgc tagagattac    300
tatgggacat cttcgccat ggactattgg ggacagggca cactggtgac tgtctctagt     360
gcctccacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacgtgca acgtagatca caagcccagc aacaccaagg tggacaagag agttgagtcc    660
aaatatggtc ccccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc caaagccaaa   1020
gggcagcccc gagagccaca ggtgtacacc ctgcccccat cccaggagga tgaccaag     1080 aaccaggtca gcctgacgtg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca gagcagatg gcaggagggg    1260 aatgtcttct catgctccgt gatgcatgag gctctgcaca accactacac acagaagagc   1320
```

```
ctctccctgt ctctgggtaa a                                          1341
```

<210> SEQ ID NO 136
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
caggtccagc tggtccagag cggagcagaa gtgaagaaac ccggaagtag cgtgaaggtg    60
tcatgcaagg caagcggcgg aacatttagt gattacgtga tctcctgggt ccgacaggct   120
ccaggacagg gactggagtg gatgggggaa atttttccta gatcaggaag cacctactat   180
aacgagaagt ttaaaggccg cgccaccatc acagcagaca agtccacttc taccgcctac   240
atggagctga gctccctgcg gagcgaagac accgccgtct actattgcgc tagagattac   300
tatgggacat ctttcgccat ggactattgg ggacagggca cactggtgac tgtctctagt   360
gcctccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacgtgca acgtagatca caagcccagc aacaccaagg tggacaagag agttgagtcc   660
aaatatggtc cccatgccc accatgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacgtg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcagatg gcaggagggg  1260
aatgtcttct catgctccgt gatgcatgag gctctgcaca accactacac acagaagagc  1320
ctctccctgt ctctgggtaa a                                           1341
```

<210> SEQ ID NO 137
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
caggtccagc tggtccagag cggagcagaa gtgaagaaac ccggaagtag cgtgaaggtg    60
tcatgcaagg caagcggcgg aacatttagt gattacgtga tctcctgggt ccgacaggct   120
ccaggacagg gactggagtg gatgggggaa atttttccta gatcaggaag cacctactat   180
aacgagaagt ttaaaggccg cgtgaccctg acagcagaca agtccacttc taccgcctac   240
```

| | | |
|---|---|---|
| atggagctga gctccctgcg gagcgaagac accgccgtct actattgcgc tagagattac | 300 | |
| tatgggacat ctttcgccat ggactattgg ggacagggca cactggtgac tgtctctagt | 360 | |
| gcctccacca agggcccatc cgtcttcccc ctggcgccct gctccaggag cacctccgag | 420 | |
| agcacagccg ccctgggctg cctggtcaag gactacttcc ccgaaccggt gacggtgtcg | 480 | |
| tggaactcag gcgccctgac cagcggcgtg cacaccttcc cggctgtcct acagtcctca | 540 | |
| ggactctact ccctcagcag cgtggtgacc gtgccctcca gcagcttggg cacgaagacc | 600 | |
| tacacgtgca acgtagatca caagcccagc aacaccaagg tggacaagag agttgagtcc | 660 | |
| aaatatggtc cccatgccc accatgccca gcacctgagt tcctggggg accatcagtc | 720 | |
| ttcctgttcc ccccaaaacc caaggacact ctcatgatct cccggacccc tgaggtcacg | 780 | |
| tgcgtggtgg tggacgtgag ccaggaagac cccgaggtcc agttcaactg gtacgtggat | 840 | |
| ggcgtggagg tgcataatgc caagacaaag ccgcgggagg agcagttcaa cagcacgtac | 900 | |
| cgtgtggtca gcgtcctcac cgtcctgcac caggactggc tgaacggcaa ggagtacaag | 960 | |
| tgcaaggtct ccaacaaagg cctcccgtcc tccatcgaga aaaccatctc caaagccaaa | 1020 | |
| gggcagcccc gagagccaca ggtgtacacc ctgcccccat cccaggagga tgaccaag | 1080 | |
| aaccaggtca gcctgacgtg cctggtcaaa ggcttctacc ccagcgacat cgccgtggag | 1140 | |
| tgggagagca atgggcagcc ggagaacaac tacaagacca cgcctcccgt gctggactcc | 1200 | |
| gacggctcct tcttcctcta cagcaggcta accgtggaca agagcagatg gcaggagggg | 1260 | |
| aatgtcttct catgctccgt gatgcatgag gctctgcaca accactacac acagaagagc | 1320 | |
| ctctcccctgt ctctgggtaa a | 1341 | |

<210> SEQ ID NO 138
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

| | | |
|---|---|---|
| caggtccagc tggtccagag cggagcagaa gtgaagaaac ccggaagtag cgtgaaggtg | 60 | |
| tcatgcaagg caagcggcgg aacatttagt gattacgtga tctcctgggt ccgacaggct | 120 | |
| ccaggacagg gactggagtg gatgggggaa attttcccta gatcaggaag cacctactat | 180 | |
| aacgagaagt ttaaaggccg cgtgaccatc acagcagaca gtccacttc taccgcctac | 240 | |
| atggagctga gctccctgcg gagcgaagac accgccgtct atttctgcgc tagagattac | 300 | |
| tatgggacat ctttcgccat ggactattgg ggacagggca cactggtgac tgtctctagt | 360 | |
| gcctccacca agggcccatc cgtcttcccc ctggcgccct gctccaggag cacctccgag | 420 | |
| agcacagccg ccctgggctg cctggtcaag gactacttcc ccgaaccggt gacggtgtcg | 480 | |
| tggaactcag gcgccctgac cagcggcgtg cacaccttcc cggctgtcct acagtcctca | 540 | |
| ggactctact ccctcagcag cgtggtgacc gtgccctcca gcagcttggg cacgaagacc | 600 | |
| tacacgtgca acgtagatca caagcccagc aacaccaagg tggacaagag agttgagtcc | 660 | |
| aaatatggtc cccatgccc accatgccca gcacctgagt tcctggggg accatcagtc | 720 | |
| ttcctgttcc ccccaaaacc caaggacact ctcatgatct cccggacccc tgaggtcacg | 780 | |
| tgcgtggtgg tggacgtgag ccaggaagac cccgaggtcc agttcaactg gtacgtggat | 840 | |
| ggcgtggagg tgcataatgc caagacaaag ccgcgggagg agcagttcaa cagcacgtac | 900 | |

| | |
|---|---|
| cgtgtggtca gcgtcctcac cgtcctgcac caggactggc tgaacggcaa ggagtacaag | 960 |
| tgcaaggtct ccaacaaagg cctcccgtcc tccatcgaga aaaccatctc caaagccaaa | 1020 |
| gggcagcccc gagagccaca ggtgtacacc ctgcccccat cccaggagga gatgaccaag | 1080 |
| aaccaggtca gcctgacgtg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggcta accgtggaca agagcagatg gcaggagggg | 1260 |
| aatgtcttct catgctccgt gatgcatgag gctctgcaca accactacac acagaagagc | 1320 |
| ctctcccctgt ctctgggtaa a | 1341 |

<210> SEQ ID NO 139
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 139

| | |
|---|---|
| caggtccagc tggtccagag cggagcagaa gtgaagaaac ccggaagtag cgtgaaggtg | 60 |
| tcatgcaagg caagcgggta tattttagt gattacgtga tctcctgggt ccgacaggct | 120 |
| ccaggacagg gactggagtg gatgggggaa atttcccta gatcaggaag cacctactat | 180 |
| aacgagaagt ttaaaggccg cgtgaccatc acagcagaca agtccacttc taccgcctac | 240 |
| atggagctga gctccctgcg gagcgaagac accgccgtct actattgcgc tagagattac | 300 |
| tatgggacat ctttcgccat ggactattgg ggacagggca cactggtgac tgtctctagt | 360 |
| gcctccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacgaagacc | 600 |
| tacacgtgca acgtagatca caagcccagc aacaccaagg tggacaagag agttgagtcc | 660 |
| aaatatggtc ccccatgccc accatgccca gcacctgagt tcctgggggg accatcagtc | 720 |
| ttcctgttcc ccccaaaacc caaggacact ctcatgatct cccggacccc tgaggtcacg | 780 |
| tgcgtggtgg tggacgtgag ccaggaagac cccgaggtcc agttcaactg gtacgtggat | 840 |
| ggcgtggagg tgcataatgc caagacaaag ccgcgggagg agcagttcaa cagcacgtac | 900 |
| cgtgtggtca gcgtcctcac cgtcctgcac caggactggc tgaacggcaa ggagtacaag | 960 |
| tgcaaggtct ccaacaaagg cctcccgtcc tccatcgaga aaaccatctc caaagccaaa | 1020 |
| gggcagcccc gagagccaca ggtgtacacc ctgcccccat cccaggagga gatgaccaag | 1080 |
| aaccaggtca gcctgacgtg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggcta accgtggaca agagcagatg gcaggagggg | 1260 |
| aatgtcttct catgctccgt gatgcatgag gctctgcaca accactacac acagaagagc | 1320 |
| ctctcccctgt ctctgggtaa a | 1341 |

<210> SEQ ID NO 140
<211> LENGTH: 1341
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 140

```
caggtccagc tgcagcagag cggccccgaa ctggtcaaac ccggaacctc cgtgaagatg      60
ccttgtaaag cctcaggata cattttcacc gattacgtga tctcttgggt caaacagcga     120
acaggacagg gactggagtg gatcggggaa attttcccca gatccggatc tacttactat     180
aacgagaagt ttaaaggcaa ggccaccctg acagctgaca gagctccaa tacagcttac      240
atgcagctgt ctagtgtgac tagtgaagac tcagcagtct atttctgcgc cagggattac     300
tatgggacaa gttttgccat ggactattgg ggacagggca cttccgtgac cgtctcaagc     360
gcctccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacgtgca acgtagatca caagcccagc aacaccaagg tggacaagag agttgagtcc     660
aaatatggtc cccatgccc accatgccca gcacctgagt tcctgggggg accatcagtc      720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacgtg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcagatg gcaggagggg    1260
aatgtcttct catgctccgt gatgcatgag gctctgcaca accactacac acagaagagc    1320
ctctccctgt ctctgggtaa a                                              1341
```

<210> SEQ ID NO 141
<211> LENGTH: 657
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141

```
gacatcgtga tgacacagtc cccactgtct ctgccgtca ctcctgggga gccagcatct       60
attagttgca gagctccca gagtctgctg aactcacgga ccagaaagaa ttacctggcc      120
tggtatctgc agaaacccgg acagagccct cagctgctga tctactgggc tagcaccagg     180
gaatccggag tgccagaccg cttcacagga tcaggaagcg gaaccgattt tacactgaag     240
atcagcgggt ggaggccga agatgtgggc gtctactatt gtaaacagtc cttctatctg      300
agaacttttg gccaggggac caaggtggag atcaaaagaa ctgtggcagc accaagcgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
```
agcagcaccc tgacgctgag caaagcagac tacgagaaac acaaagtcta cgcctgcgaa    600
gtcacccatc agggcctgag ctcgcccgtc acaaagagct caacagggg agagtgt        657

<210> SEQ ID NO 142
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gacatcgtga tgtctcagag tccactgtct ctgccagtca cccctggaga gccagcatca    60
attagctgca agagctccca gagtctgctg aactcacgga caagaaagaa ttacctggcc    120
tggtatctgc agaaacccgg acagagccct cagctgctga tctactgggc tagcacaagg    180
gaatccggag tgccagaccg cttcactgga tccggatctg gaaccgattt tacactgaag    240
atcagccggg tggaggccga agatgtgggc gtctactatt gtaaacagag tttctatctg    300
agaacttttg gccaggggac caaggtggag atcaaaagaa ctgtggcagc accaagcgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt        657

<210> SEQ ID NO 143
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gatattgtca tgtcacagtc accttcatcc ctggcagtca gcgccggaga aaaagtcact    60
atgtcttgta agtcttcaca gagcctgctg aactcccgga ccagaaagaa ttacctggca    120
tggtatcagc agaagcccgg ccagtctcct aaactgctga tctactgggc atcaacaagg    180
gagagcggag tgccagaccg cttcacaggc tctgggagtg gaactgattt taccctgaca    240
attagctccg tgcaggccga agacctggct gtctactatt gcaaacagag cttctatctg    300
cgaacttttg gcgggggaac caagctggat atcaaaagaa ctgtggcagc accaagcgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt        657

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Val Gln Ile Ile Asn Lys Lys
1               5

<210> SEQ ID NO 145
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Lys His Val Pro Gly Gly Gly Ser Val Gln Ile Val Tyr Lys Pro
1               5                   10                  15

Val Asp Leu Ser Lys Val Thr Ser Lys Cys Gly Ser Leu
            20                  25

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Val Gln Ile Val Tyr Lys
1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Gln Ile Ile Asn Lys
1               5

<210> SEQ ID NO 148
<211> LENGTH: 6
<212> TYPE: PRT
<213> ORGANISM: Homo sapiens

<400> SEQUENCE: 148

His Gln Pro Gly Gly Gly
1               5

<210> SEQ ID NO 149
<211> LENGTH: 6
<212> TYPE: PRT
<213> ORGANISM: Homo sapiens

<400> SEQUENCE: 149

His Val Pro Gly Gly Gly
1               5

<210> SEQ ID NO 150
<211> LENGTH: 6
<212> TYPE: PRT
<213> ORGANISM: Homo sapiens

```
<400> SEQUENCE: 150

His Lys Pro Gly Gly Gly
1               5

<210> SEQ ID NO 151
<211> LENGTH: 441
<212> TYPE: PRT
<213> ORGANISM: Homo sapiens

<400> SEQUENCE: 151

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350
```

```
Lys Ile Gly Ser Leu Asp Asn Ile Thr His Val Pro Gly Gly Asn
            355                 360                 365
Lys Lys Ile Glu Thr His Lys Leu Thr Phe Arg Glu Asn Ala Lys Ala
370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
            435                 440
```

<210> SEQ ID NO 152
<211> LENGTH: 412
<212> TYPE: PRT
<213> ORGANISM: Homo sapiens

<400> SEQUENCE: 152

```
Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Pro Gly Ser Glu Thr Ser
        50                  55                  60
Asp Ala Lys Ser Thr Pro Thr Ala Glu Ala Glu Glu Ala Gly Ile Gly
65                  70                  75                  80
Asp Thr Pro Ser Leu Glu Asp Glu Ala Ala Gly His Val Thr Gln Ala
                85                  90                  95
Arg Met Val Ser Lys Ser Lys Asp Gly Thr Gly Ser Asp Asp Lys Lys
            100                 105                 110
Ala Lys Gly Ala Asp Gly Lys Thr Lys Ile Ala Thr Pro Arg Gly Ala
        115                 120                 125
Ala Pro Pro Gly Gln Lys Gly Gln Ala Asn Ala Thr Arg Ile Pro Ala
130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
Glu Pro Lys Lys Val Ala Val Val Arg Thr Pro Pro Lys Ser Pro Ser
        195                 200                 205
Ser Ala Lys Ser Arg Leu Gln Thr Ala Pro Val Pro Met Pro Asp Leu
210                 215                 220
Lys Asn Val Lys Ser Lys Ile Gly Ser Thr Glu Asn Leu Lys His Gln
225                 230                 235                 240
Pro Gly Gly Gly Lys Val Gln Ile Ile Asn Lys Lys Leu Asp Leu Ser
                245                 250                 255
Asn Val Gln Ser Lys Cys Gly Ser Lys Asp Asn Ile Lys His Val Pro
            260                 265                 270
Gly Gly Gly Ser Val Gln Ile Val Tyr Lys Pro Val Asp Leu Ser Lys
        275                 280                 285
```

-continued

```
Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 153
<211> LENGTH: 410
<212> TYPE: PRT
<213> ORGANISM: Homo sapiens

<400> SEQUENCE: 153

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
```

```
                    245                 250                 255
Lys Ser Lys Ile Gly Ser Thr Glu Asn Leu Lys His Gln Pro Gly Gly
                260                 265                 270

Gly Lys Val Gln Ile Val Tyr Lys Pro Val Asp Leu Ser Lys Val Thr
                275                 280                 285

Ser Lys Cys Gly Ser Leu Gly Asn Ile His His Lys Pro Gly Gly Gly
                290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
                355                 360                 365

Ser Gly Asp Thr Ser Pro Arg His Leu Ser Asn Val Ser Ser Thr Gly
                370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 154
<211> LENGTH: 383
<212> TYPE: PRT
<213> ORGANISM: Homo sapiens

<400> SEQUENCE: 154

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
                115                 120                 125

Glu Pro Pro Lys Ser Gly Asp Arg Ser Gly Tyr Ser Ser Pro Gly Ser
                130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
                195                 200                 205
```

```
Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
                260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
    370                 375                 380

<210> SEQ ID NO 155
<211> LENGTH: 381
<212> TYPE: PRT
<213> ORGANISM: Homo sapiens

<400> SEQUENCE: 155

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
        130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205
```

```
Ser Ala Lys Ser Arg Leu Gln Thr Ala Pro Val Pro Met Pro Asp Leu
        210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
        275                 280                 285
Arg Val Gln Ser Lys Ile Gly Ser Leu Asp Asn Ile Thr His Val Pro
    290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
        355                 360                 365
Ala Asp Glu Val Ser Ala Ser Leu Ala Lys Gln Gly Leu
    370                 375                 380

<210> SEQ ID NO 156
<211> LENGTH: 352
<212> TYPE: PRT
<213> ORGANISM: Homo sapiens

<400> SEQUENCE: 156

Met Ala Glu Pro Arg Gln Glu Phe Glu Val Met Glu Asp His Ala Gly
1                   5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Ala Glu Glu Ala
        35                  40                  45
Gly Ile Gly Asp Thr Pro Ser Leu Glu Asp Glu Ala Ala Gly His Val
    50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
        115                 120                 125
Glu Pro Pro Lys Ser Gly Asp Arg Ser Gly Tyr Ser Ser Pro Gly Ser
    130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
```

```
                195                 200                 205
Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 157

His Xaa Pro Gly Gly Gly
1               5

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tgtaaaacga cggccagt                                                 18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
caggaaacag ctatgacc                                                 18

<210> SEQ ID NO 160
<211> LENGTH: 45
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 160
tgtaaaacga cggccagtat ggctgtccta gggctactct tctgc           45

<210> SEQ ID NO 161
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
caggaaacag ctatgaccca gtggatagac agatggggg                  39

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
caggaaacag ctatgaccca gtggatagac cgatggggc                  39

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
caggaaacag ctatgaccca gtggatagac tgatggggg                  39

<210> SEQ ID NO 164
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
caggaaacag ctatgaccca agggatagac agatggggc                  39

<210> SEQ ID NO 165
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tgtaaaacga cggccagtat ggattttcag gtgcagatta tcagcttc        48

<210> SEQ ID NO 166
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
caggaaacag ctatgaccac tggatggtgg gaagatgg                                    38

<210> SEQ ID NO 167
<211> LENGTH: 101
<212> TYPE: PRT
<213> ORGANISM: Mus musculus

<400> SEQUENCE: 167

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro
            100
```

<210> SEQ ID NO 168
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Tyr Leu Arg
            100
```

<210> SEQ ID NO 169
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Gln Gln Ser Gly Pro Glu Leu Val Lys Pro Gly Thr

```
                1               5                  10                 15
Ser Val Lys Met Pro Cys Lys Ala Ser Gly Tyr Ile Phe Thr Asp Tyr
                20                 25                 30

Val Ile Ser Trp Val Lys Gln Arg Thr Gly Gln Gly Leu Glu Trp Ile
            35                 40                 45

Gly Glu Ile Phe Pro Arg Ser Gly Ser Thr Tyr Tyr Asn Glu Lys Phe
        50                 55                 60

Lys Gly Lys Ala Thr Leu Thr Ala Asp Lys Ser Ser Asn Thr Ala Tyr
65                 70                 75                 80

Met Gln Leu Ser Ser Val Thr Ser Glu Asp Ser Ala Val Tyr Phe Cys
                85                 90                 95

Ala Arg

<210> SEQ ID NO 170
<211> LENGTH: 107
<212> TYPE: PRT
<213> ORGANISM: Homo sapiens

<400> SEQUENCE: 170

Arg Thr Val Ala Ala Pro Ser Val Phe Ile Phe Pro Pro Ser Asp Glu
1               5                  10                 15

Gln Leu Lys Ser Gly Thr Ala Ser Val Val Cys Leu Leu Asn Asn Phe
                20                 25                 30

Tyr Pro Arg Glu Ala Lys Val Gln Trp Lys Val Asp Asn Ala Leu Gln
            35                 40                 45

Ser Gly Asn Ser Gln Glu Ser Val Thr Glu Gln Asp Ser Lys Asp Ser
        50                 55                 60

Thr Tyr Ser Leu Ser Ser Thr Leu Thr Leu Ser Lys Ala Asp Tyr Glu
65                 70                 75                 80

Lys His Lys Val Tyr Ala Cys Glu Val Thr His Gln Gly Leu Ser Ser
                85                 90                 95

Pro Val Thr Lys Ser Phe Asn Arg Gly Glu Cys
            100                105

<210> SEQ ID NO 171
<211> LENGTH: 106
<212> TYPE: PRT
<213> ORGANISM: Homo sapiens

<400> SEQUENCE: 171

Thr Val Ala Ala Pro Ser Val Phe Ile Phe Pro Pro Ser Asp Glu Gln
1               5                  10                 15

Leu Lys Ser Gly Thr Ala Ser Val Val Cys Leu Leu Asn Asn Phe Tyr
                20                 25                 30

Pro Arg Glu Ala Lys Val Gln Trp Lys Val Asp Asn Ala Leu Gln Ser
            35                 40                 45

Gly Asn Ser Gln Glu Ser Val Thr Glu Gln Asp Ser Lys Asp Ser Thr
        50                 55                 60

Tyr Ser Leu Ser Ser Thr Leu Thr Leu Ser Lys Ala Asp Tyr Glu Lys
65                 70                 75                 80

His Lys Val Tyr Ala Cys Glu Val Thr His Gln Gly Leu Ser Ser Pro
                85                 90                 95

Val Thr Lys Ser Phe Asn Arg Gly Glu Cys
            100                105

<210> SEQ ID NO 172
```

```
<211> LENGTH: 330
<212> TYPE: PRT
<213> ORGANISM: Homo sapiens

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 173
<211> LENGTH: 327
<212> TYPE: PRT
<213> ORGANISM: Homo sapiens

<400> SEQUENCE: 173

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 174
<211> LENGTH: 19
<212> TYPE: PRT
<213> ORGANISM: Homo sapiens

<400> SEQUENCE: 174

Met Asp Trp Thr Trp Arg Phe Leu Phe Val Val Ala Ala Val Thr Gly
1               5                   10                  15

Val Gln Ser

<210> SEQ ID NO 175
<211> LENGTH: 15
<212> TYPE: PRT
<213> ORGANISM: Homo sapiens
```

<400> SEQUENCE: 175

Gln Leu Gly Leu Leu Met Leu Trp Val Ser Gly Ser Ser Gly
1               5                   10                  15

<210> SEQ ID NO 176
<211> LENGTH: 111
<212> TYPE: PRT
<213> ORGANISM: Homo sapiens

<400> SEQUENCE: 176

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Trp Thr Phe Gly Gln Gly Thr Lys Val Glu Ile Lys
                100                 105                 110

<210> SEQ ID NO 177
<211> LENGTH: 120
<212> TYPE: PRT
<213> ORGANISM: Homo sapiens

<400> SEQUENCE: 177

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Thr Val Thr Thr Gly Asp Phe Asp Tyr Trp Gly Gln
                100                 105                 110

Gly Thr Leu Val Thr Val Ser Ser
            115                 120

HUMANIZED TAU ANTIBODIES IN ALZHEIMER'S DISEASE

This application is a continuation application of U.S. application Ser. No. 16/181,088, filed on Nov. 5, 2018, which is a continuation application of U.S. application Ser. No. 15/528,333, filed on May 19, 2017, now issued U.S. Pat. No. 10,160,799, which is a national phase application based on PCT/IB2015/002610, filed Nov. 18, 2015, which claims the benefit of priority of U.S. Provisional Application No. 62/081,809, filed Nov. 19, 2014, the contents of each of which are hereby incorporated by reference in their entireties.

FIELD

The present invention is in the fields of biochemistry, molecular biology, and Alzheimer's disease diagnosis, prevention, and treatment. Provided herein are humanized antibodies against human tau that are capable of discriminating between normal (healthy) and pathological (disease-associated) tau.

BACKGROUND

Alzheimer's disease (AD) is a progressive neurodegenerative disorder that destroys higher brain structures, such as those involved in memory and cognition. The disease leads to deficits in cognitive function and declines in memory, learning, language, and in the ability to perform intentional and purposeful movements. There is a need for effective methods and compositions for treatment and prophylaxis of AD.

AD is histologically characterized by the presence of extraneuronal plaques and intracellular and extracellular neurofibrillary tangles in the brain. Plaques are composed mainly of β amyloid (Aβ), whereas tangles comprise pathological forms of tau, such as pathological tau conformers and their aggregates. A recognized role for tau in AD pathology has been demonstrated in numerous studies. For example, Braak showed that the closest correlate for AD neurodegeneration was the presence of tau tangles, and not of amyloid plaques (Braak, H., et al. Neuropathological staging of Alzheimer-related changes. Acta Neuropathol 82:239-259 (1991)).

Tau belongs to a family of intrinsically disordered proteins, characterized by the absence of a rigid three-dimensional structure in their physiological environment (Skrabana et al., 2006). However, tau truncation and hyperphosphorylation can cause pathological transformations from an intrinsically disordered state to multiple soluble and insoluble misdisordered structures, including paired helical filaments (PHFs) and other aggregates (Wischik, C. M., Novak, M., Edwards, P. C., Klug, A., Tichelaar, W., Crowther, R. A. (1988). Structural characterization of the core of the paired helical filament of Alzheimer disease, Proc Natl Acad Sci USA 85, 4884-8; Wischik, C. M., Novak, M. Thøgersen, H. C., Edwards, P. C., Runswick, M. J., Jakes, R., Walker, J. E., Milstein, C., Roth, M., Klug, A. (1988). Isolation of a fragment of tau derived from the core of the paired helical filament of Alzheimer disease, Proc Natl Acad Sci USA 85, 4506-10; Novak et al., 1993; Skrabana et al., 2006; Zilka, N., et al. Chaperone-like Antibodies Targeting Misfolded Tau Protein: New Vistas in the Immunotherapy of Neurodegenerative Foldopathies. Journal of Alzheimer's disease 15 (2008) 169-179; Kovacech B, Novak M. (2010). Tau truncation is a productive posttranslational modification of neurofibrillary degeneration in Alzheimer's disease. Curr Alzheimer Res Dec; 7(8):708-16); Kovacech B, Skrabana R, Novak M. (2010). Transition of tau protein from disordered to misordered in Alzheimer's disease. Neurodegener Dis 7: 24-27). These structural changes lead to a toxic gain of function, to a loss of physiological function of the native protein, or both (Zilka et al., 2008; Kovacech B, Novak M. (2010). Tau truncation is a productive posttranslational modification of neurofibrillary degeneration in Alzheimer's disease. Curr Alzheimer Res Dec; 7(8):708-16); Kovacech B, Skrabana R, Novak M. (2010). Transition of tau protein from disordered to misordered in Alzheimer's disease. Neurodegener Dis 7: 24-27).

Tau's physiological function is in mediating the assembly of tubulin monomers into microtubules that constitute the neuronal microtubules network (Buee, L., Bussiere, T., Buee-Scherrer, V., Delacourte, A., Hof, P. R. (2000). Tau protein isoforms, phosphorylation and role in neurodegenerative disorders. Brain Research. Brain Research Reviews. 33, 95-130). Tau binds to microtubules through repetitive regions located in the C-terminal portion of the protein. Butner K A, Kirschner M W. 1991. Tau protein binds to microtubules through a flexible array of distributed weak sites. J Cell Biol 115: 717-730; Lee G, Neve R L, Kosik K S. 1989. The microtubule binding domain of tau protein. Neuron 2: 1615-1624. These repeat domains (R1-R4), are not identical to each other, but comprise highly conserved 31-32 amino acids (Taniguchi T, Sumida M, Hiraoka S, Tomoo K, Kakehi T, Minoura K, Sugiyama S, Inaka K, Ishida T, Saito N, Tanaka C 2005 (Effects of different anti-tau antibodies on tau fibrillogenesis: RTA-1 and RTA-2 counteract tau aggregation. FEBS Lett 579:1399-1404; Taniguchi S, Suzuki N, Masuda M, Hisanaga S, Iwatsubo T, Goedert M, Hasegawa M. Inhibition of heparin-induced tau filament formation by phenothiazines, polyphenols, and porphyrins. J Biol Chem 280:7614-7623 (2005)). In the human brain, there are six unique isoforms of tau, which differ from each other in the presence or absence of certain amino acids in the N-terminal portion of tau, in combination with either three (R1, R3, and R4) or four (R1-R4) repeat domains, at the C-terminal end of the protein. See also FIG. 1, which shows the six human isoforms (2N4R, 1N4R, 2N3R, 0N4R, 1N3R, and 0N3R SEQ ID Nos. 151-156, respectively, in order of appearance)). It has been proposed that the most potent part of tau to induce microtubule polymerization are the sequences 306-VQIVYK-311 (SEQ ID NO: 146) and 274-KVQIINKK-281 region (SEQ ID NO: 144), overlapping R1-R2. (von Bergen M, Friedhoff P, Biernat J, Heberle J, Mandelkow E M, Mandelkow E. 2000. Assembly of tau protein into Alzheimer paired helical filaments depends on a local sequence motif ((306)VQIVYK (311)) forming beta structure. Proc Natl Acad Sci USA 97: 5129-5134.) Id.

In addition, tau's pathological and physiological functions appear to be influenced by the specific structural conformation, and the intrinsically disordered structure, adopted by the full length protein isoforms and their fragments. For example, Kontsekova et al. described a conformational region (encompassing residues 297-IKHVPGGGSVQI-VYKPVDLSKVTSKCGSL-325 (SEQ ID NO: 145) within certain truncated tau molecules which had a significant relationship to the function of those truncated tau molecules on microtubule assembly (WO 2004/007547).

In addition to their physiological role, tau repeats are believed to participate in the formation of pathological tau aggregates and other structures. Thus, there is a need for tau-targeted therapeutic and diagnostic approaches that are capable of discriminating between physiological and pathological microtubule binding repeat region-mediated activities. For example, the pronase resistant core of pathological paired helical filaments (PHFs) consists of the microtubule binding regions of 3- and 4-repeat tau isoforms (Jakes, R., Novak, M., Davison, M., Wischik, C. M. (1991)). Identification of 3- and 4-repeat tau isoforms within the PHF in Alzheimer's disease. EMBO J 10, 2725-2729; Wischik, et al. 1988a; Wischik, et al. 1988b). Further, Novak et al. showed that the protease resistant core of the PHFs, which is 93-95 amino acids long, was restricted to three tandem repeats (Novak, M., Kabat, J., Wischik, C. M. (1993). Molecular characterization of the minimal protease resistant tau unit of the Alzheimer's disease paired helical filament. EMBO J 12, 365-70). Von Bergen et al. determined a minimal-tau peptide/interaction motif (306-VQIVYK-311; SEQ ID NO: 146), as well as a second site on tau (275-VQIINK-280) (SEQ ID NO: 147), which form beta-sheets and are described as potentially responsible for initiating the formation of PHFs, a pathological tau aggregate (von Bergen M, Friedhoff P, Biernat J, Heberle J, Mandelkow E M, Mandelkow E. 2000. Assembly of tau protein into Alzheimer paired helical filaments depends on a local sequence motif ((306)VQIVYK(311)) forming beta structure. Proc Natl Acad Sci USA 97: 5129-5134); EP 1214598; WO 2001/18546). See FIG. 2 for a functional map of tau. Consequently, current strategies aim at generating anti-aggregating drugs that do not disrupt tau's intracellular role in microtubule stabilization.

Moreover, while under physiological circumstances tau is considered an intracellular cytoplasmic protein, intracellular tau can be released into the extracellular space and contribute to neurodegeneration (Gómez-Ramos, A., Diaz-Hernández, M., Cuadros, R., Hernández, F., and Avila, J. (2006). Extracellular tau is toxic to neuronal cells. FEBS Lett 580(20), 4842-50). Indeed, neuronal loss has been linked to the topographic distribution of neurofibrillary tangles (made up of tau protein) in AD brains (West, M. J., Coleman, P. D., Flood, D. G., Troncoso, J. C. (1994). Differences in the pattern of hippocampal neuronal loss in normal ageing and Alzheimer's disease. Lancet 344, 769-72; Gomez-Isla, T., Price, J. L., McKeel Jr, D. W., Morris, J. C., Growdon, J. H., Hyman, B. T. (1996). Profound loss of layer II entorhinal cortex neurons occurs in very mild Alzheimer's disease. J Neurosci 16(14), 4491-500, Gomez-Isla T, Hollister R, West H, Mui S, Growdon J H, Petersen R C, Parisi J E, Hyman B T. Neuronal loss correlates with but exceeds neurofibrillary tangles in Alzheimer's disease. Ann Neurol 41:17-24 (1997)). Further, the levels of total tau and phosphorylated tau are increased in the cerebrospinal fluid (CSF) of patients with AD (Hampel, H., Blennow, K., Shaw, L. M., Hoessler, Y. C., Zetterberg, H., Trojanowski, J. Q. (2010). Total and phosphorylated tau protein as biological markers of Alzheimer's disease. Exp Gerontol 45(1), 30-40), and extracellular tau has been described as "ghost tangles" in the brain (Frost, B., Diamond, M. I. (2009). The expanding realm of prion phenomena in neurodegenerative disease. Prion 3(2):74-7), indicating that intracellular tau is released into extracellular space. In addition, extracellular tau aggregates can enter cells and stimulate fibrillization of intracellular tau, further seeding tau monomer for production of pathological tau aggregates (Frost et al., 2009). Such studies have highlighted that extracellular, insoluble tau could act as a transmissible agent to spread tau pathology throughout the brain in a prion-like fashion (Frost, B., Jacks, R. L., Diamond, M. I. (2009). Propagation of tau misfolding from the outside to the inside of a cell. J Biol Chem 284(19), 12845-52, Frost et al., 2009; Frost, B., Diamond, M. I. (2009). The expanding realm of prion phenomena in neurodegenerative disease. Prion 3(2):74-7). Targeting abnormal tau can reduce tau-associated extracellular and intracellular pathology. See, Eva Kontsekova, Norbert Zilka, Branislav Kovacech, Petr Novak, Michal Novak. 2014. First-in-man tau vaccine targeting structural determinants essential for pathological tau-tau interaction reduces tau oligomerisation and neurofibrillary degeneration in an Alzheimer's disease model. *Alzheimer's Research & Therapy*, 6:44. Therefore, there is a need for treatments capable of decreasing extracellular tau, either by impeding its formation, promoting its clearance, or both, as well as for treatments that decrease intracellular disease tau. An increased understanding of the molecular mechanisms underlying the pathological transformations of tau has opened up the possibility of specifically targeting pathological modifications of tau for therapeutic purposes.

International Publication No. WO2013/041962 by Novak et al. describes the discovery of four regions of tau that promote tau-tau aggregation in AD and antibodies that prevent tau aggregation by binding to those four regions.

Although other studies have described antibodies that bind to tau sequences, and some of those antibodies also reportedly interfere with tau aggregation and clearance (Asuni A A, Boutajangout A, Quartermain D, Sigurdsson E M. Immunotherapy targeting pathological tau conformers in a tangle mouse model reduces brain pathology with associated functional improvements. J Neurosci 27:9115-9129 (2007)), no monoclonal anti-tau antibody is yet reportedly undergoing clinical trials in AD.

The success of foreign (mouse) monoclonal antibodies in human treatment has been, in part, impeded by immunogenic antiglobulin responses mounted by the human recipient against such foreign therapeutics. These complicate both the safety and pharmacokinetic properties of antibodies. These challenges have led to the development of engineered antibodies that carry a lower risk of immune reactions. A variety of patented engineering technologies (e.g., chimerization, humanization, CDR grafting, framework grafting, affinity maturation, phage display, transgenic mice) are constantly being developed to facilitate this process. For recent review, see Safdari Y1, Farajnia S, Asgharzadeh M, Khalili M. Antibody humanization methods—a review and update. 2013. Biotechnol Genet Eng Rev. 29:175-86. doi: 10.1080/02648725.2013.801235 and Almagro J C1, Fransson J. Humanization of antibodies. 2008. Front Biosci. 13:1619-33.

Humanized antibodies are designed, primarily, to retain the specificity and affinity of the parent antibody while having human constant regions, which ideally would present less of an immunogenic target to the patient. The typical humanized antibody carries the complementarity determining regions (CDRs) of a parent antibody of mouse or rat origin, and framework regions (FR) and constant regions that are mostly of human origin but have often been mutated to retain the parent antibody's binding properties. But antigen-binding affinity and specificity are not the only factors affecting the biological activity and clinical success of an antibody. Improving an antibody's activation of the patient's immune system is key to the value of some humanized antibodies, whereas for others reduction of cellular-mediated toxicity is a goal. Ultimately, an increased understanding of antibody structure and activity allows researchers to engineer, often through mutations, more advanced humanized antibodies that are more homogeneous with better antigen binding properties (binding affinity, target specificity), effector functions, stability, expression level, purification properties, pharmacokinetics, and pharmacodynamics. Many of these improvements are important for the commercial viability of a given antibody. Sometimes, after target binding affinity and specificity is achieved, it is necessary to mutate some of the amino acids in the CDRs or FRs to decrease a humanized antibody's susceptibility to aggregation. Other times, the constant regions are altered (switched or mutated) for improved effector functions. These and other aspects of antibody function and activity continue to present challenges to the development of antibodies for clinical use. Described below is a set of humanized antibodies against tau that have been engineered to possess unexpected advantageous properties. Also provided below are novel methods and compositions comprising these highly specific and highly effective antibodies having the ability to specifically recognize and bind to pathological tau, impeding its aggregation. All these antibodies, methods, and compositions are useful for diagnosis and treatment of AD and related tauopathies.

SUMMARY OF THE INVENTION

These and other objects, features and advantages of the present invention will become apparent after a review of the following detailed description of the disclosed embodiment and the appended claims.

Disclosed herein is a humanized anti-tau antibody, or a tau-binding fragment thereof, wherein said antibody or binding fragment comprises:

a heavy chain variable region comprising CDR-H1, CDR-H2, and CDR-H3 of SEQ ID NOs. 1, 2, 3, respectively, and a framework from human immunoglobulin M65092 (SEQ ID NO. 711;

a light chain variable region comprising CDR-L1, CDR-L2, and CDR-L3 of SEQ ID NOs. 4, 5, 6, respectively, and a framework from human immunoglobulin X72449 (SEQ ID NO. 65); and heavy chain and light chain constant regions each from a human immunoglobulin; and wherein said heavy chain framework has been substituted at one or more of positions selected from 9, 21, 27, 28, 30, 38, 48, 67, 68, 70, and 95; said light chain framework has either not been substituted or has been substituted at position 5; and wherein said positions are according to Kabat. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Such antibody and binding fragment is also contemplated in a form, wherein heavy chain position 9 is occupied by P, position 21 is occupied by P, position 27 is occupied by Y, position 28 is occupied by I, position 30 is occupied by T, position 38 is occupied by K, position 48 is occupied by I, position 67 is occupied by K, position 68 is occupied by A, position 70 is occupied by L, and/or position 95 is occupied by F. In one embodiment, the light chain position 5 is occupied by S. In some embodiments, only two of these 11 positions are occupied as such. In some embodiments, only three of these 11 positions are occupied as such. In some embodiments, only four of these 11 positions are occupied as such. In some embodiments, only five of these 11 positions are occupied as such. In some embodiments, only six of these 11 positions are occupied as such. In some embodiments, only seven of these 11 positions are occupied as such. In some embodiments, only eight of these 11 positions are occupied as such. In some embodiments, only nine of these 11 positions are occupied as such. In some embodiments, only ten of these 11 positions are occupied as such. In some embodiments, all 11 of these 11 positions are occupied as such. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

In some embodiments, the antibody and binding fragment are also such that the sequence of the heavy chain variable region is selected from that of RHA through RHM, SEQ ID NOs. 13-25, respectively; and the sequence of the light chain variable region is SEQ ID NO. 26 (RKA).

In some embodiments, the antibody and binding fragment are also such that the sequence of the heavy chain variable region is selected from that of RHA through RHM SEQ ID NOs. 13-25, respectively; and the sequence of the light chain variable region is SEQ ID NO. 27 (RKB).

In some embodiments, the antibody and binding fragment are also such that the sequence of the heavy chain variable region is SEQ ID NO. 13, RHA, and the sequence of the light chain variable region is SEQ ID NO. 26, RKA.

In some embodiments, the antibody and binding fragment are also such that the sequence of the heavy chain variable region is SEQ ID NO. 14, RHB, and the sequence of the light chain variable region is SEQ ID NO. 26, RKA.

In some embodiments, the antibody and binding fragment are also such that the sequence of the heavy chain variable region is SEQ ID NO. 15, RHC, and the sequence of the light chain variable region is SEQ ID NO. 26, RKA.

In some embodiments, the antibody and binding fragment are also such that the sequence of the heavy chain variable region is SEQ ID NO. 16, RHD, and the sequence of the light chain variable region is SEQ ID NO. 26, RKA.

In some embodiments, the antibody and binding fragment are also such that the sequence of the heavy chain variable region is SEQ ID NO. 17, RHE, and the sequence of the light chain variable region is SEQ ID NO. 26, RKA.

In some embodiments, the antibody and binding fragment are also such that the sequence of the heavy chain variable region is SEQ ID NO. 18, RHF, and the sequence of the light chain variable region is SEQ ID NO. 26, RKA.

In some embodiments, the antibody and binding fragment are also such that the sequence of the heavy chain variable region is SEQ ID NO. 19, RHG, and the sequence of the light chain variable region is SEQ ID NO. 26, RKA.

In some embodiments, the antibody and binding fragment are also such that the sequence of the heavy chain variable region is SEQ ID NO. 20, RHH, and the sequence of the light chain variable region is SEQ ID NO. 26, RKA.

In some embodiments, the antibody and binding fragment are also such that the sequence of the heavy chain variable region is SEQ ID NO. 21, RHI, and the sequence of the light chain variable region is SEQ ID NO. 26, RKA.

In some embodiments, the antibody and binding fragment are also such that the sequence of the heavy chain variable region is SEQ ID NO. 22, RHJ, and the sequence of the light chain variable region is SEQ ID NO. 26, RKA.

In some embodiments, the antibody and binding fragment are also such that the sequence of the heavy chain variable region is SEQ ID NO. 23, RHK, and the sequence of the light chain variable region is SEQ ID NO. 26, RKA.

In some embodiments, the antibody and binding fragment are also such that the sequence of the heavy chain variable region is SEQ ID NO. 24, RHL, and the sequence of the light chain variable region is SEQ ID NO. 26, RKA.

In some embodiments, the antibody and binding fragment are also such that the sequence of the heavy chain variable region is SEQ ID NO. 25, RHM, and the sequence of the light chain variable region is SEQ ID NO. 26, RKA.

In some embodiments, the antibody and binding fragment are also such that the sequence of the heavy chain variable region is SEQ ID NO. 13, RHA, and the sequence of the light chain variable region is SEQ ID NO. 27, RKB.

In some embodiments, the antibody and binding fragment are also such that the sequence of the heavy chain variable region is SEQ ID NO. 14, RHB, and the sequence of the light chain variable region is SEQ ID NO. 27, RKB.

In some embodiments, the antibody and binding fragment are also such that the sequence of the heavy chain variable region is SEQ ID NO. 15, RHC, and the sequence of the light chain variable region is SEQ ID NO. 27, RKB.

In some embodiments, the antibody and binding fragment are also such that the sequence of the heavy chain variable region is SEQ ID NO. 16, RHD, and the sequence of the light chain variable region is SEQ ID NO. 27, RKB.

In some embodiments, the antibody and binding fragment are also such that the sequence of the heavy chain variable region is SEQ ID NO. 17, RHE, and the sequence of the light chain variable region is SEQ ID NO. 27, RKB.

In some embodiments, the antibody and binding fragment are also such that the sequence of the heavy chain variable region is SEQ ID NO. 18, RHF, and the sequence of the light chain variable region is SEQ ID NO. 27, RKB.

In some embodiments, the antibody and binding fragment are also such that the sequence of the heavy chain variable region is SEQ ID NO. 19, RHG, and the sequence of the light chain variable region is SEQ ID NO. 27, RKB.

In some embodiments, the antibody and binding fragment are also such that the sequence of the heavy chain variable region is SEQ ID NO. 20, RHH, and the sequence of the light chain variable region is SEQ ID NO. 27, RKB.

In some embodiments, the antibody and binding fragment are also such that the sequence of the heavy chain variable region is SEQ ID NO. 21, RHI, and the sequence of the light chain variable region is SEQ ID NO. 27, RKB.

In some embodiments, the antibody and binding fragment are also such that the sequence of the heavy chain variable region is SEQ ID NO. 22, RHJ, and the sequence of the light chain variable region is SEQ ID NO. 27, RKB.

In some embodiments, the antibody and binding fragment are also such that the sequence of the heavy chain variable region is SEQ ID NO. 23, RHK, and the sequence of the light chain variable region is SEQ ID NO. 27, RKB.

In some embodiments, the antibody and binding fragment are also such that the sequence of the heavy chain variable region is SEQ ID NO. 24, RHL, and the sequence of the light chain variable region is SEQ ID NO. 27, RKB.

In some embodiments, the antibody and binding fragment are also such that the sequence of the heavy chain variable region is SEQ ID NO. 25, RHM, and the sequence of the light chain variable region is SEQ ID NO. 27, RKB.

In some embodiments, the antibody and binding fragment are also such that the sequence of the heavy chain variable region is SEQ ID NO. 14, RHB, the sequence of the light chain variable region is SEQ ID NO. 26, RKA, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 26, RKA, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 26, RKA, and the constant region is of the IgG1 isotype.

In some embodiments, the antibody and binding fragment are also such that the sequence of the heavy chain variable region is SEQ ID NO. 25, RHM, the sequence of the light chain variable region is SEQ ID NO. 26, RKA, and the constant region is of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

Also contemplated is a humanized anti-tau antibody, or a tau-binding fragment thereof, wherein said antibody or binding fragment comprises:

a heavy chain variable region comprising CDR-H1, CDR-H2, and CDR-H3 of SEQ ID NOs. 1, 2, 3, respectively, and a framework from human immunoglobulin M65092 (SEQ ID NO. 71); and a light chain variable region comprising CDR-L1, CDR-L2, and CDR-L3 of SEQ ID NOs. 4, 5, 6, respectively, and a framework from human immunoglobulin X72449 (SEQ ID NO. 65); and heavy chain and light chain constant regions from a human immunoglobulin, preferably IgG1 or IgG4.

Further contemplated is an anti-tau antibody, or a tau-binding fragment thereof, wherein said antibody or binding fragment comprises the following complete chains:

a heavy chain having the amino acid sequence of any one of SEQ ID NO. 28-40; and a light chain variable domain having the amino acid sequence of any one of SEQ ID NO. 26 and 27. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:

a heavy chain having the amino acid sequence of any one of SEQ ID NO. 43-55; and a light chain comprising a light chain variable domain having the amino acid sequence of any one of SEQ ID NO. 26 and 27. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of any one of SEQ ID NO. 43-55; and
a light chain having the amino acid sequence of any one of SEQ ID NO. 57 and 58. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 31; and
a light chain having the amino acid sequence of SEQ ID NO. 57. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 32; and
a light chain having the amino acid sequence of SEQ ID NO. 57. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 31; and
a light chain having the amino acid sequence of SEQ ID NO. 58. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 32; and
a light chain having the amino acid sequence of SEQ ID NO. 58 or 57. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 46; and
a light chain having the amino acid sequence of SEQ ID NO. 57. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 47; and
a light chain having the amino acid sequence of SEQ ID NO. 57. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 46; and
a light chain having the amino acid sequence of SEQ ID NO. 58. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

Further contemplated is an anti-tau antibody, or a tau-binding fragment thereof, wherein said antibody or binding fragment comprises the following complete chains:
a heavy chain having the amino acid sequence of SEQ ID NO. 47; and
a light chain having the amino acid sequence of SEQ ID NO. 58. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

It is also contemplated an antibody comprising:
a heavy chain variable region comprising CDR-H1, CDR-H2, and CDR-H3 of SEQ ID NOs 1, 2, 3, and being at least 85% identical to any one of SEQ ID NO. RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;
and a mature light chain variable region comprising CDR-L1, CDR-L2, and CDR-L3 of SEQ ID NOs 4, 5, 6, respectively, and being at least 85% identical to SEQ ID NO. 26, RKA, wherein the antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

It is also contemplated an antibody comprising:
a heavy chain variable region comprising CDR-H1, CDR-H2, and CDR-H3 of SEQ ID NOs 1, 2, 3, and being at least 90% identical to any one of SEQ ID NO:RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;
and a mature light chain variable region comprising CDR-L1, CDR-L2, and CDR-L3 of SEQ ID NOs 4, 5, 6, respectively, and being at least 90% identical to SEQ ID NO: 26, RKA, wherein the antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

It is also contemplated an antibody comprising:

a heavy chain variable region comprising CDR-H1, CDR-H2, and CDR-H3 of SEQ ID NOs 1, 2, 3, and being at least 95% identical to any one of SEQ ID NO:RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;

and a mature light chain variable region comprising CDR-L1, CDR-L2, and CDR-L3 of SEQ ID NOs 4, 5, 6, respectively, and being at least 95% identical to SEQ ID NO: 26, RKA, wherein the antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

Such antibody and binding fragment, according to the three previous paragraphs, is also contemplated in a form, wherein heavy chain position 9 is occupied by P, position 21 is occupied by P, position 27 is occupied by Y, position 28 is occupied by I, position 30 is occupied by T, position 38 is occupied by K, position 48 is occupied by I, position 67 is occupied by K, position 68 is occupied by A, position 70 is occupied by L, and/or position 95 is occupied by F. In one embodiment, the light chain position 5 is occupied by S. In some embodiments, only two of these 11 positions are occupied as such. In some embodiments, only three of these 11 positions are occupied as such. In some embodiments, only four of these 11 positions are occupied as such. In some embodiments, only five of these 11 positions are occupied as such. In some embodiments, only six of these 11 positions are occupied as such. In some embodiments, only seven of these 11 positions are occupied as such. In some embodiments, only eight of these 11 positions are occupied as such. In some embodiments, only nine of these 11 positions are occupied as such. In some embodiments, only ten of these 11 positions are occupied as such. In some embodiments, all 11 of these 11 positions are occupied as such. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

And also contemplated is an antibody comprising:

a heavy chain variable region comprising CDR-H1, CDR-H2, and CDR-H3 of SEQ ID NOs. 1, 2, 3, and being at least 85% identical to any one of SEQ ID NO:RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;

and a mature light chain variable region comprising CDR-L1, CDR-L2, and CDR-L3 of SEQ ID NOs 4, 5, 6, respectively, and being at least 85% identical to SEQ ID NO: 27, RKB, wherein the antibody antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

And also contemplated is an antibody comprising:

a heavy chain variable region comprising CDR-H1, CDR-H2, and CDR-H3 of SEQ ID NOs. 1, 2, 3, and being at least 90% identical to any one of SEQ ID NO:RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;

and a mature light chain variable region comprising CDR-L1, CDR-L2, and CDR-L3 of SEQ ID NOs 4, 5, 6, respectively, and being at least 90% identical to SEQ ID NO: 27. RKB, wherein the antibody antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

And also contemplated is an antibody comprising:

a heavy chain variable region comprising CDR-H1, CDR-H2, and CDR-H3 of SEQ ID NOs. 1, 2, 3, and being at least 95% identical to any one of SEQ ID NO:RHA, SEQ ID RHB, SEQ ID RHC, SEQ ID RHD, SEQ ID RHE, SEQ ID RHF, SEQ ID RHG, SEQ ID RHH, SEQ ID RHI, SEQ ID RHJ, SEQ ID RHL, SEQ ID RHM, i.e., SEQ ID NOs. 13-25;

and a mature light chain variable region comprising CDR-L1, CDR-L2, and CDR-L3 of SEQ ID NOs 4, 5, 6, respectively, and being at least 95% identical to SEQ ID NO: 27, RKB, wherein the antibody antibody binds one or two epitopes chosen from HQPGGG (SEQ ID NO: 148), HVPGGG (SEQ ID NO: 149), and HKPGGG (SEQ ID NO: 150). In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

Such antibody and binding fragment, according to the three previous paragraphs, is also contemplated in a form, wherein heavy chain position 9 is occupied by P, position 21 is occupied by P, position 27 is occupied by Y, position 28 is occupied by I, position 30 is occupied by T, position 38 is occupied by K, position 48 is occupied by I, position 67 is occupied by K, position 68 is occupied by A, position 70 is occupied by L, and/or position 95 is occupied by F. In one embodiment, the light chain position 5 is occupied by S. In some embodiments, only two of these 11 positions are occupied as such. In some embodiments, only three of these 11 positions are occupied as such. In some embodiments, only four of these 11 positions are occupied as such. In some embodiments, only five of these 11 positions are occupied as such. In some embodiments, only six of these 11 positions are occupied as such. In some embodiments, only seven of these 11 positions are occupied as such. In some embodiments, only eight of these 11 positions are occupied as such. In some embodiments, only nine of these 11 positions are occupied as such. In some embodiments, only ten of these 11 positions are occupied as such. In some embodiments, all 11 of these 11 positions are occupied as such. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody in all the previous paragraphs of this section (Summary of the Description), wherein said antibody or binding fragment is a Fab, Fab', F(ab')2, Fd, scFv, (scFv)$_2$, or scFv-Fc. In some embodiments, such an antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody in the previous paragraphs of this section, wherein said antibody or binding fragment is an IgG1, IgG2, IgG3, or IgG4 antibody. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody in the previous paragraphs of this section, wherein said antibody or binding fragment is an IgG1 antibody. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody in the previous paragraphs of this section, wherein said antibody or binding fragment is glycosylated. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody in the previous paragraphs of this section, wherein said antibody or binding fragment binds to Tau 151-391/4R with an affinity ($K_D$) of at least $5\times10^{-7}$. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized. In some embodiments, the binding affinity is measured by SPR. In some embodiments, the binding affinity is measured by ELISA.

The present disclosure also provides or contemplates an antibody as in the previous paragraphs of this section, wherein said antibody or binding fragment binds to tau with at least 80% of the same binding affinity, substantially the same binding affinity, or better binding affinity, than the DC8E8 antibody secreted by hybridoma PTA-11994, deposited at the American Type Culture Collection. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized. In some embodiments, the binding affinity is measured by SPR. In some embodiments, the binding affinity is measured by ELISA.

The present disclosure also provides or contemplates an antibody as in the previous paragraphs of this section, wherein said antibody competes for binding to tau, at at least one of the same epitope(s), with the DC8E8 antibody secreted by hybridoma PTA-11994, deposited at the American Type Culture Collection. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

The present disclosure also provides or contemplates an antibody as in the previous paragraphs of this section, wherein said antibody is recombinantly produced. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes. In some embodiments, the antibody is chimeric. In some embodiments, the antibody is humanized.

In some embodiments, the antibody and binding fragment of the previous four paragraphs are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment of the first four of the previous five paragraphs are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment of the first four of the previous six paragraphs are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment of the first four of the previous seven paragraphs are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In some embodiments, the antibody and binding fragment of the first four of the previous eight paragraphs are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment of the first four of the previous nine paragraphs are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment of the first four of the previous ten paragraphs are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment of the first four of the previous eleven paragraphs are also such that the sequence of the heavy chain variable region is SEQ ID NO. 17, RHE, the sequence of the light chain variable region is SEQ ID NO. 27, RKB, and the constant region is of the IgG4 isotype.

The present disclosure also provides or contemplates an antibody as in the previous paragraphs of this section, wherein said antibody is recombinantly produced in a Chinese Hamster Ovary (CHO) cell line. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The present disclosure also provides or contemplates an antibody as in the previous paragraphs of this section, wherein said antibody or binding fragment contains an Fc region that has been modified to alter effector function, half-life, proteolysis, and/or glycosylation. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The following are fourteen exemplary additional embodiments of the previous two paragraphs:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

The present disclosure also provides or contemplates an antibody in the previous paragraphs of this section, wherein said antibody or binding fragment is modified to modulate a functional characteristic selected from the group consisting of antibody-dependent cellular cytotoxicity, complement-dependent cytotoxicity, serum half-life, biodistribution, and binding to Fc receptors. In some embodiments, the antibody binds one or two epitopes chosen from HQPGGG (SEQ ID NO: 148), HVPGGG (SEQ ID NO: 149), and HKPGGG (SEQ ID NO: 150). In some embodiments, the antibody binds all three epitopes.

The following are fourteen exemplary additional embodiments of the previous paragraph:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

The present disclosure also provides or contemplates an antibody as in the previous paragraphs of this section, wherein said antibody has a thermostability temperature equal to or greater than 69° C.

The following are fourteen exemplary additional embodiments of the previous paragraph:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In another aspect of the present disclosure, it contemplates a composition comprising one of the antibodies and/or binding fragments of the present disclosure and another component.

In another aspect of the present disclosure, it contemplates a pharmaceutical composition comprising the antibody or binding fragment as described in this section and a pharmaceutically acceptable carrier, diluent, excipient, or stabilizer.

The following are fourteen exemplary additional embodiments of the previous two paragraphs:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

Also contemplated is a further version of any of the previous composition, wherein the composition comprises a lyophilized powder of the antibody or binding fragment.

Also contemplated are any of the previous compositions, wherein the composition is formulated for infusion or subcutaneous administration.

Also contemplated are any of these compositions, further comprising a second therapeutic agent (also called combinations).

The following are fourteen exemplary additional composition embodiments of the previous three paragraphs:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In some of these compositions, the therapeutic agent and the antibody or binding fragment are chemically conjugated.

In some of these compositions, the second therapeutic agent is useful in the prophylaxis and/or treatment of AD.

It is also contemplated that the second therapeutic agent be selected from, for example, beta-amyloid peptides (e.g., N-terminal amyloid beta peptides), which might or might not be conjugated to other compounds, such as mutated diphtheria toxin; other anti-tau antibodies, antibodies against beta-amyloid, such as bapineuzumab, solaneuzumab, gantenerumab, crenezumab, and IVIG immunoglobulin, other immunization therapies targeting Abeta oligomers, compounds preventing the hyperphosphorylation of tau, compounds preventing tau oligomerization and aggregation or depolymerize tau oligomers (e.g. methylthioninium, rember or LMTX) and other active and passive immunization therapies targeting tau aggregates; and any pharmaceutically acceptable salts thereof.

It is also contemplated that the second therapeutic agent be selected from amyloid-beta aggregation inhibitors (e.g., Tramiprosate), gamma-secretase inhibitors (e.g., semagacestat), and gamma-secretase modulators (tarenflurbil); and any pharmaceutically acceptable salts thereof.

The following are fourteen exemplary additional embodiments of the previous four paragraphs:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some instances, the second therapeutic agent is selected from acetylcholinesterase inhibitors (e.g., donepezil, rivastigmine, galantamine, tacrine, nutritive supplements), N-Methyl-D-aspartate (NMDA) receptor antagonists (e.g., memantine), inhibitors of DNA repair (e.g., pirenzepine or a metabolite thereof), transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of anti-mitochondrial dysfunction drugs, neurotrophins, inhibitors of heat shock proteins, inhibitors of Lipoprotein-associated phospholipase $A_2$, memantine, an anti-apoptotic compound, a metal chelator, an inhibitor of DNA repair, 3-amino-1-propanesulfonic acid (3APS), 1,3-propanedisulfonate (1,3PDS), a secretase activator, a beta-secretase inhibitor, a gamma-secretase inhibitor, a beta-amyloid peptide, a beta-amyloid antibody, a tau peptide, a neurotransmitter, a beta-sheet breaker, an anti-inflammatory molecule; and any pharmaceutically acceptable salts thereof.

The following are fourteen exemplary additional embodiments of the previous paragraph:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

Also contemplated are compositions wherein the second therapeutic agent is selected from compounds described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), antipsychotics and anti-depressants (pages 80-82), nutritional supplements (pages 83-89) and compounds increasing the availability of biologically active substances in the brain (see pages 89-93) and prodrugs (pages 93 and 94); and any pharmaceutically acceptable salts thereof.

Also contemplated are compositions wherein the second therapeutic agent is selected from compounds preventing tau oligomerization and aggregation and compounds that depolymerize tau oligomers (e.g. methylthioninium, rember or LMTX).

The following are fourteen exemplary additional embodiments of the previous two paragraphs:

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In another aspect, the disclosure provides a diagnostic reagent comprising an antibody or binding fragment according to the embodiments disclosed herein and a carrier, diluent, excipient, or stabilizer.

In some embodiments of these diagnostic reagents, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments of these diagnostic reagents, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments of these diagnostic reagents, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments of these diagnostic reagents, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments of these diagnostic reagents, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments of these diagnostic reagents, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments of these diagnostic reagents, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments of these diagnostic reagents, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments of these diagnostic reagents, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments of these diagnostic reagents, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments of these diagnostic reagents, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments of these diagnostic reagents, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments of these diagnostic reagents, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments of these diagnostic reagents, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

In yet another aspect, the disclosure provides an immunoconjugate having the formula (A)-(L)-(C), wherein: (A) is an antibody or binding fragment thereof according to the embodiments disclosed herein; (L) is a linker; and (C) is an agent; and wherein said linker (L) links (A) to (C). In some cases, (C) is a therapeutic agent, an imaging agent, a detectable agent, or a diagnostic agent. In some cases, (C) is a therapeutic agent.

In some embodiments of these immunoconjugates, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 isotype.

In some other embodiments of these immunoconjugates, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 isotype.

In some other embodiments of these immunoconjugates, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 isotype.

In some other embodiments of these immunoconjugates, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 isotype.

In some embodiments of these immunoconjugates, the antibody and binding fragment are also such that the sequence of the heavy chain variable region is SEQ ID NO. 26, RHD, the sequence of the light chain variable region is SEQ ID NO. 27, RKB, and the constant region is of the IgG1 isotype.

In some embodiments of these immunoconjugates, the antibody and binding fragment are also such that the sequence of the heavy chain variable region is SEQ ID NO. 17, RHE, the sequence of the light chain variable region is SEQ ID NO. 27, RKB, and the constant region is of the IgG1 isotype.

In some embodiments of these immunoconjugates, the antibody and binding fragment are also such that the sequence of the heavy chain variable region is SEQ ID NO. 16, RHD, the sequence of the light chain variable region is SEQ ID NO. 27, RKB, and the constant region is of the IgG4 isotype.

In some embodiments of these immunoconjugates, the antibody and binding fragment are also such that the sequence of the heavy chain variable region is SEQ ID NO. 17, RHE, the sequence of the light chain variable region is SEQ ID NO. 27, RKB, and the constant region is of the IgG4 isotype.

In some embodiments of these immunoconjugates, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG4 isotype.

In some other embodiments of these immunoconjugates, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG4 isotype.

In some other embodiments of these immunoconjugates, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG4 isotype.

In some other embodiments of these immunoconjugates, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG4 isotype.

In some embodiments of these immunoconjugates, the antibody and binding fragment are also such that the sequence of the heavy chain variable region is SEQ ID NO. 14, RHB, the sequence of the light chain variable region is SEQ ID NO. 27, RKB, and the constant region is of the IgG1 isotype.

In some embodiments of these immunoconjugates, the antibody and binding fragment are also such that the sequence of the heavy chain variable region is SEQ ID NO. 14, RHB, the sequence of the light chain variable region is SEQ ID NO. 27, RKB, and the constant region is of the IgG4 isotype.

The invention contemplates nucleic acid molecules (RNA or DNA) encoding any of the antibodies and tau-binding fragments disclosed above. In one embodiment, such nucleic acid molecules comprise one or more of nucleic acid sequences chosen from SEQ ID NOs. 96-124, 141-142, and 127-140. In other embodiments, such nucleic acid molecules comprise one or more of nucleic acid sequences chosen from sequences that are at least 85% identical to any one of SEQ ID NOs. 96-124, 141-142, and 127-140. In other embodiments, such nucleic acid molecules comprise one or more of nucleic acid sequences chosen from sequences that are at least 90% identical to any one of SEQ ID NOs. 96-124, 141-142, and 127-140. In other embodiments, such nucleic acid molecules comprise one or more of nucleic acid sequences chosen from sequences that are at least 95% identical to any one of SEQ ID NOs. 96-124, 141-142, and 127-140. In other embodiments, such nucleic acid molecules comprise one or more of nucleic acid sequences chosen from sequences that are at least 96% identical to any one of SEQ ID NOs. 96-124, 141-142, and 127-140. In other embodiments, such nucleic acid molecules comprise one or more of nucleic acid sequences chosen from sequences that are at least 97% identical to any one of SEQ ID NOs. 96-124, 141-142, and 127-140. In other embodiments, such nucleic acid molecules comprise one or more of nucleic acid sequences chosen from sequences that are at least 98% identical to any one of SEQ ID NOs. 96-124, 141-142, and 127-140. In other embodiments, such nucleic acid molecules comprise one or more of nucleic acid sequences chosen from sequences that are at least 99% identical to any one of SEQ ID NOs. 96-124, 141-142, and 127-140.

In one embodiment, the disclosure contemplates a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of anyone of SEQ ID NO: RHA through SEQ ID NO. RHM, i.e., SEQ ID NOs. 13-25. In each of these embodiments, it can also be the case that the antibody or fragment thereof comprises a heavy chain further comprising an IgG1 constant region. In other embodiments, the antibody or fragment thereof comprises a heavy chain further comprising an IgG4 constant region.

A nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 26, RKA, or SEQ ID NO: 27, RKB. In each of these embodiments, it can also be the case that the antibody or fragment thereof comprises a heavy chain further comprising a kappa constant region.

In one embodiment, the disclosure contemplates a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is identical to the amino acid sequence of anyone of SEQ ID NO: RHA through SEQ ID NO. RHM, i.e., SEQ ID NOs. 13-25. In each of these embodiments, it can also be the case that the antibody or fragment thereof comprises a heavy chain further comprising an IgG1 constant region. In other embodiments, the antibody or fragment thereof comprises a heavy chain further comprising an IgG4 constant region.

A nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is identical to the amino acid sequence of SEQ ID NO: 26, RKA, or SEQ ID NO. 27, RKB. In each of these embodiments, it can also be the case that the antibody or fragment thereof comprises a heavy chain further comprising a kappa constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO: 14, RHB. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO: 16, RHD. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO: 17, RHE. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO: 25, RHM. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is identical to the amino acid sequence of SEQ ID NO: 14, RHB. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is identical to the amino acid sequence of SEQ ID NO: 16, RHD. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is identical to the amino acid sequence of SEQ ID NO: 17, RHE. In each of these embodiments, it can also be the case that the antibody or fragment thereof comprises a heavy chain further comprising an IgG1 constant region.

Also contemplated is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is identical to the amino acid sequence of SEQ ID NO: 25, RHM. In each of these embodiments, it can also be the case that the antibody or fragment thereof comprises a heavy chain further comprising an IgG1 constant region.

In some embodiments, any of the nucleic acid molecules just described in this section is such that the antibody or fragment thereof comprises a heavy chain further comprising an IgG1 constant region.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 26, RKA. In each of these embodiments, it can also be the case that the antibody or fragment thereof comprises a heavy chain further comprising a kappa constant region.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: RKB. In each of these embodiments, it can also be the case that the antibody or fragment thereof comprises a heavy chain further comprising a kappa constant region.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is identical to the amino acid sequence of SEQ ID NO: 26, RKA. In each of these embodiments, it can also be the case that the antibody or fragment thereof comprises a heavy chain further comprising a kappa constant region.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is identical to the amino acid sequence of SEQ ID NO: RKB. In each of these embodiments, it can also be the case that the antibody or fragment thereof comprises a heavy chain further comprising a kappa constant region.

In some embodiments, the nucleic acid sequence encodes the HCVR of any one of SEQ ID NO: 13-25 (RHA through RHM).

In yet another set of embodiments, the nucleic acid sequence encodes the HCVR of SEQ ID NO. 14, RHB.

In one embodiment of these nucleic acids, the nucleic acid sequence encodes the HCVR of SEQ ID NO. 16, RHD.

In one embodiment of these nucleic acids, the nucleic acid sequence encodes the HCVR of SEQ ID NO. 17, RHE.

In one embodiment of these nucleic acids, the nucleic acid sequence encodes the HCVR of SEQ ID NO. 25, RHM.

In one embodiment of these nucleic acids, the nucleic acid sequence encodes the LCVR of any one of SEQ ID NO. 26, RKA, and SEQ ID NO. 27, RKB.

Also contemplated is a nucleic acid sequence comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of anyone of SEQ ID NO: RHA through SEQ ID NO. RHM (i.e., SEQ ID NO. 13-25), and further such that the nucleic acid sequence comprises a nucleotide sequence that hybridizes under stringent conditions to a complementary strand of any one of SEQ ID NO: RHA through SEQ ID NO. RHM (i.e., SEQ ID NO. 96-108), wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid sequence comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO. 14, RHB, and further such that the nucleic acid sequence comprises a nucleotide sequence that hybridizes under stringent conditions to a complementary strand of SEQ ID NO. 97, RHB, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid sequence comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO. 16, RHD, and further such that the nucleic acid sequence comprises a nucleotide sequence that hybridizes under stringent conditions to a complementary strand of SEQ ID NO. 99, RHD, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid sequence comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO. 17, RHE, and further such that the nucleic acid sequence comprises a nucleotide sequence that hybridizes under stringent conditions to a complementary strand of SEQ ID NO. 100, RHE, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid sequence comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of SEQ ID NO. 25, RHM, and further such that the nucleic acid sequence comprises a nucleotide sequence that hybridizes under stringent conditions to a complementary strand of SEQ ID NO. 108, RHM, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 26, RKA; and further such that the nucleic acid sequence comprises a nucleotide sequence that hybridizes under stringent conditions to a complementary strand of SEQ ID NO: 109, RKA, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 14, RKB, and further such that the nucleic acid sequence comprises a nucleotide sequence that hybridizes under stringent conditions to a complementary strand of SEQ ID NO: 110, RKB, wherein the stringent hybridization conditions comprise hybridization in 5×SSPE, 1% SDS, 1×Denhardts solution at 65° C. and washing in 2×SSC, 1% SDS and subsequently with 0.2×SSC at 65° C.

Also contemplated is a population of nucleic acid molecules comprising a first nucleic acid molecule and a second nucleic acid molecule, wherein:

the first nucleic acid molecule is a nucleic acid molecule comprising a nucleotide sequence encoding a heavy chain variable region (HCVR) or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3, and wherein said HCVR or fragment thereof comprises an amino acid sequence that is at least 98% identical to the amino acid sequence of anyone of SEQ ID NO: RHA through SEQ ID NO. RHM (i.e., SEQ ID NO. 13-25);

and wherein the second nucleic acid molecule comprises a nucleotide sequence encoding an LCVR or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6.

Also contemplated is a population of nucleic acid molecules comprising a first nucleic acid molecule and a second nucleic acid molecule, wherein:

a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 26, RKA;

and wherein the second nucleic acid molecule comprises a nucleotide sequence encoding an HCVR or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3.

Also contemplated is a population of nucleic acid molecules comprising a first nucleic acid molecule and a second nucleic acid molecule, wherein:

a nucleic acid molecule comprising a nucleotide sequence encoding a light chain variable region (LCVR) or a tau-binding fragment thereof of an anti-tau antibody, wherein said LCVR or fragment thereof comprises: (i) a framework derived from human immunoglobulin X72449 (SEQ ID NO. 65), (ii) an LCVR CDR1 comprising the amino acid sequence of SEQ ID NO: 4, (iii) an LCVR CDR2 comprising the amino acid sequence of SEQ ID NO: 5, and (iv) an LCVR CDR3 comprising the amino acid sequence of SEQ ID NO: 6, and wherein said LCVR or fragment thereof comprises an amino acid sequence that is at least 98% identical to the amino acid sequence of SEQ ID NO: 27, RKB;

and wherein the second nucleic acid molecule comprises a nucleotide sequence encoding an HCVR or a tau-binding fragment thereof of an anti-tau antibody, wherein said HCVR or fragment thereof comprises: (i) a framework derived from human immunoglobulin M65092 (SEQ ID NO. 71), (ii) an HCVR CDR1 comprising the amino acid sequence of SEQ ID NO: 1, (iii) an HCVR CDR2 comprising the amino acid sequence of SEQ ID NO: 2, and (iv) an HCVR CDR3 comprising the amino acid sequence of SEQ ID NO: 3.

Also contemplated are nucleic acid molecules encoding any of heavy chain variable regions RHA-RHM (SEQ ID NOs 13-25), wherein those nucleic acid sequences are selected from any of SEQ ID NOs. 28-40, respectively, or 43-55, respectively. Any of these nucleic acid molecules can be combined with the nucleic acid molecules of the following paragraph.

Also contemplated are nucleic acid molecules encoding any of light chains RKA or RKB, wherein the nucleic acid molecules encode a sequence selected from SEQ ID NOs. 57 and 58, respectively.

All possible combinations of the nucleic acids disclosed above, that encode an amino acid or tau-binding fragment thereof, a light chain variable, a complete light chain, a heavy chain variable, a complete heavy chain, as disclosed herein, are contemplated.

In some examples of such nucleic acid populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 14, RHB, and the second nucleic acid molecule comprises a nucleotide sequence encoding a LCVR or a tau-binding fragment thereof of SEQ ID NO. 26, RKA.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 16, RHD, and the second nucleic acid molecule comprises a nucleotide sequence encoding a LCVR or a tau-binding fragment thereof of SEQ ID NO. 26, RKA.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 17, RHE, and the second nucleic acid molecule comprises a nucleotide sequence encoding a LCVR or a tau-binding fragment thereof of SEQ ID NO. 26, RKA.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 25, RHM, and the second nucleic acid molecule comprises a nucleotide sequence encoding a LCVR or a tau-binding fragment thereof of SEQ ID NO. 26, RKA.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 16, RHD, and the second nucleic acid molecule comprises a nucleotide sequence encoding a LCVR or a tau-binding fragment thereof of SEQ ID NO. 27, RKB.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 17, RHE, and the second nucleic acid molecule comprises a nucleotide sequence encoding a LCVR or a tau-binding fragment thereof of SEQ ID NO. 27, RKB.

In some examples of such populations, they comprise a first nucleic acid molecule and a second nucleic acid molecule, wherein the first nucleic acid molecule comprises a nucleotide sequence encoding an HCVR or a tau-binding fragment thereof of an anti-tau antibody of SEQ ID NO. 14, RKB, and the second nucleic acid molecule comprises a nucleotide sequence encoding a LCVR or a tau-binding fragment thereof of SEQ ID NO. 27, RKB.

Also contemplated is a set of vectors each comprising a nucleic acid encoding the heavy chain of the antibody or binding fragment as described in the previous paragraphs of this section. Another set of vectors contemplated are those comprising a nucleic acid encoding the light chain of the antibody or binding fragment as described in any of the previous paragraphs of this section. Another set of vectors contemplated are those comprising a nucleic acid encoding the light chain of the antibody or binding fragment as described in any of the previous paragraphs of this section and heavy chain of the antibody or binding fragment as described in the previous paragraphs of this section.

Host cells comprising any of these vectors are also contemplated. In some embodiments, the host cell is prokaryotic. In other embodiments, the host cell is eukaryotic. A host cell comprising any of the population of nucleic acid molecules described above are also contemplated.

In some embodiments of these host cells, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of these host cells, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of these host cells, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of these host cells, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of these host cells, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of these host cells, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of these host cells, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

In some other embodiments of these host cells, the antibody and binding fragment are also such that the sequence of the heavy chain variable region is SEQ ID NO. 17, RHM, and the sequence of the light chain variable region is SEQ ID NO. 26, RKA. Optionally, the antibody and binding fragment are of the IgG1 or IgG4 isotype.

Any of the above contemplated nucleic acids, antibodies, vectors, and host cells, and their respective compositions is contemplated for use as a drug for:

the prevention or treatment of AD or another tauopathy;

treating Alzheimer's Disease or another tauopathy in a subject having, suspected of having, or being prone to have Alzheimer's Disease or another tauopathy;

slowing progression of AD or another tauopathy in a subject having, suspected of having, or being prone to have Alzheimer's Disease or another tauopathy;

ameliorating the symptoms of AD or a related in a subject having, suspected of having, or being prone to have Alzheimer's Disease or another tauopathy; and reducing the risk or delaying the onset of AD or another tauopathy in a subject having, suspected of having, or being prone to have Alzheimer's Disease or another tauopathy.

Another aspect of the present disclosure is a method of producing an antibody or tau-binding fragment thereof that binds to human tau comprising culturing any of the host cells just described so that the nucleic acid is expressed and the antibody or tau-binding fragment thereof produced.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

Another aspect contemplates a method of treating Alzheimer's Disease or another tauopathy in a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

Another aspect contemplates a method of promoting clearance of tau aggregates from the brain of a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

Another aspect contemplates a method of slowing progression of AD or another tauopathy in a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

Another aspect contemplates a method of ameliorating the symptoms of AD or a related in a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

Another aspect contemplates a method of treating, preventing, or reversing cognitive in a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

Another aspect contemplates a method of reducing the risk or delaying the onset of AD or another tauopathy in a subject having, suspected of having, or being prone to have Alzheimer's Disease or another tauopathy, comprising administering to the subject a therapeutically effective amount of a composition comprising any of the antibodies or binding fragments described in this section.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 14, RHB, and the sequence of the light chain variable region is SEQ ID NO. 27, RKB. Optionally, the antibody and binding fragment are of the IgG1 or IgG4 isotype.

In some embodiments, any of these compositions, antibodies, and/or binding fragments is administered via injection. In other embodiments, any of these compositions, antibodies, and/or binding fragments is administered via intravenous infusion.

Also contemplated are embodiments wherein any of these compositions, antibodies, and/or binding fragments is administered to said subject at a dose of antibody or binding fragment of 0.1 mg/kg of body weight to 20 mg/kg of body weight and a frequency of between weekly and monthly, thereby treating the subject. In a preferred embodiment, the antibody or binding fragment is administered at a dose of 0.1 mg/kg of body weight to 10 mg/kg of body weight. In some preferred embodiments, the antibody or binding fragment is administered over a period of at least three months, preferably at least six months, likely at least twelve months, possibly for twenty four months, at any of these previous doses. In another embodiment, any of these compositions, antibodies, and/or binding fragments is administered to said subject at a dose of antibody or binding fragment of 0.1 mg/kg of body weight to 10 mg/kg of body weight and a frequency of between weekly and monthly, preferably every two weeks, thereby treating the subject. In another embodiment, any of these compositions, antibodies, and/or binding fragments is administered to said subject at a dose of antibody or binding fragment of 0.01 mg/kg of body weight to 100 mg/kg of body weight and a frequency of between weekly and monthly, thereby treating the subject.

In some embodiments of these two methods, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments these two methods, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments these two methods, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments these two methods, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments these two methods, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments these two methods, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In another aspect, any of the therapeutic methods just described in this section further comprise monitoring the subject for treatment progression by at least one type of assessment selected from the group consisting of Mini-Mental State Exam (MMSE), Alzheimer's Disease Assessment Scale-cognitive (ADAS-COG), Clinician Interview-Based Impression (CIBI), Neurological Test Battery (NTB), Disability Assessment for Dementia (DAD), Clinical Dementia Rating-sum of boxes (CDR-SOB), Neuropsychiatric Inventory (NPI), Positron Emission Tomography (PET Imaging) scan, and Magnetic Resonance Imaging (MRI) scan. In one embodiment, the type of assessment is a Neurological Test Battery (NTB). In another embodiment, the type of assessment is a Mini-Mental State Exam (MMSE).

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some embodiments, the practice of any of these methods further comprises administering to said subject, concurrently or sequentially, an effective amount of at least one additional therapeutic agent.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

For example, in some of these embodiments, the additional therapeutic agent is selected from the group consisting of an anti-apoptotic compound, a metal chelator, an inhibitor of DNA repair, 3-amino-1-propanesulfonic acid (3APS), 1,3-propanedisulfonate (1,3PDS), a secretase activator, a beta-secretase inhibitor, a gamma-secretase inhibitor, a beta-amyloid peptide, an anti-beta-amyloid antibody, a neurotransmitter, a beta-sheet breaker, an anti-inflammatory molecule, and a cholinesterase inhibitor; and any pharmaceutically acceptable salts thereof.

In some other of these embodiments, the cholinesterase inhibitor is tacrine, rivastigmine, donepezil, galantamine, or a nutritive supplement; and any pharmaceutically acceptable salts thereof.

In some embodiments of these two methods, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In yet some other of these embodiments, the additional therapeutic agent is selected from beta-amyloid peptides (e.g., N-terminal amyloid beta peptides), which might or might not be conjugated to other compounds, such as mutated diphtheria toxin; antibodies against beta-amyloid, such as bapineuzumab, solaneuzumab, gantenerumab, crenezumab, ponezumab, and IVIG immunoglobulin, other immunization therapies targeting Abeta oligomers, compounds preventing the hyperphosphorylation of tau, a compound preventing tau oligomerization and aggregation or promoting depolymerization of tau oligomers (e.g. methylthioninium, rember or LMTX) and other active and passive immunization therapies targeting pathological forms of tau (e.g. aggregates); and any pharmaceutically acceptable salts thereof.

In some of these other embodiments, the additional therapeutic agent is selected from amyloid-beta aggregation inhibitors (e.g., Tramiprosate), gamma-secretase inhibitors (e.g., semagacestat), and gamma-secretase modulators (tarenflurbil); and any pharmaceutically acceptable salts thereof.

In some embodiments of these two methods, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some of these embodiments, the additional therapeutic agent is selected from acetylcholinesterase inhibitors (e.g., donepezil, rivastigmine, galantamine, tacrine, nutritive supplements), N-Methyl-D-aspartate (NMDA) receptor antagonists (e.g., memantine), inhibitors of DNA repair (e.g., pirenzepine or a metabolite thereof), transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of anti-mitochondrial dysfunction drugs, neurotrophins, inhibitors of heat shock proteins, inhibitors of Lipoprotein-associated phospholipase $A_2$, memantine, an anti-apoptotic compound, a metal chelator, an inhibitor of DNA repair, 3-amino-1-propanesulfonic acid (3APS), 1,3-propanedisulfonate (1,3PDS), a secretase activator, a beta-secretase inhibitor, a gamma-secretase inhibitor, a beta-amyloid peptide, a beta-amyloid antibody, a neurotransmitter, a beta-sheet breaker, an anti-inflammatory molecule; and any pharmaceutically acceptable salts thereof.

In some embodiments of these two methods, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

In some of these embodiments, the additional therapeutic agent is selected from BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors, cholesterol absorption inhibitors, and any pharmaceutically acceptable salts thereof.

In some of these embodiments, the additional therapeutic agent is a second antibody. In yet other embodiments, the second antibody is selected from bapineuzumab, solaneuzumab, gantenerumab, crenezumab, ponezumab, and IVIG immunoglobulin.

In some embodiments of these two methods, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of these two methods, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of these two methods, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

Also contemplated is a method of evaluating a subject having, suspected of having, or being prone to have Alzheimer's Disease or another tauopathy, the method comprising the step of detecting binding of any of the antibodies or tau-binding fragment described in this section to a component of a biological sample from the subject, wherein the detection of binding to the biological sample is indicative of Alzheimer's Disease or another tauopathy in the subject. In some of these embodiments, the biological sample is a biopsy, a CSF, blood, serum, or plasma sample.

In some embodiments of this method, the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

In some other embodiments of this method, the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

In some other embodiments of this method, the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 14, RHB, and the sequence of the light chain variable region is SEQ ID NO. 26, RKA. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 16, RHD, and the sequence of the light chain variable region is SEQ ID NO. 26, RKA. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 17, RHE, and the sequence of the light chain variable region is SEQ ID NO. 26, RKA. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 25, RHM, and the sequence of the light chain variable region is SEQ ID NO. 26, RKA. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 16, RHD, and the sequence of the light chain variable region is SEQ ID NO. 27, RKB. Optionally, the antibody and binding fragment are of the IgG1 or IgG4 isotype.

It is also contemplated that any of the therapeutic methods described in the previous paragraphs can be practiced with an antibody or tau-binding fragment, wherein the antibody and binding fragment are also such that the sequence of the heavy chain variable region is SEQ ID NO. 17, RHM, and the sequence of the light chain variable region is SEQ ID NO. 27, RKB. Optionally, the antibody and binding fragment are of the IgG1 or IgG4 isotype.

BRIEF DESCRIPTION OF THE DRAWINGS

FIG. 3: Protein (SEQ ID NO: 8) and DNA sequence (SEQ ID NO: 91) of DC8E8 Kappa Light Chain Variable Region FIG. 4: Protein (SEQ ID NO: 7) and DNA Sequence (SEQ ID NO: 90) of DC8E8 Heavy Chain Variable Region FIG. 5: DC8E8 Kappa Light Chain Germ Line Analysis (SEQ ID NOS 167 and 168, respectively, in order of appearance)

FIG. 6: DC8E8 Heavy Chain Germ Line Analysis (SEQ ID NOS 66 and 169, respectively, in order of appearance)

FIG. 8: DC8E8 Heavy Chain Humanization Strategy. Structurally important residues (Proline, Cysteine and Asparagine) are highlighted by bold typeface and italicised. Bold underlined residues indicate back-translations to the Mouse Residue. CDR regions are in lowercase letters and indicated by dots in the table header. Residues within 4 Å of a CDR are indicated by stars in the table header. FIG. 8 discloses SEQ ID NOS 7, 71 and 13-25, respectively, in order of appearance. Note that SEQ ID NO. 71 (accession number M65092 in the IMGT database) is shown without the leader peptide MDWTWRFLFVVAAVTGVQS (SEQ ID NO. 174).

FIG. 9: DC8E8 Kappa Light Chain Humanization Strategy. Structurally important residues (Proline, Cysteine and Asparagine) are highlighted by bold typeface and italicised. Bold underlined residues indicate back-translations to the Mouse Residue. CDR regions are in lowercase letters and indicated by dots in the table header. Residues within 4 Å of a CDR are indicated by stars in the table header. FIG. 9 discloses SEQ ID NOs. 8, 65 and 26-27, respectively, in order of appearance. Note that SEQ ID NO. 65 (accession number X72449 in the IMGT database) is shown without the leader peptide QLLGLLMLWVSGSSG (SEQ ID NO. 175).

FIG. 22: Binding kinetics of DC8E8 antibodies analysed by surface plasmon resonance: $K_D$ determination: Humanized DC8E8 RHE/RKB (AX017), FIG. 23: Biacore Results Summary FIG. 24A. AX004 (DA); FIG. 24B. AX005 (EA); FIG. 24C. AX016 (DB); FIG. 24D. AX017 (EB).

FIG. 28A. AX004 (DA); FIG. 28B. AX005 (EA); FIG. 28C. AX0016 (DB); FIG. 28D. AX017 (EB).

FIGS. 29A-29C: Binding of (FIG. 29A) chimeric DC8E8 and (FIG. 29B) mouse DC8E8 to misdisordered truncated tau 151-391/4R and physiological tau 2N4R as determined by ELISA. (FIG. 29C) EC50 values of chimeric and mouse antibody for analyzed tau proteins.

(FIG. 31C) EC50 values of chimeric and mouse antibody for analyzed tau peptides.

FIGS. 33A-33F: Binding of humanized leads of DC8E8 (IgG4 isotype) and chimeric DC8E8 to misdisordered tau 151-391/4R and full length physiological tau 2N4R, as determined by ELISA. (FIG. 33A) Binding of humanized antibody AX004, (FIG. 33B) Binding of humanized antibody AX005, (FIG. 33C) Binding of humanized antibody AX016, (FIG. 33D) Binding of humanized antibody AX017. (FIG. 33E) Binding of chimeric DC8E8. (FIG. 33F) EC50 values of chimeric DC8E8 and humanized leads AX004, AX005, AX016, AX017 to the analyzed tau proteins.

(FIG. 34A) Binding of humanized antibody AX004, (FIG. 34B) Binding of humanized antibody AX005, (FIG. 34C) Binding of humanized antibody AX016, (FIG. 34D) Binding of humanized antibody AX017. (FIG. 34E) EC50 values of humanized leads AX004, AX005, AX016, AX017 to the analyzed tau proteins.

(FIG. 35A) IgG4 versions, (FIG. 35B) IgG1 versions.

FIGS. 36A-36F: Binding of humanized antibodies (of IgG4 isotype) to tau peptides derived from the microtubule-binding repeat region of protein tau, as determined by ELISA. (FIG. 36A) Binding of humanized antibody AX004, (FIG. 36B) Binding of humanized antibody AX005, (FIG. 36C) Binding of humanized antibody AX016, (FIG. 36D) Binding of humanized antibody AX017. (FIG. 36E) Binding of chimeric DC8E8. (FIG. 36F) EC50 values of chimeric DC8E8 and humanized version AX004, AX005, AX016, AX017 for analyzed tau proteins.

(FIG. 37A) Binding of humanized antibody AX004, (FIG. 37B) Binding of humanized antibody AX005, (FIG. 37C) Binding of humanized antibody AX016, (FIG. 37D) Binding of humanized antibody AX017. (FIG. 37E) EC50 values of chimeric DC8E8 and humanized version AX004, AX005, AX016, AX017 for analyzed tau proteins.

(FIG. 38A) Inhibition of pathological aggregation induced by humanized DC8E8 leads of IgG4 isotype and (FIG. 38B) inhibition of pathological aggregation induced by humanized antibodies of IgG1 isotype.

FIGS. 39A-39F: Immunohistochemical staining of Alzheimer's disease brain using humanized DC8E8 antibodies (IgG1) Both DC8E8 (FIG. 39A) and chimeric DC8E8 (FIG. 39B) recognized high load of neurofibrillary pathology in the human AD hippocampus (CA1). Humanized antibodies AX004 (FIG. 39C) and AX016 (FIG. 39E) displayed the same staining pattern as DC8E8. In general humanized antibodies AX005 (FIG. 39D) and AX017 (FIG. 39F) recognized less pathological structures in AD brain. Tool bar: 100 μm FIGS. 40A-40F: Immunohistochemical staining of Alzheimer's disease brain using humanized DC8E8 antibodies (IgG4) Both DC8E8 (FIG. 40A) and chimeric DC8E8 (FIG. 40B) recognized high load of neurofibrillary pathology in the human AD hippocampus (CA1). Humanized antibodies AX004 (FIG. 40C) and AX016 (FIG. 40E) displayed the same staining pattern as DC8E8. In general humanized antibodies AX005 (FIG. 40D) and AX017 (FIG. 40F) recognized less pathological structures in AD brain. Tool bar: 100 μm FIGS. 41A-41F: Immunohistochemical staining of FTDP-17 brain (tau mutation at R406W) using humanized DC8E8 antibodies (IgG1) Both DC8E8 (FIG. 41A) and chimeric DC8E8 (FIG. 41B) recognized high load of neurofibrillary pathology in the human entorhinal cortex. Humanized antibodies AX004 (FIG. 41C) and AX016 (FIG. 41E) displayed the similar staining pattern as DC8E8. In general humanized antibodies AX005 (FIG. 41D) and AX017 (FIG. 41F) recognized less pathological structures in FTDP-17 brain. Tool bar: 100 μm FIGS. 42A-42F: Immunohistochemical staining of FTDP-17 brain (tau mutation at R406W) using humanized DC8E8 antibodies (IgG4) Both DC8E8 (FIG. 42A) and chimeric DC8E8 (FIG. 42B) recognized high load of neurofibrillary pathology in the human entorhinal cortex. Humanized antibodies AX004 (FIG. 42C) and AX016 (FIG. 42E) displayed the same staining pattern as DC8E8. AX005 (FIG. 42D) and AX017 (FIG. 42F) did not recognize any pathological structures in FTDP-17 brain. Tool bar: 100 μm FIGS. 43A-43F: Immunohistochemical staining of corticobasal degeneration using humanized DC8E8 antibodies (IgG1) Both DC8E8 (FIG. 43A) and chimeric DC8E8 (FIG. 43B) recognized high number of glial tau pathology in the human nucleus caudatus. Humanized antibodies AX004 (FIG. 43C) and AX016 (FIG. 43E) displayed the same staining pattern as DC8E8. In general humanized antibodies AX005 (FIG. 43D) and AX017 (FIG. 43F) recognized less pathological structures in CBD brain, however the intensity of staining is comparable to DC8E8. Tool bar: 50 μm FIGS. 44A-44F: Immunohistochemical staining of corticobasal degeneration using humanized DC8E8 antibodies (IgG4) Both DC8E8 (FIG. 44A) and chimeric DC8E8 (FIG. 44B) recognized high number of glial tau pathology in the human nucleus caudatus. Humanized antibodies AX004 (FIG. 44C) and AX016 (FIG. 44E) displayed the same staining pattern as DC8E8. In general humanized antibodies AX005 (FIG. 44D) and AX017 (FIG. 44F) recognized less pathological structures in CBD brain, however the intensity of staining is comparable to DC8E8. Tool bar: 50 μm FIGS. 45A-45F: Immunohistochemical staining of progressive supranuclear palsy using humanized DC8E8 antibodies (IgG1) Both DC8E8 (FIG. 45A) and chimeric DC8E8 (FIG. 45B) recognized high number of glial tau pathology in the human nucleus caudatus. Humanized antibodies AX004 (FIG. 45C) and AX016 (FIG. 45E) displayed the same staining pattern as DC8E8. In general humanized antibodies AX005 (FIG. 45D) and AX017 (FIG. 45F) recognized slightly less pathological structures. The intensity of staining is comparable to DC8E8. Tool bar: 50 μm FIGS. 46A-46F: Immunohistochemical staining of progressive supranuclear palsy using humanized DC8E8 antibodies (IgG4) Both DC8E8 (FIG. 46A) and chimeric DC8E8 (FIG. 46B) recognizes high number of glial tau pathology in the human nucleus caudatus. Humanized antibodies AX004 (FIG. 46C) and AX016 (FIG. 46E) displayed the same staining pattern as DC8E8. In general humanized antibodies AX005 (FIG. 46D) and AX017 (FIG. 46F) recognized slightly less pathological structures. The intensity of staining is comparable to DC8E8. Tool bar: 50 μm The amino acid sequences corresponding to the human tau isoforms are given in SEQ ID NOs. 151-156, respectively, in order of appearance:

Figure 1:
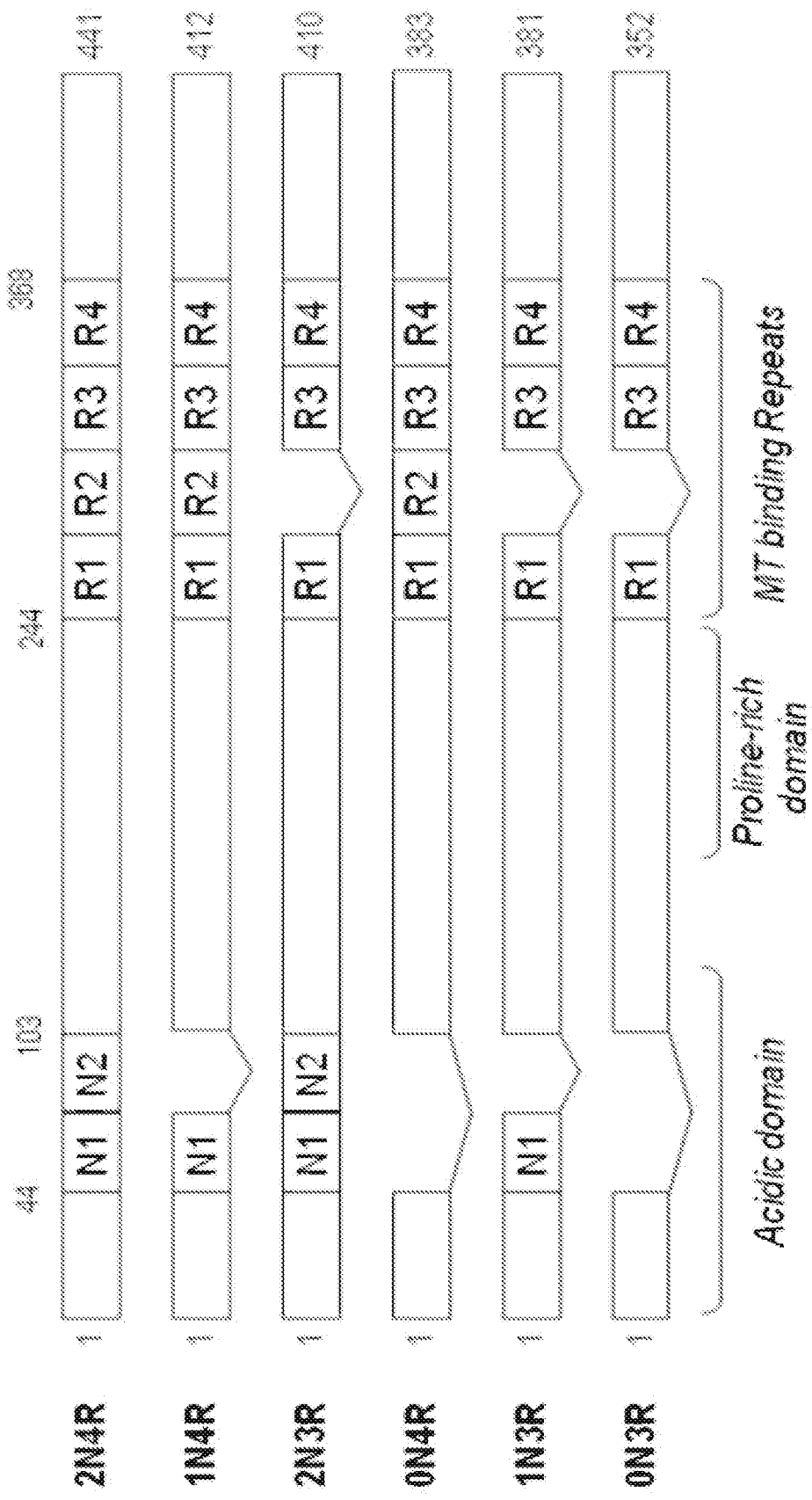
FIG. 1: Schematic of six isoforms of human tau

```
SEQ ID NO: 151 (2N4R):
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L

SEQ ID NO: 152 (1N4R):
MAEPRQEFEV MEDHAGTYGL GDRKDQGGYT MHQDQEGDTD

AGLKESPLQT PTEDGSEEPG SETSDAKSTP TAEAEEAGIG

DTPSLEDEAA GHVTQARMVS KSKDGTGSDD KKAKGADGKT

KIATPRGAAP PGQKGQANAT RIPAKTPPAP KTPPSSGEPP

KSGDRSGYSS PGSPGTPGSR SRTPSLPTPP TREPKKVAVV

RTPPKSPSSA KSRLQTAPVP MPDLKNVKSK IGSTENLKHQ

PGGGKVQIIN KKLDLSNVQS KCGSKDNIKH VPGGGSVQIV

YKPVDLSKVT SKCGSLGNIH HKPGGGQVEV KSEKLDFKDR

VQSKIGSLDN ITHVPGGGNK KIETHKLTFR ENAKAKTDHG

AEIVYKSPVV SGDTSPRHLS NVSSTGSIDM VDSPQLATLA

DEVSASLAKQ GL

SEQ ID NO: 153 (2N3R):
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIVYK

PVDLSKVTSK CGSLGNIHHK PGGGQVEVKS EKLDFKDRVQ

SKIGSLDNIT HVPGGGNKKI ETHKLTFREN AKAKTDHGAE

IVYKSPVVSG DTSPRHLSNV SSTGSIDMVD SPQLATLADE

VSASLAKQGL

SEQ ID NO: 154 (0N4R):
MAEPRQEFEV MEDHAGTYGL GDRKDQGGYT MHQDQEGDTD

AGLKAEEAGI GDTPSLEDEA AGHVTQARMV SKSKDGTGSD

DKKAKGADGK TKIATPRGAA PPGQKGQANA TRIPAKTPPA

PKTPPSSGEP PKSGDRSGYS SPGSPGTPGS RSRTPSLPTP

PTREPKKVAV VRTPPKSPSS AKSRLQTAPV PMPDLKNVKS

KIGSTENLKH QPGGGKVQII NKKLDLSNVQ SKCGSKDNIK

HVPGGGSVQI VYKPVDLSKV TSKCGSLGNI HHKPGGGQVE

VKSEKLDFKD RVQSKIGSLD NITHVPGGGN KKIETHKLTF

RENAKAKTDH GAEIVYKSPV VSGDTSPRHL SNVSSTGSID

MVDSPQLATL ADEVSASLAK QGL

SEQ ID NO: 155 (1N3R):
MAEPRQEFEV MEDHAGTYGL GDRKDQGGYT MHQDQEGDTD

AGLKESPLQT PTEDGSEEPG SETSDAKSTP TAEAEEAGIG

DTPSLEDEAA GHVTQARMVS KSKDGTGSDD KKAKGADGKT

KIATPRGAAP PGQKGQANAT RIPAKTPPAP KTPPSSGEPP

KSGDRSGYSS PGSPGTPGSR SRTPSLPTPP TREPKKVAVV

RTPPKSPSSA KSRLQTAPVP MPDLKNVKSK IGSTENLKHQ

PGGGKVQIVY KPVDLSKVTS KCGSLGNIHH KPGGGQVEVK

SEKLDFKDRV QSKIGSLDNI THVPGGGNKK IETHKLTFRE

NAKAKTDHGA EIVYKSPVVS GDTSPRHLSN VSSTGSIDMV

DSPQLATLAD EVSASLAKQG L

SEQ ID NO: 156 (0N3R):
MAEPRQEFEV MEDHAGTYGL GDRKDQGGYT MHQDQEGDTD

AGLKAEEAGI GDTPSLEDEA AGHVTQARMV SKSKDGTGSD

DKKAKGADGK TKIATPRGAA PPGQKGQANA TRIPAKTPPA

PKTPPSSGEP PKSGDRSGYS SPGSPGTPGS RSRTPSLPTP

PTREPKKVAV VRTPPKSPSS AKSRLQTAPV PMPDLKNVKS
```

```
            -continued
KIGSTENLKH QPGGGKVQIV YKPVDLSKVT SKCGSLGNIH

HKPGGGQVEV KSEKLDFKDR VQSKIGSLDN ITHVPGGGNK

KIETHKLTFR ENAKAKTDHG AEIVYKSPVV SGDTSPRHLS

NVSSTGSIDM VDSPQLATLA DEVSASLAKQ GL
```

DETAILED DESCRIPTION OF THE INVENTION

Definitions

The term "affinity" refers to the strength of the sum total of noncovalent interactions between a single binding site of a molecule (e.g., an antibody) and its binding partner (e.g., an antigen). The affinity of a molecule X for its partner Y can generally be represented by the equilibrium dissociation constant ($K_D$) (or its inverse equilibrium association constant, $K_A$). Affinity can be measured by common methods known in the art, including those described herein. See, for example, Pope M E, Soste M V, Eyford B A, Anderson N L, Pearson T W. (2009) J Immunol Methods. 341(1-2):86-96 and methods described herein. Specific illustrative and exemplary embodiments for measuring binding affinity are described below.

The term "amino acid" refers to naturally occurring, modified, and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Suitable amino acids include, without limitation, both the D- and L-isomers of the 20 common naturally occurring amino acids found in peptides as well as the naturally occurring and unnaturally occurring amino acids prepared by organic synthesis or other metabolic routes. Examples of such unnaturally occurring amino acids include, but are not limited to, N-acetylglucosaminyl-L-serine, N-acetylglucosaminyl-L-threonine, and O-phosphotyrosine. Modified amino acids include, but are not limited to, hydroxyproline, pyroglutamate, gamma-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term amino acid also includes naturally occurring amino acids that are metabolites in certain organisms but are not encoded by the genetic code for incorporation into proteins. Such amino acids include, but are not limited to, ornithine, D-ornithine, and D-arginine.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc.gamma.RIII only, whereas monocytes express Fc.gamma.RI, Fc.gamma.RIII and Fc.gamma.RIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821, 337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

A "back mutation" is a mutation introduced in a nucleotide sequence which encodes a humanized antibody, the mutation results in an amino acid corresponding to an amino acid in the parent antibody (e.g., donor antibody, for example, a murine antibody). Certain framework residues from the parent antibody may be retained during the humanization of the antibodies of the disclosure in order to substantially retain the binding properties of the parent antibody, while at the same time minimizing the potential immunogenicity of the resultant antibody. In one embodiment disclosed herein, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, J. Mol. Biol. 224, 487-499), and those close to CDR H3.

The term "chimeric" antibodies refers to antibodies in which a portion of the heavy and/or light chain is identical with or homologous to corresponding sequences in antibodies derived from a particular species or belonging to a particular antibody class or subclass (e.g., chimeric humanized, class-switched antibodies), while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). In one embodiment, the term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are sometimes preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now known in the art. See, e.g., Morrison, S. L., et al., Proc. Natl. Acad Sci. USA 81 (1984) 6851-6855; U.S. Pat. Nos. 5,202,238 and 5,204,244.

"Competitive binding" is determined in an assay in which the immunoglobulin/antibody/binding fragment under testing inhibits specific binding of a reference antibody to a common antigen, such as tau (e.g., tau 151-391/4R). Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using $I^{125}$ label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

The term "conjugation," as used herein, refers to a bond or chemical moiety formed from a chemical reaction between a functional group of a first molecule (e.g., an antibody) with a functional group of a second molecule (e.g., a therapeutic agent or drug). Such bonds include, but are not limited to, covalent linkages and non-covalent bonds, while such chemical moieties include, but are not limited to, esters, carbonates, imines phosphate esters, hydrazones, acetals, orthoesters, peptide linkages, and oligonucleotide linkages. "Hydrolytically stable linkages" means that the linkages are substantially stable in water and do not react with water at useful pH values, including but not limited to, under physiological conditions for an extended period of time. "Hydrolytically unstable or degradable linkages" means that the linkages are degradable in water or in aqueous solutions, including for example, blood. "Enzymatically unstable or degradable linkages" means that the linkages are degraded by one or more enzymes. By way of example only, certain PEG and related polymers include degradable linkages in the polymer backbone or in a linker group between the PEG polymer backbone and one or more of the terminal functional groups of protein, polypeptide or peptide provided herein. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide The term "DC8E8" refers to an antibody described in WO2013/041962 and produced by the hybridoma deposited under American Type Culture Collection Patent Deposit no. PTA-11994. Disclosed in WO2013/041962 is the discovery that antibodies (e.g., DC8E8) that specifically bind to one or more of four previously unidentified functional regions of tau selected from 268-HQPGGG-273 (SEQ ID NO: 148) (within $1^{st}$ repeat domain of tau protein), 299-HVPGGG-304 (SEQ ID NO: 149) (within $2^{nd}$ repeat domain of tau protein), 330-HKPGGG-335 (SEQ ID NO: 150) (within $3^{rd}$ repeat domain of tau protein), and 362-HVPGGG-367 (SEQ ID NO: 149) (within $4^{th}$ repeat domain of tau protein) are capable of inhibiting formation of pathological tau aggregates, and of detecting various pathological forms of tau, some of which are the earliest formed in the disease (e.g., pathological monomers). Hybridomas produced against human misdisordered tau II (Tau 151-391/4R), which is also referred in this application as tauΔ(1-150; 392-441)/4R, were screened for the production of monoclonal antibodies specific to human paired helical filaments (PHFs) both by immunohistochemistry (IHC) and Enzyme-linked Immuno Assays (ELISAs). The resulting set included mouse monoclonal antibody (mAb) DC8E8, which is of the IgG1 subclass. Epitope mapping of DC8E8 revealed it to bind four previously unidentified epitopes on human tau. Moreover, further functional analysis of DC8E8 revealed that each epitope represents a distinct functional region within tau. These regions, which were described as novel targets for AD diagnosis and therapy, are comprised within functional regions of tau selected from 268-HQPGGG-273 (SEQ ID NO: 148) (within 1st repeat domain of tau protein), 299-HVPGGG-304 (SEQ ID NO: 149) (within $2^{nd}$ repeat domain of tau protein), 330-HKPGGG-335 (SEQ ID NO: 150) (within $3^{rd}$ repeat domain of tau protein), and 362-HVPGGG-367 (SEQ ID NO: 149) (within $4^{th}$ repeat domain of tau protein).

The terms "diagnosing" and "diagnosis" as used herein refer to methods by which the skilled artisan can estimate and even determine whether or not a subject is suffering from a given disease or condition, in this case Alzheimer's disease and related tauopathies. The skilled artisan often makes a diagnosis on the basis of one or more diagnostic indicators, such as for example a biomarker, the amount (including presence or absence) of which is indicative of the presence, severity, or absence of the condition.

Along with diagnosis, clinical disease monitoring and prognosis is also an area of great concern and interest. It is important to know the stage and rapidity of advancement of the AD in order to plan the most effective therapy. If a more accurate prognosis can be made, appropriate therapy, and in some instances less severe therapy for the patient can be chosen. Measurement of pathological tau levels as disclosed herein can be useful in order to categorize subjects according to advancement of AD who will benefit from particular therapies and differentiate from other subjects where alternative or additional therapies can be more appropriate.

For example, DC8E8 is able to discriminate between preclinical AD, clinically incipient AD and fully developed final stage AD (see WO2013/041962). DC8E8 displayed staining of early stages (tau monomers, dimers) of pathological tau in human preclinical AD—Braak's Stage I. The antibody recognized the stage of pathological tau oligomers and the stage of pathological tau polymers (tangles). In fully developed Alzheimer's disease (final stage—Braak's Stage VI), DC8E8 recognized mainly pathological tau polymers in forms of the neurofibrillary tangles, neuritic plaques and neuritic threads. DC8E8 recognized all developmental stages of tangle formation in Alzheimer's disease. DC8E8 recognized early developmental stages of tangle formation—monomeric, dimeric and early oligomeric stage, and late oligomeric, pre-tangle stage, as well as late developmental stages of pathological tau polymers—intracellular and extracellular neurofibrillary tangles.

Accordingly, "diagnosing" or "making a diagnosis," as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the measure of pathological tau levels.

Antibody "effector functions" refer to those biological activities attributable to an Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC), phagocytosis; and down regulation of cell surface receptors (e.g. B cell receptor; BCR).

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids, often in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, G. E. Morris, Ed. (1996). A "conformational epitope" is an epitope to which the antibody or tau-binding fragment thereof binds in a conformational-specific manner. In the case of protein-based epitopes, the binding can depend on the epitope-carrying-protein's secondary, tertiary, or quaternary structure. In other words, the antibody binds in a structure-specific manner, a tertiary-structure-specific manner, or a quaternary-structure-specific manner. A conformational epitope is one that is present in pathological tau (e.g., present in Tau 151-391/4R).

The antibodies and tau-binding fragments described herein have as their "epitope" any one or more of the following four tau sites, some or all of which are conformational epitopes: 268-HQPGGG-273 (SEQ ID NO: 148) (within 1st repeat domain of tau protein), 299-HVPGGG-304 (SEQ ID NO: 149) (within $2^{nd}$ repeat domain of tau protein), 330-HKPGGG-335 (SEQ ID NO: 150) (within $3^{rd}$ repeat domain of tau protein), and 362-HVPGGG-367 (SEQ ID NO: 149) (within $4^{th}$ repeat domain of tau protein). These epitopes are also referred herein as QT1, QT2, QT3, and QT4, respectively. DC8E8 binds to all of QT1-QT4; in fact, the epitope of DC8E8 is HXPGGG, wherein X is any amino acid (SEQ ID NO. 157).

Papain digestion of antibodies produces two identical antigen-binding fragments, called "Fab" fragments, each with a single antigen-binding site, and a residual "Fc" fragment, whose name reflects its ability to crystallize readily (fragment crystallizable). Pepsin treatment yields an F(ab')$_2$ fragment that has two antigen-binding sites and is still capable of cross-linking antigen. "Fv" is that portion of the heavy chain that is included in a Fab fragment. Any of these fragments can also be produced recombinantly. The Fc portion of an antibody is associated with the antibody's effector functions, including antibody-dependent cellular cytotoxicity (ADCC) and complement-dependent cytotoxicity or phagocytosis. Alterations (e.g., mutations or glycosylation changes) in the Fc region of an antibody can be used to modulate any of its effector functions as well as increase its serum half-life and other pharmacokinetic properties.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The term "Fc", as used herein, includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains C gamma 2 and C gamma 3 (Cgamma2 and Cgamma3) and the hinge between C gamma 1(Cgamma1) and C gamma 2 (Cgamma2). Although the boundaries of the Fc region may vary, the human IgG heavy chain Fc region is usually defined to comprise residues C226 or P230 to its carboxyl-terminus, wherein the numbering is according to the EU numbering system. For human IgG1 the Fc region is herein defined, in one embodiment, to comprise residue P232 to its carboxyl-terminus, wherein the numbering is according to the EU numbering system (Edelman G M et al., (1969) Proc Natl Acad Sci USA, 63(1): 78-85). The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Fc may refer to this region in isolation or this region in the context of an Fc polypeptide, for example an antibody. The Fc may be a native sequence Fc or a variant Fc. Replacements of amino acid residues in the Fc portion to alter antibody effector function are known in the art (see, e.g., Winter et al., U.S. Pat. Nos. 5,648,260 and 5,624,821). One suitable Fc, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc.gamma.RI, Fc.gamma.RIII, and Fc.gamma.RIII subclasses, including allelic variants and alternatively spliced forms of these receptors. Fc.gamma.RIII receptors include Fc.gamma.RIIA (an "activating receptor") and Fc.gamma.RIIB (an "inhibiting receptor"), which have similar amino acid sequences that differ primarily in the cytoplasmic domains thereof. Activating receptor Fc.gamma.RIIA contains an immunoreceptor tyrosine-based activation motif (ITAM) in its cytoplasmic domain. Inhibiting receptor Fc.gamma.RIIB contains an immunoreceptor tyrosine-based inhibition motif (ITIM) in its cytoplasmic domain (see review M. in Daeron, Annu. Rev. Immunol 15:203-234 (1997)). FcRs are reviewed in Ravetch and Kinet, Annu. Rev. Immunol 9:457-92 (1991); Capel et al, Immunomethods 4:25-34 (1994); and de Haas et al, J. Lab. Olin; Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)), and regulates homeostasis of immunoglobulins.

"Fv" is also the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

As used herein, a humanized antibody that comprises a heavy or light chain variable "framework region" from a particular human germline immunoglobulin sequence may contain amino acid differences as compared to the heavy or light chain variable framework region of the particular germline sequence, due to, for example, naturally-occurring somatic mutations or intentional introduction of site-directed mutation. However, a selected humanized antibody typically is at least 90% identical in amino acid sequence of the heavy or light chain variable framework region to an amino acid sequence encoded by the heavy or light chain variable framework region of a human germline immunoglobulin gene and contains amino acid residues that identify the humanized antibody as being derived from human when compared to the germline immunoglobulin amino acid sequences of other species (e.g., murine germline sequences). In certain cases, a humanized antibody may be preferably at least 90%, more preferably at least 95%, more preferably at least 96%, most preferably at least 97%, in particular at least 98%, most particular at least 99%, identical in amino acid sequence of the heavy or light chain variable framework region to the amino acid sequence of the heavy or light chain variable framework region encoded by the germline immunoglobulin gene. Typically, the heavy or light chain variable framework region of a humanized antibody derived from a particular human germline sequence will display no more than 11 amino acid, preferably no more than 5, or even more preferably no more than 4, 3, 2, or 1 differences from the amino acid sequence of the heavy or light chain variable framework region encoded by the human germline immunoglobulin gene.

"Human effector cells" are leukocytes that express one or more FcRs and perform effector functions. Preferably, the cells express at least Fc.gamma.RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

"Human germline sequences" are found naturally in the human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001). Publicly available, well-known, databases exist for all known germline sequences.

The term "hinge" or "hinge region" or "antibody hinge region" herein includes the flexible polypeptide comprising the amino acids between the first and second constant domains of an antibody or tau-binding fragment thereof. The "hinge region" as referred to herein is a sequence region of 6-62 amino acids in length, only present in IgA, IgD and IgG, which encompasses the cysteine residues that bridge the two heavy chains. Structurally, in one embodiment, the IgG CH1 domain ends at EU position 220, and the IgG CH2 domain begins at residue EU position 237. Thus, for IgG the antibody hinge is herein defined, in one embodiment, to include positions 221 (D221 in IgG1) to 231 (A231 in IgG1), wherein the numbering is according to the EU numbering system.

The term "humanized antibody" refers to antibodies in which the framework regions (FR) and/or the complementarity determining regions (CDR) have been modified to comprise the CDR of an immunoglobulin of different specificity (mouse) as compared to that of the parent immunoglobulin (human). In one embodiment, a murine CDR is grafted into the framework region of a human antibody to prepare the "humanized antibody." In another embodiment, human frameworks are "grafted" or spliced into mouse antibodies, preserving the CDRs of the mouse antibody and replacing its frameworks with frameworks of human origin. Grafting and splicing can be done by various recombinant DNA technologies, including PCR and mutagenesis. Various humanization methods exist in the art (e.g., CDR grafting, reshaping, transgenic animals, combinatorial libraries). See, e.g., Riechmann, L., et al., Nature 332 (1988) 323-327; Neuberger, M. S., et al., Nature 314 (1985) 268-270; Sastry L, Alting-Mess M, Huse W D, Short J M, Sorge J A, Hay B N, Janda K D, Benkovic S J, Lerner R A (1989) Cloning of the immunological repertoire in for generation of monoclonal catalytic antibodies: construction of a heavy chain variable region-specific cDNA library. Proc Natl Acad Sci USA 86, 5728-5732; and Huse W D, Sastry S, Iverson S A, Kang A S, Alting-Mees M, Burton D R, Benkovic S J, Lerner R A (1989) Generation of a large combinatorial library of the immunoglobulin repertoire in phage lambda. Science 246, 1275-1281. Humanized antibodies result from genetically engineering another antibody to make it more human-like while retaining its original antigen-binding properties. Presta, L. G. Engineering of therapeutic antibodies to minimize immunogenicity and optimize function. Advanced Drug Delivery Reviews, Volume 58, Issues 5-6: 640-656 (2006). The choice of human variable domains, both light and heavy, to be used in making the humanized antibodies is very important to reduce antigenicity. According to the so-called "best-fit" method, the sequence of the variable domain of a rodent antibody is screened against a library of known human variable-domain sequences or a library of human germline sequences. The human sequence that is closest to that of the rodent can then be accepted as the human framework region for the humanized antibody (Sims et al., J. Immunol. 1993; 151:2296 et seq.; Chothia et al, Chothia and Lesk, J. Mol. Biol. 1987; 196:901-917). Another method uses a particular framework region derived from the consensus sequence of all human antibodies of a particular subgroup of light or heavy chains. The same framework may be used for several different humanized antibodies (Carter et al., PNAS USA, 1992; 89:4285 et seq.; Presta et al., J Immunol 1993; 151:2623 et seq.). Other methods designed to reduce the immunogenicity of the antibody molecule in a human patient include veneered antibodies (see, e.g., U.S. Pat. No. 6,797,492 and U.S. patent application publications 20020034765 and 20040253645) and antibodies that have been modified by T-cell epitope analysis and removal (see, e.g., U.S. patent application publications 20030153043 and U.S. Pat. No. 5,712,120).

Particularly preferred CDRs of the humanized antibodies described herein correspond to the CDR sequences of the mouse monoclonal DC8E8 antibody, namely SEQ ID NOs.1-6. A copy of the humanized antibodies and tau-binding fragments thereof described herein (e.g. an immunoglobulin with the same heavy or light chain variable region as those described herein), made by recombinant methods or any other methods (except a naturally existing antibody), is also a humanized antibody or tau-binding fragment thereof within the scope of the term.

The term "hypervariable region" when used herein refers to the amino acid residues of an antibody that are responsible for antigen-binding. In one embodiment, according to Kabat, the hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)).

"Framework Region" or "FR" residues are those variable domain residues other than the hypervariable region residues as herein defined. In the IMGT unique numbering system, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). See, e.g., Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003). In another embodiment, the IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become important information. The IMGT unique numbering is used in 2D graphical representations, designated as IMGT Colliers de Perles. See, e.g., Ruiz, M. and Lefranc, M.-P., Immunogenetics, 53, 857-883 (2002); Kaas, Q. and Lefranc, M.-P., Current Bioinformatics, 2, 21-30 (2007). It is also used for representing 3D structures. See, e.g., IMGT/3D structure-DB Kaas, Q., Ruiz, M. and Lefranc, M.-P., T cell receptor and MHC structural data. Nucl. Acids. Res., 32, D208-D210 (2004). Framework or FR residues are those variable domain residues other than and bracketing the hypervariable regions.

Using the Kabat numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "immunogenicity" or immunogenic, as used herein, refers to an antibody response to administration of a therapeutic drug. The immunogenicity toward the antibodies and tau-binding fragments provided herein is obtained using quantitative and qualitative assays for detection of antibodies against said therapeutic proteins, polypeptides and peptides in biological fluids. Such assays include, but are not limited to, Radioimmunoassay (RIA), Enzyme-linked immunosorbent assay (ELISA), luminescent immunoassay (LIA), and fluorescent immunoassay (FIA). Analysis of such immunogenicity involves comparing the antibody response upon administration of antibodies and tau-binding fragments provided herein to the antibody response upon administration of a control therapeutic protein, polypeptide or peptide or of the delivery vehicle or delivery buffer.

The "light chains" of antibodies from any vertebrate species can be assigned to one of two clearly distinct types, called kappa (κ) and lambda (λ), based on the amino acid sequences of their constant domains.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "nucleic acid" as used herein, is intended to include DNA molecules and RNA molecules. A nucleic acid molecule may be single-stranded or double-stranded, but preferably is double-stranded DNA.

The "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P). For example, the identity of a sequence can exist over a region that is at least about 75-100 sequential units in length, over a region that is about 50 sequential units in length, or, where not specified, across the entire sequence of a polypeptide sequence.

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, for example between the two complete sequences, dividing the number of identical positions by the total number of positions in the alignment window and multiplying the result by 100 to obtain the percentage identity between the two sequences. In one embodiment, percentage sequence identities between antibodies are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/bl2.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, for example 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated. As a non-limiting example, the table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |

TABLE 1-continued

| Original residue | Substitution(s) |
| --- | --- |
| Tyr (Y) | Phe, Trp |
| Val (V) | Leu, Ala |

In the context of this disclosure, the terms "pathological tau" and "disease tau" include pathological tau conformers and structures and encompasses all of the following: Tau Type IA, IB, IIA, and IIB (described in detail in WO2004/007547 A2), misordered, misdisordered tau (monomer, dimer, trimer, oligomer), misdisordered soluble tau, sarkosyl-insoluble tau, extracellular tau deposits, tau aggregates, paired helical filaments, neurofibrillary pathology, including neurofibrillary lesions, tangles, threads, fibrils, axonal spheroids, highly phosphorylated forms of truncated tau and of full-length tau, or any other form of tau associated with AD or another tauopathy that is detectable by the antibodies and/or tau-binding fragments described herein. Tau 151-391/4R (also referred to as tauΔ(1-150; 392-441)/4R) represents a form of pathological tau.

The term "pharmaceutically acceptable" means biologically or pharmacologically compatible for in vivo use in animals or humans, and preferably means approved by a regulatory agency of the Federal or a state government or listed in the U.S. Pharmacopeia or other generally recognized pharmacopeia for use in animals, and more particularly in humans.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "another tauopathy" encompasses all neurological diseases that are accompanied by the appearance of abnormal forms of microtubule associated protein tau in the brains of patients. The term includes, but is not limited to, the following diseases: Alzheimer's disease, Gerstmann-Sträussler-Scheinker disease, British dementia, Danish dementia, Pick's disease, Progressive supranuclear palsy, Corticobasal degeneration, Argyrophilic grain disease, Guam Parkinsonism-dementia complex, Tangle-only dementia, White matter tauopathy with globular glial inclusions, Frontotemporal dementia (e.g., FTDP-17), and Parkinsonism linked to chromosome 17. See, e.g., Goedert M, Clavaguera F and Tolnay M. The propagation of prion-like protein inclusions in neurodegenerative diseases. Trends Neurol. Sci. In one embodiment, one or more of those abnormal forms of tau is recognized by one of the antibodies or binding fragments described herein in at least one assay. In some embodiments, the assay is IHC. In other embodiments, the assay is ELISA.

As used herein "specifically binds" in reference to an antibody means that the antibody binds to its target antigen or epitope with greater affinity that it does to a structurally different antigen(s) or epitope.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "treatment" as used herein, is defined as the application or administration of a therapeutic agent to a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease. Moreover, as long as the compositions of the disclosure either alone or in combination with another therapeutic agent cure, heal, alleviate, relieve, alter, remedy, ameliorate, improve or affect at least one symptom of Alzheimer's Disease or another tauopathy being treated as compared to that symptom in the absence of use of the humanized anti-tau antibody or tau-binding fragment thereof composition, the result should be considered a treatment of the underlying disorder regardless of whether all the symptoms of the disorder are cured, healed, alleviated, relieved, altered, remedied, ameliorated, improved or affected or not.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions (HVR) in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure.

Humanized Antibodies that Bind to Disease Tau

Provided herein are the first humanized antibodies against human disease/pathological tau that are capable of recognizing four different regions of tau in a conformation-dependent manner. More particularly, the humanized antibodies described herein are capable of binding at least one, two, three, or four of QT1-QT4 in such manner that they discriminate between wild-type/normal tau and conformations of tau that are associated with AD (disease tau). In some embodiments, two, three, or four of the QT1-QT4 may be simultaneously occupied by these antibodies. In other words, the antibodies and tau-binding fragments described herein have as their "epitope" any one or more of the following four tau sites, some or all of which are conformational epitopes: 268-HQPGGG-273 (SEQ ID NO: 148) (within 1st repeat domain of tau protein), 299-HVPGGG-304 (SEQ ID NO: 149) (within $2^{nd}$ repeat domain of tau protein), 330-HKPGGG-335 (SEQ ID NO: 150) (within $3^{rd}$ repeat domain of tau protein), and 362-HVPGGG-367 (SEQ ID NO: 149) (within $4^{th}$ repeat domain of tau protein). These epitopes are also referred herein as QT1, QT2, QT3, and QT4, respectively. DC8E8 binds to all of QT1-QT4; in fact, the epitope of DC8E8 is HXPGGG, wherein X is any amino acid.

In one embodiment, the antibodies and tau-binding fragments have affinities for Tau 151-139/4R that are at least 80% as good if not better than that of the parent mouse monoclonal antibody DC8E8. In one embodiment, the antibodies and tau-binding fragments retain specificity for the epitopes recognized by the mouse DC8E8 antibody. In one embodiment, these antibodies have one or more advantageous biochemical properties (e.g., human constant regions and thus reduced immunogenicity, high expression levels, high solubility, lack of significant protein aggregation upon purification, high stability) that render them optimal for use in the clinic for treatment of AD and related tauopathies in humans.

Humanization of DC8E8 was empirically optimized by manipulation of framework residues. The initial humanized version RHA/RKA (AX001) exhibited a 10-fold decrease in binding affinity for tau, relative to the chimeric DC8E8 construct. These data implied that one or more framework amino acid residues are important in order to humanize DC8E8 with little resultant loss in binding activity. In contrast, a single framework back-mutation was sufficient to restore binding affinity in the RHD (AX004) humanized antibody. This superiority was unexpected. Other single point back-mutations did not have the same unexpected advantage in binding affinity. See, for example, RHF/RKA (AX006) and RHG/RKA (AX007) constructs. And the next best antibody carried 10 back-mutations. See AX002. Of all back-mutation combinations tested, AX004 proved to have the best binding affinity for tau (in the assay described herein), despite having a single back-mutation, and unlike other single back-mutation constructs. Other humanized constructs of improved affinity include, for example, AX002, AX005, AX037 and AX014, AX016, AX017, AX038, in RKA and RKB light chain versions, respectively.

Also provided are tau-binding fragments (e.g. antibody portions) of the humanized antibodies described herein. These fragments are also capable of binding to at least one, two, three, or four of QT1-QT4 (defined above) in such manner that they discriminate between wild-type/normal tau and conformations of tau that are associated with AD. In some embodiments, all four of the QT1-QT4 epitopes may be occupied by four of the antibodies or tau-binding fragments described herein. In some embodiments, the fragments or portions bind to tau with the same affinity and properties of the mouse monoclonal antibody DC8E8. For example, antibody fragments or portions capable of binding to one or more of QT1-QT4, include, but are not limited to Fab (e.g., by papain digestion), Fd, Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and re-aggregation), Fv or scFv (e.g., by molecular biology techniques) fragments, are provided by the present invention. See also, William E. Paul (ed.) Fundamental Immunology, $6^{th}$ Edition, Lippincott Williams & Wilkins, NY, N.Y. (2008), incorporated herein by reference in its entirety. Any other fragments whose half-life has been increased by conjugation to other molecules, including PEGylated fragments, are also within the scope of this invention. Certain fragments can be produced by enzymatic cleavage, synthetic or recombinant techniques, as routinely known in the art, or as provided herein. Antibodies can also be produced in a variety of truncated forms using antibody genes in which one or more stop codons have been introduced upstream of the natural stop site. For example, a combination gene encoding an F(ab')$_2$ heavy chain portion can be designed to include DNA sequences encoding the CH1 domain and/or hinge region of the heavy chain. The various portions of antibodies can be joined together chemically by conventional techniques, or can be prepared as a contiguous protein using routine genetic engineering techniques.

Depending on the amino acid sequence of the constant domain of their heavy chains, intact antibodies can be assigned to different "classes". In one embodiment, there are six major classes of intact antibodies: IgA, IgD, IgE, IgG, IgY, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha (α), delta (δ), epsilon (ε), gamma (γ), and mu (μ), respectively. The subunit structures and three-dimensional configurations of different classes of immunoglobulins are well known. In one embodiment, the antibodies described herein have constant regions of any of the existing immunogenic isotypes. For example, the constant regions can be of the lambda or kappa region and the gamma-1, gamma-2, gamma-3, or gamma 4 regions. Constant regions of mixed isotypes are also within the scope of this disclosure (e.g., IgG1 mixed with IgG4). It has been perceived that some isotypes are superior over the others. Bruggemann M, Williams G T, Bindon C I, Clark M R, Walker M R, Jefferis R, Waldmann H, Neuberger M S (1987) Comparison of the effector functions of human immunoglobulins using a matched set of chimeric antibodies. J. Exp. Med. 166, 1351-1361; Bindon C I, Hale G, Bruggemann M, Waldmann H (1988) Human monoclonal IgG isotypes differ incomplement activating function at the level of C4 as well as C1q. J. Exp. Med. 168, 127-42; Shaw D R, Khazaeli M B, LoBuglio A F (1988) Mouse/human chimeric antibodies to a tumor associated antigen: biologic activity of the four human IgG subclasses. J. Natl. Cancer Inst. 80, 1553-9; Steplewski Z, Sun L K, Shearman C W, Ghrayeb J, Daddona P, Koprowski, H (1988) Biological activity of human-mouse IgG1, IgG2, IgG3, and IgG4 chimeric monoclonal antibodies with antitumor specificity. Proc. Natl. Acad. Sci. USA 85, 4852-6. In one set of experiments, described in these references, the human isotypes IgM, IgG1, IgG2, IgG3 (two allotypes), IgG4, IgA and IgE were compared for autologous complement mediated lysis as well as for antibody dependent cell mediated cytotoxicity (ADCC). For complement mediated lysis, human IgM and IgG1 proved to be the most effective with the two allotypes of IgG3 being next best. IgG2 gave poor lysis while the other isotypes seemed to give no lysis. The results for ADCC were that IgG1 was again very effective followed by either IgG2, IgG3, or IgG4, depending on the assay (e.g., cell type). The other isotypes, including IgM, were ineffective. But antibodies have many other activities (e.g., promoting opsonization by macrophages), and ultimately it is difficult or even not possible to predict which isotype is going to have the best set of properties for its desired use.

Another factor influencing the immunogenicity of a humanized antibody is the existence of polymorphic determinants in the constant region. These differences can be minimized for reduced antigenicity. There are 18 allotypes of human IgG observed with reasonable frequencies in the population: IgG1 has 4; IgG2 has 1; IgG3 has 13; IgG4 has 0. WHO (1976) Review of the notation for the allotypic and related markers of human immunoglobulins. Eur. J. Immunol. 6, 599-601. In addition there are three allotypes of human k light chains. Some allotypes are present in some individuals and not in others. Some are predominantly expressed amongst the Japanese population.

Many methods for humanizing non-human antibodies have been described in the art. In one embodiment, a humanized antibody has one or more amino acid residues introduced into it from a source which is non-human. These non-human amino acid residues are often referred to as "import" residues, which are typically taken from an "import" variable domain. In one embodiment, humanization can be essentially performed following the method of Winter and co-workers (Jones et al, Nature, 321:522-525 (1986); Riechmann et al, Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In some embodiments, humanized antibodies are human antibodies in which some hypervariable region residues and possibly some FR residues are substituted by residues from analogous sites in rodent antibodies.

The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence (entire variable region or just the frameworks) that is closest to that of the rodent is then accepted as the human framework region (FR) for the humanized antibody (Sims et al, J. Immunol., 151:2296 (1993); Chothia et al, J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol, 151:2623 (1993)).

In some embodiments, it is important that antibodies be humanized with retention of high affinity for the antigen and other favorable biological properties of the parent (e.g., mouse antibody). To achieve this goal, according to one embodiment, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

TABLE 2

| POLYPEPTIDE | SEQ ID NO. | VARIABLE REGION ONLY | SEQ ID NO. |
|---|---|---|---|
| CDR-H1 | 1 | HEAVY DC8E8 | 7 |
| CDR-H2 | 2 | LIGHT DC8E8 | 8 |
| CDR-H3 | 3 | HEAVY CHIMERIC | 9 (identical to 7) |
| CDR-L1 | 4 | LIGHT CHIMERIC | 10 (identical to 8) |
| CDR-L2 | 5 | HEAVY DC8E8 OPTIMIZED | 11 (identical to 7) |
| CDR-L3 | 6 | LIGHT DCBE8 OPTIMIZED | 12 (identical to 8) |

The previous table 2 provides the SEQ ID NOs. for some of the amino acid sequences described herein. In another embodiment, a humanized antibody or tau-binding fragment, as described herein, comprises SEQ ID NOs. 1, 2, 3, as the heavy chain CDRs 1, 2, and 3, respectively, and SEQ ID Nos. 4, 5, 6, as the light chain CDRs 1, 2, and 3, respectively. In some embodiments, this antibody or fragment comprises at least one CDR, as defined according to Kabat, whose sequence has at least 80%, preferable at least 85%, 90%, 95%, and 98% identity after optimal alignment with a CDR of any one of SEQ ID NOs. 1 to 6.

In one embodiment, the antibody (AX001) or tau-binding fragment thereof comprises heavy chain variable region RHA (SEQ ID NO. 13) and light chain variable region RKA (SEQ ID NO. 26). This antibody is provided with either IgG1 (AX001-IgG1) or IgG4 (AXON001-IgG4) constant regions.

In one embodiment, the antibody (AX002) or tau-binding fragment thereof comprises heavy chain variable region RHB (SEQ ID NO. 14) and light chain variable region RKA (SEQ ID NO. 26). This antibody is provided with either IgG1 (AX002-IgG1) or IgG4 (AXON002-IgG4) constant regions.

In one embodiment, the antibody (AX003) or tau-binding fragment thereof comprises heavy chain variable region RHC (SEQ ID NO. 15) and light chain variable region RKA (SEQ ID NO. 26). This antibody is provided with either IgG1 (AX003-IgG1) or IgG4 (AXON003-IgG4) constant regions.

In one embodiment, the antibody (AX004) or tau-binding fragment thereof comprises heavy chain variable region RHD (SEQ ID NO. 16) and light chain variable region RKA (SEQ ID NO. 26). This antibody is provided with either IgG1 (AX004-IgG1) or IgG4 (AXON004-IgG4) constant regions.

In one embodiment, the antibody (AX005) or tau-binding fragment thereof comprises heavy chain variable region RHE (SEQ ID NO. 17) and light chain variable region RKA (SEQ ID NO. 26). This antibody is provided with either IgG1 (AX005-IgG1) or IgG4 (AXON005-IgG4) constant regions.

In one embodiment, the antibody (AX006) or tau-binding fragment thereof comprises heavy chain variable region RHF (SEQ ID NO. 18) and light chain variable region RKA (SEQ ID NO. 26). This antibody is provided with either IgG1 (AX006-IgG1) or IgG4 (AXON006-IgG4) constant regions.

In one embodiment, the antibody (AX007) or tau-binding fragment thereof comprises heavy chain variable region RHG (SEQ ID NO. 19) and light chain variable region RKA (SEQ ID NO. 26). This antibody is provided with either IgG1 (AX007-IgG1) or IgG4 (AXON007-IgG4) constant regions.

In one embodiment, the antibody (AX008) or tau-binding fragment thereof comprises heavy chain variable region RHH (SEQ ID NO. 20) and light chain variable region RKA (SEQ ID NO. 26). This antibody is provided with either IgG1 (AX008-IgG1) or IgG4 (AXON008-IgG4) constant regions.

In one embodiment, the antibody (AX009) or tau-binding fragment thereof comprises heavy chain variable region RHI (SEQ ID NO. 21) and light chain variable region RKA (SEQ ID NO. 26). This antibody is provided with either IgG1 (AX009-IgG1) or IgG4 (AXON009-IgG4) constant regions.

In one embodiment, the antibody (AX010) or tau-binding fragment thereof comprises heavy chain variable region RHJ (SEQ ID NO. 22) and light chain variable region RKA (SEQ ID NO. 26). This antibody is provided with either IgG1 (AX010-IgG1) or IgG4 (AXON010-IgG4) constant regions.

In one embodiment, the antibody (AX011) or tau-binding fragment thereof comprises heavy chain variable region RHK (SEQ ID NO. 23) and light chain variable region RKA (SEQ ID NO. 26). This antibody is provided with either IgG1 (AX011-IgG1) or IgG4 (AXON011-IgG4) constant regions.

In one embodiment, the antibody (AX012) or tau-binding fragment thereof comprises heavy chain variable region RHL (SEQ ID NO. 24) and light chain variable region RKA (SEQ ID NO. 26). This antibody is provided with either IgG1 (AX012-IgG1) or IgG4 (AXON012-IgG4) constant regions.

In one embodiment, the antibody (AX013) or tau-binding fragment thereof comprises heavy chain variable region RHA (SEQ ID NO. 13) and light chain variable region RKB (SEQ ID NO. 27). This antibody is provided with either IgG1 (AX013-IgG1) or IgG4 (AXON013-IgG4) constant regions.

In one embodiment, the antibody (AX014) or tau-binding fragment thereof comprises heavy chain variable region RHB (SEQ ID NO. 14) and light chain variable region RKB (SEQ ID NO. 27). This antibody is provided with either IgG1 (AX014-IgG1) or IgG4 (AXON014-IgG4) constant regions.

In one embodiment, the antibody (AX015) or tau-binding fragment thereof comprises heavy chain variable region RHC (SEQ ID NO. 15) and light chain variable region RKB (SEQ ID NO. 27). This antibody is provided with either IgG1 (AX015-IgG1) or IgG4 (AXON015-IgG4) constant regions.

In one embodiment, the antibody (AX016) or tau-binding fragment thereof comprises heavy chain variable region RHD (SEQ ID NO. 16) and light chain variable region RKB (SEQ ID NO. 27). This antibody is provided with either IgG1 (AX016-IgG1) or IgG4 (AXON016-IgG4) constant regions.

In one embodiment, the antibody (AX017) or tau-binding fragment thereof comprises heavy chain variable region RHE (SEQ ID NO. 17) and light chain variable region RKB (SEQ ID NO. 27). This antibody is provided with either IgG1 (AX017-IgG1) or IgG4 (AXON017-IgG4) constant regions.

In one embodiment, the antibody (AX018) or tau-binding fragment thereof comprises heavy chain variable region RHF (SEQ ID NO. 18) and light chain variable region RKB (SEQ ID NO. 27). This antibody is provided with either IgG1 (AX018-IgG1) or IgG4 (AXON018-IgG4) constant regions.

In one embodiment, the antibody (AX019) or tau-binding fragment thereof comprises heavy chain variable region RHG (SEQ ID NO. 19) and light chain variable region RKA (SEQ ID NO. 27). This antibody is provided with either IgG1 (AX019-IgG1) or IgG4 (AXON019-IgG4) constant regions.

In one embodiment, the antibody (AX020) or tau-binding fragment thereof comprises heavy chain variable region RHH (SEQ ID NO. 20) and light chain variable region RKB (SEQ ID NO. 27). This antibody is provided with either IgG1 (AX020-IgG1) or IgG4 (AXON020-IgG4) constant regions.

In one embodiment, the antibody (AX021) or tau-binding fragment thereof comprises heavy chain variable region RHI (SEQ ID NO. 21) and light chain variable region RKB (SEQ ID NO. 27). This antibody is provided with either IgG1 (AX021-IgG1) or IgG4 (AXON021-IgG4) constant regions.

In one embodiment, the antibody (AX022) or tau-binding fragment thereof comprises heavy chain variable region RHJ (SEQ ID NO. 22) and light chain variable region RKB (SEQ ID NO. 27). This antibody is provided with either IgG1 (AX022-IgG1) or IgG4 (AXON022-IgG4) constant regions.

In one embodiment, the antibody (AX023) or tau-binding fragment thereof comprises heavy chain variable region RHK (SEQ ID NO. 23) and light chain variable region RKB (SEQ ID NO. 27). This antibody is provided with either IgG1 (AX023-IgG1) or IgG4 (AXON023-IgG4) constant regions.

In one embodiment, the antibody (AX024) or tau-binding fragment thereof comprises heavy chain variable region RHL (SEQ ID NO. 24) and light chain variable region RKB (SEQ ID NO. 27). This antibody is provided with either IgG1 (AX024-IgG1) or IgG4 (AXON024-IgG4) constant regions.

In one embodiment, the antibody (AX025) or tau-binding fragment thereof comprises heavy chain variable region RHA (SEQ ID NO. 13) and light chain variable region VK (SEQ ID NO. 8)). This antibody is provided with either IgG1 (AX025-IgG1) or IgG4 (AXON025-IgG4) constant regions.

In one embodiment, the antibody (AX026) or tau-binding fragment thereof comprises heavy chain variable region RHB (SEQ ID NO. 14) and light chain variable region VK (SEQ ID NO.8). This antibody is provided with either IgG1 (AX026-IgG1) or IgG4 (AXON026-IgG4) constant regions.

In one embodiment, the antibody (AX027) or tau-binding fragment thereof comprises heavy chain variable region RHC (SEQ ID NO. 15) and light chain variable region VK (SEQ ID NO.8). This antibody is provided with either IgG1 (AX027-IgG1) or IgG4 (AXON027-IgG4) constant regions.

In one embodiment, the antibody (AX028) or tau-binding fragment thereof comprises heavy chain variable region RHD (SEQ ID NO. 16) and light chain variable region VK (SEQ ID NO.8). This antibody is provided with either IgG1 (AX028-IgG1) or IgG4 (AXON028-IgG4) constant regions.

In one embodiment, the antibody (AX029) or tau-binding fragment thereof comprises heavy chain variable region RHE (SEQ ID NO. 17) and light chain variable region VK (SEQ ID NO.8). This antibody is provided with either IgG1 (AX029-IgG1) or IgG4 (AXON029-IgG4) constant regions.

In one embodiment, the antibody (AX030) or tau-binding fragment thereof comprises heavy chain variable region RHF (SEQ ID NO. 18) and light chain variable region VK (SEQ ID NO.8). This antibody is provided with either IgG1 (AX030-IgG1) or IgG4 (AXON030-IgG4) constant regions.

In one embodiment, the antibody (AX031) or tau-binding fragment thereof comprises heavy chain variable region RHG (SEQ ID NO. 19) and light chain variable region VK (SEQ ID NO.8). This antibody is provided with either IgG1 (AX031-IgG1) or IgG4 (AXON031-IgG4) constant regions.

In one embodiment, the antibody (AX032) or tau-binding fragment thereof comprises heavy chain variable region RHH (SEQ ID NO. 20) and light chain variable region VK (SEQ ID NO.8). This antibody is provided with either IgG1 (AX032-IgG1) or IgG4 (AXON032-IgG4) constant regions.

In one embodiment, the antibody (AX033) or tau-binding fragment thereof comprises heavy chain variable region RHI (SEQ ID NO. 21) and light chain variable region VK (SEQ ID NO.8). This antibody is provided with either IgG1 (AX033-IgG1) or IgG4 (AXON033-IgG4) constant regions.

In one embodiment, the antibody (AX034) or tau-binding fragment thereof comprises heavy chain variable region RHJ (SEQ ID NO. 22) and light chain variable region VK (SEQ ID NO.8). This antibody is provided with either IgG1 (AX034-IgG1) or IgG4 (AXON034-IgG4) constant regions.

In one embodiment, the antibody (AX035) or tau-binding fragment thereof comprises heavy chain variable region RHK (SEQ ID NO. 23) and light chain variable region VK (SEQ ID NO.8). This antibody is provided with either IgG1 (AX035-IgG1) or IgG4 (AXON035-IgG4) constant regions.

In one embodiment, the antibody (AX036) or tau-binding fragment thereof comprises heavy chain variable region RHL (SEQ ID NO. 24) and light chain variable region VK (SEQ ID NO.8). This antibody is provided with either IgG1 (AX036-IgG1) or IgG4 (AXON036-IgG4) constant regions.

In one embodiment, the antibody (AX037) or tau-binding fragment thereof comprises heavy chain variable region RHM (SEQ ID NO. 25) and light chain variable region RKA (SEQ ID NO. 26). This antibody is provided with either IgG1 (AX037-IgG1) or IgG4 (AXON037-IgG4) constant regions.

In one embodiment, the antibody (AX038) or tau-binding fragment thereof comprises heavy chain variable region RHM (SEQ ID NO. 25) and light chain variable region RKB (SEQ ID NO. 27). This antibody is provided with either IgG1 (AX037-IgG1) or IgG4 (AXON037-IgG4) constant regions.

In another embodiment, the invention provides an antibody heavy chain comprising a variable region chosen from any one of heavy chain variable regions RHA, RHB, RHC, RHD, RHE, RHF, RHG, RHH, RHI, RHJ, RHK, RHL, and RHM. Any of these variable regions can be linked to a constant region of any human isotype, including constant regions with mixed isotypes.

In another embodiment, the invention provides an antibody light chain comprising a variable region chosen from RKA and RKB. Any of these variable regions can be linked to a constant region of any human isotype, including constant regions with mixed isotypes.

In another embodiment, the invention provides an antibody heavy chain of any one of SEQ ID NO. 28-40 and 43-55.

In another embodiment, the invention provides an antibody light chain chosen from SEQ ID NO. 57-59.

The heavy and light chain variable regions of humanized antibodies can be linked to at least a portion of a human constant region. As described above in the Definitions, the choice of constant region depends, in part, whether antibody-dependent cell-mediated cytotoxicity, antibody dependent cellular phagocytosis and/or complement dependent cytotoxicity are desired. In one embodiment, human isotopes IgG1 and IgG3 have complement-dependent cytotoxicity and human isotypes IgG2 and IgG4 do not. In one embodiment, human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO: 170. The N-terminal arginine of SEQ ID NO:170 can be omitted, in which case light chain kappa constant region has the amino acid sequence of SEQ ID NO:171. An exemplary human IgG1 heavy chain constant region has the amino acid sequence of SEQ ID NO:172. An exemplary human IgG4 heavy chain constant region has the amino acid sequence of SEQ ID NO:173. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

cDNA sequences encoding the constant regions of human antibodies are known to one of ordinary skill in the art. In one embodiment, exemplary cDNA sequences available via, e.g., GenBank, each of which incorporated by reference in its entirety, are as follows: Human IgG1 constant heavy chain region: GenBank accession No.: J00228; Human IgG2 constant heavy chain region: GenBank accession No.: J00230; Human IgG3 constant heavy chain region: GenBank accession No.: X04646; Human IgG4 constant heavy chain region: GenBank accession No.: K01316; and Human kappa light chain constant region: GenBank accession No.:

J00241. In one embodiment, the constant region may further be modified according to known methods. For example, in an IgG4 constant region, residue S241 may be mutated to a proline (P) residue to allow complete disulphide bridge formation at the hinge (see, e.g., Angel et al., Mol. Immunol. 1993; 30:105-8).

For more clarity, the table 3 below summarizes the various amino acid sequences corresponding to the various variable regions of some of the humanized antibodies described herein.

TABLE 3

| HUMANIZED VARIABLE HEAVY REGION ONLY | SEQ ID NO. | HUMANIZED VARIABLE LIGHT REGION ONLY | SEQ ID NO. |
|---|---|---|---|
| RHA | 13 | RKA | 26 |
| RHB | 14 | RKB | 27 |
| RHC | 15 | | |
| RHD | 16 | | |
| RHE | 17 | | |
| RHF | 18 | | |
| RHG | 19 | | |
| RHH | 20 | | |
| RHI | 21 | | |
| RHJ | 22 | | |
| RHK | 23 | | |
| RHL | 24 | | |
| RHM | 25 | | |

Table 4 below summarizes the amino acid sequences corresponding to the various full length sequences of the mouse and humanized antibodies described herein.

TABLE 4

| COMPLETE VARIABLE AND HEAVY CONSTANT IgG1 | SEQ ID NO. | COMPLETE VARIABLE AND HEAVY CONSTANT IgG4 | SEQ ID NO. |
|---|---|---|---|
| RHA | 28 | RHA | 43 |
| RHB | 29 | RHB | 44 |
| RHC | 30 | RHC | 45 |
| RHD | 31 | RHD | 46 |
| RHE | 32 | RHE | 47 |
| RHF | 33 | RHF | 48 |
| RHG | 34 | RHG | 49 |
| RHH | 35 | RHH | 50 |
| RHI | 36 | RHI | 51 |
| RHJ | 37 | RHJ | 52 |
| RHK | 38 | RHK | 53 |
| RHL | 39 | RHL | 54 |
| RHM | 40 | RHM | 55 |
| cDC8E8 | 41 | cDC8E8 | 56 |
| Mouse DC8E8 | 42 | | |

The table 5 below summarizes the various amino acid sequences corresponding to the various full length sequences of the light chains of the humanized antibodies described herein.

TABLE 5

| COMPLETE HUMANIZED VARIABLE LIGHT CONSTANT K | SEQ ID NO. |
|---|---|
| RKA | 57 |
| RKB | 58 |
| cDC8E8 kappa | 59 |

Also provided are chimeric antibodies and tau-binding fragments thereof. In one embodiment, the chimeric antibody or tau-binding fragment thereof comprises heavy chain variable region DC8E8 VH (SEQ ID NO. 9) and light chain variable region DC8E8 VK (SEQ ID NO. 10) together with a human IgG1 constant region (SEQ ID NO. 172) for the heavy chain and a kappa constant region (SEQ ID NO. 170) for the light chain. In another embodiment, the chimeric antibody or tau-binding fragment thereof comprises heavy chain variable region DC8E8 VH (SEQ ID NO. 9) and light chain variable region DC8E8 VK (SEQ ID NO. 10) together with a human IgG4 constant region (SEQ ID NO. 173) for the heavy chain and a kappa constant region (SEQ ID NO. 170) for the light chain.

In one embodiment, the humanized antibody or a tau-binding fragment/portion thereof is made recombinantly. In another embodiment, the humanized antibody or a tau-binding fragment/portion thereof is made, at least partially, by chemical synthesis. In one embodiment, the chimeric antibody or a tau-binding fragment/portion thereof is made recombinantly. In another embodiment, the chimeric antibody or a tau-binding fragment/portion thereof is made, at least partially, by chemical synthesis.

Table 6 summarizes the sequences for some of the other humanization-related molecules described herein.

TABLE 6

| MOLECULE | AMINO ACID SEQ ID NO. | NUCLEIC ACID SEQ ID NO. |
|---|---|---|
| Y15982 Igkv8-21*01 | 60 | 72 |
| L17135 Igkv8-28*02 | 61 | 73 |
| Y15980 IGKV8-19*01 | 62 | 74 |
| AJ235948 IGKV8-30*01 | 63 | 75 |
| AJ235947 IGKV8-28*01 | 64 | 76 |
| X72449 | 65 | 77 |
| AC160990 Musmus IGHV1-81*01 | 66 | 78 |
| AC160473 Musmus IGHV1-77*01 | 67 | 79 |
| AC160990 Musmus IGHV1-83*01 | 68 | 80 |
| AC160473 Musmus IGHV1-75*01 | 69 | 81 |
| X02064 Musmus IGHV1-54*02 | 70 | 82 |
| M65092 | 71 | 83 |

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Also comprised by the present disclosure are antibodies and binding fragments the sequence of which has been altered by introducing at least one, particularly at least two, more particularly at least 3 or more conservative substitutions into the sequences of SEQ ID NOs: 13-25 and SEQ ID NOs: 26 and 27 respectively, such that the antibody essentially maintains its full functionality.

Certain amino acids from the human mature variable region framework residues can be selected for substitution based on their possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, among other reasons. One of ordinary skill in the art would know how to pick certain amino acids for substitution and then assess the result of such substitution. In many embodiments, positions for substitution within frameworks and amino acids to substitute are selected empirically.

Amino acid substitutions can also be made in the CDRs. One possible variation is to substitute certain residues in the CDRs of the mouse DC8E8 antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41:863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

In one embodiment, antibodies and tau-binding fragments thereof comprise a heavy chain variable region comprising CDR-H1, CDR-H2, and CDR-H3 of SEQ ID NOs 1, 2, and 3, respectively, and being at least 90% identical to the mature heavy chain of SEQ ID NO. 28-40 (complete RHA-RHM); and a light chain variable region comprising CDR-L1, CDR-L2, and CDR-L3 of SEQ ID NOs. 4, 5, and 6 respectively, and being at least 90% identical to the mature light chain of SEQ ID NO. 57 (RKA) or SEQ ID NO. 58 (RKB). In some embodiments, the mature heavy chain is at least 95%, 96%, 97%, 98%, or 99% identical to any one of SEQ ID NO. 28-40. In some embodiments, the mature light chain is at least 95%, 96%, 97%, 98%, or 99% identical to any one of SEQ ID NO. 57 or SEQ ID NO. 58.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to another therapeutic agent. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. In one embodiment, the sites of greatest interest for substitutional mutagenesis include the hypervariable regions, but FR alterations are also contemplated. Conservative substitutions are shown in a table above as well as below. More substantial changes, denominated in amino acid classes may be introduced and the products screened.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on other common side-chain properties:
(1) hydrophobic: Norleucine, Met, Ala, Val, Leu, Ile,
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions typically entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human tau. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0693621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the half-life of the antibodies or tau-binding fragments of the disclosures. In one embodiment, one or more Fc amino acids are mutated to increase the half-life of the antibody in the blood, or wherein one or more sugar moieties of the Fc have been deleted, or one or more sugar moieties added to increase the blood half-life of the antibody. Common plasma proteins such as human serum albumin (HSA) and immunoglobulins (Igs), including humanized antibodies, show long half-lifes, typically of 2 to 3 weeks, which is attributable to their specific interaction with the neonatal Fc receptor (FcRn), which leads to endosomal recycling (Ghetie (2002) Immunol Res, 25:97-113). In contrast, most other proteins of pharmaceutical interest, in particular recombinant antibody fragments, hormones, and interferons suffer from rapid (blood) clearance. This is particularly true for proteins whose size is below the threshold value for kidney filtration of about 70 kDa (Caliceti (2003) Adv Drug Deliv Rev 55:1261-1277). In these cases the plasma half-life of an unmodified pharmaceutical protein may be considerably less than an hour. This can limit their use in most therapeutic applications. In order to achieve sustained pharmacological action and also improved patient compliance—with required dosing intervals extending to several days or even weeks—several strategies have been established and described in the art for purposes of biopharmaceutical drug development.

In other embodiments, the antibodies or tau-binding fragments thereof may be modified to affect half-life or circulation time through PEGylation or other conjugation to other polymers. The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 Da. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999). Polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Figure 2:
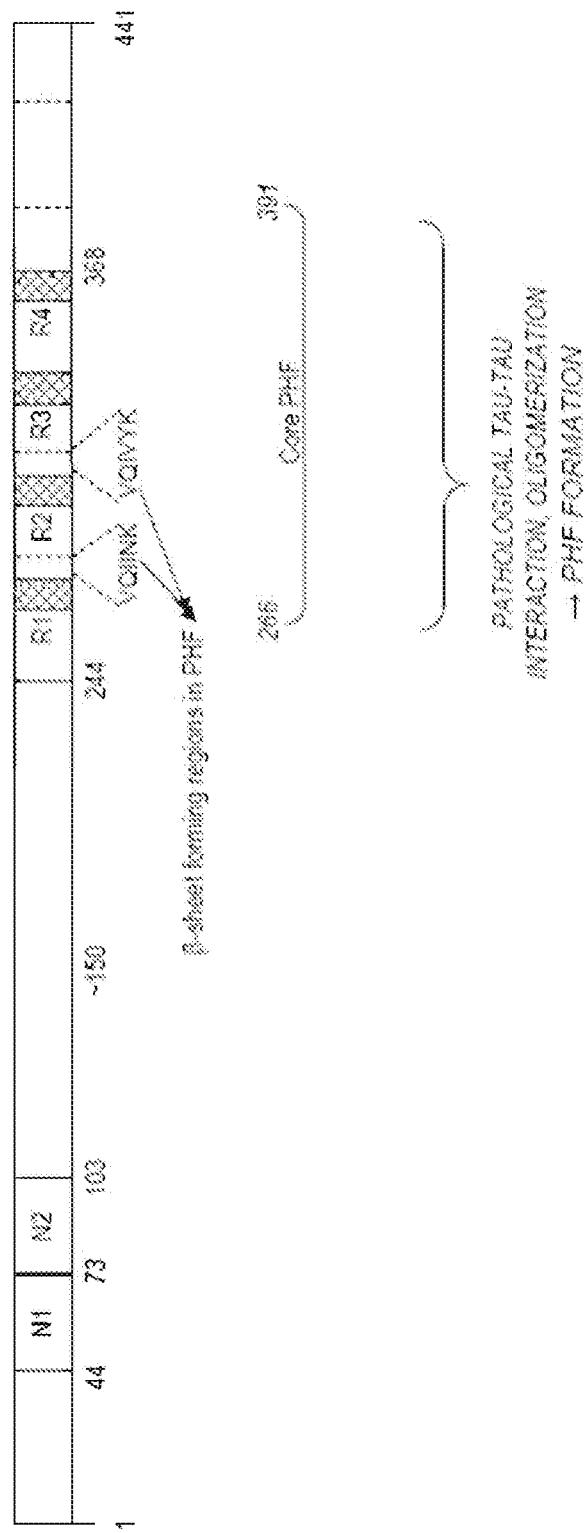
FIG. 2: Schematic functional map of human tau (2N4R); discloses "VQIINK" and "VQIVYK" as SEQ ID NOS 147 and 146, respectively.

Alternatively, antibodies or fragments thereof may have increased in vivo half lives via fusion with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) or other circulating blood proteins such as transferrin or ferritin. In one embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. Polynucleotides encoding fusion proteins of the disclosure are also encompassed by the invention.

Antibodies or tau-binding fragments thereof may also be chemically modified to provide additional advantages such as increased solubility, stability and circulating time (in vivo half-life) of the polypeptide, or decreased immunogenicity (See, e.g, U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and tau-binding fragments thereof may be modified at random positions within the molecule, or at predetermined positions within the molecule and may include one, two, three or more attached chemical moieties It may be desirable to modify the antibodies or tau-binding fragments of the disclosures with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al, J. Exp Med. 176:1191-1195 (1992) and Shopes, B. J. Immunol. 148:2918-2922 (1992). Alternatively, an antibody can be engineered which has dual Fc regions and may thereby have enhanced complement lysis and ADCC capabilities. See Stevenson et al. Anti-Cancer Drug Design 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. Nos. 6,194,551B1, 6,242,195B1, 6,528, 624B1 and 6,538,124 (Idusogie et al.). The antibodies comprise an amino acid substitution at one or more of amino acid positions 270, 322, 326, 327, 329, 313, 333 and/or 334 of the Fc region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Antibodies with improved binding to the neonatal Fc receptor (FcRn), and increased half-lives, are described in WO00/42072 (Presta, L.). These antibodies comprise a Fc region with one or more substitutions therein which improve binding of the Fc region to FcRn. For example, the Fc region may have substitutions at one or more of positions 238, 256, 265, 272, 286, 303, 305, 307, 311, 312, 317, 340, 356, 360, 362, 376, 378, 380, 382, 413, 424 or 434. The preferred Fc region-comprising antibody variant with improved FcRn binding comprises amino acid substitutions at one, two or three of positions 307, 380 and 434 of the Fc region thereof.

In one embodiment, the humanized antibody or a tau-binding fragment/portion thereof is monoclonal. The monoclonal antibodies (mAbs) described herein are antibodies obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant (epitope) on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods. In other cases, the monoclonal antibodies are made from the growth of a single cell clone, such as a eukaryotic host cell transfected with a DNA molecule encoding for the antibody or a tau-binding fragment or portion thereof. Nucleic acids encoding antibodies and fragments of the disclosure can also be delivered to a host subject for expression of the antibody and fragments by cells of the host subject. Examples of strategies for polynucleotide delivery to and expression of anti-senilin antibodies in the central nervous system of a host subject are described in PCT application No. WO98/44955, published Oct. 15, 1998. Any nucleic acid may be modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queuosine and wybutosine, as well as acetyl-, methyl-, thio- and other modified forms of adenine, cytidine, guanine, thymine and uridine.

In one aspect, an antibody or tau-binding fragment as described herein is capable of displaying a higher affinity for pathological tau than for physiological tau.

In another aspect, an antibody or tau-binding fragment as described herein is capable of inhibiting tau-tau aggregation.

In another aspect, an antibody or tau-binding fragment as described herein is capable of mediating uptake and degradation of pathological tau protein by microglia.

In one aspect, an antibody or tau-binding fragment as described herein is capable of displaying a higher affinity for pathological tau than for physiological tau and inhibiting tau-tau aggregation.

In one aspect, an antibody or tau-binding fragment as described herein is capable of displaying a higher affinity for pathological tau than for physiological tau, inhibiting tau-tau aggregation, and mediating uptake and degradation of pathological tau protein by microglia.

The tables 7, 8, and 9 below summarize the nucleic acid sequences of the CDRs and variable regions and complete chains of some of the antibodies described herein:

TABLE 7

| NUCLEIC ACID | SEQ ID NO. | VARIABLE REGION | SEQ ID NO. |
|---|---|---|---|
| CDR-H1 | 84 | HEAVY DC8E8 | 90 |
| CDR-H2 | 85 | LIGHT DC8E8 | 91 |
| CDR-H3 | 86 | HEAVY CHIMERIC | 92 |
| CDR-L1 | 87 | LIGHT CHIMERIC | 93 |
| CDR-L2 | 88 | HEAVY DC8E8 OPTIMIZED | 94 (identical to 92) |
| CDR-L3 | 89 | LIGHT DCBE8 OPTIMIZED | 95 (identical to 93) |

TABLE 8

| HUMANIZED VARIABLE HEAVY REGION ONLY | SEQ ID NO. | HUMANIZED VARIABLE LIGHT REGION ONLY | SEQ ID NO. |
|---|---|---|---|
| RHA | 96 | RKA | 109 |
| RHB | 97 | RKB | 110 |
| RHC | 98 | | |
| RHD | 99 | | |
| RHE | 100 | | |
| RHF | 101 | | |
| RHG | 102 | | |
| RHH | 103 | | |
| RHI | 104 | | |
| RHJ | 105 | | |
| RHK | 106 | | |
| RHL | 107 | | |
| RHM | 108 | | |

TABLE 9

| COMPLETE VARIABLE HEAVY CONSTANT IgG1 | SEQ ID NO. | COMPLETE VARIABLE HEAVY CONSTANT IgG4 | SEQ ID NO. |
|---|---|---|---|
| RHA | 111 | RHA | 127 |
| RHB | 112 | RHB | 128 |
| RHC | 113 | RHC | 129 |
| RHD | 114 | RHD | 130 |
| RHE | 115 | RHE | 131 |
| RHF | 116 | RHF | 132 |
| RHG | 117 | RHG | 133 |
| RHH | 118 | RHH | 134 |
| RHI | 119 | RHI | 135 |
| RHJ | 120 | RHJ | 136 |
| RHK | 121 | RHK | 137 |
| RHL | 122 | RHL | 138 |
| RHM | 123 | RHM | 139 |
| cDC8E8 | 124 | cDC8E8 | 140 |
| Mouse DC8E8 | 125 | | |
| Codon optimized mouse DC8E8 | 126 (identical to 124) | | |

In a different set of embodiments, the invention provides nucleic acids encoding the antibodies described herein, or parts thereof. The nucleic acids encoding heavy chain variable regions DC8E8 VH, RHA, RHB, RHC, RHD, RHE, RHF, RHG, RHH, RHI, RHJ, RHK, RHL, and RHM and light chain variable regions DC8E8 VK, RKA, and RKB have been codon optimized, using GeneScript's proprietary technology. In the context of this application, codon optimization is the process of modifying a nucleotide sequence in a manner that improves its expression, G/C content, RNA secondary structure, and translation in eukaryotic cells, without altering the amino acid sequence it encodes.

In one embodiment, the invention provides nucleic acids (DNA or RNA) that encode a humanized antibody heavy chain variable region as described herein. In one embodiment, the nucleic acid comprises a DNA that encodes any one of heavy chain variable regions RHA, RHB, RHC, RHD, RHE, RHF, RHG, RHH, RHI, RHJ, RHK, RHL, and RHM. These nucleic acids are represented in the tables below. Nucleic acids exhibiting a percent identity of at least 80%, at least 85%, at least 90%, at least 95%, and at least 98% are also within the scope of this embodiment.

The table 10 below summarizes the various nucleic acid sequences corresponding to the various full length sequences of the light chains of the humanized antibodies described herein.

TABLE 10

| COMPLETE HUMANIZED VARIABLE LIGHT CONSTANT K | SEQ ID NO. |
|---|---|
| RKA | 141 |
| RKB | 142 |
| cDC8E8 kappa | 143 |

In another embodiment, the invention provides nucleic acids (DNA or RNA) that encode a humanized antibody light chain variable region as described herein. In one embodiment, the nucleic acid comprises a DNA that encodes any one of light chain variable regions RKA and RKB. These nucleic acids are represented in the tables above. Nucleic acids exhibiting a percent identity of at least 80%, at least 85%, at least 90%, at least 95%, and at least 98% are also within the scope of this embodiment.

It will be appreciated by those of ordinary skill in the art that, as a result of the degeneracy of the genetic code, there are many nucleotide sequences that encode an antibody or tau-binding fragment thereof as described herein. Some of these nucleic acids bear minimal homology to the nucleotide sequence of any "wild-type" antibody or tau-binding fragment thereof as described herein. Nonetheless, nucleic acids that vary due to differences in codon usage are specifically contemplated by the present invention.

In one embodiment, the invention provides nucleic acids (DNA or RNA) that encode a humanized antibody heavy chain variable region as described herein. In one embodiment, the nucleic acid comprises a DNA that encodes any one of heavy chains variable regions RHA, RHB, RHC, RHD, RHE, RHF, RHG, RHH, RHI, RHJ, RHK, RHL, and RHM linked to a human IgG1 constant region. Nucleic acids exhibiting a percent identity of at least 80%, at least 85%, at least 90%, at least 95%, and at least 98% are also within the scope of this embodiment.

In one embodiment, the invention provides nucleic acids (DNA or RNA) that encode a humanized antibody heavy chain variable region as described herein. In one embodiment, the nucleic acid comprises a DNA that encodes any one of heavy chains variable regions RHA, RHB, RHC, RHD, RHE, RHF, RHG, RHH, RHI, RHJ, RHK, RHL, and RHM linked to a human IgG4 constant region. Nucleic acids exhibiting a percent identity of at least 80%, at least 85%, at least 90%, at least 95%, and at least 98% are also within the scope of this embodiment.

In another embodiment, the invention provides nucleic acids (DNA or RNA) that encode a humanized antibody light chain variable region as described herein. In one embodiment, the nucleic acid comprises a DNA that encodes any one of light chain variable regions RKA and RKB linked to a human kappa region. Nucleic acids exhibiting a percent identity of at least 80%, at least 85%, at least 90%, at least 95%, and at least 98% are also within the scope of this embodiment.

In another embodiment, the invention provides nucleic acids (DNA or RNA) that encode each of DC8E8's CDRs in a codon optimized manner.

Nucleic sequences exhibiting a percentage identity of at least 80%, for example 85%, 90%, 95% and 98%, after optimal alignment with a preferred sequence, means nucleic sequences exhibiting, with respect to the reference nucleic sequence, certain modifications such as, in particular, a deletion, a truncation, an extension, a chimeric fusion and/or a substitution, notably punctual. In some embodiments, these are sequences which code for the same amino acid sequences as the reference sequence, this being related to the degeneration of the genetic code, or complementarity sequences that are likely to hybridize specifically with the reference sequences, for example under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

Expression Systems

The antibodies and tau-binding fragments thereof can be made synthetically or by any of the multiple expression systems known to those of ordinary skill in the art. To this end, also provided are embodiments that cover cloning vectors, expression vectors, host cells, and transgenic animals (other than human) transfected, transformed, or otherwise genetically or recombinantly modified to contain one or more of the nucleic acid sequences described above. In one embodiment, the host cells are eukaryotic. In another embodiment, the host cells are prokaryotic. In another embodiment, the host cells express one or more of the antibodies and tau binding fragments thereof. Selected cells may be cultured and if required, the protein product of the gene of interest isolated from the culture using conventional techniques. In some embodiments, the expression systems have been adapted to express the antibody or tau-binding fragment thereof at an optimal level. In some embodiments, the antibodies and tau-binding fragments thereof are expressed by contract-based antibody expression companies (e.g., Lonza) that use proprietary technologies to express the antibodies and tau-binding fragments thereof as a service. In another embodiment, the antibodies and tau-binding fragments thereof are expressed in a cell-free system.

Examples of routinely used antibody expression systems include recombinant baculovirus, lentivirus, protozoa (e.g., eukaryotic parasite *Leishmania tarentolae*), microbial expression systems, including yeast-based (e.g. *Pichia pastoris, Saccharomyces cerevisiae, Yarrowia lipolytica, Hansenula polymorpha, Aspergillus* and *Trichoderma* Fungi) and bacterial-based (e.g. *E. coli, Pseudomonas fluorescens, Lactobacillus, Lactococcus, Bacillus megaterium, Bacillus subtilis, Brevibacillus, Corynebacterium glutamicum*), Chinese hamster ovary (CHO) cells, CHOK1SVNSO (Lonza), BHK (baby hamster kidney), PerC.6 or Per.C6 (e.g., Percivia, Crucell), different lines of HEK 293, Expi293F™ cells (Life Technologies), GenScript's YeastHIGH™ Technology (GenScript), human neuronal precursor cell line AGE1.HN (Probiogen) and other mammalian cells, plants (e.g., corn, alfalfa, and tobacco), insect cells, avian eggs, algae, and transgenic animals (e.g., mice, goats, sheep, pigs, cows).

The glycosylation pattern of the antibodies expressed by these various systems varies considerably with the expression system. For example, the glycosylation machinery of CHO cells is somewhat similar to the human glycosylation machinery, with some differences. In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art and can be used to alter the antibodies and tau-binding fragments thereof described herein.

The advantages and disadvantages of these various systems have been reviewed in the literature and are known to one of ordinary skill in the art. Some of these have been described in the following references, all of which are incorporated herein by reference in their entirety: Chadd et al. Therapeutic antibody expression technology. Curr Opin Biotechnol. 2001 April; 12(2):188-94; Ma et al. Human antibody expression in transgenic rats: comparison of chimeric IgH loci with human VH, D and JH but bearing different rat C-gene regions. J Immunol Methods. 2013 Dec. 31; 400-401:78-86; Zhang et al. Monoclonal antibody expression in mammalian cells. Methods Mol Biol. 2012; 907:341-58.

Pharmaceutical Compositions and Formulations

Provided herein are compositions comprising a humanized antibody or a tau-binding fragment thereof, as described herein, and another component, such as a carrier. Also provided are pharmaceutical compositions/therapeutic formulations comprising a humanized antibody or a tau-binding fragment thereof, as described herein, and an excipient and/or a pharmaceutical carrier. In one embodiment, the carrier is not a naturally existing compound. In one embodiment, the excipient is not a naturally existing compound. In another embodiment, the diluent is not a naturally existing compound. In another embodiment, the formulation comprising the humanized antibody or a tau-binding fragment thereof, as described herein, does not contain a naturally existing compound, except, optionally, water.

In one embodiment, therapeutic formulations of the antibodies used in accordance with the present invention are prepared for storage and/or administration by mixing an antibody our tau-binding fragment thereof having the desired degree of purity with optional pharmaceutically acceptable carriers, diluents, excipients or stabilizers (Remington's Pharmaceutical Sciences 16th edition, Osol, A. Ed. (1980)), in the form of lyophilized formulations or aqueous solutions. In one embodiment, acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN, PLURONICS or polyethylene glycol (PEG). Examples of lyophilized antibody formulations are described in WO 97/04801, expressly incorporated herein by reference.

In a further embodiment, the formulation further comprises a surfactant. The surfactant may, for example, be selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, N alpha.- acylated derivatives of lysine, arginine or histidine, or side-chain acylated derivatives of lysine or arginine, Nalpha.- acylated derivatives of dipeptides comprising any combination of lysine, arginine or histidine and a neutral or acidic amino acid, Nalpha-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl .beta.-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. In one embodiment, the surfactant is not a naturally existing compound. Each one of these specific surfactants constitutes an alternative embodiment of the disclosure.

One embodiment provides for stable formulations of the antibodies and/or tau-binding fragments thereof, which comprise preferably a phosphate buffer with saline or a chosen salt, as well as preserved solutions and formulations containing a preservative, as well as multi-use preserved formulations suitable for pharmaceutical or veterinary use, comprising at least one the antibodies and/or tau-binding fragments thereof in a pharmaceutically acceptable formulation. In one embodiment, preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like. In one embodiment, the preservative or preservatives are not naturally existing compounds.

In one embodiment, the antibodies and tau-binding fragments thereof of the disclosure can be incorporated into pharmaceutical compositions suitable for administration to a subject. In one common embodiment, the pharmaceutical composition comprises an antibody or tau-binding fragment thereof of the invention and a pharmaceutically acceptable carrier. In one embodiment, "pharmaceutically acceptable carrier" includes any and all solvents, dispersion media, coatings, antibacterial and antifungal agents, isotonic and absorption delaying agents, and the like that are physiologically compatible. Additional examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or tau-binding fragment thereof.

In one embodiment, an appropriate amount of a pharmaceutically-acceptable salt is used in the formulation to render the formulation isotonic. Examples of the carrier include saline, Ringer's solution and dextrose solution. In one embodiment, the pH of the solution is from about 5 to about 8. In another embodiment, the pH is from about 7 to about 7.5. Further carriers include sustained release preparations such as semipermeable matrices of solid hydrophobic polymers containing the antibody or tau-binding fragment thereof, which matrices are in the form of shaped articles, e.g., films, liposomes or microparticles. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It will be apparent to those persons skilled in the art that certain carriers may be more preferable depending upon, for instance, the route of administration and concentration of antibody being administered.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. In some embodiments, such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Antibodies and tau-binding fragments thereof may also be encapsulated within liposomes using well-known technologies.

Dosage forms suitable for internal administration generally contain from about 0.1 milligram to about 500 milligrams of antibody or tau-binding fragment thereof (the active ingredient) per unit or container. In these pharmaceutical compositions, the active ingredient will ordinarily be present in an amount of about 0.5-99.999% by weight based on the total weight of the composition.

Therapeutic compositions/formulations typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or tau-binding fragment thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The preferred dosage form depends on the intended mode of administration and therapeutic application. One of ordinary skill in the art is familiar with the procedures for determining such dosages. Typical compositions are in the form of injectable or infusible solutions, such as compositions similar to those used for passive immunization of humans with other antibodies. The most typical mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The antibodies and tau-binding fragments thereof of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the antibody or tau-binding fragment thereof may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody or tau-binding fragment thereof of the invention may be orally administered, for example, with an inert diluent or an assimilable edible carrier. The antibody or tau-binding fragment thereof (and other ingredients, if desired) may also be enclosed in a hard or soft shell gelatin capsule, compressed into tablets, or incorporated directly into the subject's diet. For oral therapeutic administration, the antibody or tau-binding fragment thereof may be incorporated with excipients and used in the form of ingestible tablets, buccal tablets, troches, capsules, elixirs, suspensions, syrups, wafers, and the like. To administer an antibody or tau-binding fragment thereof of the invention by other than parenteral administration, it may be necessary to coat the antibody or tau-binding fragment thereof with, or co-administer the antibody or tau-binding fragment thereof with, a material to prevent its inactivation.

Certain embodiments of the invention provide for the antibody or tau-binding fragment thereof to traverse the blood-brain barrier. Certain neurodegenerative diseases, including AD and related tauopathies, are associated with an increase in permeability of the blood-brain barrier, such that the antibody or tau-binding fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or or tau-binding fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or tau-binding fragment thereof (see, e.g., U.S. Patent Publication No. 2003/0083299).

Lipid-based methods of transporting the antibody or tau-binding fragment thereof across the blood-brain barrier include, but are not limited to, encapsulating the antibody or tau-binding fragment thereof in liposomes that are coupled to active fragments thereof that bind to receptors on the vascular endothelium of the blood-brain barrier (see, e.g., U.S. Patent Application Publication No. 20020025313), and coating the antibody or tau-binding fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or tau-binding fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

A variety of other approaches are known in the art to effect administration of compounds to the brain. For example, the antibody or tau-binding fragment thereof may be administered by direct intraventricular or intrathecal injection, preferably via slow infusion to minimize impact on brain parenchyma. The desired antibody or tau-binding fragment thereof may also be delivered using a slow release implant in the brain, or implanted recombinant cells that produce the antibody or tau-binding fragment thereof. The blood brain barrier (BBB) may be permeabilized concomitant with the antibody or tau-binding fragment thereof administration, to permit movement of the antibody or tau-binding fragment thereof across the BBB. Permeabilizing agents include osmotic agents, such as hypertonic mannitol, or another permeabilizing agent such as bradykinin, an alkylglycerol, ultrasound, electromagnetic radiation or parasympathetic innervation.

In addition, and without being bound by any specific mechanism, it has also been considered that it is possible that an antibody, in the blood, could have a "sink-like" effect in removing its target protein from the brain. See, e.g., US Published Application US 20110158986, paragraph [0017]. If that is the case, the antibodies and tau-binding fragments thereof could be useful to remove pathological tau from the brain out into the circulation, effectively preventing it from causing further damage to the neuronal cells and tissues.

Supplementary or combination active compounds or therapeutic agents as disclosed elsewhere in this application can also be incorporated into the compositions, administered concurrently, or administered sequentially with the antibody or tau-binding fragment thereof. In certain embodiments, an antibody or tau-binding fragment thereof of the invention is coformulated with and/or coadministered with one or more additional therapeutic agents. These additional therapeutic agents can also be chemically conjugates to the antibodies or tau-binding fragments thereof described herein.

In one embodiment, an immunoconjugate is provided having the formula (A)-(L)-(C), wherein: (A) is an antibody or binding fragment thereof according to the embodiments disclosed herein; (L) is a linker; and (C) is an agent; and wherein said linker (L) links (A) to (C). In one embodiment, (C) is an effector molecule, e.g., therapeutic agent, an imaging agent, a detectable agent, or a diagnostic agent. In some embodiments, these conjugates are referred to herein as antibody-drug-conjugates (ADCs).

A (L) linker, as used herein, is a molecule that is used to join the (A) to (C). The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. In yet other embodiments, the linker unit is not cleavable and the drug is released, for example, by antibody degradation.

A number of different reactions are available for covalent attachment of drugs and/or linkers to antibodies or fragments thereof. This is often accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in 191P4D12-expressing cells. Other examples of such linkers are described, e.g., in U.S. Pat. No. 6,214,345. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10): 1305-12).

In yet other embodiments, the linker unit is not cleavable and the drug is released by antibody degradation. (See U.S. Publication No. 2005/0238649).

In one embodiment, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the antibody-drug conjugate compound as described herein).

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Some examples of antibody-drug conjugates (ADCs) currently existing in the clinic can be found in Feng, Y. et al. Conjugates of Small Molecule Drugs with Antibodies and Other Proteins. Biomedicines 2014, 2, 1-13; doi:10.3390/biomedicines2010001.

In view of the large number of methods that have been reported for attaching a variety of therapeutic agents, imaging agents, detectable agents, diagnostic agents, radiodiagnostic compounds, radiotherapeutic compounds, drugs, toxins, and other agents to antibodies and fragments thereof, one skilled in the art will be able to determine a suitable method for attaching a given agent to an antibody or tau-binding fragment thereof. In another embodiment, (A) and (C) are directly bound to each other.

In another embodiment, (L) is a spacer group or a linkage group such as polyaldehyde, glutaraldehyde, ethylenediaminetetraacetic acid (EDTA) or diethylenetriaminepentaacetic acid (DPTA). Other techniques for linking an antibody or fragment to another compound include the formation of disulfide linkages using N-succinimidyl-3-(2-pyridyl-thio) propionate (SPDP) and succinimidyl 4-(N-maleimidomethyl)cyclohexane-1-carboxylate (SMCC) or derivatives (if the peptide lacks a sulfhydryl group, this can be provided by addition of a cysteine residue). These reagents create a disulfide linkage between themselves and peptide cysteine resides on one protein and an amide linkage through the .epsilon.-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Drug loading is represented by p and is the average number of Drug moieties per antibody in a molecule (e.g., A-L-Dp). Drug loading may range from 1 to 20 drug moieties (D) per antibody. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay. The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See U.S. Pat. No. 7,498,298.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488.

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., Hamblett, K J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

In some exemplary embodiments, an antibody or tau-binding fragment thereof described herein may be coformulated and/or coadministered with one or more additional compounds that are also useful in the prophylaxis and/or treatment of AD. These include, without limitation, compounds that are useful in active and passive immunotherapies for AD, such as beta-amyloid peptides (e.g., N-terminal amyloid beta peptides), tau peptides, which might or might not be conjugated to other compounds, such as mutated diphtheria toxin; antibodies against beta-amyloid, such as bapineuzumab, solaneuzumab, gantenerumab, crenezumab, ponezumab, and IVIG immunoglobulin, other immunization therapies targeting Abeta oligomers, other tau antibodies, compounds preventing the hyperphosphorylation of tau, and other active and passive immunization therapies targeting tau aggregates Other drugs that should be helpful in combination therapy with the antibodies and tau-binding fragments described herein are amyloid-beta aggregation inhibitors (e.g., Tramiprosate), gamma-secretase inhibitors (e.g., semagacestat), and gamma-secretase modulators (tarenflurbil). Furthermore, one or more antibodies of the invention may be used in combination with two or more of the foregoing therapeutic agents. At early stages of the disease, combination therapies can be advantageous. Combination therapies are also advantageous at later stages of the disease, such as combination of hAb and growth factors and other biologically active molecules inducing neuronal plasticity and regeneration. Such combination therapies may advantageously utilize lower dosages of the administered therapeutic agents, thus avoiding possible toxicities or complications associated with the various monotherapies. According to a related embodiment, an antibody or tau-binding fragment thereof described herein is used in combination (one administered separately, before, simultaneously with or after the other) with at least one combination agent chosen from acetylcholinesterase inhibitors (e.g., donepezil, rivastigmine, galantamine, tacrine, nutritive supplements), N-Methyl-D-aspartate (NMDA) receptor antagonists (e.g., memantine), inhibitors of DNA repair (e.g., pirenzepine or a metabolite thereof), transition metal chelators, growth factors, hormones, non-steroidal anti-inflammatory drugs (NSAID), antioxidants, lipid lowering agents, selective phosphodiesterase inhibitors, inhibitors of tau aggregation, inhibitors of protein kinases, inhibitors of anti-mitochondrial dysfunction drugs, neurotrophins, inhibitors of heat shock proteins, inhibitors of Lipoprotein-associated phospholipase $A_2$, and any pharmaceutically acceptable salts thereof. In one embodiment, the treatment with an antibody and/or tau-binding fragment thereof is combined with treatment with cholinesterase inhibitors (ChEI) and/or memantine, which offer modest symptomatic benefit. In one embodiment, the combination therapeutic agent is selected from the group consisting of an anti-apoptotic compound, a metal chelator, an inhibitor of DNA repair, 3-amino-1-propanesulfonic acid (3APS), 1,3-propanedisulfonate (1,3PDS), a secretase activator, a beta-secretase inhibitor, a gamma-secretase inhibitor, a beta-amyloid peptide, a beta-amyloid antibody, a neurotransmitter, a beta-sheet breaker, an anti-inflammatory molecule, and a cholinesterase inhibitor. In one embodiment, the cholinesterase inhibitor is tacrine, rivastigmine, donepezil, galantamine, or a nutritive supplement. In another embodiment, the additional therapeutic agent is selected from BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors.

Other compounds that can be suitably used in combination with the antibody and tau-binding fragment described herein are described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94).

In one embodiment, the antibody and/or tau-binding fragment thereof is used in combination with the current standard of treatment at the time of treatment, which includes cholinesterase inhibitors and memantine (Namenda) NMDA antagonist.

The pharmaceutical compositions of the invention may include a "therapeutically effective amount" or a "prophylactically effective amount" of an antibody or tau-binding fragment thereof of the invention. A "therapeutically effective amount" refers to an amount effective, at dosages and for periods of time necessary, to achieve the desired therapeutic result. A therapeutically effective amount of the antibody or tau-binding fragment thereof may vary according to factors such as the disease state, age, sex, and weight of the individual, and the ability of the antibody or tau-binding fragment thereof to elicit a desired response in the individual. A therapeutically effective amount is also one in which any toxic or detrimental effects of the antibody or tau-binding fragment thereof are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, an infusion protocol, or a single bolus, may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active compound calculated to produce the desired therapeutic effect in association with the required pharmaceutical carrier. The specifications for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

For example, effective doses of the compositions of the present disclosure, for the treatment of the conditions described below, vary depending upon many factors, including means of administration, target site, physiological state of the patient, whether the patient is human or an animal, other medications administered, and whether the treatment is prophylactic or therapeutic. Usually, the patient is a human. Treatment dosages need to be titrated to optimize safety and efficacy. Accordingly, treatment with an antibody or tau-binding fragment thereof will typically entail multiple dosages over a period of time.

An exemplary, non-limiting range for a therapeutically or prophylactically effective amount of an antibody or tau-binding fragment thereof of the invention for humans is 0.1-20 mg/kg, more preferably 1-10 mg/kg. In one preferred embodiment, the antibody is administered in multiple dosages over a period of at least three months, preferably at least six months, and a dose between 1 and 10 mg/kg. Optionally the antibody or tau-binding fragment thereof is administered at a dose of 0.01-0.6 mg/kg and a frequency of between weekly and monthly. Optionally, the antibody or tau-binding fragment thereof is administered at a dose of 0.05-0.5 mg/kg. Optionally, the antibody or tau-binding fragment thereof is administered at a dose of 0.05-0.25 mg/kg. Optionally, the antibody or tau-binding fragment thereof is administered at a dose of 0.015-0.2 mg/kg weekly to biweekly. Optionally, the antibody or tau-binding fragment thereof is administered at a dose of 0.05-0.15 mg/kg weekly to biweekly. Optionally, the antibody or tau-binding fragment thereof is administered at a dose of 0.05-0.07 mg/kg weekly. Optionally, the antibody or tau-binding fragment thereof is administered at a dose of 0.06 mg/kg weekly. Optionally, the antibody or tau-binding fragment thereof is administered at a dose of 0.1 to 0.15 mg/kg biweekly. Optionally, the antibody or tau-binding fragment thereof is administered at a dose of 0.1 to 0.3 mg/kg monthly. Optionally, the antibody or tau-binding fragment thereof is administered at a dose of 0.2 mg/kg monthly. Optionally, the antibody or tau-binding fragment thereof is administered once a year. Optionally, the antibody or tau-binding fragment thereof is administered at a dose of 1-40 mg and a frequency of between weekly and monthly. Optionally, the antibody or tau-binding fragment thereof is administered at a dose of 5-25 mg. Optionally, the antibody or tau-binding fragment thereof is administered at a dose of 2.5-15 mg. Optionally, the antibody or tau-binding fragment thereof is administered at a dose of 1-12 mg weekly to biweekly. Optionally, the antibody or tau-binding fragment thereof is administered at a dose of 2.5-10 mg weekly to biweekly. Optionally, the antibody or tau-binding fragment thereof is administered at a dose of 2.5-5 mg weekly. Optionally, the antibody or tau-binding fragment thereof is administered at a dose of 4-5 mg weekly. Optionally, the antibody or tau-binding fragment thereof is administered at a dose of 7-10 mg biweekly.

In other passive immunization embodiments with an antibody or tau-binding fragment as described herein, the dosage ranges from about 0.0001 to 100 mg/kg, and more usually 0.01 to 5 mg/kg of the host body weight. In some applications, the amount of antibody or tau-binding fragment thereof can be administered at a dosage of at least 0.1 mg/kg of body weight, at a dosage of at least 0.5 mg/kg of body weight, 1 mg/kg of body weight, or any combination of dosages between 0.1 and 10 mg/kg of body weight. In some methods, the antibody or tau-binding fragment thereof can be administered in multiple dosages (equal or different) over a period of at least 1 month, at least 3 months, or at least 6 months. The total number of doses over any one treatment period can be, for example, between 4 and 6, although other numbers can be used depending on the factors discussed above. Treatment can be monitored by any of the methods described further below.

Suitable antibody formulations can also be determined by examining experiences with other already developed therapeutic monoclonal antibodies. For example, several monoclonal antibodies have been shown to be efficient in clinical situations, such as Rituxan (Rituximab), Herceptin (Trastuzumab), Xolair (Omalizumab), Bexxar (Tositumomab), Campath (Alemtuzumab), Zevalin, Oncolym, Remicade (infliximab), Lucentis (Ranibizumab), Synagis (Palivizumab), Soliris (Eculizumab), Kadcyla (ado-trastuzumab emtansine), Avastin (Bevacizumab), Erbitux (cetuximab), Simponi (Golimumab), Tysabri (natalizumab), MabThera (Rituximab), Stelara (Ustekinumab), Pritumumab, and Aducanumab, and similar formulations may be used with the antibodies of this disclosure. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Methods of Treatment and Prophylaxis

The antibodies and compositions described herein can be used for various methods of treatment and prophylaxis of AD and related tauopathies. In addition to the advantageous property of reduced immunogenicity, these antibodies have at least 80% of the binding affinity for disease tau than the parent mouse DC8E8 antibody. Mouse DC8E8 was extensively characterized in WO2013/041962, where it was shown that it possesses therapeutic properties in an in vivo model of AD. Thus, there is a reasonable basis to believe that humanized DC8E8 will also be useful in the therapy and prophylaxis of human AD, while potentially eliciting a less detrimental immunologic response.

In one embodiment, the method comprises administering the antibodies, nucleic acids encoding them, or pharmaceutical compositions as described above to the subject/patient. In prophylactic applications, pharmaceutical compositions or medicaments are administered to a patient susceptible to, or otherwise at risk of, Alzheimer's disease or another tauopathy in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in amount sufficient to cure, or at least partially arrest, the symptoms of the disease (biochemical, histologic and/or behavioral), including its complications and intermediate pathological phenotypes in development of the disease.

As defined above, treatment encompasses the application or administration of a therapeutic agent to a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease. Moreover, as long as the compositions of the disclosure either alone or in combination with another therapeutic agent cure, heal, alleviate, relieve, alter, remedy, ameliorate, improve or affect at least one symptom of Alzheimer's Disease or another tauopathy being treated as compared to that symptom in the absence of use of the humanized anti-tau antibody or tau-binding fragment thereof composition, the result should be considered an effective treatment of the underlying disorder regardless of whether all the symptoms of the disorder are cured, healed, alleviated, relieved, altered, remedied, ameliorated, improved or affected or not.

An individual "at risk" may or may not have detectable disease, and may or may not have displayed detectable disease prior to the treatment methods described herein. "At risk" denotes that an individual has one or more so-called risk factors, which are measurable parameters that correlate with development of Alzheimer's disease. An individual having one or more of these risk factors has a higher probability of developing Alzheimer's disease than an individual without these risk factor(s). These risk factors include, but are not limited to, age, sex, race, diet, history of previous disease, presence of precursor disease, genetic (i.e., hereditary) considerations, and environmental exposure, and are well-known to one of ordinary skill in the art.

In one embodiment, the disclosure provides a method of treating or preventing the progression of Alzheimer's disease or another tauopathy in a subject, the method comprising administering to said subject an effective amount of at least one antibody and/or tau-binding fragment thereof as provided herein. In some embodiments, the method is capable of reducing motor impairment, improving motor function, reducing cognitive impairment, improving cognitive function, or a combination thereof.

In other embodiments, the disclosure provides a method of ameliorating at least one of the symptoms associated with Alzheimer's disease or another tauopathy in a subject, the method comprising administering to said subject an effective amount of at least one antibody and/or tau-binding fragment thereof as provided herein.

In one embodiment, the disclosure provides a method of delaying the progression of Alzheimer's disease. In one embodiment, "delaying" development of Alzheimer's disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. In one embodiment, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects.

Patients, subjects, or individuals include mammals, such as human, bovine, equine, canine, feline, porcine, and ovine animals. The subject is preferably a human, and may or may not be afflicted with disease or presently show symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient.

In one embodiment, the patient herein is optionally subjected to a diagnostic test prior to therapy. In one embodiment, the present methods are useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy (1997) Trends Neurosci. 20:154-9). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Amyloid-beta42 levels. Elevated tau and decreased Amyloid-beta42 levels signify the presence of AD. In one embodiment, individuals suffering from Alzheimer's disease can be diagnosed by ADRDA (Alzheimer's Disease and Related Disorders Association) criteria. In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by various ways known in the art over time. In the case of potential Down's syndrome patients, treatment can begin antenatally by administering therapeutic agent to the mother or shortly after birth.

Patient selection can be done by any of the selection criteria applied in the art of treating AD and related tauopathies. In one embodiment, the criteria are those determined by a particular clinical trial. In another embodiment, the criteria are those determined by an approved treatment regimen. A combination of inclusion and exclusion criteria may be applied. Examples of inclusion criteria include, but are not limited to: diagnosis of probable Alzheimer's disease based on the NINCDS/ADRDA criteria; confirmed AD of mild to moderate degree if the MMSE score is in the range of 15 to 26; the result of the Magnetic Resonance Imaging scan (MRI) of the patient's brain is consistent with the diagnosis of AD; presence of tau pathology in the patients' brains determined by suitable imaging methods, e.g. by using (11)C-PBB3 or lansoprazole-based radiopharmaceuticals; and age between 50 and 85 years.

In one embodiment, patient selection follows the method described in Rollin-Sillaire et al. Reasons that prevent the inclusion of Alzheimer's disease patients in clinical trials. Br J Clin Pharmacol. April 2013; 75(4): 1089-1097.

A number of outcome measures and primary endpoints are provided herein for some embodiments of how treatment is evaluated and effective amount determined. In one embodiment, the primary outcome measures at a given time frame include Mean change in Alzheimer's Disease Activity Scale-Cognitive subscale 13 (ADAS-Cog13) scores and Mean change in Alzheimer's Disease Cooperative Study-Activities of Daily Living (ADCS-ADL) scores and the secondary outcome measures include Change in biomarkers (total-tau, phosphorylated-tau, Abeta 1-42 levels) in cerebral spinal fluid, Change in MRI volumetry, assessed on structural MRI, Change in Clinical Dementia Rating (CDR-SB/CDR-GS), Change in neuropsychiatric behavior: Neuropsychiatric Inventory (NPI) total and domain scores, Change in cognition: MMSE total score, and/or Safety: Incidence of adverse events, serious adverse events and treatment discontinuations. In another embodiment, the primary end points include any of the following: time to the occurrence of death, institutionalization, loss of ability to perform activities of daily living, severe dementia, slowing of the rate of progression of the disease, ADCS-ADL, ADAS-cog score, MMSE scores, cognitive performance, plasma CSF biomarkers, ADAS-total score, Quality of life assessed by Quality of Life Alzheimer's disease scale, behavioral test scores, and the US FDA's Clinical Dementia Rating-sum of boxes.

In one embodiment, treating Alzheimer's disease refers to decreasing or preventing behavioral, functional, and cognitive deterioration over time. In some embodiments, behavioral, functional, and cognitive aspects of Alzheimer's Disease can be evaluated by any one or more of a series of standardized tests known to persons of ordinary skill in the art including, but not limited to, neuropsychological testing, the Mini-Mental State Exam, Mini-cog exam, Neuropsychiatric Inventory, Blessed Roth Dementia Rating Scale, Spanish and English Neuropsychological Assessment Scales (SE-NAS), Psychiatric Behavioral Assessment, Functional Assessment, Clock Drawing Test, Boston Naming Test, California Verbal Learning Test, Cognitive Symptoms Checklist, Continuous Performance Test, Controlled Oral Word Association Test, Cognistat, d2 Test of Attention, Delis-Kaplan Executive Function System, Dementia Rating Scale, Digit Vigilance Test, Figural Fluency Test, Finger Tapping Test, Halstead Category Test, Halstead-Reitan Neuropsychological Battery, Hooper Visual Organization Test, Kaplan Baycrest Neurocognitive Assessment, Kaufman Short Neuropsychological Assessment, Luria-Nebraska Neuropsychological Battery, Memory Assessment Scales, Quick Neurological Screening Test, Repeatable Battery for the Assessment of Neuropsychological Status, Stroop Test, Symbol Digit Modalities Test, Tactual Performance Test, Thematic Apperception Test, Tower of London, Trail Making Tests A and B, Verbal (Word) Fluency Tests, and Wisconsin Card Sort Test. Additional tests for depression, anxiety, aphasia, agitation, and behavioral parameters known to persons of ordinary skill in the art are also used.

In another embodiment, the treatment of Alzheimer's disease is determined by the improvement, or no deterioration, or a reduction in the rate of deterioration in at least one of the assessments selected from the group consisting of Alzheimer's Disease Assessment Scale-cognitive subscale (ADAS-cog), the Clinical Dementia Rating Sum of Boxes (CDR-sb), the Alzheimer's Disease Cooperative Study Activities of Daily Living Scale (ADCS-ADL), the Neuropsychiatric Inventory (NPI), and the Mini-Mental State Evaluation (MMSE). In some embodiments, the treatment results in a reduction in the rate of deterioration in ADAS-cog scores. In other embodiments, the treatment results in a median reduction in the rate of deterioration of ADAS-cog scores of two to five points.

In one embodiment, patients are identified and/or selected based on the FDA's "Guidance for Industry, Alzheimer's Disease: Developing Drugs for the Treatment of Early Stage Disease," available in updated form from the U.S. Food and Drug Administration.

In one embodiment, diagnosis of Alzheimer's disease in human subjects is made according to criteria of the National Institute of Neurologic and Communicative Disorders and Stroke-Alzheimer's disease and Related Disorders Association (NINCDS-ADRDA).

Periodic use of one or more of these tests can advise a physician or other medical professional as to the progression, or regression of Alzheimer's Disease and related tauopathies and the need for further treatment. The choice of test and the determination of success of treatment are within the expertise of medical professionals in the Alzheimer's Disease field. An improved score in one or more tests is an indication of decrease in severity of the Alzheimer's Disease in that subject.

Methods of Diagnosis

Because of their ability to detect pathological forms of tau, the antibodies and tau-binding fragments thereof described herein are useful for numerous other practical applications. Examples of such applications include, but are not limited to, pathological tau association analysis, disease predisposition screening, disease diagnosis, disease prognosis, disease progression monitoring, determining therapeutic strategies based on an individual's type and level of pathological tau, developing therapeutic agents based on pathological tau levels and type associated with a disease or likelihood of responding to a drug, stratifying a patient population for clinical trial for a treatment regimen, and predicting the likelihood that an individual will respond to a therapeutic agent. In vitro methods for detection of the pathological tau proteins associated with Alzheimer's disease and related tauopathies with the antibodies and tau-binding fragments that are disclosed herein include, but are not limited to, enzyme linked immunosorbent assays (ELISAs), radioimmunoassays (RIA), Western blots, immunoprecipitations, immunofluorescence, sandwich assays, and tissue arrays.

In one embodiment, the antibodies and tau-binding fragments thereof described herein can be used to assess pathological tau abnormal tissue distribution, abnormal expression during development, or expression in an abnormal condition, such as Alzheimer's disease and related tauopathies. Additionally, antibody detection of circulating pathological tau can be used to identify tau turnover during treatment of AD and related tauopathies.

In related embodiments, the invention provides a method of diagnosing or screening a subject for the presence of Alzheimer's disease or another tauopathy in a subject, or for determining a subject's risk for developing Alzheimer's disease or another tauopathy, the method comprising:
 a) contacting the subject, or a cell, tissue, organ, fluid, or any other sample of the subject, with an effective amount of at least one antibody and/or tau-binding fragment thereof as provided herein; and
 b) determining the presence of a complex comprising pathological tau and the antibody and/or tau-binding fragment thereof, wherein the presence of the complex is diagnostic of Alzheimer's disease or another tauopathy associated with the presence of pathological tau.

In some embodiments, the antibodies and/or tau-binding fragments thereof can be used to detect pathological tau in vivo, ex vivo, in situ, in vitro, in a bodily fluid (e.g., blood, serum, urine, plasma, cerebrospinal fluid, saliva), or in a cell lysate or supernatant in order to evaluate the amount and pattern of expression. In one embodiment, the antibodies and tau-binding fragments thereof are used for in vivo diagnostic assays, such as in vivo imaging. In some of those embodiments, the antibody is labeled with a radionuclide (such as $^{111}$In, $^{99}$Tc, $^{14}$C, $^{131}$I, $^{125}$I, or $^{3}$H) so that the cells or tissue of interest marked by the presence of the antibody (and pathological tau) can be localized using immunoscintiography. Other detectable labels include a label which is observable using analytical techniques including, but not limited to, fluorescence, chemiluminescence, electron-spin resonance, ultraviolet/visible absorbance spectroscopy, infrared spectroscopy, mass spectrometry, nuclear magnetic resonance, magnetic resonance, radiometric and electrochemical methods.

In one embodiment, the antibodies and tau-binding fragments thereof can be used in a method for evaluating the efficacy of a treatment of Alzheimer's disease or another tauopathy. In one embodiment, the method comprises using one of the antibodies and tau-binding fragments thereof for monitoring the presence of pathological tau before, throughout, and after the treatment. In one embodiment, a decrease in the level of, or type of, pathological tau is indicative of a positive response to the given treatment. In another embodiment, a lack of change or an increase in the level of, or type of, pathological tau is indicative that the treatment should continue.

In some embodiments, a first time point can be selected prior to initiation of a prophylaxis or treatment and a second time point can be selected at some time after initiation of the prophylaxis or treatment. Pathological tau levels can be measured in each of the samples taken from different time points and qualitative and/or quantitative differences noted. A change in the amounts of one or more of the measured pathological tau levels from the first and second samples can be correlated with prognosis, used to determine treatment efficacy, and/or used to determine progression of the disease in the subject.

Detection of an antibody or tau-binding fragment thereof as described herein can be facilitated by coupling (i.e., physically linking) the antibody or tau-binding fragment thereof to a detectable substance. Detectable substances include, but are not limited to, various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{113}I$, $^{35}S$ and $^{3}H$.

Other Uses

The antibodies and tau-binding fragments described herein can also be used to isolate the pathological tau proteins from a natural cell source or from recombinant host cells by standard techniques, such as affinity chromatography or immunoprecipitation. In another embodiment, the antibodies and tau-binding fragments described herein can be used to identify other antibodies that bind to pathological tau by competition assays.

In one embodiment, the antibodies may be used as affinity-purification agents. In one embodiment, the antibodies or tau-binding fragments thereof are immobilized on a solid phase such as a SEPHADEX™ resin or magnetic beads (e.g. of Dynal brand) or filter paper, using methods well known in the art. The immobilized antibody is contacted with a sample containing the tau (or fragment thereof) to be purified, and thereafter the support is washed with a suitable solvent that will remove substantially all the material in the sample except the tau protein, which is bound to the immobilized antibody. Finally, the support is washed with another suitable solvent, such as glycine buffer, pH 5.0, which will release the tau protein from the antibody.

Also provided are kits for using antibodies and tau-binding fragments thereof, such as kits for detecting the presence of pathological tau in a test sample. An exemplary kit can comprise antibodies and tau-binding fragments thereof such as a labeled or labelable antibody and a compound or agent for detecting variant proteins in a biological sample; means for determining the amount, or presence/absence of variant protein in the sample; means for comparing the amount of variant protein in the sample with a standard; and instructions for use.

In some embodiments, the invention provides a medical device comprising an antibody or tau-binding fragment as provided herein, wherein the device is suitable for contacting or administering the antibody or tau-binding fragment by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, and transdermal. In one embodiment, the device comprises a syringe (e.g., a pre-filled syringe). In another embodiment, the device comprises a patch. In another embodiment, the device comprises a pump (e.g., a mini-pump). In another embodiment, the device comprises an inhaler. In another embodiment, the device comprises a nebulizer.

In another embodiment, an article of manufacture containing materials useful for treatment of AD and related tauopathies is provided. The article of manufacture may comprise a vial with a fixed dose of the humanized antibody and/or tau-binding fragment thereof contained therein and, optionally, a package insert. The vial may be formed from a variety of materials such as glass or plastic, and may be sealed by a stopper pierceable by a syringe. For example, the vial may be a formal vitrum type I glass vial (e.g. 20 cc vial for a certain fixed dose or 50 cc vial for another fixed dose), with DAIKYO GREY fluoro-resin laminated stopper, and 20 mm flip top aluminum cap. The article of manufacture may further include other materials desirable from a commercial and user standpoint, including other buffers, diluents, filters, needles, and syringes, and the like. In one embodiment, the article of manufacture comprises two vials, wherein a first vial contains a given fixed dose of the humanized antibody and/or tau-binding fragment thereof, and a second vial contains a different fixed dose of the humanized antibody and/or tau-binding fragment thereof.

The antibodies can be used to generate anti-idiotype antibodies. (see, e.g., Greenspan & Bona, FASEB J. 7(5): 437-444, 1989; and Nissinoff, J. Immunol. 147:2429-2438, 1991). Such anti-idiotype antibodies can be utilized in pharmacokinetics, pharmacodynamics, biodistribution studies as well as in studies of clinical human-anti-human antibody (HAHA) responses in individuals treated with the antibodies. For example, anti-idiotypic antibodies bind specifically the variable region of humanized DC8E8 antibodies and therefore can be used to detect humanized DC8E8 antibodies in pharmacokinetic studies and help to quantify human-anti-human antibody (HAHA) responses in treated individuals.

All publications, patent applications, and patents cited in this specification are herein incorporated by reference as if each individual publication, patent application, or patent were specifically and individually indicated to be incorporated by reference. In particular, all publications, patent applications, and patents cited herein are expressly incorporated herein by reference for the purpose of describing and disclosing compositions and methodologies that might be used in connection with the disclosed inventions.

The following abbreviations apply to the Examples provided below.

Expi293 Human Embryonic Kidney (HEK293 High density/serum free) cells
A Adenine
bp base pairs
° C. Centigrade
C Cytosine
MEM Minimal Essential Medium
DNA Deoxyribonucleic acid
ELISA Enzyme linked immuno-adsorbent assay
EC50 Concentration of antibody providing half-maximal response
EC80 Concentration of antibody providing 80% of maximal response
ECD extracellular domain
g grams
G Guanine
HRP Horseradish peroxidase
IgG Immunoglobulin-G
K G or T (IUPAC convention)
min minute
M A or C (IUPAC convention)
nm nanometre
OD optical density PBS Phosphate Buffered Saline
PCR Polymerase chain reaction
R A or G (IUPAC convention)
RNA Ribonucleic acid
RT Room Temperature
s second
S C or G (IUPAC convention)
T Thymine
TBS Tris Buffered Saline
UV Ultra Violet
V A or C or G (IUPAC convention)
VH Immunoglobulin heavy chain variable region
VK Immunoglobulin kappa light chain variable region
W A or T (IUPAC convention)
Y C or T (IUPAC convention)

EXAMPLES

Example 1: Generation of a Chimeric Version of the DC8E8 Antibody

Total RNA was isolated from DC8E8 hybridoma cells using the RNeasy Mini protocol for isolation of total RNA (Qiagen). DC8E8 RNA (3 μg) was reverse-transcribed to produce DC8E8 cDNA using the GE Life Sciences 1st strand cDNA synthesis kit following the manufacturer's protocol. DC8E8 cDNA was amplified by PCR in 3 separate reactions as described in Section 8.3. Immunoglobulin heavy chain variable region (VH) cDNA was PCR-amplified with heavy chain primers M13-MHV6 plus MHCmix and kappa light chain PCR primers M13-MKV5 plus MKC using the Phusion High-Fidelity PCR Master Mix (Thermo Scientific). The result of each PCR reaction was a single amplification product that was purified using the QIAquick PCR purification kit and sequenced in both directions using the M13-Forward (TGTAAAACGACGGCCAGT (SEQ ID NO: 158)) and M13-Reverse primers (CAGGAAACAGC-TATGACC (SEQ ID NO: 159)).

| Name | Sequence (5'→3') | |
|---|---|---|
| MHV6 | TGTAAAACGACGGCCAGTATGGC TGTCCTAGGGCTACTCTTCTGC | (SEQ ID NO: 160) |
| MHCG1 | CAGGAAACAGCTATGACCCA GTGGATAGACAGATGGGGG | (SEQ ID NO: 161) |
| MHCG2a | CAGGAAACAGCTATGACCCAGT GGATAGACCGATGGGGC | (SEQ ID NO: 162) |
| MHCG2b | CAGGAAACAGCTATGACCCA GTGGATAGACTGATGGGGG | (SEQ ID NO: 163) |
| MHCG3 | CAGGAAACAGCTATGACCAA GGGATAGACAGATGGGGC | (SEQ ID NO: 164) |

MHV indicates primers that hybridize to the leader sequences of mouse heavy chain variable region genes, MHCG indicates primers that hybridize to the mouse constant region genes. Italicised sequence indicates the M13 Forward or the M13 Reverse Sequencing Primer.

| Name | Sequence (5'→3') | |
|---|---|---|
| MKV5 | TGTAAAACGACGGCCAGTATGGAT TTTCAGGTGCAGATTATCAGCTTC | (SEQ ID NO: 165) |
| MKC | CAGGAAACAGCTATGACCAC TGGATGGTGGGAAGATGG | (SEQ ID NO: 166) |

Figure 3:
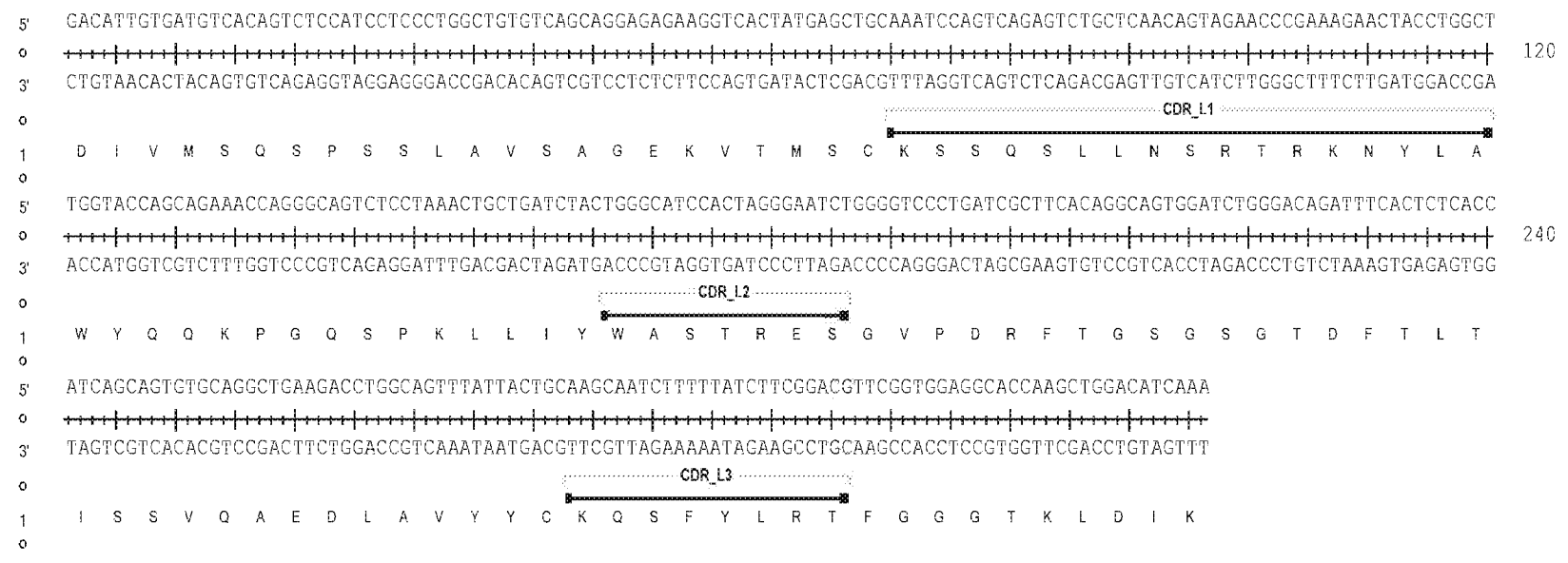
Figure 4:
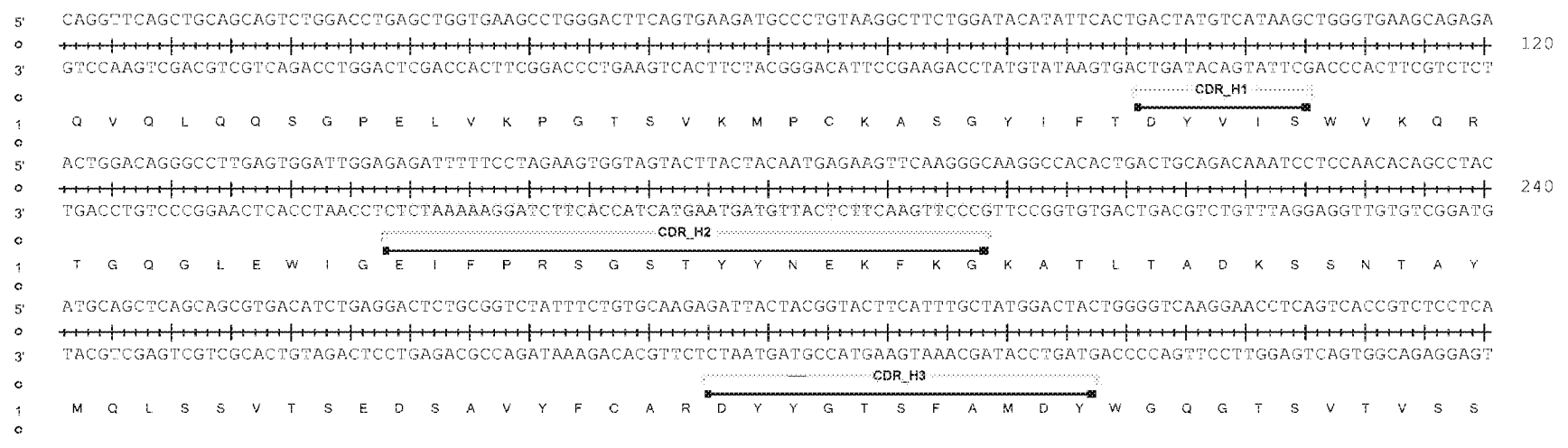

MKV indicates primer that hybridizes to leader sequences of the mouse kappa light chain variable region genes; MKC indicates the primer that hybridizes to the mouse kappa constant region gene. Coloured section indicates the M13 Forward or the M13 Reverse Sequencing Primer. The consensus sequence of DC8E8 VK PCR was designated DC8E8 VK (FIG. 3) and the consensus DNA sequence of VH designated DC8E8 VH (FIG. 4). Germ Line analysis of the sequences shows that the Kappa Light Chain is a Murine VK8, with no somatic mutations (FIG. 5). The Heavy Chain is a Murine VH1, and shows a number of somatic mutations in both the CDR's and Frameworks (FIG. 6). The appearance of two Proline residues in Framework 1 was considered to be significant. These residues may have a structural role outside of the 4 Å Proximity Residues.

Construction of chimeric expression vectors entailed routine cloning the amplified variable regions into IgG/kappa vectors (herein labeled pHuG1, pHuG4 and pHuK, a variety of which are commercially available). The clones generating the correct constructs were selected and sequenced.

Expi293 (Invitrogen) suspension cells growing in Expi293 transfection medium and antibiotics were co-transfected with DC8E8 VH.pHuG1 and DC8E8 VK.pHuK or DC8E8 VH.pHuG4 and DC8E8 VK.pHuK (50 μg DNA each) using ExpiFectamine 293 Reagent. The cells were grown in 100 ml growth medium for 10 days. The presence of γ1κ and γ4κ (chimeric DC8E8 antibodies) was measured in the conditioned medium by routine ELISA methods.

Figure 7:
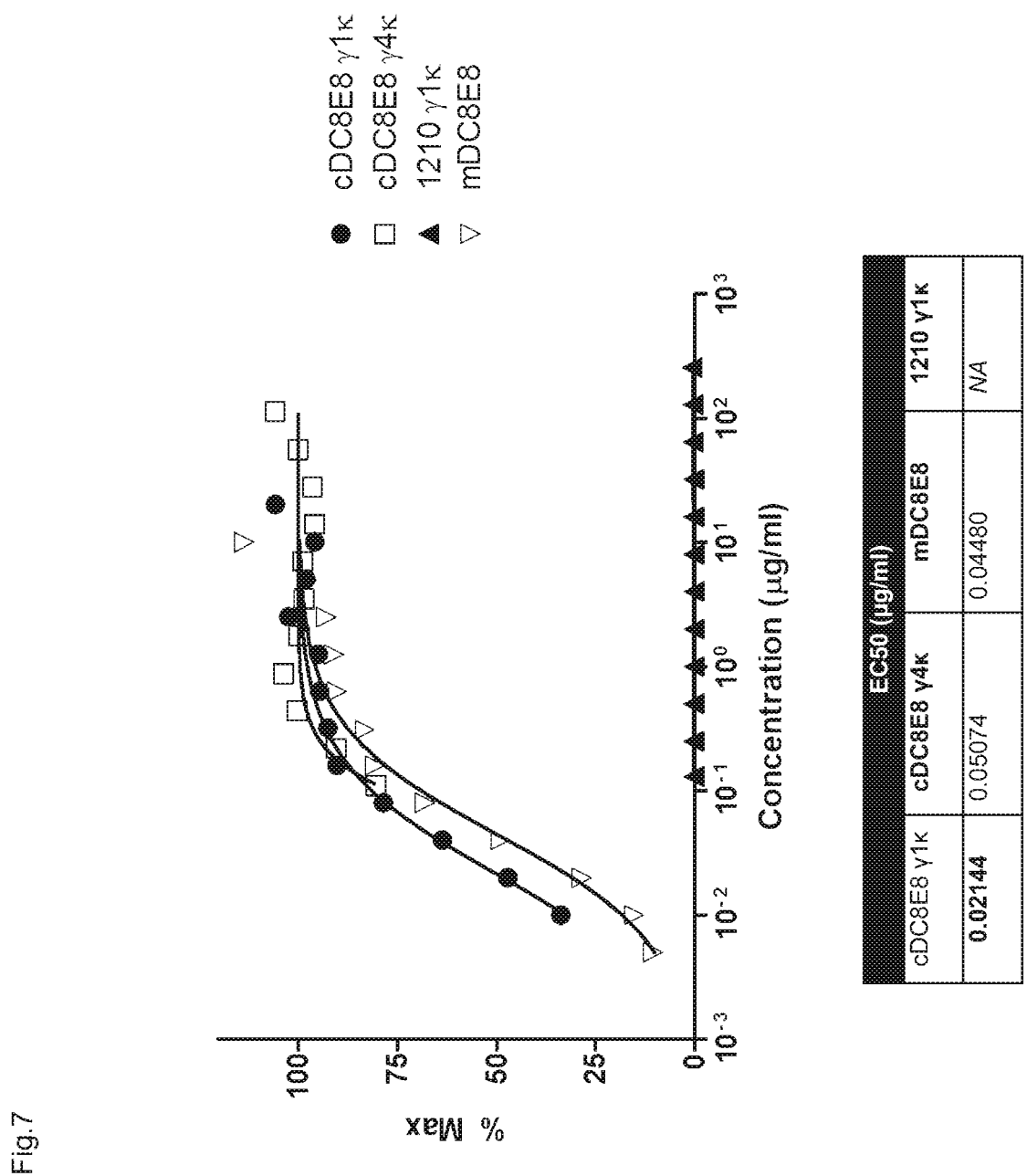
FIG. 7: Binding of chimeric and murine DC8E8 to Tau 151-391/4R

The tau protein-binding activity of each chimeric antibody was measured by Binding ELISA and compared to that of the original mouse DC8E8 antibody. Each well of a 94-well MaxiSorp plate (Nunc) was coated with 50 μL aliquots of 330 ng/mL of Tau 151-391/4R in PBS and incubated overnight at 4° C. Wells were washed 3× with PBS-T (0.1% Tween20). A fresh plate was blocked with 250 μL of PBS/0.2% BSA/0.05% Tween20 per well and incubated for 1 hour at RT. Wells were washed 3× with PBS-T (0.1% Tween20). 240 uL were added of antibody (diluted in PBS/0.2% BSA/0.05% Tween20 if necessary) to wells in column 1; 120 μL of buffer (PBS/0.2% BSA/0.05% Tween20) in the other wells. 120 μL were transferred from column 1 to the neighboring wells in column 2. The procedure was continued to column 12 with a series of 2-fold dilutions of the experimental samples. 100 μL per well were transferred from the dilution plate to the experimental plate. Plates were incubated for 1 hour at RT. Wells were washed 3× with PBS-T. The goat anti-human Fc peroxidase conjugate was diluted 10000-fold (or anti-mouse at 10000-fold dilution) in PBS/0.2% BSA/0.05% Tween20 and 100 μL added to each well. Plates were incubated 1 hour at RT and repeated washing step. 150 μL of substrate (K-Blue) were added per well and incubated for 150 minutes at RT. The reaction was stopped by adding 50 μl of RED STOP solution to each well. The optical density was read at 650 nm. Both chimeric antibodies bound Tau 151-391/4R with comparable $EC_{50}$ values, comparable with the murine DC8E8 antibody (FIG. 7). The sequence was used to design the humanized version of the DC8E8 antibody.

Example 2: Humanized Variants of Mouse DC8E8

The immunoglobulin sequence M65092 was chosen as the human donor candidate for the humanized heavy chain framework (FW) due to its higher sequence identity and similarity to the DC8E8 variable heavy chain region (VH). The sequence alignment of these two variable regions can be found in FIG. 8. The next step was to graft CDR1, 2, and 3 from DC8E8 VH into the acceptor FW of M65092. The human residues at Kabat positions 9, 21, 27, 28, 30, 38, 48, 67, 68, 70 and 95 are not conserved in the wild-type variable heavy chain region (RHA) of M65092. Due to their position (within 4 Å of a Kabat CDR using the program Discovery Studio (Accelrys), except for Pro at positions 9 and 21) these residues were tested for their importance in tau binding. This step is one of the most unpredictable procedures in the humanization of monoclonal antibodies, and necessitates the identification of critical framework residues from the parent antibody that need to be retained in order to substantially retain the binding properties of the parent antibody while at the same time minimizing the potential immunogenicity of the resultant humanized antibody. Each of these non-conserved residues was back-mutated to the DC8E8 mouse equivalent residue, resulting in the various recombinant variable heavy chain regions RHA through RHM. (FIG. 8).

In order to humanize the light chain a human kappa (light) chain was identified in a similar process to that of the heavy chain. Initial analysis found several potential donor candidates, but all these proved to be Human VK4, which show poor expression. Extending the analysis to include CDR1 with one less residue resulted in a single candidate, X72449, which showed a higher degree of sequence homology to the murine antibody than the VK4 candidates. The sequence of DC8E8 variable kappa light chain (VK) was aligned with the variable kappa light chain of X72449. FIG. 9. RKA shows the recombinant variable light chain having DC8E8's CDRs grafted onto the X72449 framework. In an alternative variant, RKB, DC8E8's CDRs grafted onto the X72449 framework and Kabat residue 5 was back mutated to the corresponding DC8E8 light chain mouse residue.

The genes for RHA through RHM, RKA, and RKB were synthesized by GenScript and/or PCR mutagenesis. The genes were codon optimized by silent mutagenesis to use codons preferentially utilized by human cells, using software algorithms proprietary to GenScript. Each of the RHA through RHM genes was then inserted into human IgG1 and IgG4 expression vectors, using methods typically done in the art. RKA and RKB genes were inserted into a K light chain expression vector in the same manner. Multiple examples of such expression vectors are well known and commercially available to one of ordinary skill in the art. Clones were sequenced and expression plasmid DNA prepared using QIAGEN Plasmid Miniprep/Maxiprep Kits. Expression plasmid preparations encoding all different humanized and chimeric VH and VK sequences were used to transfect Expi293 cells using Invitrogen's Expi293 expression system kit, cultured for 10 days in serum free media, whereupon the condition medium containing each secreted antibody was harvested. When desired, the concentrations of IgG1k and IgG4k antibodies in Expi293 conditioned media were measured by ELISA using routine methods of antibody quantification.

Example 3: Properties of the Humanized Versions of DC8E8

Tau Protein Binding by DC8E8 Antibodies

Figure 10:
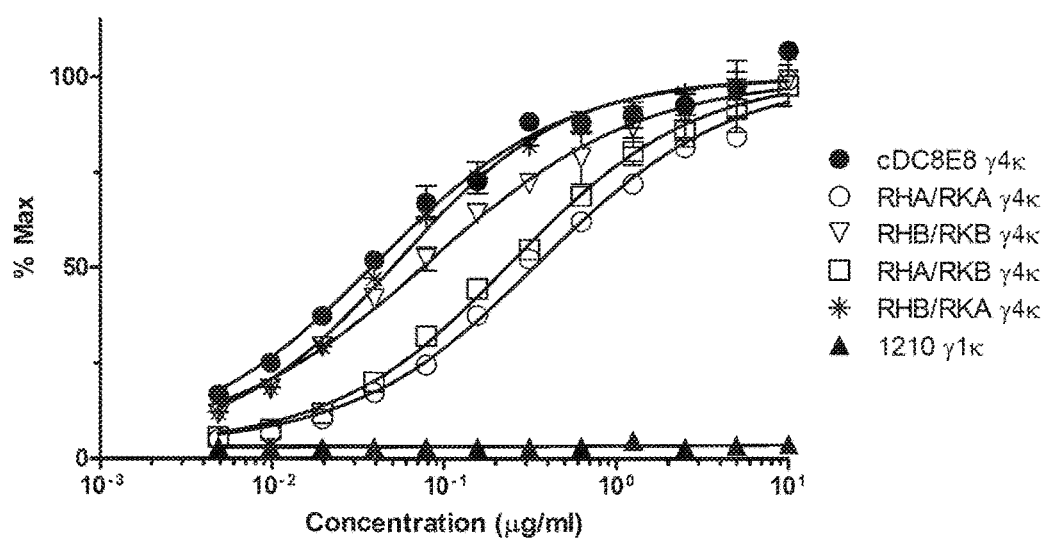
FIG. 10: Binding of humanized and chimeric DC8E8 to Tau 151-391/4R. Comparison of antibody binding by antibodies encoded by combinations of DC8E8 RHA or DC8E8 RHB co-expressed with DC8E8 RKA or DC8E8 RKB with the fully chimeric antibody.

Binding activity to Tau protein (151-139/4R) was measured by Binding ELISA, as described in Example 5. The data shown in FIG. 10 show the binding potency of the initial versions of the humanized DC8E8. Although all versions bound to the Tau protein, of this initial set, those antibodies containing the RHB version of the heavy chain appeared to bind better. This version of the heavy chain contains back-mutations to murine residues at all of Kabat positions 9, 21, 27, 28, 30, 38, 48, 67, 68, 70 and 95, indicating that one or more of these residues is important for retaining full antibody binding activity.

Figure 11:
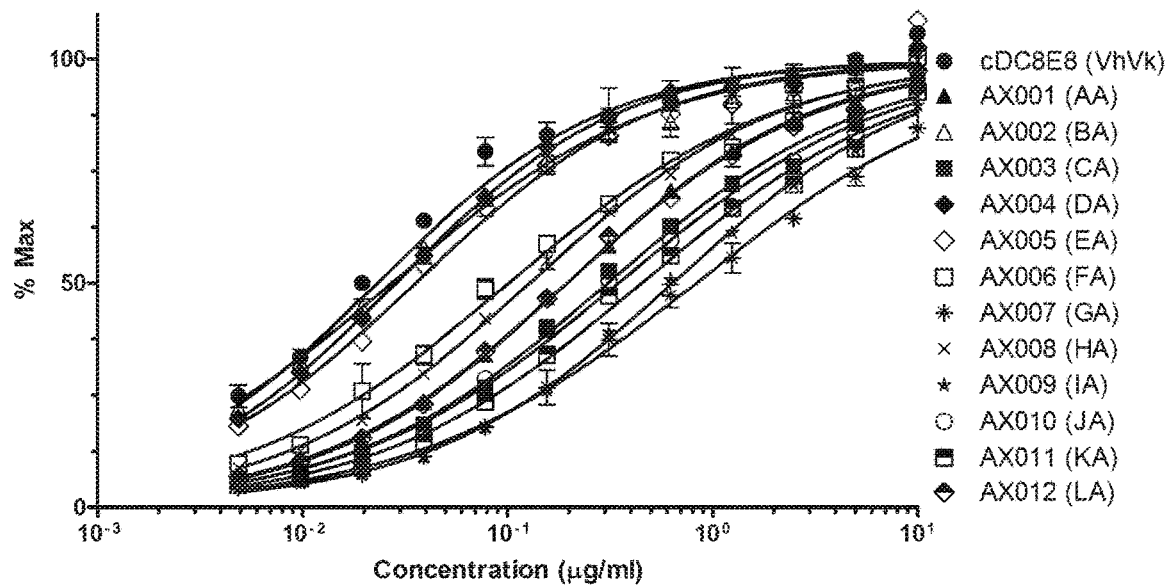
FIG. 11: Binding of humanized and chimeric DC8E8 to Tau 151-391/4R: RKA Versions.
Figure 12:
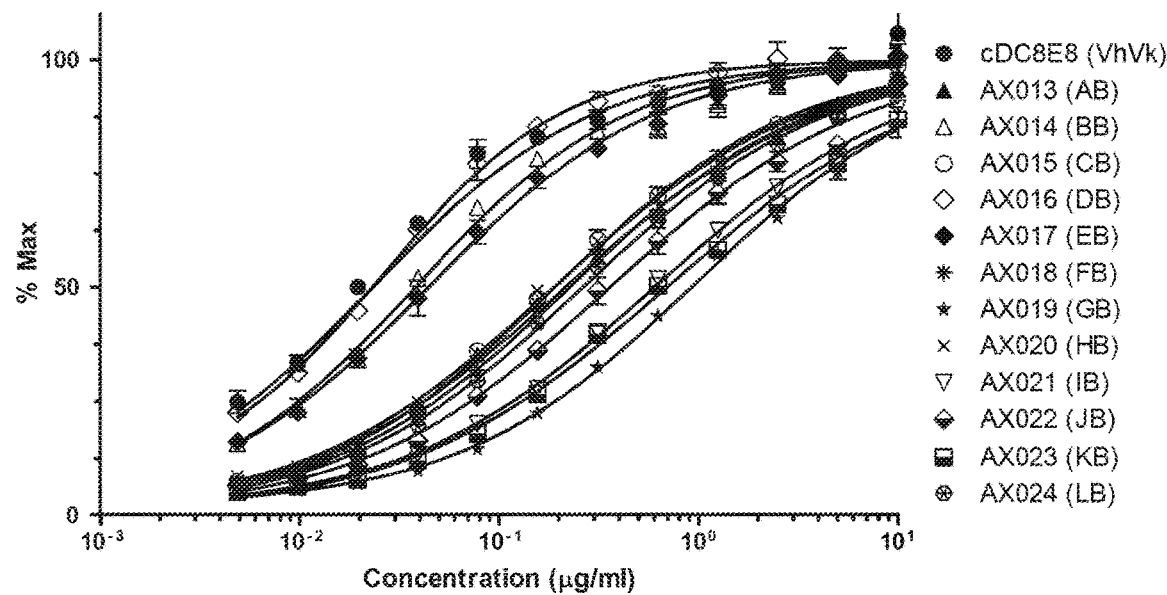
FIG. 12: Binding of humanized and chimeric DC8E8 to Tau 151-391/4R: RKB Versions.
Figure 13:
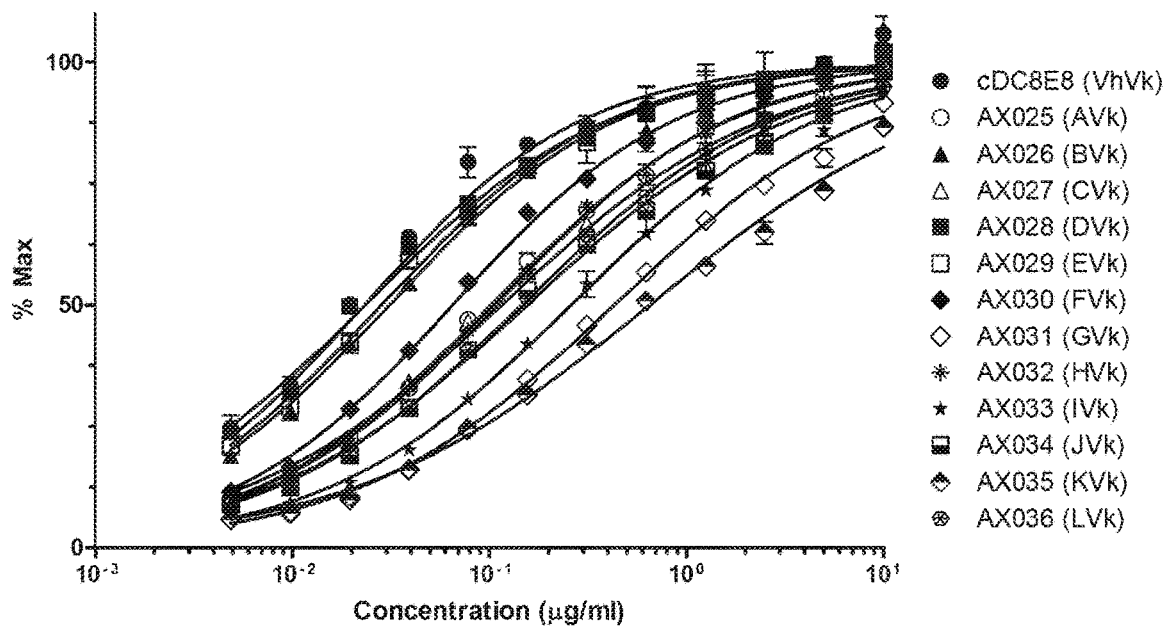
FIG. 13: Binding of humanized and chimeric DC8E8 to Tau 151-391/4R: Vk Versions (with chimeric light chain).

Further versions of the humanized heavy chain were synthesized, each with a single back-mutation, and were tested for binding by ELISA. Results for the IgG4 versions are shown and summarized in FIGS. 11, 12, and 13. Versions of the antibody having RHB, RHD and RHE were consistently better, with either of the humanized light chains (RKA and RKB) or chimeric light chain (cDC8E8). As the RHD and RHE versions contain only a single murine back-mutation, as opposed to the 11 murine back-mutations in version RHB, these two versions were chosen as possible lead candidates, in conjunction with the RKA light chain version (no murine back-mutations). It was surprising that these back-mutants would have been sufficient to restore binding affinity to the humanized antibodies. Combining RHD and RHE mutations (version RHM) did not result in a marked improvement in pathological tau-binding properties, relative to each individual mutation.

Figure 14:
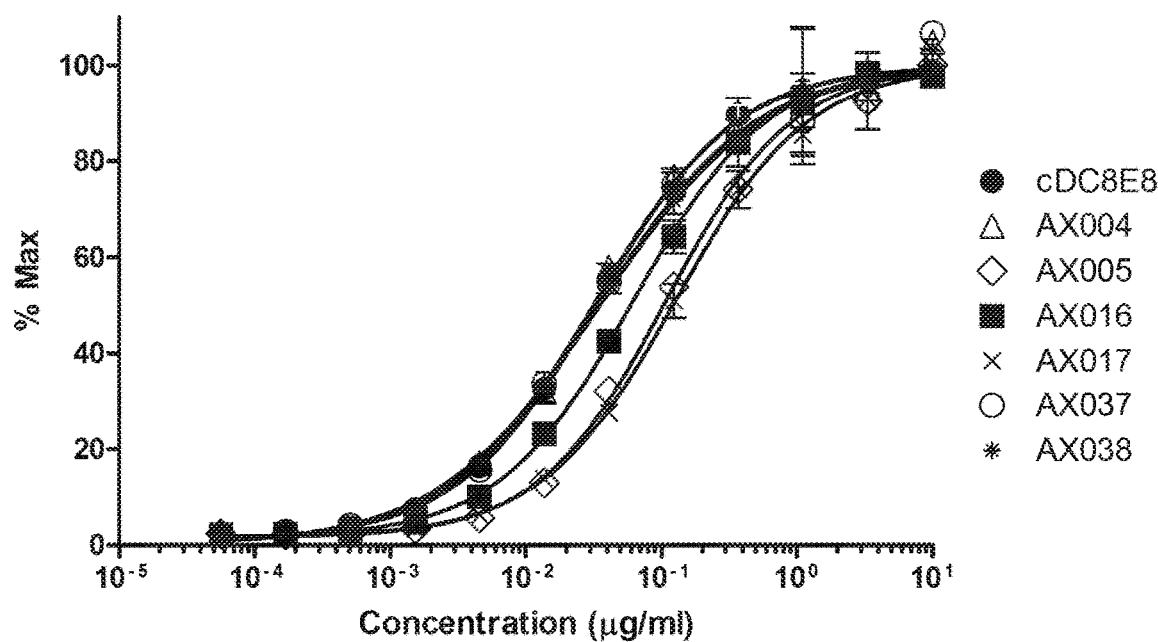
FIG. 14: Binding of humanized and chimeric DC8E8 to Tau 151-391/4R: RHM Versions.

In light of the results described above, a heavy chain version (RHM) containing both murine back-mutations present in RHD and RHE was generated by site-directed mutagenesis. FIG. 14 shows the Tau protein 151-391/4R binding of the RHM versions of the humanized DC8E8 antibody, and indicates that the affinity for the protein is no better than the lead candidate, AX004 (RHD/RKA).

Thermo Stability of Humanized Candidate Antibodies to High Temperatures

Figure 15:
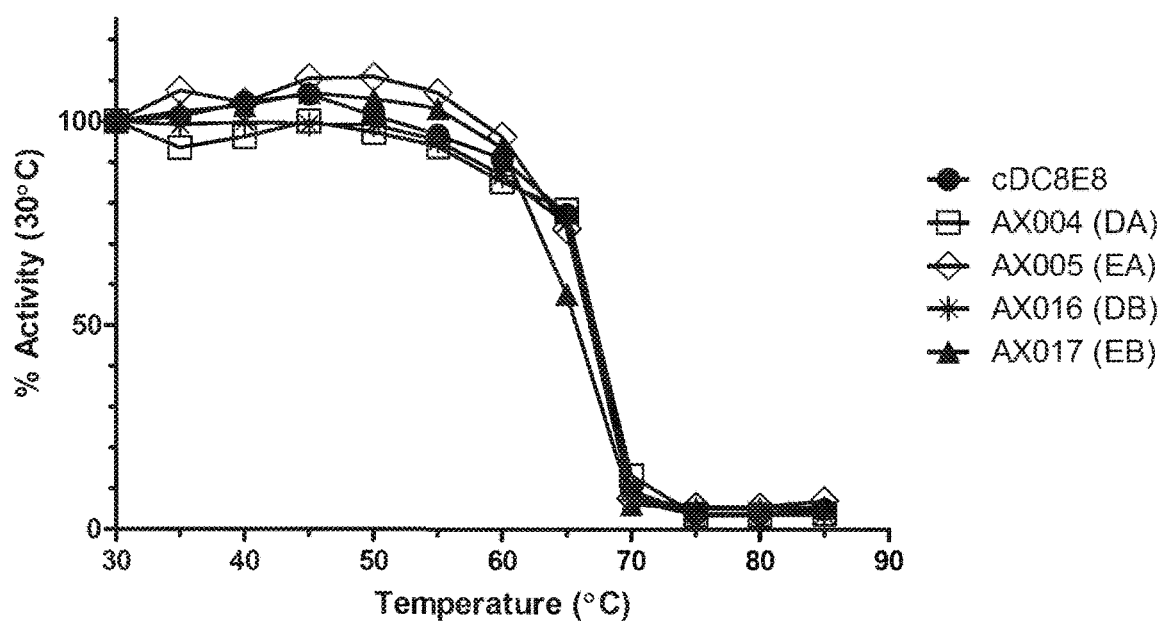
FIG. 15: Thermal stability of candidate humanized DC8E8 antibodies: Purified antibodies were heated for 10 min at the indicated temperature, then cooled to 4° C. before performing the Tau Binding ELISA.

The aim of this experiment is to compare the thermo stability of the humanized antibodies. When subjected to higher temperatures, varying from 30° to 85° C. for 10 minutes, cooled to 4° C. and used in an Binding ELISA assay at the EC80 concentration of each candidate. All the antibodies tested appear equally stable (FIG. 15), all becoming inactive only at 70° C., but without any untoward effect on tau-binding properties before then.

Determination of Humanized Candidate Antibodies Tm

Figure 16:
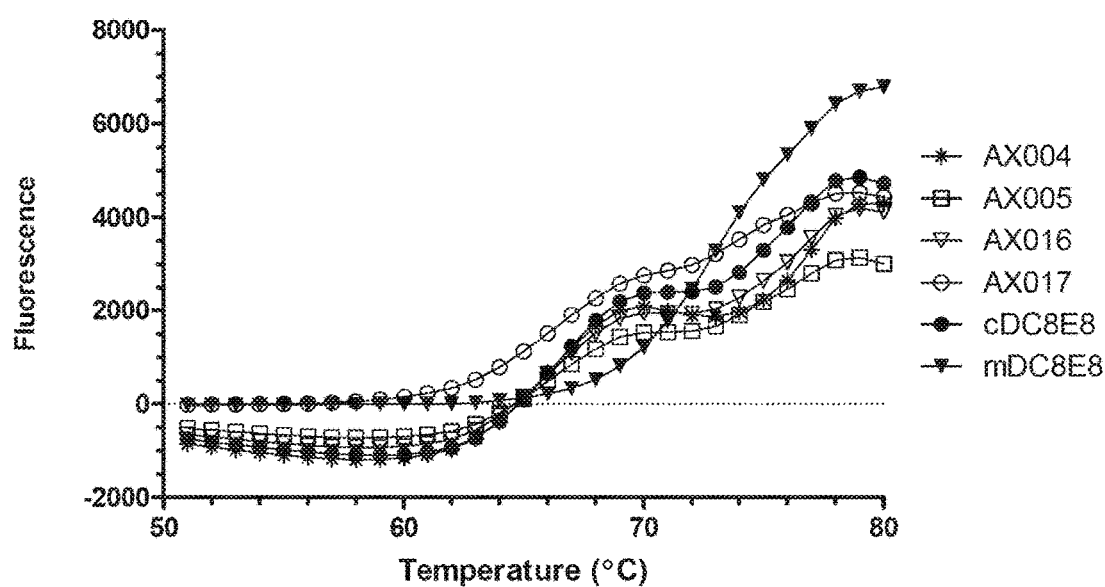
FIG. 16: Thermal shift analysis of the purified humanized candidate DC8E8 antibodies: Determination of the purified candidate antibodies Tm and comparison to chimeric and murine DC8E8.
Figure 17:
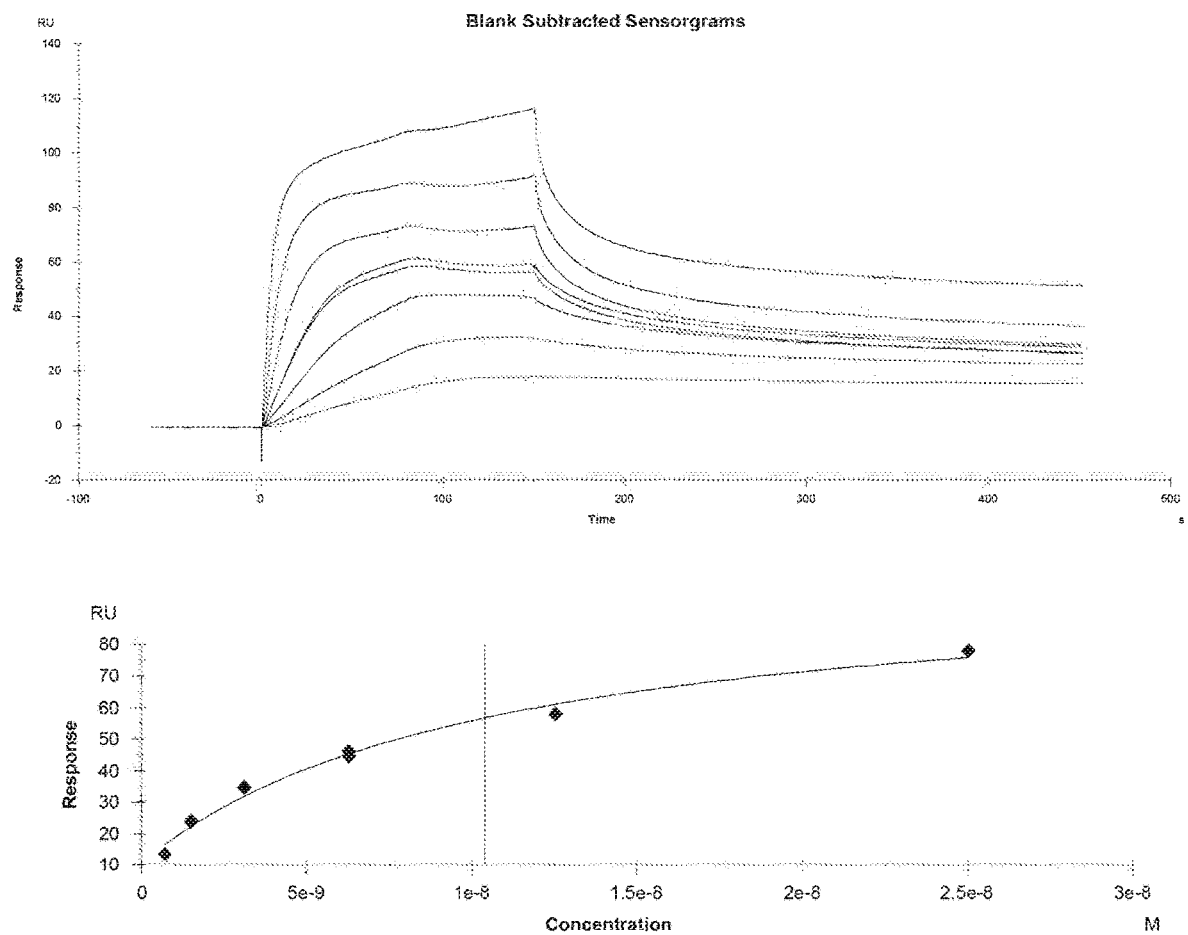
FIG. 17: Binding kinetics of DC8E8 antibodies analysed by surface plasmon resonance: KD determination: Murine DC8E8.
Figure 18:
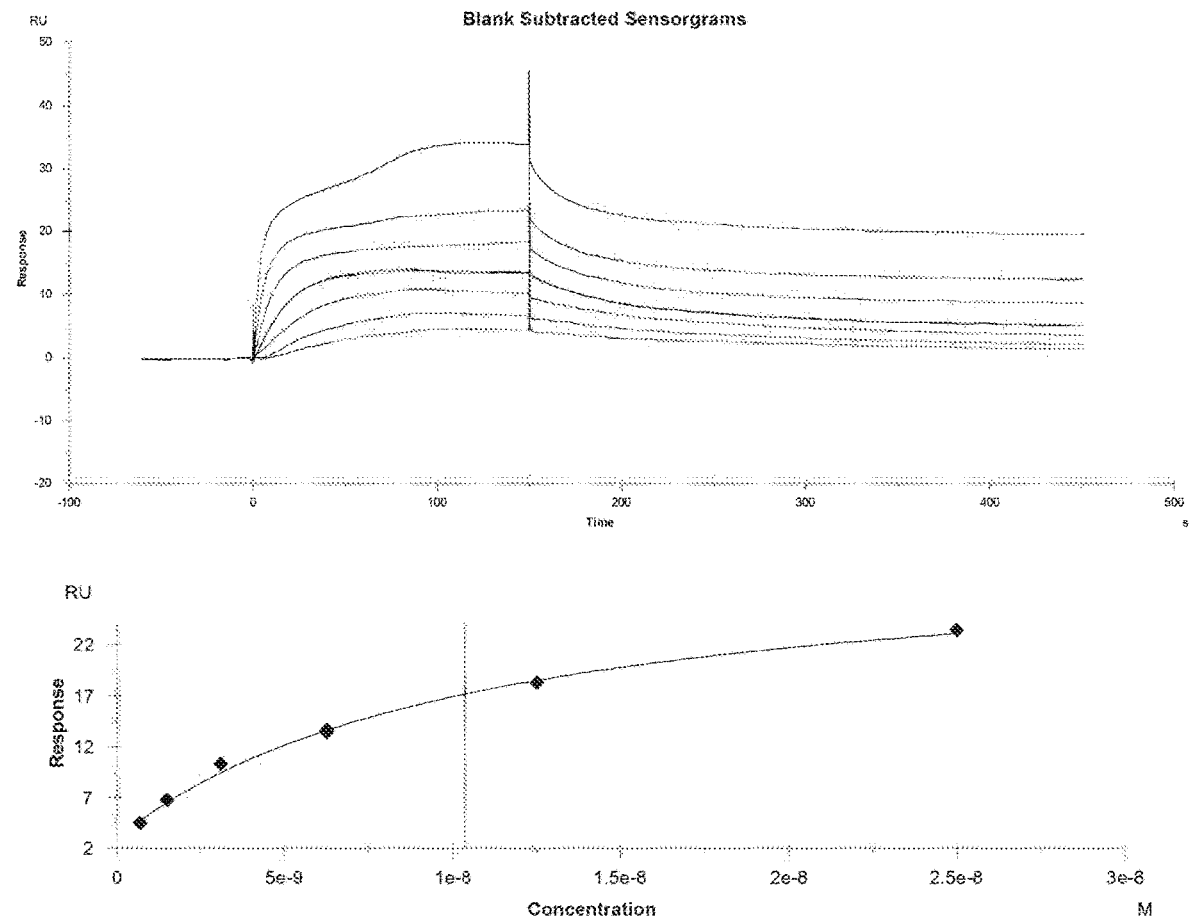
FIG. 18: Binding kinetics of DC8E8 antibodies analysed by surface plasmon resonance: $K_D$ determination: Chimeric DC8E8
Figure 19:
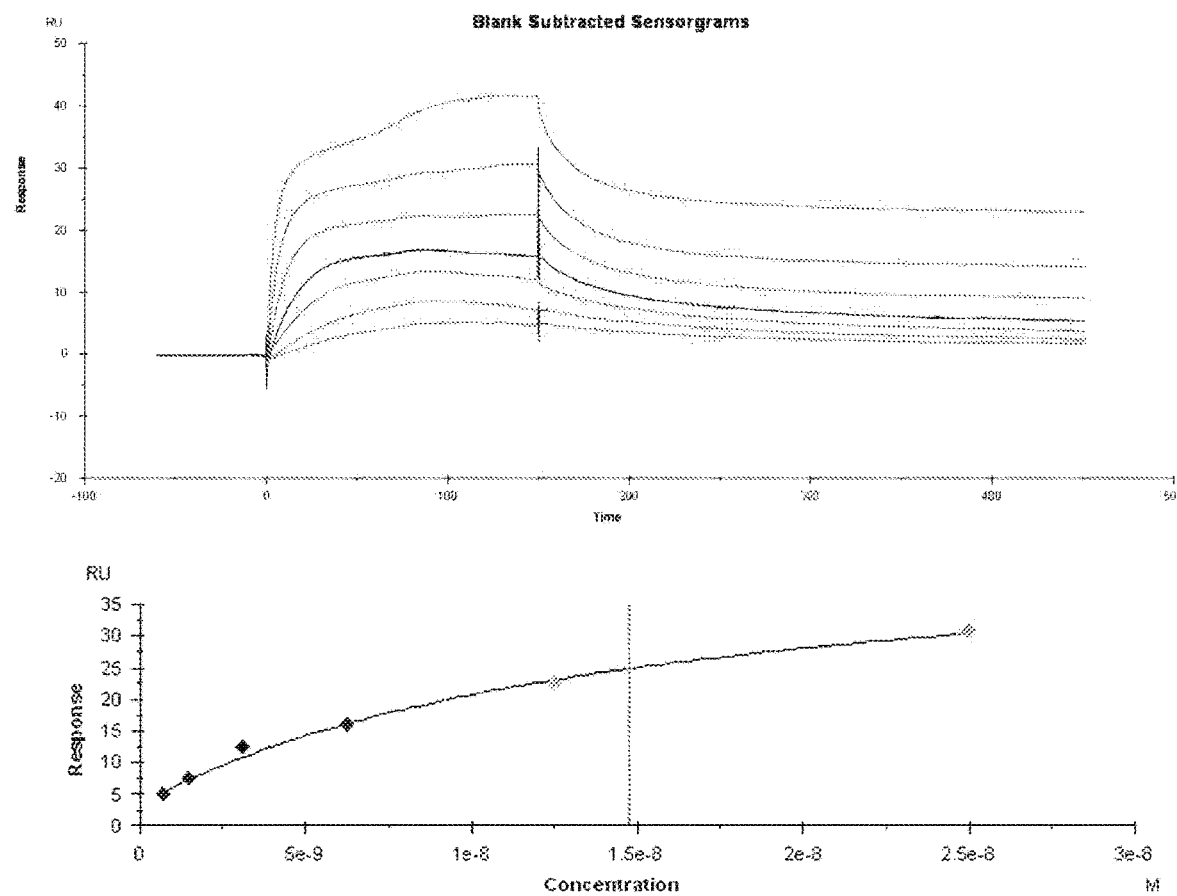
FIG. 19: Binding kinetics of DC8E8 antibodies analysed by surface plasmon resonance: $K_D$ determination: Humanized DC8E8 RHD/RKA (AX004)
Figure 20:
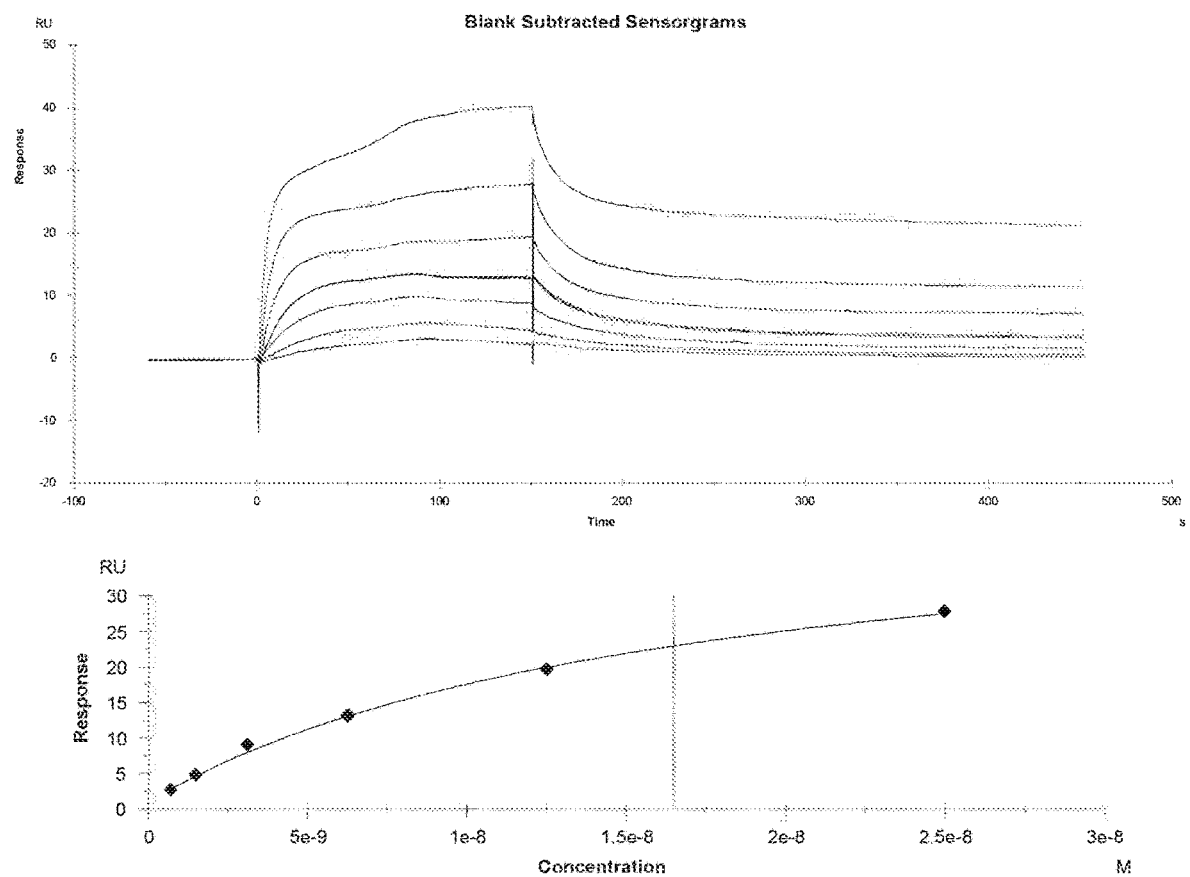
FIG. 20: Binding kinetics of DC8E8 antibodies analysed by surface plasmon resonance: $K_D$ determination: Humanized DC8E8 RHE/RKA (AX005)
Figure 21:
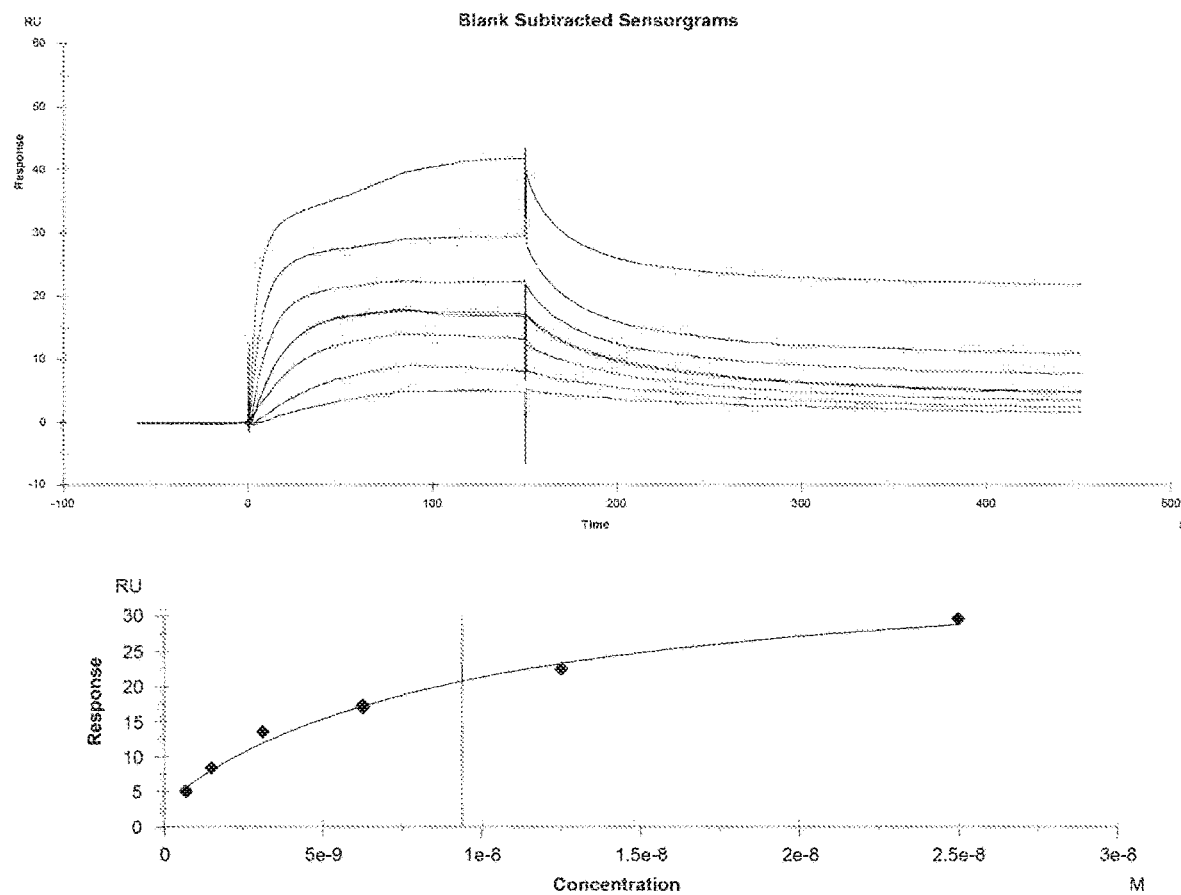
FIG. 21: Binding kinetics of DC8E8 antibodies analysed by surface plasmon resonance: $K_D$ determination: Humanized DC8E8 RHD/RKB (AX016)
Figure 24A:
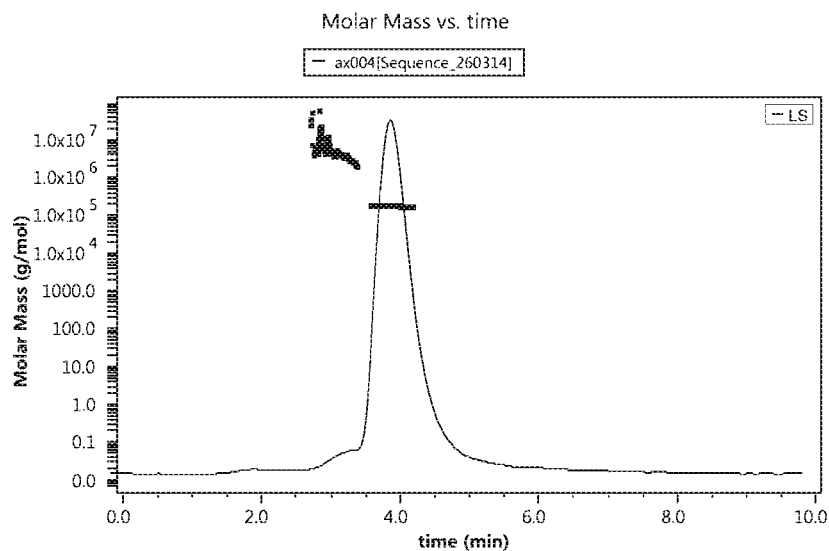
FIGS. 24A-24D: Fully humanized antibody candidates aggregation analysis.
Figure 24B:
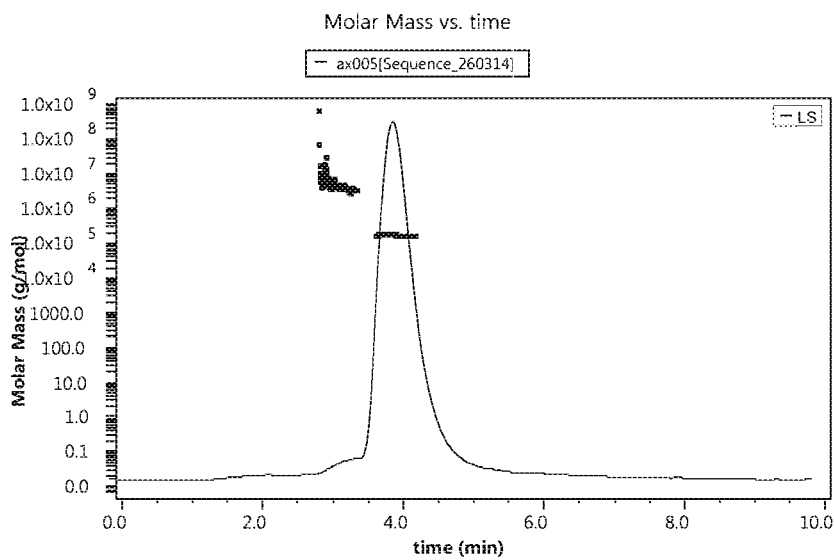
Figure 24C:
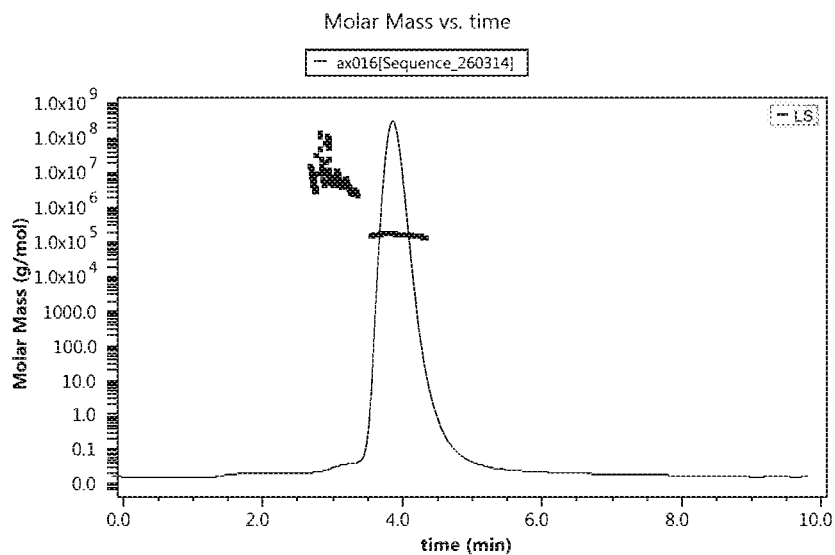
Figure 24D:
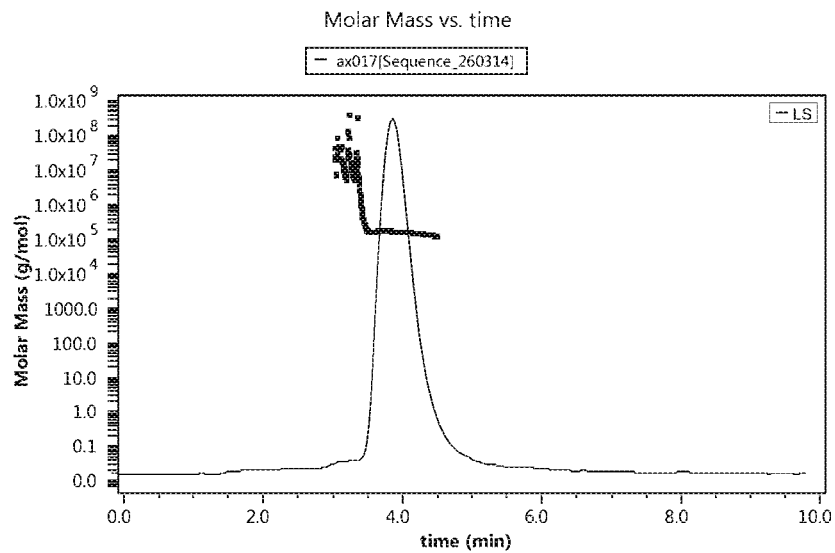

In order to determine the melting temperature of the lead antibodies AX004 (DA), AX005 (EA), AX016 (DB) and AX017 (DE), the humanized, chimeric, and mouse antibodies were purified in a 2-step affinity chromatography and gel filtration system (as described in Example 4) and tested in a thermal shift. This thermal shift assay is a microplate binding assay for monitoring thermal melting curves. The method uses an environmentally sensitive dye SYPRO Orange, whose protein binding properties increase with denaturation of the protein. Therefore, upon heat-induced denaturation of the analyzed protein the binding of the dye increases and reaches maximum when the protein is fully denatured/unfolded. The fluorescence intensity plotted as a function of temperature thus generates a typical sigmoid curve, where inflection point (half maximal intensity) corresponds to the melting temperature (Tm) of the protein Samples were incubated with a fluorescent dye (Sypro Orange) for 71 cycles with 1° C. increase per cycle in a qPCR thermal cycler. Tm for the chimeric and the four humanized antibodies are indicated in FIG. 16 and confirm the results obtained in the thermo stability assay: all of the candidate antibodies have very similar Tms (69-70° C.) and are similar to those of the chimeric antibody (70° C.) but slightly lower than that for the mouse (73° C.) antibody.

Affinity of Humanized Candidate Antibodies

Antibody affinity determination was carried out by SPR analysis using a Biacore T200. Anti-human IgG (GE Healthcare, cat. no. BR-1008-39) or anti-murine IgG (GE Healthcare, cat. no. BR-1008-38) was covalently immobilized to a CM5 chip (Cat. no. BR-1005-30) to the point of saturation and in accordance with the manufacturer's instructions. The antibodies mouse DC8E8, chimeric DC8E8, AX004, AX005, AX016 and AX017 were diluted in HBS-EP buffer [0.01 M HEPES pH 7.4, 0.15 M NaCl, 3 mM EDTA, 0.005% v/v Surfactant P20, GE HEalthcare] and immobilized by affinity binding to a level of between 144 and 177 RU. Recombinant monomeric tau 151-391/4R (in PBS saturated with Argon) was diluted in HBS-EP, in concentrations ranging from 20 nM to 0.312 nM in doubling dilutions and then injected at a flow rate of 100 µL/min. Association time was set at 150 sec and disassociation time 300 sec. Tau concentrations were chosen empirically in order to obtain curvature during the association phase. The kinetics of binding/dissociation was initially analyzed according to the 1:1 interaction model using BIAcore T200 evaluation software package 2.0.

Sensograms are shown in FIGS. 17-22. Unfortunately, due to the biphasic nature of the dissociation phase, and some evidence of extra binding during the association phase, it was not possible to analyze the kinetics. The data shown was obtained using a Steady State Analysis. Both the murine and chimeric DC8E8 show an affinity of approximately 10 nM. The lead humanized antibodies show similar affinities, ranging from 9 mM (RHD/RKB) to approximately 16 nM (RHE/RKA), summarized in FIG. 23. These results suggest that the humanization has successfully retained the binding activity within the desired parameters.

Aggregation of Humanized Candidate Antibodies

Aggregation is considered a serious problem in drug development, as aggregation may lower yield during production, limit shelf-life and result in reduced potency in patients due to increased immunogenicity. Antibody samples were injected at 0.4 mL/min into a size exclusion column in an HPLC system and analyzed by multi-angle light scattering to determine the absolute molar masses and check for aggregation (see FIGS. 24A, 24B, 24C, and 24D). All variants show no signs of aggregation with an average molecular weight ranging from 160-169.8 kDa, which is the expected range for an IgG monomer in this analysis setup. All samples are monodispersed (Mw/Mn<1.05). The mass recoveries are between 99.6-99.9% (calculated mass over injected mass), which indicates good protein recovery and that the samples do not seem to stick to the column or contain insoluble aggregates, which would be retained by the guard column. Overall the data suggest there are no aggregation concerns in any of the anti-DC8E8 antibody samples analyzed.

Solubility of Humanized Candidate Antibodies

Figure 25:
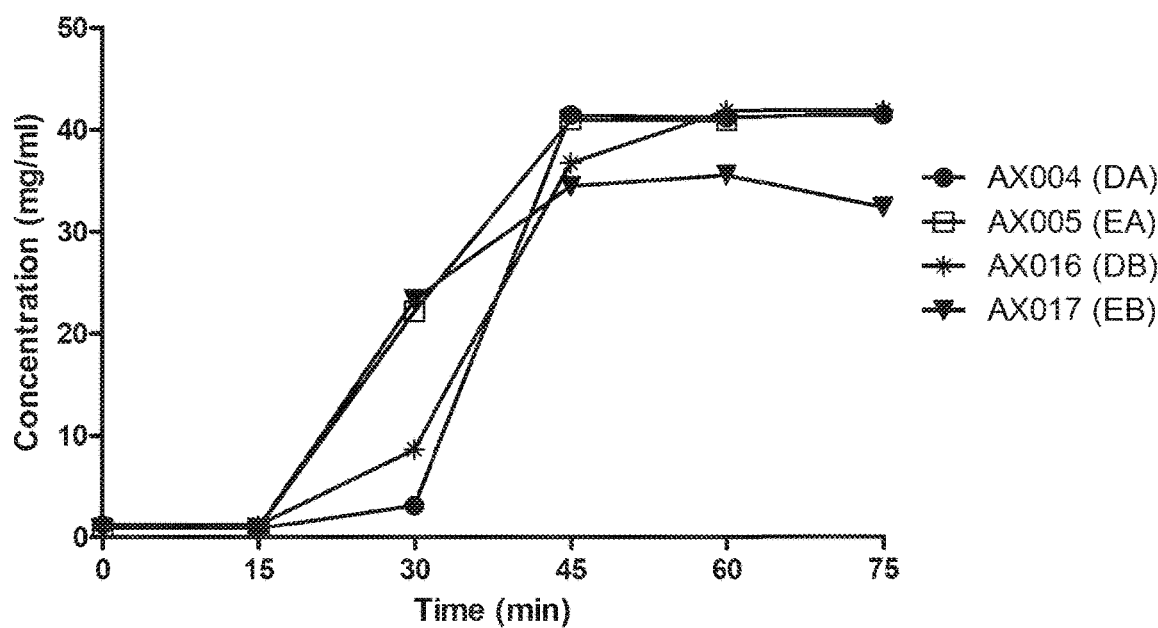
FIG. 25: Purified humanized antibody candidates of DC8E8 assessed for solubility: Solubility Profile during concentration.
Figure 26:
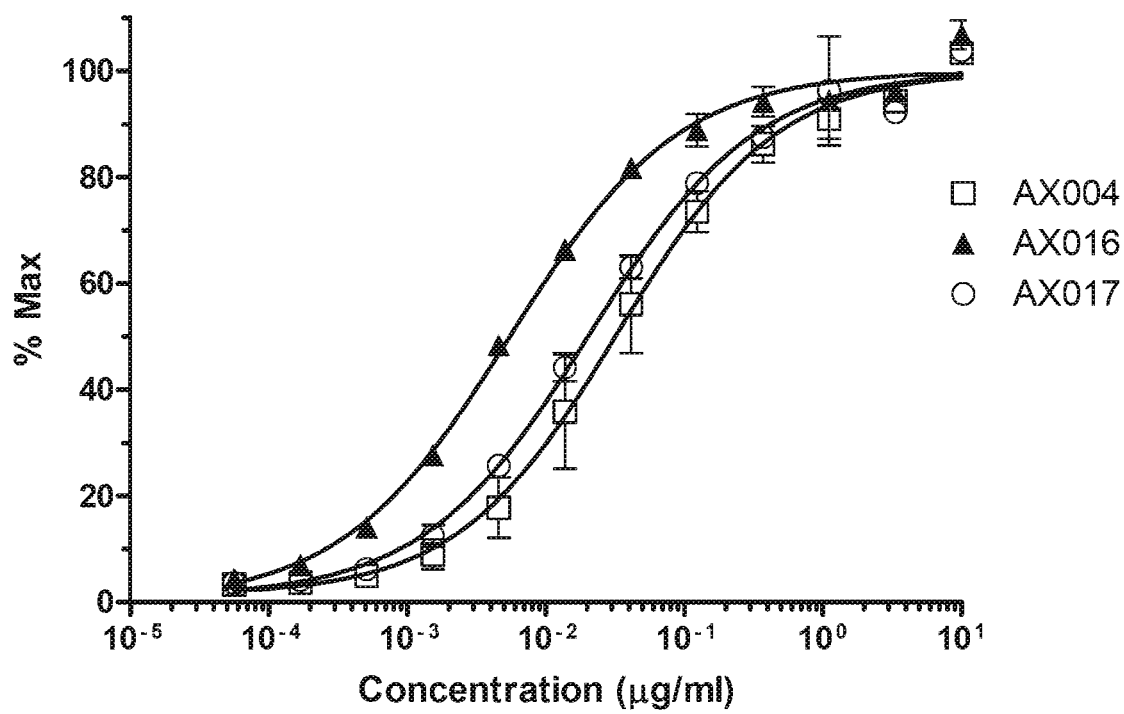
FIG. 26: Purified humanized antibody candidates of DC8E8 assessed for solubility: Solubility Profile during concentration: Binding activity after concentration.

The purified candidate antibodies were concentrated using solvent absorption concentrators (MWCO 7500 kDa) and the concentration measured at timed intervals. All of the samples were concentrated to between 35 and 41 mg/ml without apparent precipitation, and tested in Binding ELISA that showed that none had lost binding potency to Tau Peptide (FIGS. 25 and 26). The data suggest that the antibodies are not prone to precipitation at concentrations up to at least 35 mg/ml.

Freeze/Thaw Stress Analysis of Candidate Antibodies

Figure 27:
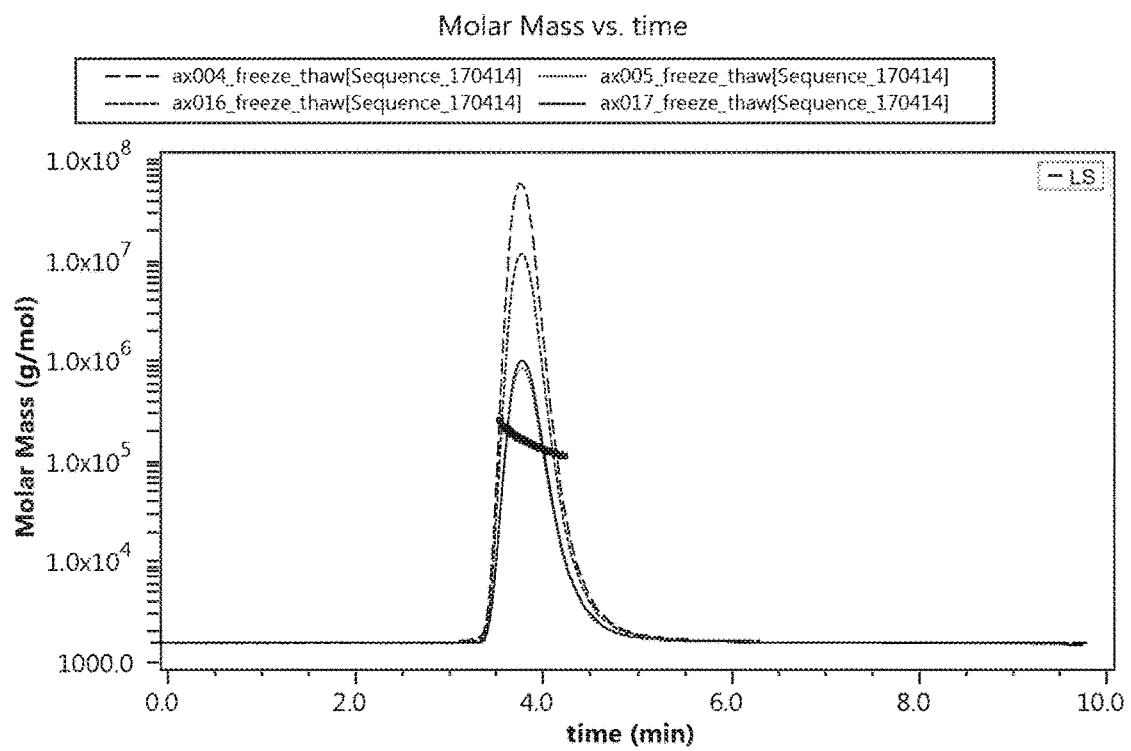
FIG. 27: Freeze/thaw stress analysis of humanized candidate antibodies.
Figure 28A:
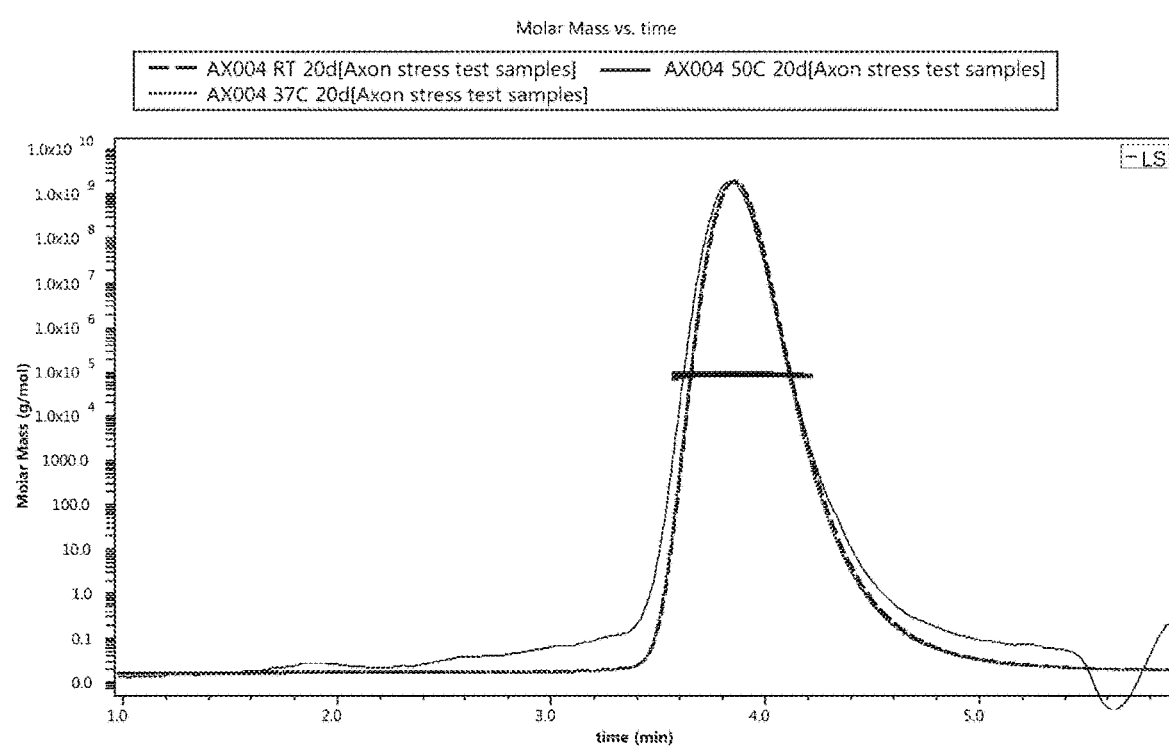
FIGS. 28A-28D: Heat induced stress analysis of fully humanized antibody candidates.
Figure 28B:
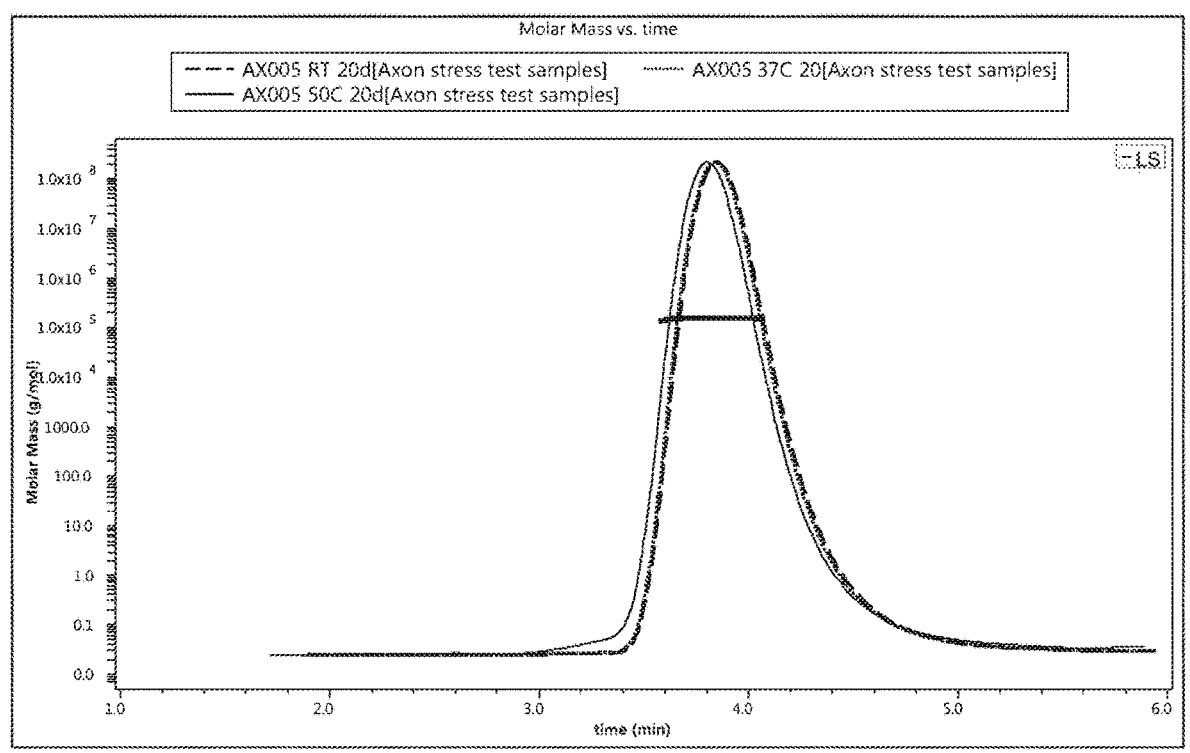
Figure 28C:
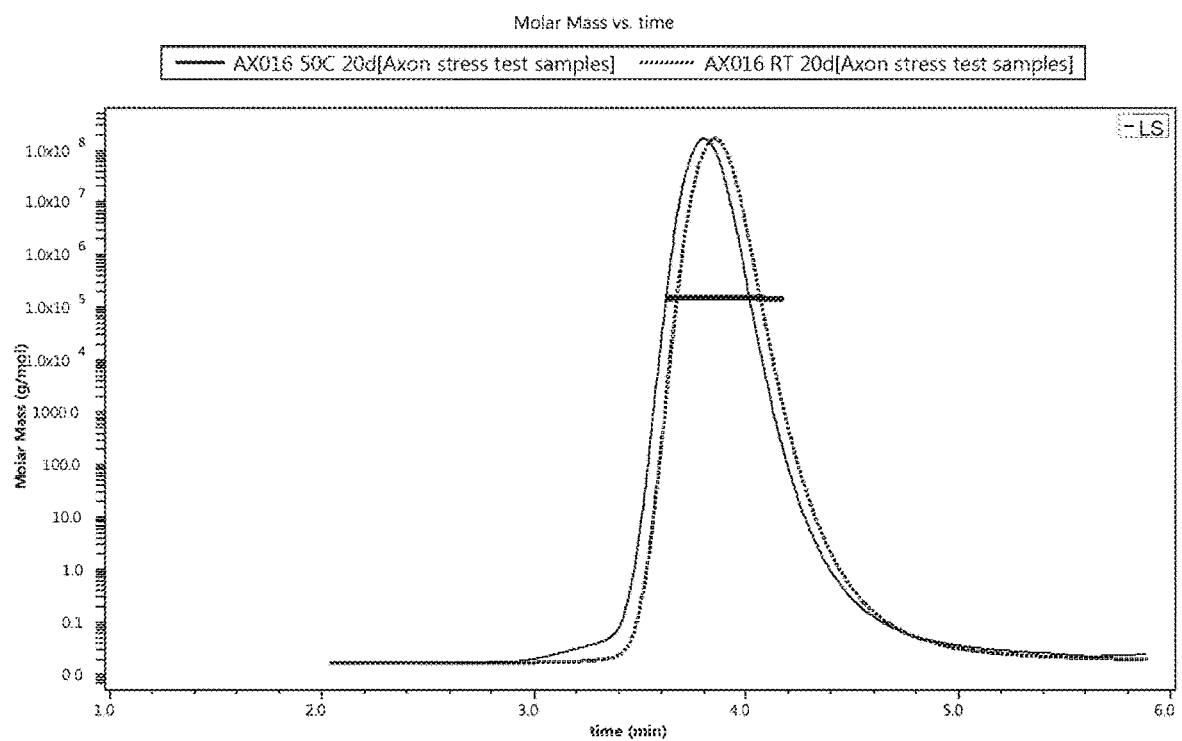
Figure 28D:
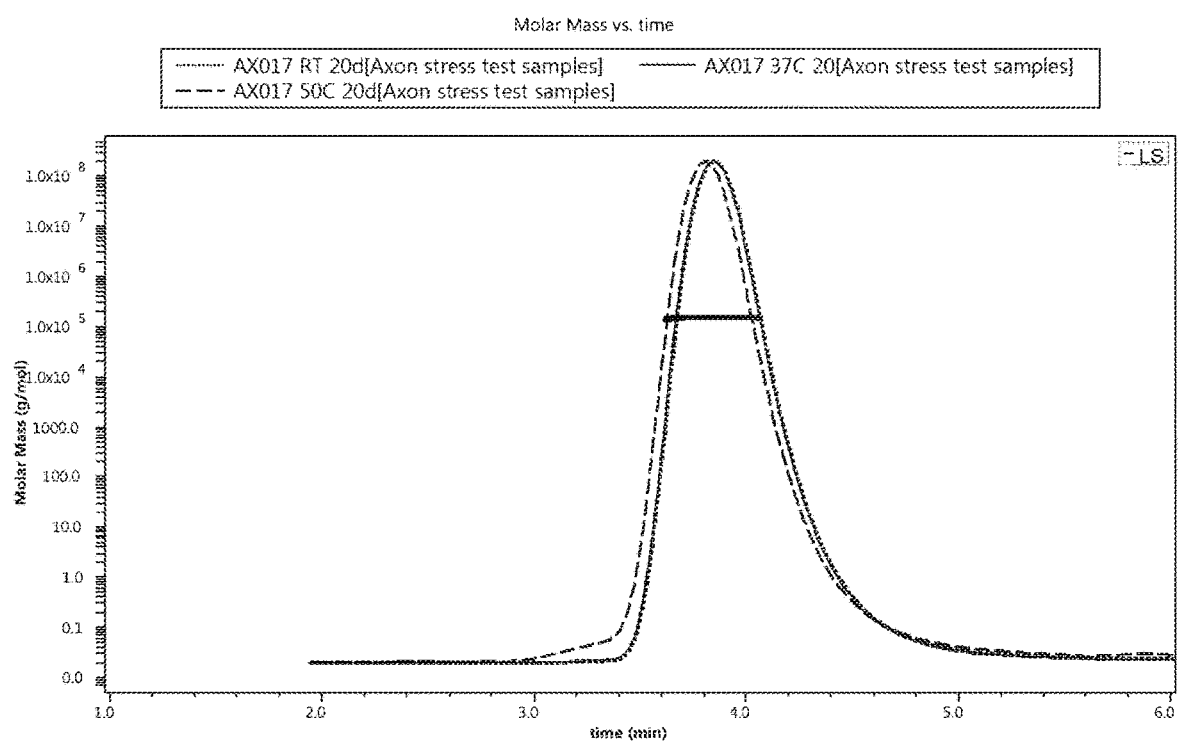

Samples of the purified candidate antibodies were subjected to 10 cycles of 15 minutes at −80° C. followed by thawing for 15 minutes at Room Temperature. Samples were then analyzed by SEC-MALS to analyze for aggregation (FIG. 27). The data suggests that freeze/thaw does not induce aggregation for all four antibodies tested. Overall, the data suggest there are no aggregation concerns in any of the anti-DC8E8 antibody samples analyzed.

Heat-Induced Stress Analysis of Candidate Antibodies

Samples of the purified candidate antibodies were heat exposed at a) Room Temperature, b) 37° C. and c) 50° C. for 20 days. Samples were then analyzed by SEC-MALS to analyze for aggregation (FIGS. 28A-28D). Overall, the data suggest there are no aggregation concerns in any of the anti-DC8E8 antibody samples analyzed.

Example 4: Preparation of Recombinant Full-Length Tau Isoform 2N4R and Misdisordered Tau 151-391/4R Recombinant tau proteins were generated from clone τ40 (Goedert, 1989), which was subcloned into the expression plasmid pET-17b (Novagen) and expressed in bacteria. The misdisordered tau 151-391/4R and all tau peptides are numbered according to the longest human tau isoform 2N4R, which is 441 amino acids in length and thus is also called tau441 (D'Souza, 2005). Production of tau proteins involved the following steps: a) expression of tau in bacteria; b) tau purification by ion exchange chromatography; c) tau purification by gel-filtration; d) concentration and storage of isolated tau;

a) Bacterial expression of human full-length tau 2N4R and misdisordered tau151-391/4R: expression plasmids were transformed into *Escherichia coli* production strain BL21(DE3). Bacterial cells containing the appropriate expression plasmid were cultivated and induced as described in "Molecular Cloning: A Laboratory Manual" by Sambrook and Russell (2001). A single colony of BL21(DE3) bacteria, transformed with pET-17b plasmid driving expression of a tau protein or its fragment, were grown at 37° C. in 500 ml of Luria broth medium with 100 µg/ml ampicillin at 300 rpm and induced by the addition of isopropyl-β-D-1-thiogalactopyranoside (IPTG) to a final concentration of 0.4 mM. After further incubation at 37° C. for 3 hours, bacteria were collected by centrifugation at 3,000×g for 15 min at 4° C.

b) Cation-exchange chromatography purifications of the basic and neutral tau proteins (full-length tau isoforms and tau 151-391/4R) were done essentially as previously described (Krajciova et al., 2008). After expression, the bacterial pellets were resuspended in 10 ml of lysis buffer (50 mM 1,4-piperazinediethanesulfonic acid (PIPES) pH 6.9, 50 mM sodium chloride (NaCl), 1 mM ethylenediaminetetraacetic acid (EDTA), 5 mM dithiothreitol (DTT), 0.1 mM phenylmethylsulfonyl fluoride (PMSF), 5% (v/v) glycerol), quickly frozen in liquid nitrogen, and stored at −80° C. until used for purification of tau proteins. For tau protein purification, the frozen bacterial suspensions were quickly thawed and placed on ice. Bacterial cell walls were broken by sonication on ice by using Sonopuls HD 2200, tip TT-13 (Bandelin, Germany) set to 50% duty cycle, 50 W power output, 6 times for 30 s with 30 s pauses. The lysates were clarified by centrifugation (21,000×g for 15 min at 4° C.) and the supernates were filtered through a 0.45 µm membrane filter. Large-scale purification of the recombinant tau proteins was done at 6° C. using an ÄKTA-FPLC workstation (Amersham Biosciences, Sweden). The filtered lysates were loaded at a 3 ml/min flow rate onto a 5-ml HiTrap SP HP column (GE Healthcare, Uppsala, Sweden) equilibrated with the lysis buffer, and washed extensively with 60 ml of the lysis buffer until the baseline at 280 nm became stable. Bound tau proteins were eluted by a gradient (0-30% within 15 ml) of Buffer B (lysis buffer supplemented with 1 M NaCl). Individual 1 ml fractions were collected and analyzed by sodium dodecyl sulfate-polyacrylamide gel electrophoresis (SDS-PAGE). To remove nucleic acids, which copurify with positively charged tau proteins, the fractions containing tau protein were pooled and purified by a second cation-exchange chromatography step, using a 5-ml HiTrap SP HP column (GE Healthcare, Uppsala, Sweden) with a less steep gradient of Buffer B (0-30% in 45 ml).

c) In the final gel-filtration step of purification (the same for all tau proteins), pooled tau protein fractions obtained by ion exchange chromatography, were injected onto a gel-filtration column (HiLoad 26/60 Superdex 200 prep grade column, GE Healthcare) at 3 ml/min in either PIPES or Histidine lysis buffer for basic/neutral or acidic tau proteins, respectively, supplemented with 100 mM NaCl. Eluted tau proteins were pooled.

d) For tau protein concentration after gel-filtration purification, pooled fractions were diluted with 1.5 volumes of 2.5% glycerol, and loaded again on a HiTrap SP HP column (basic and neutral tau proteins) or on a HiTrap Q HP column (acidic tau proteins). The concentrated recombinant tau protein was then eluted from the column with a 1 M NaCl step gradient. Finally, the buffer was exchanged to phosphate-buffered saline (PBS, 8.09 mM disodium phosphate ($Na_2HPO_4$), 1.47 mM potassium dihydrogen phosphate ($KH_2PO_4$), 136.89 mM NaCl, 2.7 mM potassium chloride (KCl)) saturated with argon, using a 5 ml HiTrap Desalting column (GE Healthcare). Protein quantitation of purified samples was done using bicinchoninic acid (BCA) quantitation kits (Pierce, USA), with bovine serum albumin (BSA) as a standard. Tau proteins were aliquoted into working aliquots, snap-frozen in liquid nitrogen, and stored at −70° C.

Example 5: Properties of Chimeric DC8E8 a/ Chimeric DC8E8 Displays Higher Affinity for Misdisordered Tau 151-391/4R than for Full Length Tau 2N4R.

The discriminatory capacity of chimeric DC8E8 between immunoreactivity with pathological tau and physiological tau was determined by ELISA and by surface plasmon resonance (SPR).

For ELISA and SPR experiments, mouse DC8E8 was purified from serum-free hybridoma supernate on a Protein G affinity column, as follows. The hybridoma supernate was adjusted to pH 7.5 by adding 0.2 volume of PBS and checking with pH paper strip (if necessary, pH is further adjusted by adding 4 M NaOH), the solution was precleared by centrifugation (20,000×g, 4° C., 10 minutes), filtered through a 0.45 µm membrane filter, and loaded onto a 5 ml Protein G Sepharose column (at a flow rate of 1-0.5 ml/min). DC8E8 was eluted from the column with 0.1 M Glycine-HCl, pH 2.7. Eluted fractions were immediately neutralized with 1M Tris-HCl pH 9.0. Pooled fractions were dialyzed against PBS, concentrated by ultrafiltration, and stored at −70° C. The concentration of the antibody was determined by measuring absorbance at 280 nm, using the formula c (mg/ml)=A280 nm/1.43.

The chimeric DC8E8 was expressed in Expi293 cells and purified from serum-free conditioned media by affinity chromatography and size-exclusion chromatography as described above for mouse DC8E8 with a few modifications. The cell culture medium was adjusted to pH 7.5, precleared by centrifugation, filtered through a 0.45 µm membrane filter, and loaded onto a 1 ml HiTrap MabSelect SuRe Protein A column, using Dulbecco PBS as binding and washing buffer. Chimeric DC8E8 mAb was eluted from the column with 0.1M sodium citrate pH 2.5 supplemented with 150 mM NaCl. Eluted fractions were immediately neutralized with 1M Tris-HCl pH 9.0. Pooled fractions were polished by size exclusion chromatography on the HiLoad 16/600 Superdex 200 pg column, Dulbecco PBS as running buffer. The concentration of the antibody was determined by measuring absorbance at 280 nm, using the formula c (mg/ml)=A280 nm/1.37.

For direct ELISA assays, mis-disordered tau151-391/4R or full length tau 2N4R were immobilized on ELISA plates (Nunc, MediSorp) at 5 µg/ml in PBS, 50 µl/well, and incubated overnight at 37° C. After blocking with PBS-0.05% Tween 20 (1 hr at 20-25° C.) to reduce nonspecific binding, the plates were incubated with 50 µl/well of three-fold serial antibody dilutions (concentration range of 10000 ng/ml-0.17 ng/ml) in the blocking buffer (PBS, 0.05% Tween 20) for 1 hr at 37° C. After incubation and washing, peroxidase-conjugated secondary antibody (anti-human Ig, Pierce, ThermoScientific) was diluted 1:4000 in PBS-Tween buffer and applied to the wells (50 µ/well) for 1 hr at 37° C. After washing, the reaction was developed for 20 min with colorburst blue solution (50 µ/well) as a peroxidase substrate and stopped with 50 µl of 2 M $H_2SO_4$. Absorbance was measured at 450 nm using a Multiscan MCC/340 ELISA reader (Labsystems). Readouts with an absorbance value of at least twice the value of the negative controls (PBS) were considered positive.

Figure 29A:
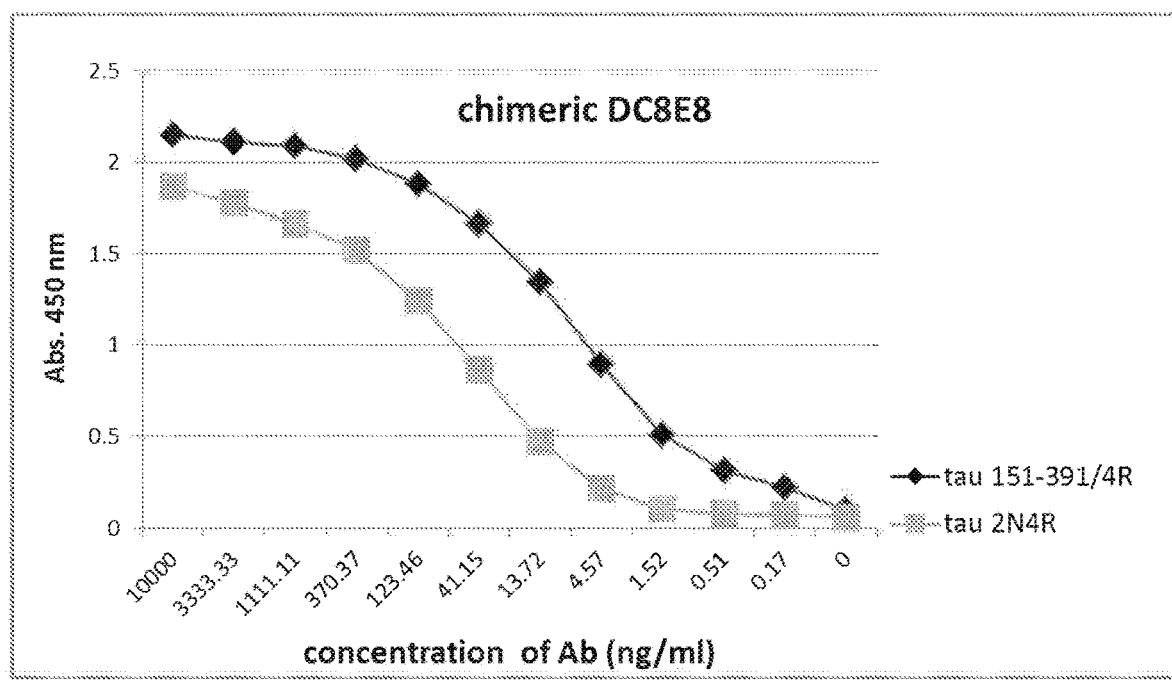
Figure 29B:
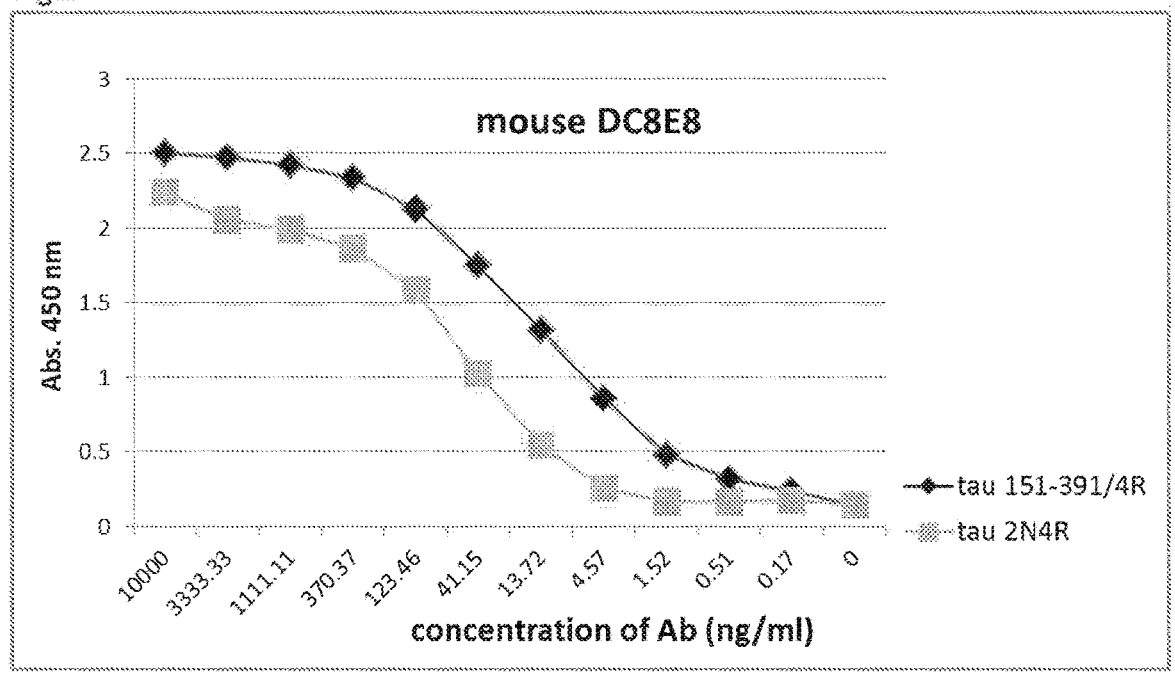

The analysis showed that chimeric antibody DC8E8 was able to discriminate between the misdisordered tau 151-391/4R and physiological tau 2N4R (FIG. 29A). Chimeric DC8E8 recognized the physiological tau 2N4R to a much lesser extent than it recognized the pathological/misdisordered tau 151-391/4R. Importantly, the immunoreactivity of chimeric DC8E8 was comparable with immunoreactivity of mouse DC8E8 (FIG. 29B). Both chimeric and mouse DC8E8 bound analyzed tau proteins (pathological and physiological tau) with similar ECK values as indicated in FIG. 29C. Together, these findings suggest that binding properties of chimeric DC8E8 are comparable with binding properties of original mouse DC8E8.

Surface plasmon resonance (SPR) is used for the detection and quantification of protein binding and for determination of the thermodynamic parameters of protein complexes (e.g., antibody-antigen complexes) by direct monitoring of the binding event in real time. This technology is routinely used to characterize both diagnostic and therapeutic antibodies (See, e.g., Karlsson and Larsson, Affinity Measurement Using Surface Plasmon Resonance, in Methods in Molecular Biology, Vol. 248: Antibody Engineering: Methods and Protocols. Edited by: B. K. C. Lo © Humana Press Inc., Totowa, N.J., (2008)).

A BIACORE3000 instrument with a CM5 sensor chip (Biacore AB, Uppsala) was used for the SPR assays. Amine-coupling reagents (EDC, NHS, ethanolamine pH 8.5), P20 detergent, and 10 mM sodium acetate pH 5.0 were obtained from Biacore AB. These experiments were done at 25° C. in PBS pH 7.4 with 0.005% of P20 (PBS-P) as the running buffer. For chimeric DC8E8, goat anti-human-Fc polyclonal antibody (SIGMA, Cat. no. 12136) was coupled at pH 5.0 via primary amines simultaneously in two flow cells to 5,000 RU (response units), one of which was used for reference measurement. For mouse DC8E8, analytical flow cell was coated with polyclonal anti-mouse antibody (No. Z 0420; DakoCytomation, Glostrup, Denmark).

In each analysis cycle, purified chimeric DC8E8 and mouse DC8E8 were separately captured in the analytical flow cell to reach an immobilization level of 200-250 RU. For determinations of equilibrium association binding constant ($K_A$) as well as for the determination of the kinetic rate constants (kON and kOFF), two-fold serial dilutions of either tau151-391/4R and physiological tau 2N4R (against which DC8E8 affinity was tested), or PBS-P as a control, were injected at a flow rate of 100 μl/min over the sensor chip. Kinetic binding data were double referenced as described by Myszka (1999) and fitted by BIA evaluation software 4.1 (Biacore AB) separately to obtain dissociation rate constant and association rate constant. Equilibrium association constant $K_A$ was obtained as a ratio of association and dissociation rate constants.

Figure 30:
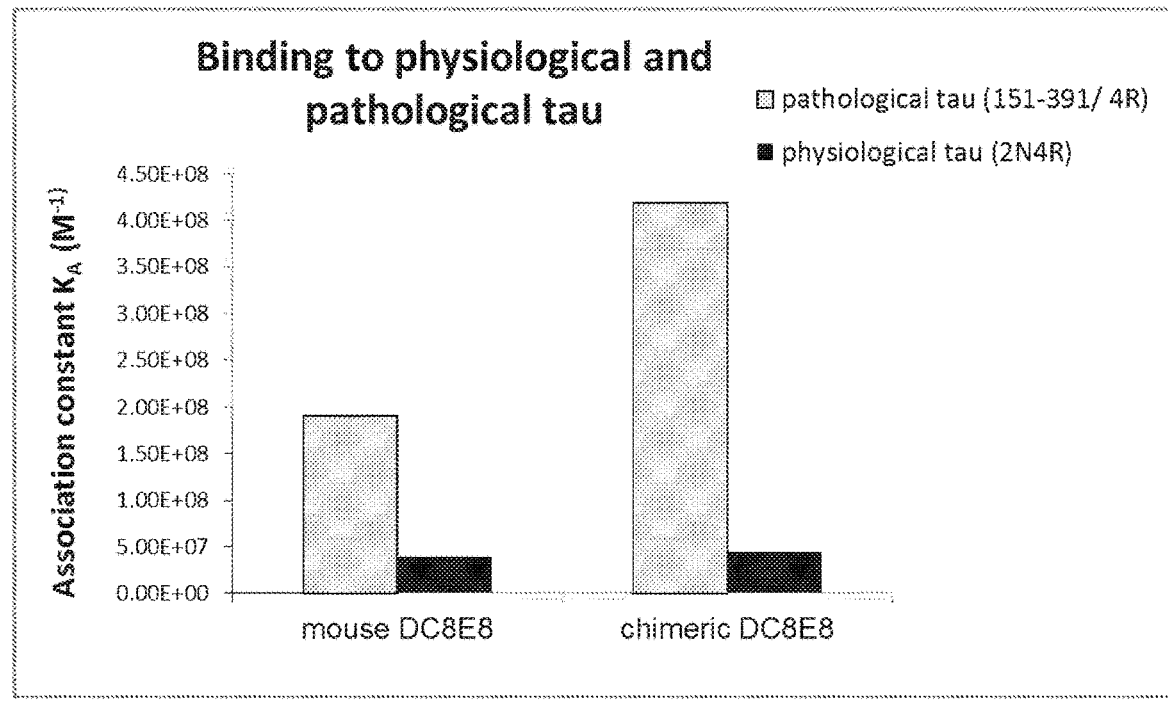
FIG. 30: Mouse and chimeric DC8E8 equilibrium association binding constants to misdisordered truncated tau 151-391/4R and full length physiological tau 2N4R were determined by surface plasmon resonance.
Figure 31A:
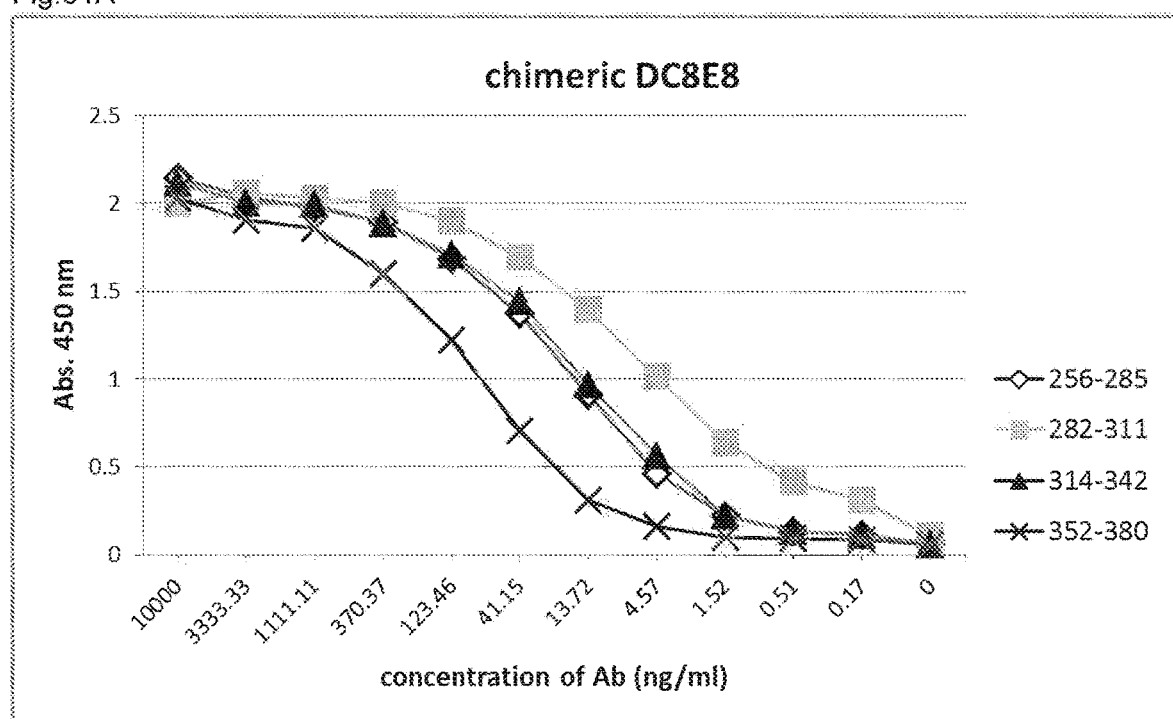
FIGS. 31A-31C: Binding of (FIG. 31A) chimeric DC8E8 and (FIG. 31B) mouse DC8E8 to tau peptides derived from repeat domains of protein tau, determined by ELISA.
Figures 31B, 31C:
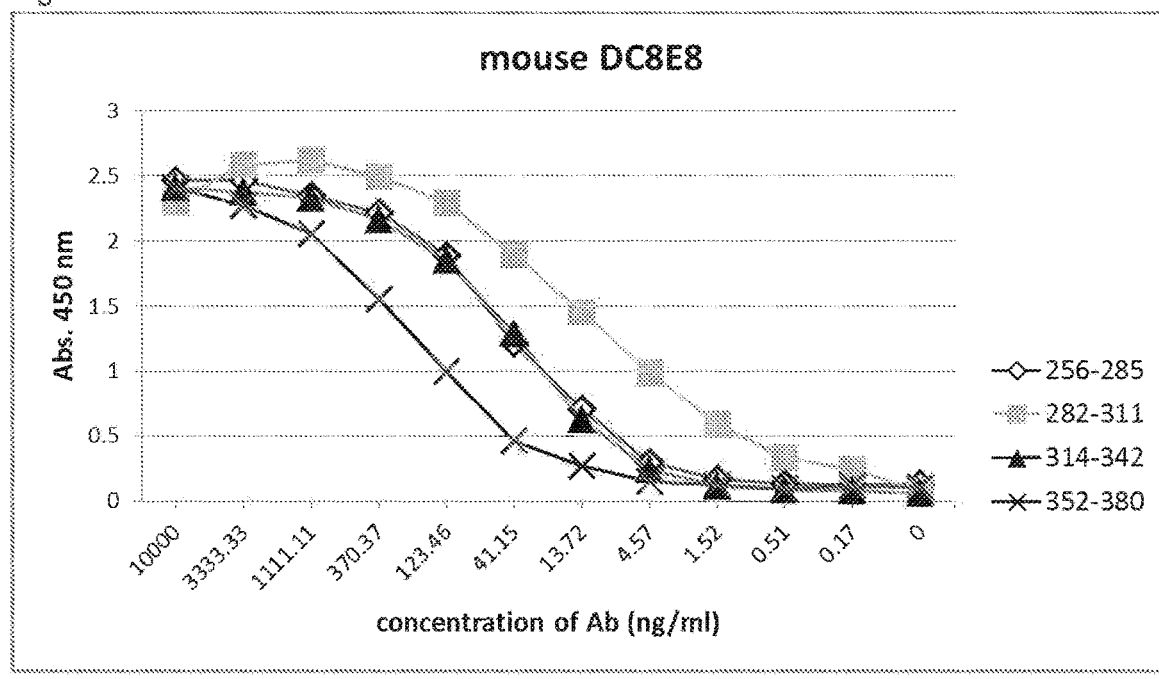

In order to quantify chimeric DC8E8's affinity for tested tau proteins, the association equilibrium binding constants ($K_A$) were determined for DC8E8 binding to the physiological, four repeat tau protein isoform 2N4R as well as to pathological, misdisordered tau 151-391/4R. Both tau proteins used for SPR were prepared as described in Example 4. Chimeric DC8E8 antibody discriminates between misdisordered tau151-391/4R protein and the physiological tau protein 2N4R (FIG. 30). The extent of discriminatory potency of chimeric DC8E8 is even slightly higher than that of the original mouse DC8E8 antibody. These results confirmed: (1) the specificity of humanized DC8E8 for the misdisordered form of tau, and (2) the selectivity of DC8E8 for misdisordered tau (i.e., disease or pathological tau) over the full-length tau (i.e., normal or physiological tau).

b/ Chimeric DC8E8 Binds Tau Peptides Each Carrying One of the Four DC8E8 Epitopes in the Repeat Regions of Microtubule-Binding Domain of Protein Tau Previous results showed that mouse DC8E8 has four binding sites or epitopes (267-273, 298-304, 329-335 and 361-367) on human tau, each of which is separately located within one of the repeats in the microtubule-binding domain of tau (WO/2013/041962, Kontsekova et al., 2014). With the aim to test the capability of chimeric DC8E8 to bind to any one of the four epitopes, tau peptides 256-285, 282-311, 314-342, 352-380 were synthetized by EZBiolabs (USA) with purity higher than 95%. Each of the peptides encompassed one of the four separate DC8E8 epitopes. Binding activity of chimeric DC8E8 to the tau peptides was measured by direct ELISA, as described in Example 5 a/. Chimeric DC8E8 bound all tested MTBRs-derived peptides (FIG. 31A), similarly to original mouse DC8E8 (FIG. 31B). Importantly, the highest immunoreactivity showed chimeric and mouse DC8E8 to peptide 282-311, which was derived from MTBRII and which comprises DC8E8 epitope within position 298-304. The immunoreactivity of chimeric antibody to additional tested peptides (256-285, 314-342, 352-380) was even slightly higher, than that of original mouse DC8E8, as indicate $EC_{50}$ values (FIG. 31C).

c/ Chimeric DC8E8 Inhibits Pathological Tau-Tau Interaction

An in vitro tau fibrillization assay was used to determine whether chimeric antibody had an inhibitory effect on pathological tau-tau interactions. The assay is based on an intrinsic property of tau proteins, namely their ability to undergo a conformational change upon interaction with polyanions, such as the sulfated glycosaminoglycan heparin. This altered conformation on one tau molecule further leads to its pathological interactions with another tau molecule, stabilization of the tau-tau complex through formation of cross-β sheet structures in the microtubule binding regions of the interacting tau molecules, and, lastly, formation of Alzheimer's disease-like paired helical filaments (PHFs) (Skrabana, R., Sevcik, I., Novak, M. (2006). Intrinsically disordered proteins in the neurodegenerative processes: formation of tau protein paired helical filaments and their analysis. Cell Mol Neurobiol 26, 1085-1097). The formation of the beta-sheet-rich structures can be detected by fluorescent dyes, like Thioflavin T (Friedhoff P, Schneider A, Mandelkow E M, Mandelkow E. Rapid assembly of Alzheimer-like paired helical filaments from microtubule-associated protein tau monitored by fluorescence in solution. Biochemistry 37(28): 10223-30 (1998)).

Figure 32:
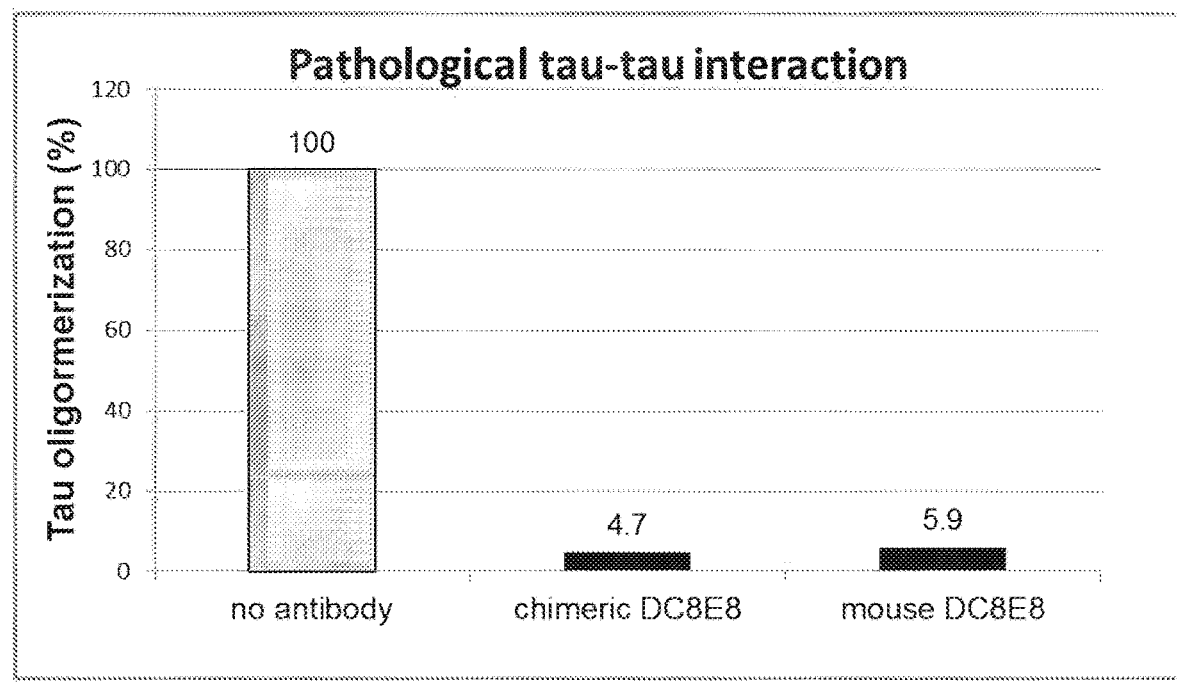
FIG. 32: Chimeric DC8E8 inhibits pathological tau-tau interaction in in vitro tau fibrillization assay. Misdisordered truncated tau 151-391/4R was induced by heparin to undergo a conformational change and fibrilize, extent of which was measured by Thioflavin T fluorescence; chimeric DC8E8 was tested for its ability to prevent the pathological conformational change and tau-tau interaction.
Figure 33A:
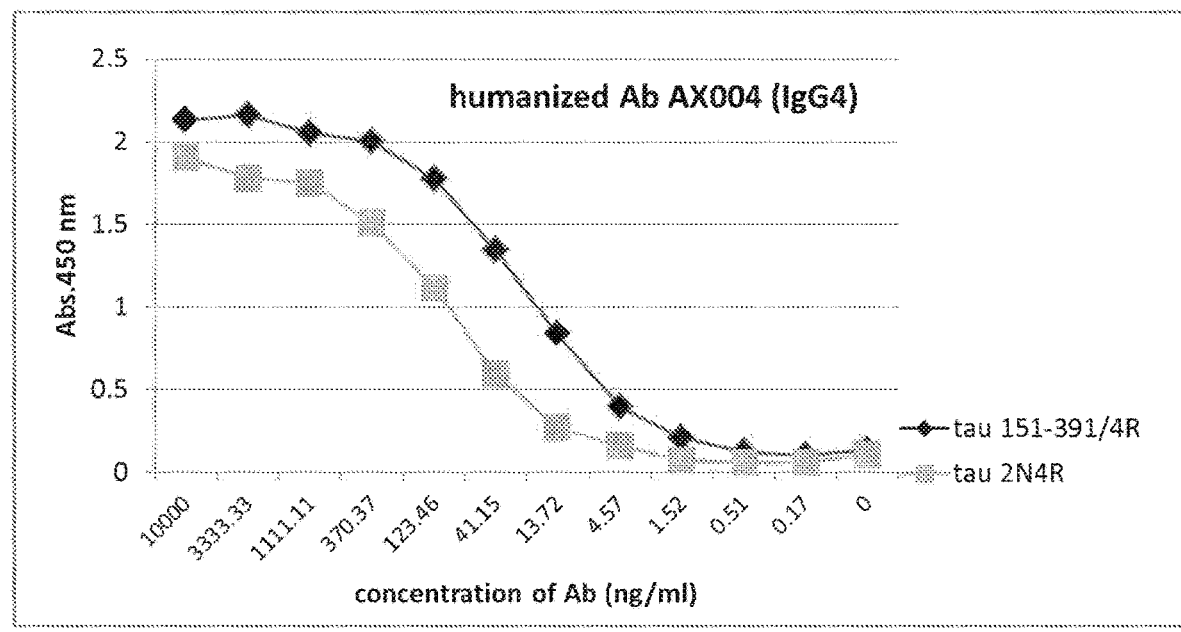
Figure 33B:
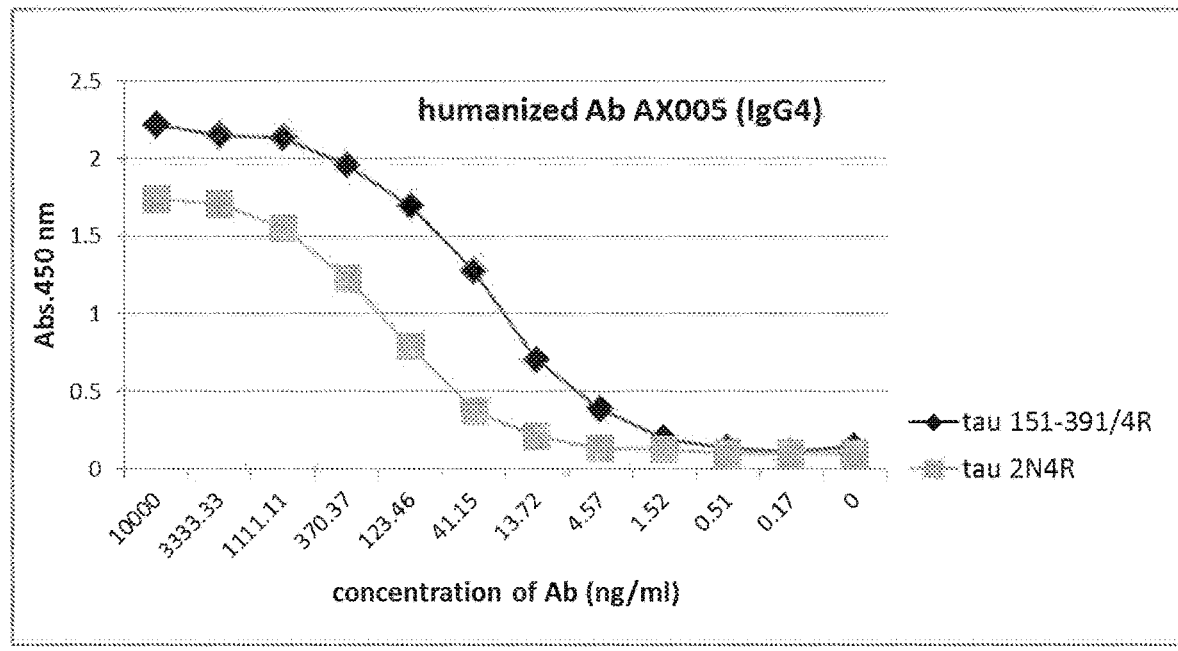
Figure 33C:
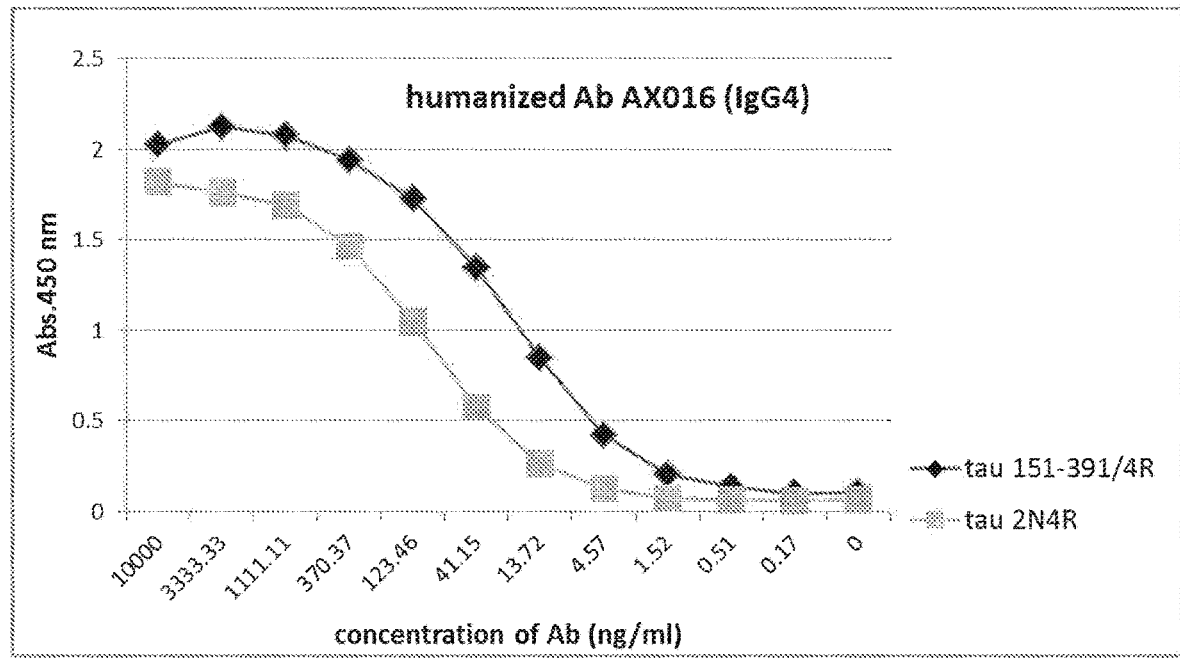
Figure 33D:
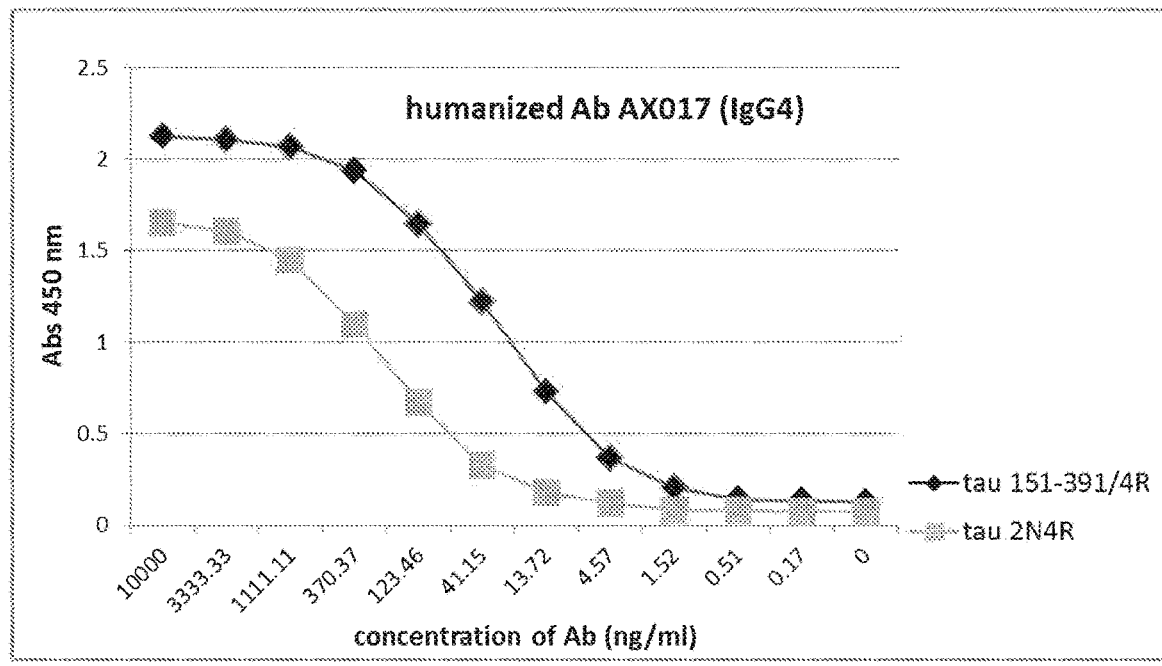
Figure 33E:
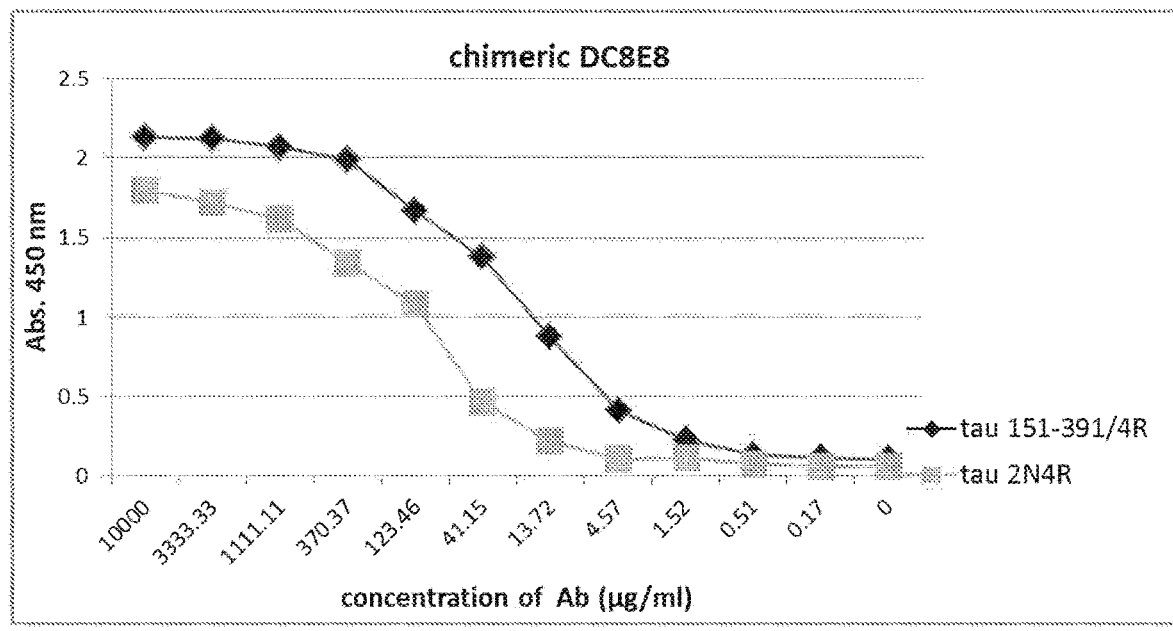

For in vitro tau fibrillization assay, mouse and chimeric DC8E8 were purified by methods described in Example 5. The assay to measure the effect of chimeric DC8E8 on pathological tau-tau interactions was setup in PBS (filtered through a 0.2 μm filter) containing: 10 μM (final concentration) of the misdisordered tau 151-391/4R; 10 μM heparin (Heparin sodium salt from porcine intestinal mucosa, ≥150 IU/mg, dry basis, average molecular weight 6000 Da, from SIGMA); and 12.5 μM (final concentration) Thioflavin T. Each reaction (50 μl final volume) was incubated for 20 h at 37° C. in sealed black solid polystyrene plates (384 wells, Greiner BioOne). Thioflavin T fluorescence was measured using a fluorescence reader (Fluoroskan Ascent FL (Labsystems)), with excitation wavelength of 450 nm, emission at 510 nm, and 200 ms measurement time. For determination of the inhibitory activity of chimeric DC8E8 on pathological tau-tau interactions, purified chimeric DC8E8 was added to the reaction mix at 10 μM final concentration, prior to the incubation at 37° C. The amount of conformationally altered and fibrillized tau was measured by Thioflavin T fluorescence in the absence ("no antibody") and in the presence of the chimeric antibody (FIG. 32). Both chimeric DC8E8 and mouse DC8E8, added at 10 μM final concentration, prevented the pathological conformational change and fibrillization of the misdisordered tau protein. Chimeric DC8E8 reduced the amount of fibrillized pathological tau forms to less than 5.9%, mouse DC8E8 reduced the amount of fibrillized pathological tau forms to less than 4.7%. The data shows that chimeric antibody prevented the pathological conformational change and fibrillization of misdisordered tau protein with the comparable capacity as that of parental DC8E8.

Example 6: Properties of the Humanized Versions of DC8E8 a/ Humanized Versions of DC8E8 Exhibit Higher Affinity for Misdisordered Tau 151-391/4R than for Full Length Tau 2N4R.

To assess the discriminatory capacity of humanized versions of DC8E8 between immunoreactivity with pathological and physiological tau proteins, ELISA and SPR were used, as described in Example 5. All humanized variants of DC8E8, namely AX004, AX005, AX016, AX017 (in both isotypes IgG4 and IgG1), were purified according to the method for purification of chimeric DC8E8 described in Example 5.

Figure 34A:
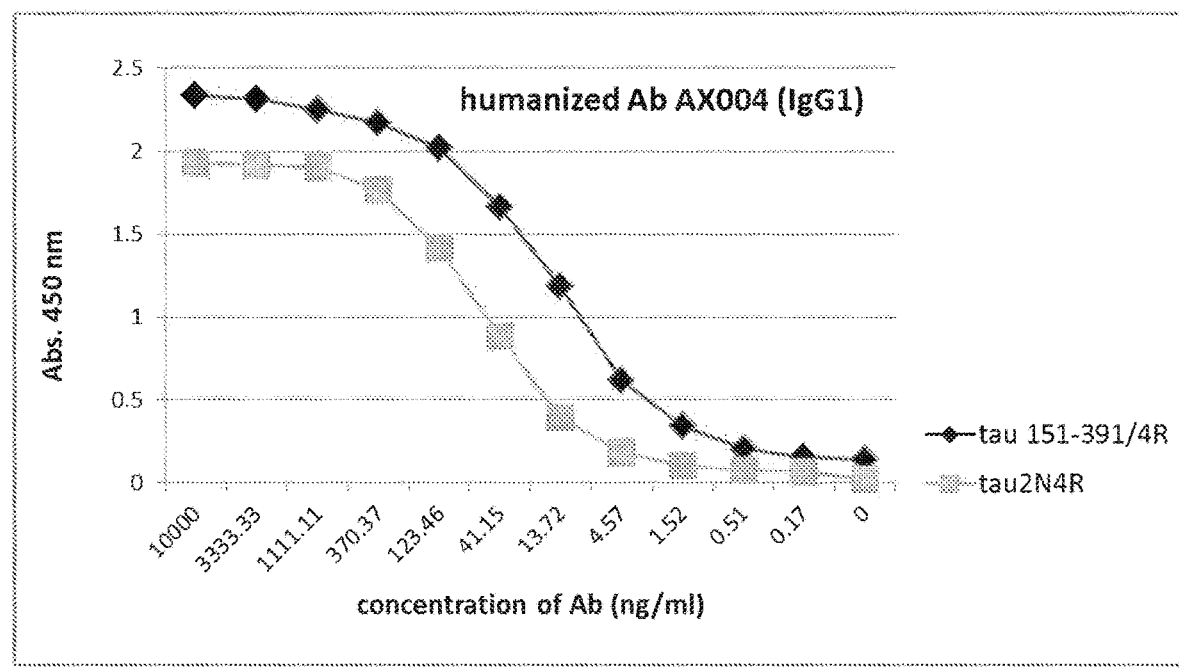
FIGS. 34A-34E: Binding of humanized leads of DC8E8 (IgG1 isotype) to misdisordered tau 151-391/4R and full length physiological tau 2N4R, as determined by ELISA.
Figure 34B:
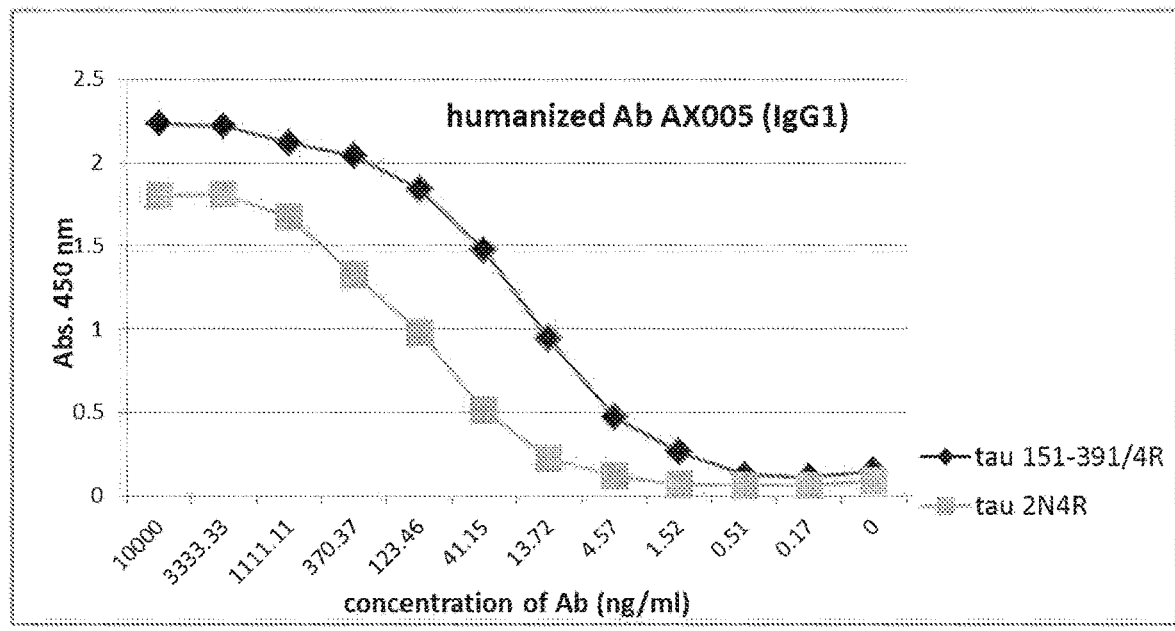
Figure 34C:
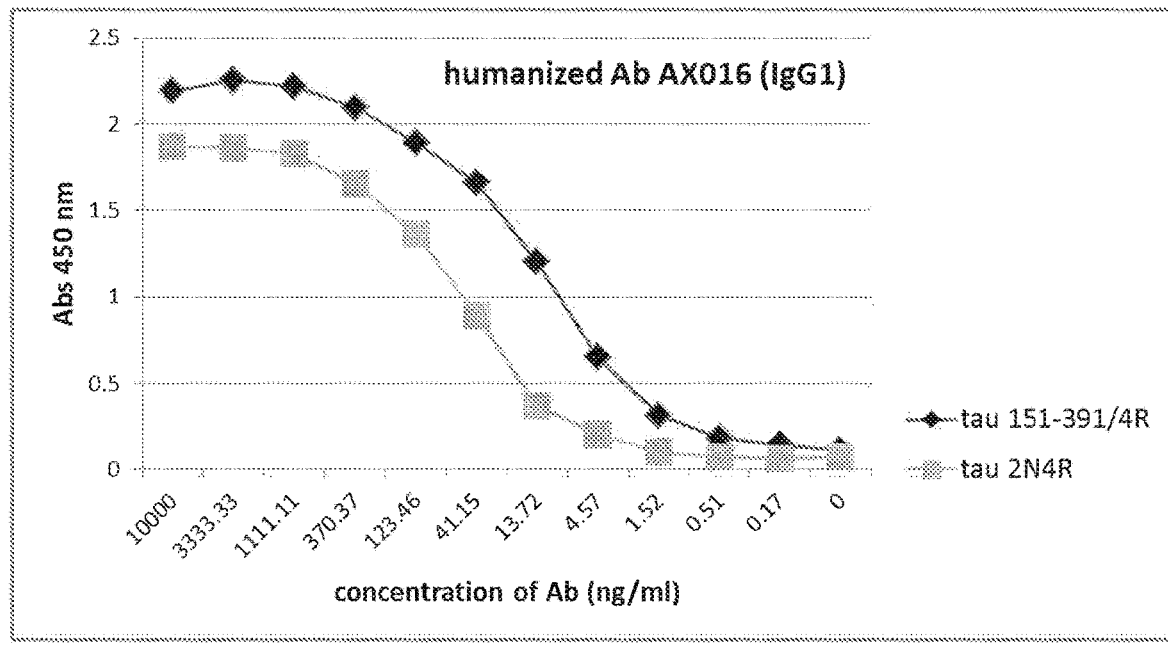
Figures 34D, 34E:
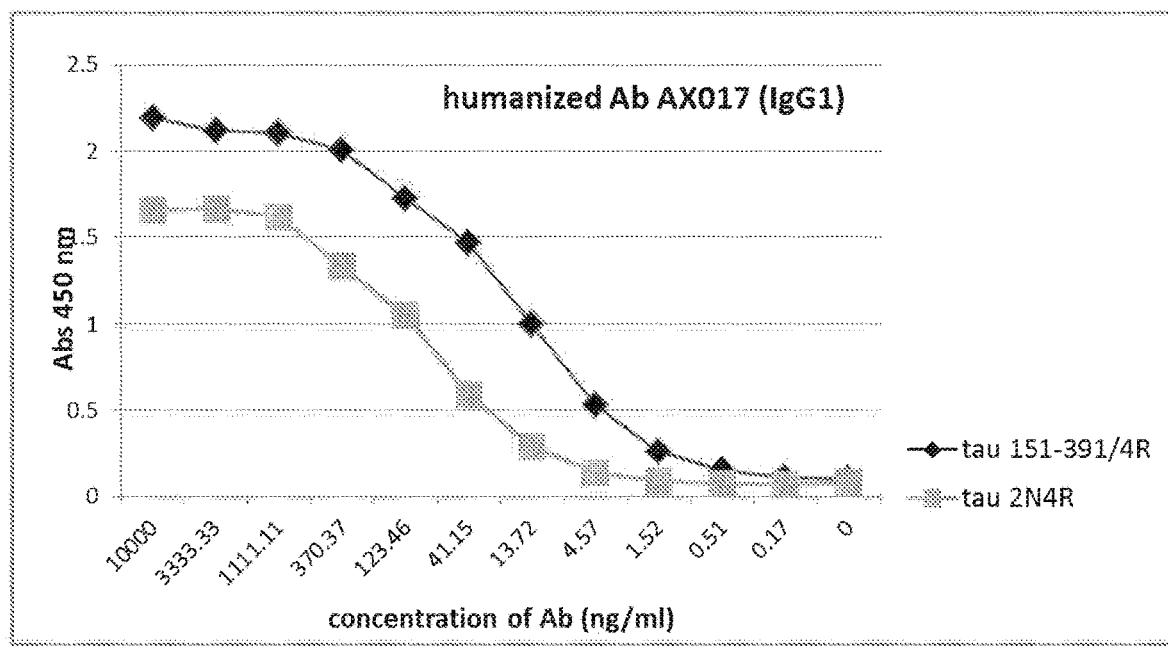

The ELISA showed that all humanized leads AX004, AX005, AX016 and AX017 (of both IgG4 and IgG1 isotypes) were able to recognize pathological tau151-391/4R (FIGS. 33A-33D; FIGS. 34A-34D). Importantly, the binding of each humanized DC8E8 variant was higher for pathological tau 151-391/4R than for the physiological tau 2N4R. However, the leads containing the RHE version of heavy chain (AX005 and AX017) appeared to bind the physiological tau weaker than leads AX004 and AX016 containing the RHD version of heavy chain (FIG. 33F; FIG. 34E). Although AX005 and AX017 bind the physiological tau weaker, the extent of discriminatory potency of humanized leads AX004, AX005, AX016 and AX017 is similar to that of chimeric DC8E8 antibody, as indicated by ECK values. Altogether, binding properties of the tested humanized antibodies are comparable with binding properties of chimeric antibody (and parental mouse DC8E8, FIGS. 29A-29C).

Figure 35A:
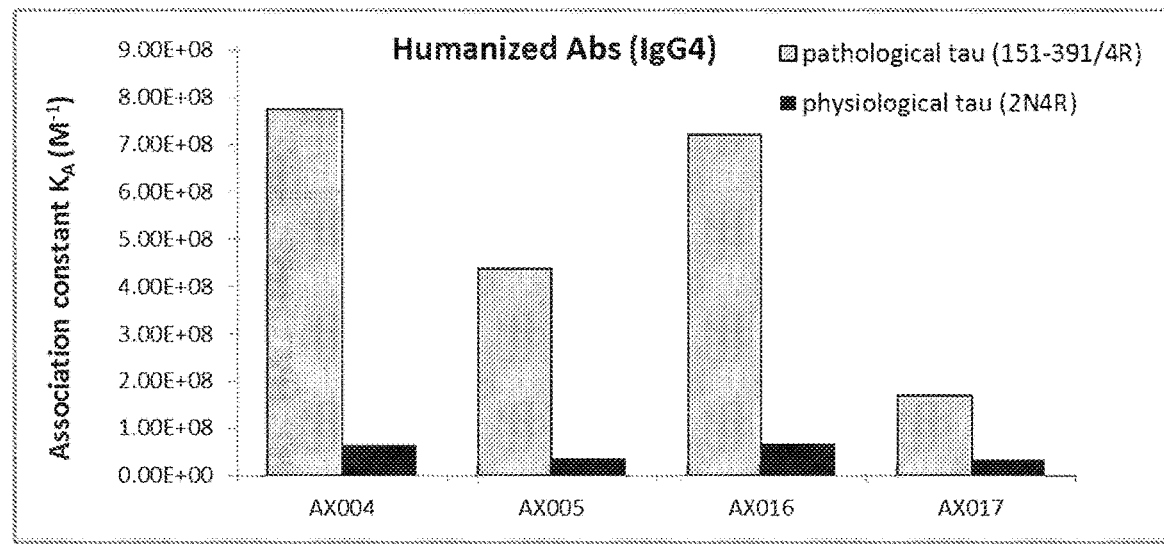
FIGS. 35A-35B: Surface plasmon resonance (SPR) to characterize humanized DC8E8 leads AX004, AX005, AX016, AX017, binding to mis-disordered tau151-391/4R and full length 2N4R.
Figure 35B:
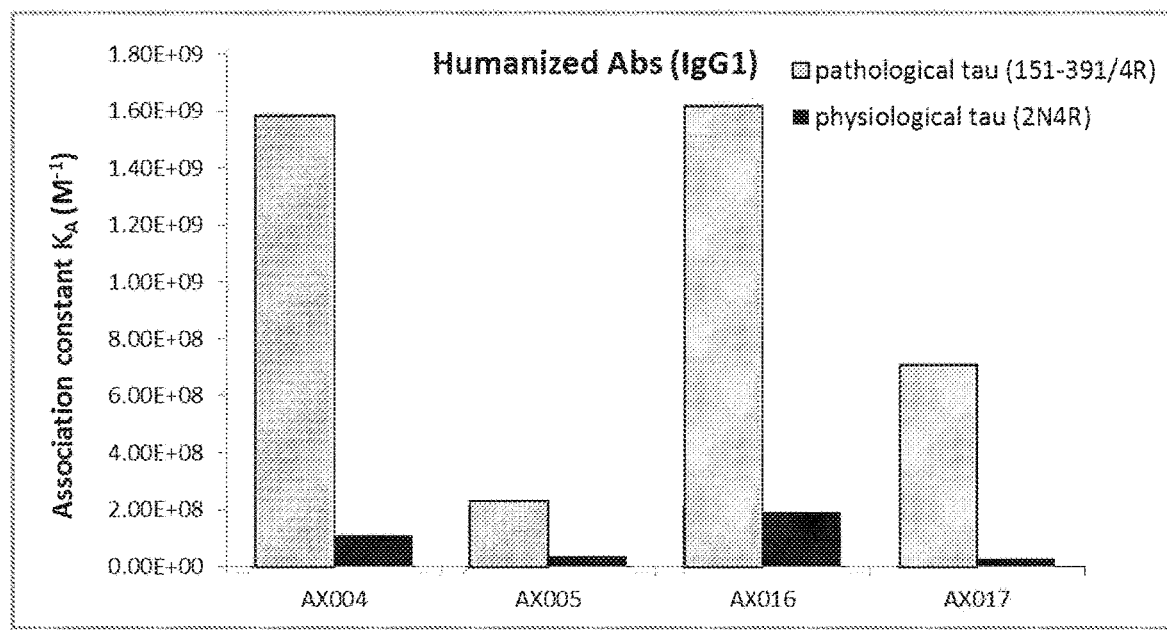
Figure 36A:
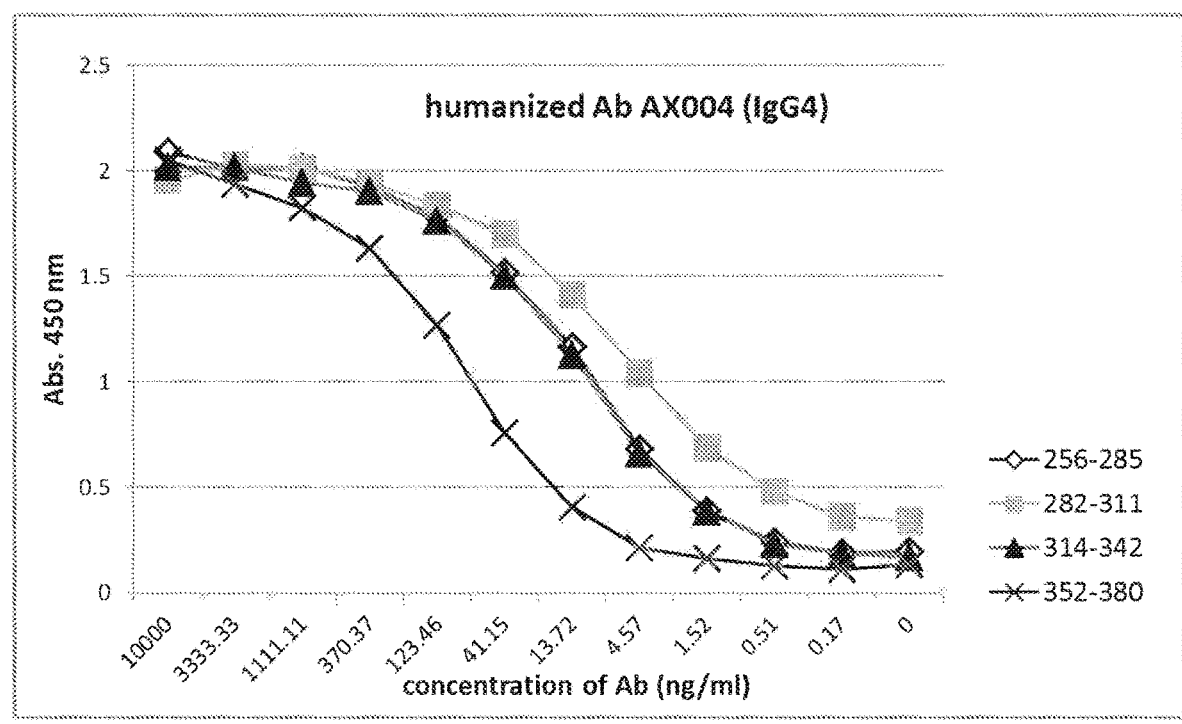
Figure 36B:
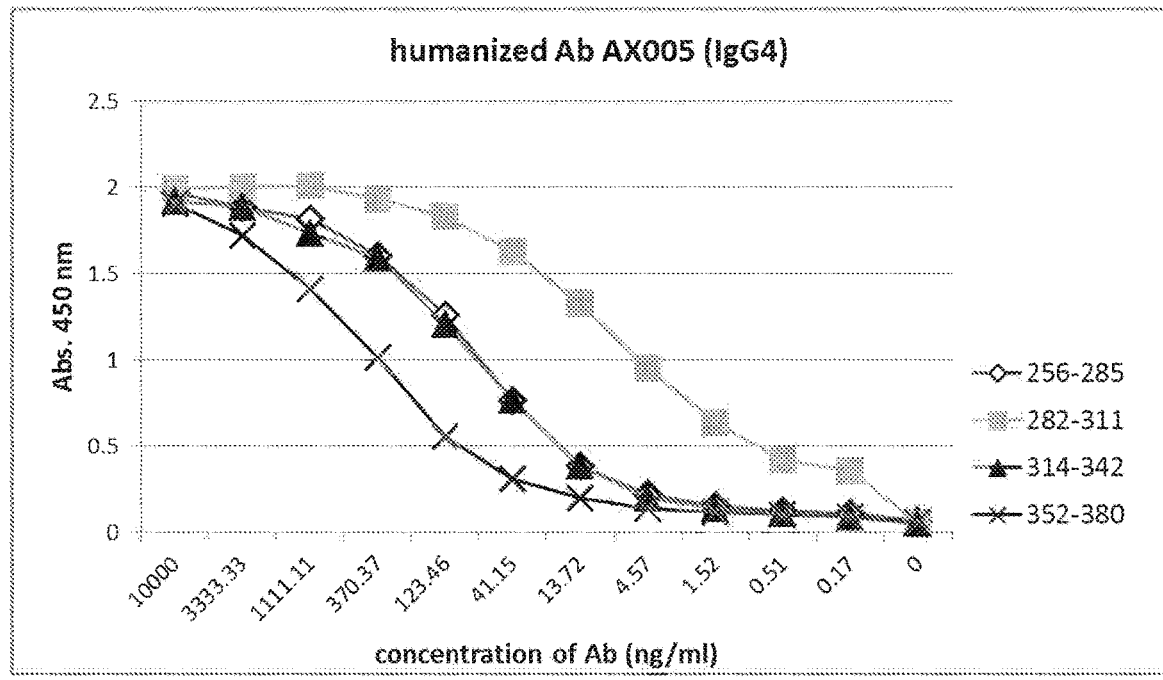
Figure 36C:
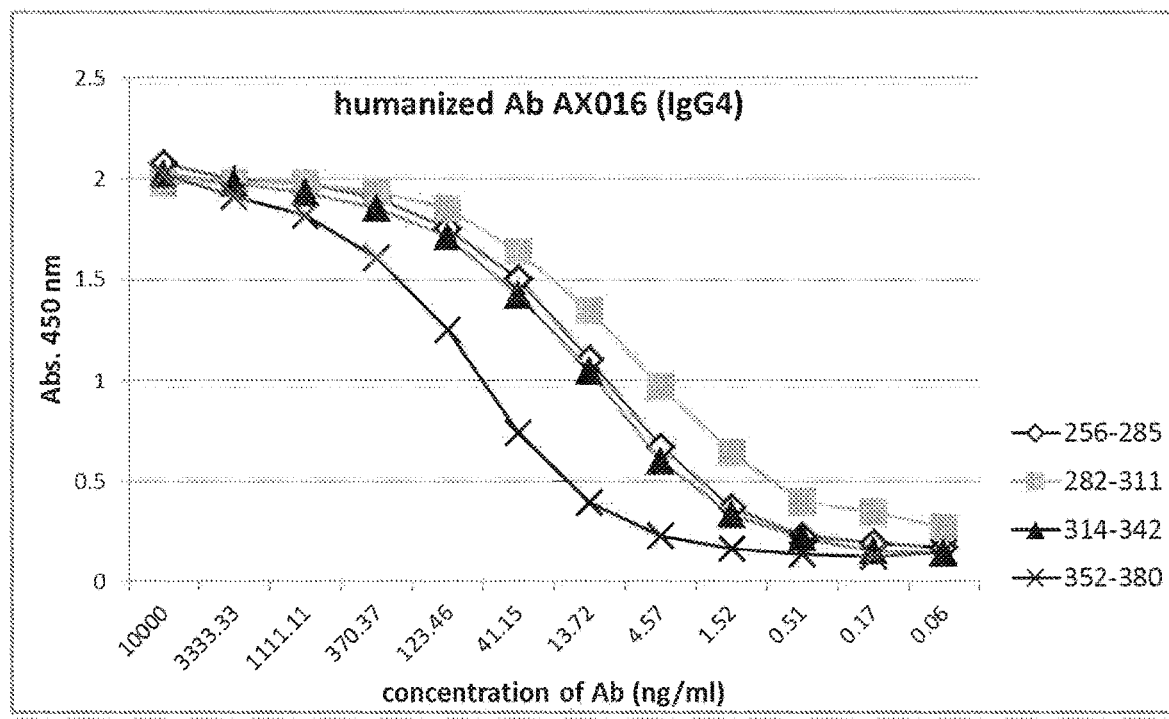
Figure 36D:
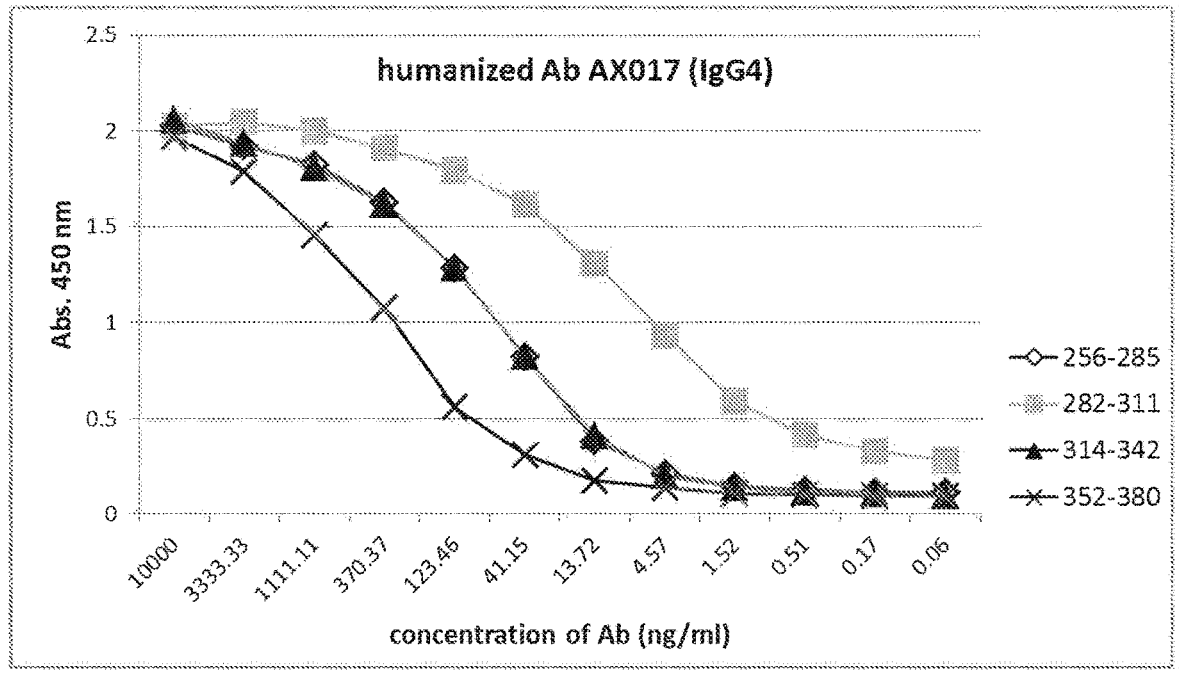
Figure 36E:
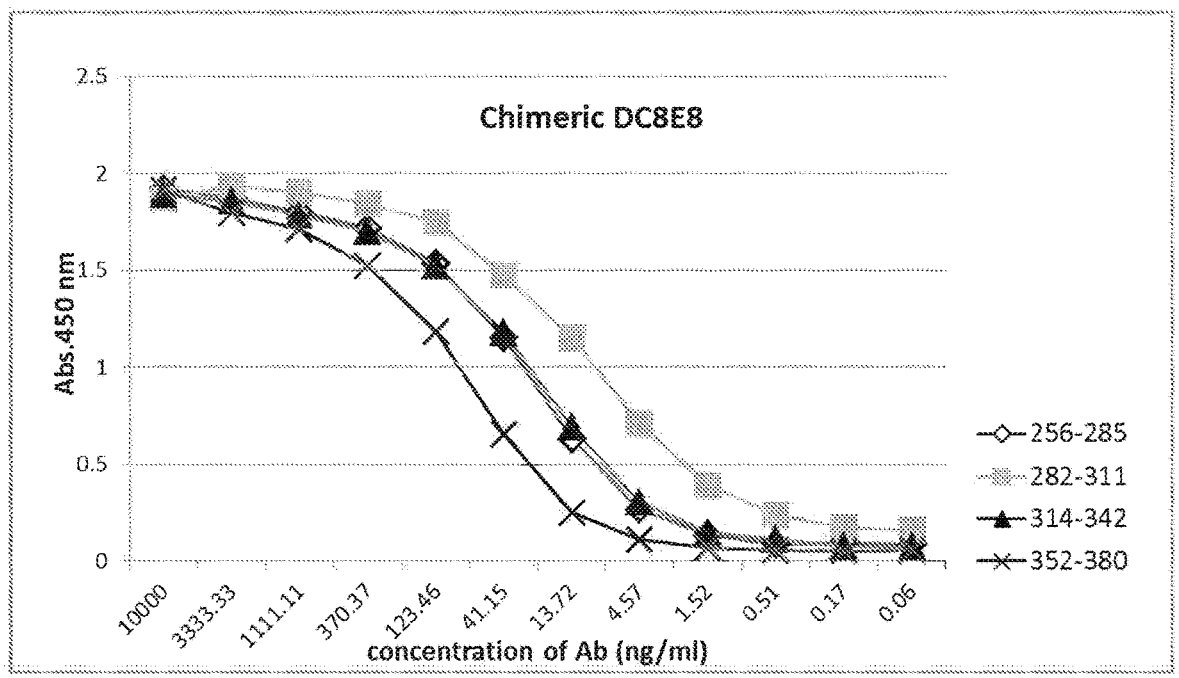
Figure 37A:
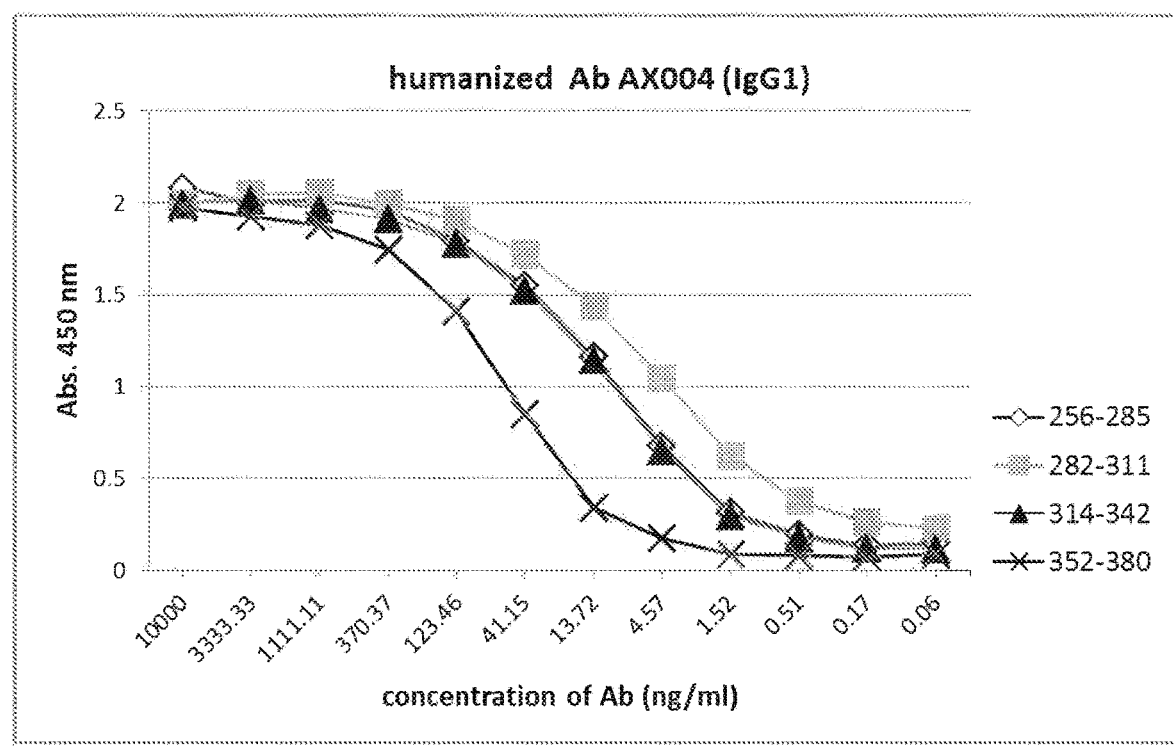
FIGS. 37A-37E: Binding of humanized antibodies (of IgG1 isotype) to tau peptides derived from the microtubule-binding repeat region of protein tau, as determined by ELISA.
Figure 37B:
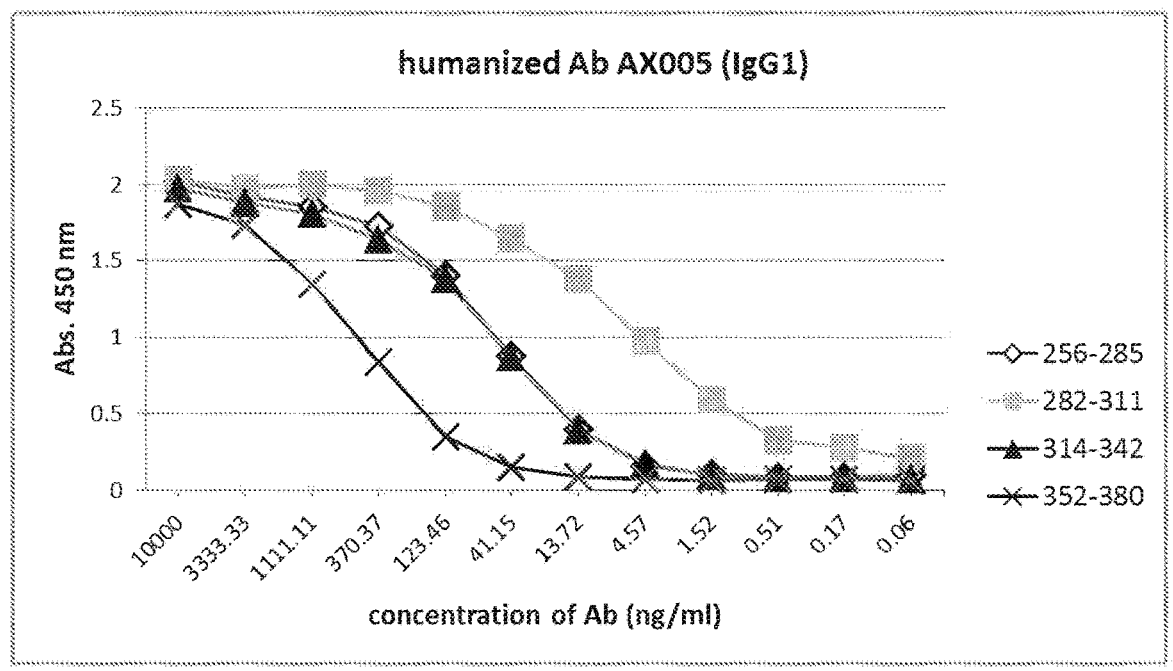
Figure 37C:
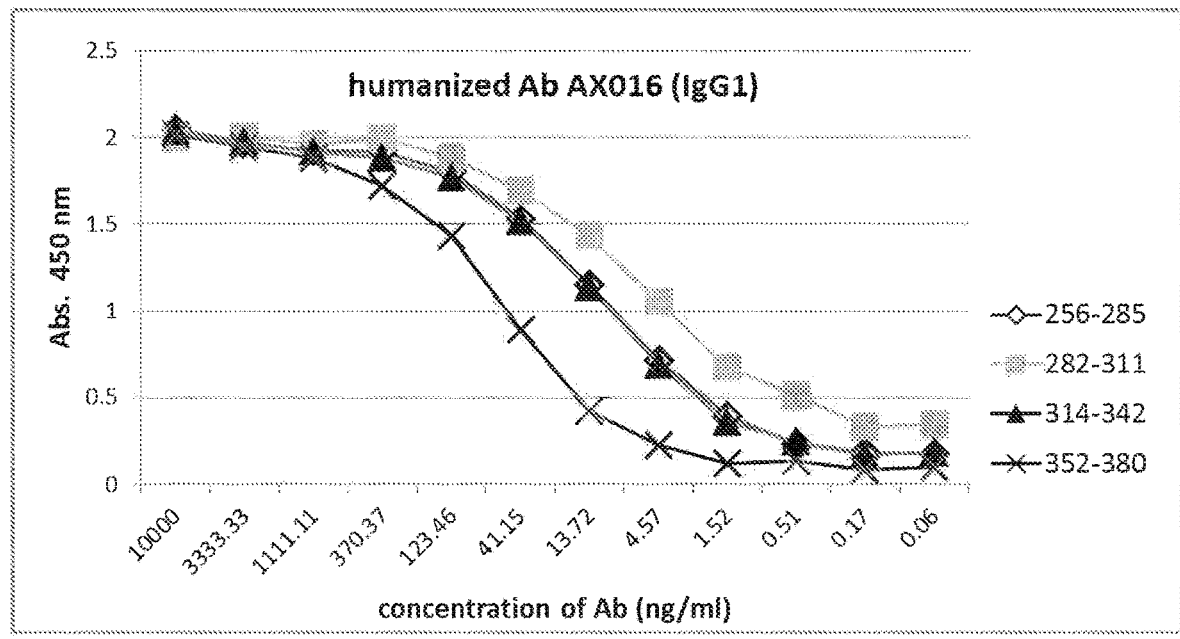
Figures 37D, 37E:
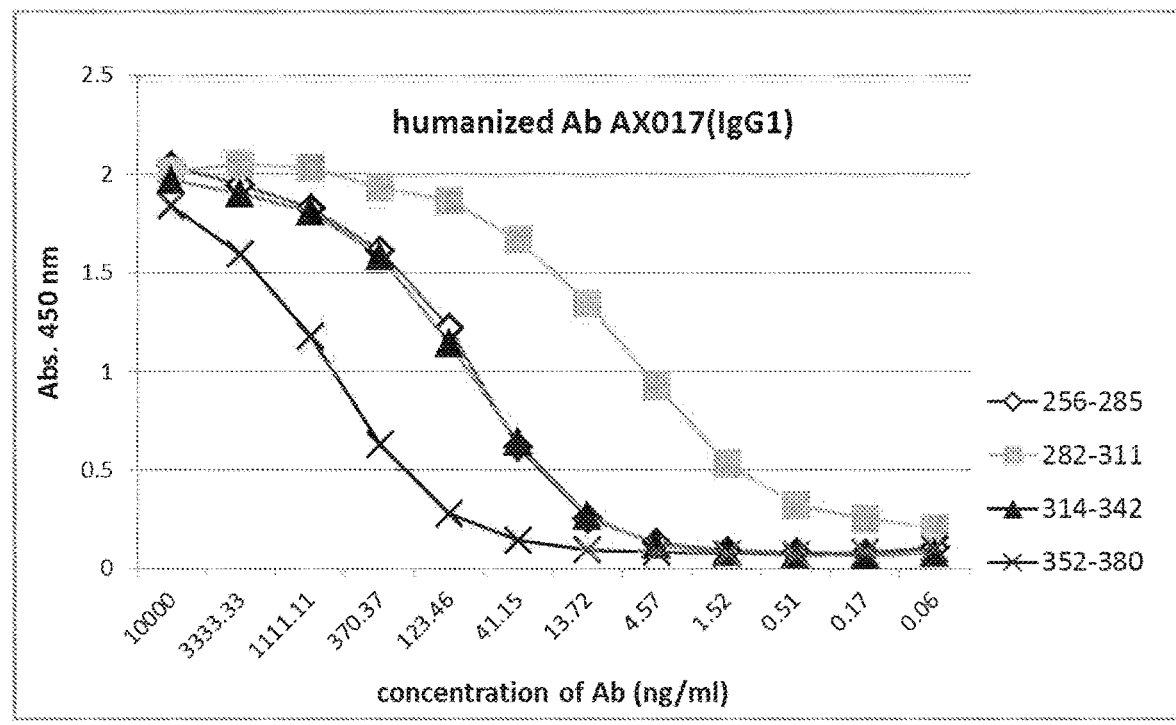

For SPR experiments performed as described above for chimeric DC8E8, the humanized variants of DC8E8 monoclonal antibody and chimeric DC8E8 were used. In each analysis cycle, purified humanized version of DC8E8 was captured in the analytical flow cell to reach the immobilization levels of 200-250 RU. In order to quantify humanized DC8E8's affinity for each of the tested tau proteins, the association equilibrium binding constants (KA) were determined for the antibodies binding to the physiological, four repeat tau protein isoform 2N4R as well as to pathological misdisordered tau151-391/4R. All tau proteins used for SPR were prepared according to Example 4. The affinity of each humanized DC8E8 variant was higher for misdisordered tau 151-391/4R then for the full-length tau 2N4R. (FIGS. 35A, 35B). These results confirmed: (1) the specificity of humanized DC8E8 for the misdisordered form of tau, and (2) the selectivity of DC8E8 for misdisordered tau (i.e., disease or pathological tau) over the full-length tau (i.e., normal or physiological tau).

b/ Humanized Versions of DC8E8 Bind Tau Peptides Each Carrying One of the Four DC8E8 Epitopes in the Microtubule-Binding Domain of Tau The aim of this experiment was to determine the capability of the humanized leads of DC8E8 (AX004, AX005, AX016, AX017, isotype IgG4 and isotype IgG1), to bind tau peptides 256-285, 282-311, 314-342, 352-380. Each of these peptides encompassed one of the four separate DC8E8 epitopes in the microtubule-binding repeats (MTBRs) of tau. Binding activity of humanized leads of DC8E8 to the tau peptides was measured by ELISA, as described in Example 5. Each of the tested humanized antibodies bound all MTBRs-derived peptides (FIGS. 36A-36D; FIGS. 37A-37D), similarly to chimeric DC8E8 (FIG. 36E). This was true for both IgG1 and IgG4 isotype versions. The humanized candidate antibodies showed the highest immunoreactivity to peptide 282-311, which was derived from MTBRII and which comprises DC8E8 epitope within positions 298-304, as indicated by $EC_{50}$ values (FIG. 36F; FIG. 37E). The leads containing the RHE version of heavy chain (AX005 and AX017) bind the other tested peptides (256-285, 314-342, 352-380) weaker than the leads AX004 and AX016 containing the RHD version of the heavy chain (FIG. 36F; FIG. 37E). Overall the data suggest that the immunoreactivity of humanized antibody AX004 and AX016 to the tested peptides is similar to that of chimeric DC8E8, as indicated by $EC_{50}$ values (FIG. 36F).

c/ Humanized Versions of DC8E8 are Capable of Inhibiting Pathological Tau-Tau Interaction In order to determine the effect of humanized candidate antibodies (namely AX004, AX005, AX016, AX017, isotype IgG4 and isotype IgG1) on tau fibrillization and on the formation of tau aggregates, in vitro tau fibrillization assay was performed (as described in Example 5). All humanized leads of DC8E8 were purified as described in Example 5. Pathological tau protein 151-391/4R used for fibrillization assay was prepared according to Example 4.

Figure 38A:
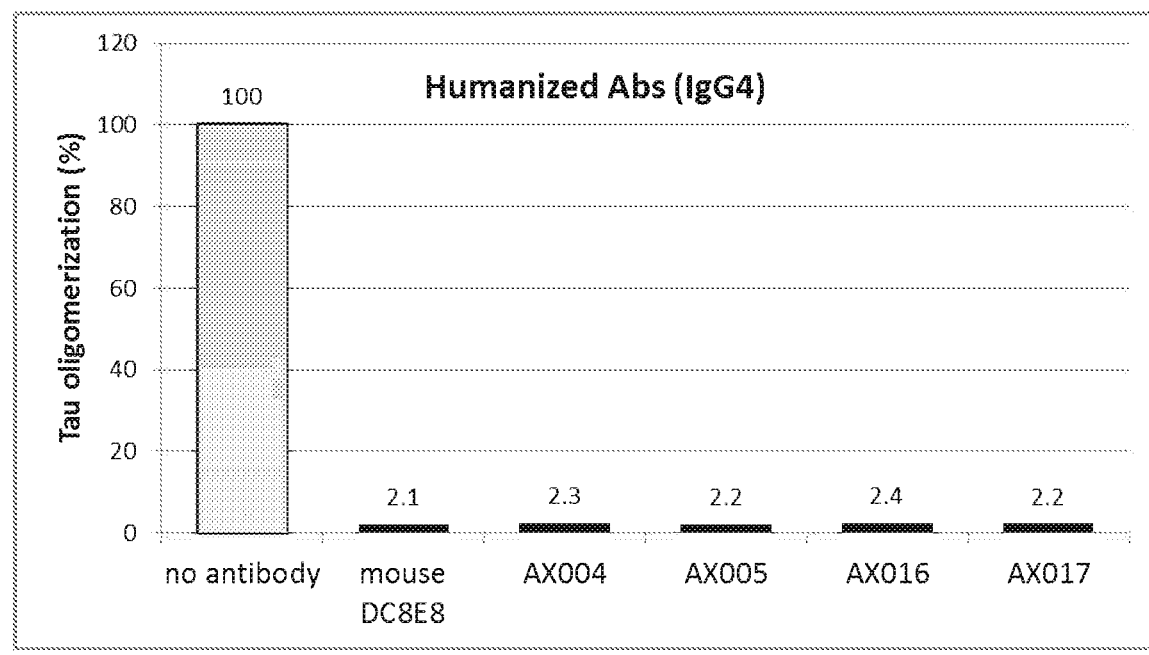
FIGS. 38A-38B: Humanized DC8E8 leads inhibit pathological tau-tau interaction in fluorescence-based tau fibrillization assay. Mis-disordered tau 151-391/4R was induced to undergo a conformational change and fibrilize as measured by Thioflavin T fluorescence; humanized antibodies were added to the fibrillization reaction and tested for their ability to prevent the pathological conformational change. All tested humanized antibodies are capable of inhibiting pathological tau-tau aggregation.
Figure 38B:
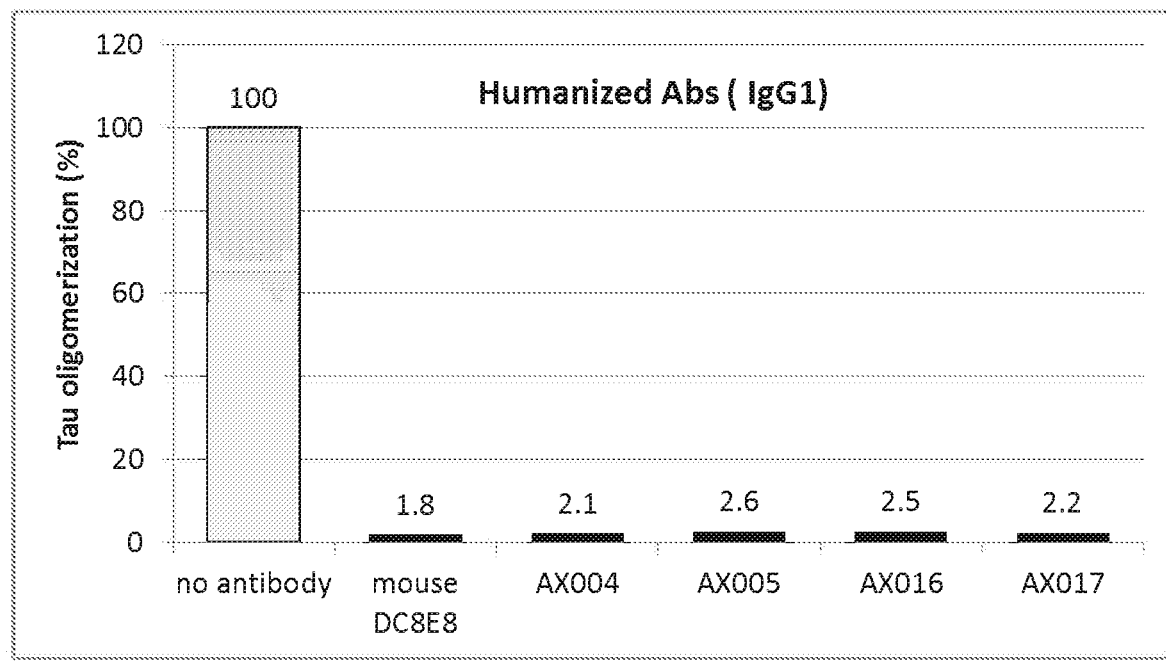

For determining the inhibitory activity of humanized candidate antibodies on pathological tau-tau interactions, purified humanized leads AX004, AX005, AX016, AX017 (isotype IgG4 and isotype IgG1) were separately added to the reaction mix at 10 µM final concentration, prior to the incubation at 37° C. The amount of conformationally altered and fibrillized tau was measured by Thioflavin T fluorescence in the absence ("no antibody") and in the presence of the tested antibodies. Results shown, that all of the humanized antibodies, added at 10 µM final concentration, prevented the pathological conformational change and fibrillization of the misdisordered tau protein (FIGS. 38A, 38B). Isotype of the antibodies did not influence the inhibitory potential of humanized antibodies. Humanized leads AX004, AX005, AX016 and AX017, both IgG4 and IgG1 isotype versions, reduced the amount of fibrillized pathological tau forms to less than 3%. The data suggest that humanized antibodies prevented the pathological conformational change and fibrillization of misdisordered tau protein with the comparable capacity as that of the original mouse DC8E8.

Example 7: Chimeric DC8E8 and Humanized Versions of DC8E8 Recognize Pathology in Human Alzheimer's Disease Brain and Other Tauopathies Human brain tissue samples (on paraffin blocks) were obtained from the Netherlands brain bank. The blocks were cut on a microtome. Paraffin-sections (8 µm) of the hippocampus-entorhinal cortex from Alzheimer's disease brain (Braak's stage VI) and FTDP17 (R406W mutation), nucleus caudatus from corticobasal degeneration and progressive supranuclear palsy were used for the study. The sections were treated with cold (+4° C.) 98% formic acid for 1 min followed by heat treatment in the pressure cooker (2100 Retriever) for 20 min at 121° C. The tissue sections were incubated in blocking solution (Section block, Aptum) for 10 min. at room temperature and then overnight with primary mouse antibody DC8E8 (1:200), human antibodies AX004, AX005, AX016, AX017 and chimeric DC8E8 (all 1:1000). Subsequently, the sections were incubated with a biotinylated secondary antibody (Vectastain Elite ABC Kit, Vector Laboratories) at room temperature for an hour and then reacted with avidin-biotin peroxidase-complex for 60 minutes (Vectastain Elite ABC Kit, Vector Laboratories), both at room temperature (25° C.). The immunoreaction was visualized with peroxidase substrate kit (Vector VIP, Vector laboratories, Ca, USA) and counterstained with methyl green (Vector Laboratories). The assessment of immunoreactivity was carried out under light microscopy at ×100-400 magnification. The morphological details of tau-immunopositive lesions were defined based on the cellular localization and the pattern of staining. Digital images were taken using an Olympus BX51 microscope equipped with an Olympus DP50 digital camera (Olympus Optical Co., Ltd., Tokyo, Japan).

Immunohistochemical staining of human brains of Alzheimer's disease, progressive supranuclear palsy, corticobasal degeneration and FTDP-17 patients revealed that chimeric DC8E8 antibody displayed the same staining pattern as mouse DC8E8 (FIGS. 39A, 39B, 40A, 40B, 41A, 41B, 42A, 42B, 43A, 43B, 44A, 44B, 45A, 45B, 46A, 46B). We compared the immunohistochemical staining of chimeric antibody with humanized DC8E8 antibodies—AX004, AX005, AX016 and AX017. In general, humanized antibodies AX004 and AX016 (IgG1 and IgG4) displayed the very similar staining pattern as mouse or chimeric DC8E8. Humanized antibodies AX004 and AX016 recognized extensive number of neurofibrillary tangles, neuropil threads and neuritic plaques in human AD brain (FIGS. 39C, 39E; FIGS. 40C, 40E). In human FTDP-17 case bearing mutation on tau protein at R406W, AX004 and AX016 immunolabeled neurofibrillary tangles and neuropil threads in entorhinal and temporal cortex (FIGS. 41C, 41E; FIGS. 42C, 42E). In corticobasal degeneration, AX004 and AX016 stained glial tau pathology in nucleus caudatus (FIGS. 43C, 43E; FIGS. 44C, 44E). In progressive supranuclear palsy, AX004 and AX016 recognized high number of oligodendroglial coiled bodies and astrocytic plaques (FIGS. 45C, 45E; FIGS. 46C, 46E). In contrast AX005 and AX017 displayed reduced immunostaining in Alzheimer's disease (FIGS. 39D, 39F; FIGS. 40D, 40F), in FTDP-17 (FIGS. 41D, 41F), in corticobasal degeneration (FIGS. 43D, 43F; FIGS. 44D, 44F) and in progressive supranuclear palsy (FIGS. 45D, 45F; FIGS. 46D, 46F). Interestingly, isotype IgG4 of AX005 and AX017 did not stain pathological structures in FTDP17 (FIGS. 42D, 42F). In summary, humanized antibodies AX004 and AX016 have the same staining pattern as DC8E8.

We claim:

1. An anti-tau antibody or a tau-binding fragment thereof, wherein the antibody or fragment comprises:
   a heavy chain variable region comprising SEQ ID NO: 13 or a sequence that differs from SEQ ID NO: 13 at one or more positions selected from 9, 21, 27, 28, 30, 38, 48, 67, 68, 70, and 95;
   a light chain variable region comprising SEQ ID NO: 26 or a sequence that differs from SEQ ID NO: 26 at position 5; and
   heavy chain and light chain constant regions, each from a human immunoglobulin;
   wherein position numbering is according to Kabat.

2. The antibody or fragment of claim 1, wherein the heavy chain variable region position 9 is P, the heavy chain variable region position 21 is P, the heavy chain variable region position 27 is Y, the heavy chain variable region position 28 is I, the heavy chain variable region position 30 is T, the heavy chain variable region position 38 is K, the heavy chain variable region position 48 is I, the heavy chain variable region position 67 is K, the heavy chain variable region position 68 is A, the heavy chain variable region position 70 is L, and/or the heavy chain variable region position 95 is F; wherein position numbering is according to Kabat.

3. The antibody or fragment of claim 1, wherein the heavy chain variable region position 9 is A, the heavy chain variable region position 21 is S, the heavy chain variable region position 27 is Y, the heavy chain variable region position 28 is T, the heavy chain variable region position 30 is S, the heavy chain variable region position 38 is R, the heavy chain variable region position 48 is M, the heavy chain variable region position 67 is R, the heavy chain variable region position 68 is V, the heavy chain variable region position 70 is I, and/or the heavy chain variable region position 95 is Y; wherein position numbering is according to Kabat.

4. The antibody or fragment of claim 1, wherein the light chain variable region position 5 is S; wherein position numbering is according to Kabat.

5. The antibody or fragment of claim 1, wherein the heavy chain variable region comprises any one of SEQ ID NOs: 14-25; and of the light chain variable region comprises SEQ ID NO: 26.

6. The antibody or fragment of claim 1, wherein the heavy chain variable region comprises any one of SEQ ID NOs: 14-25; and the light chain variable region comprises SEQ ID NO: 27.

7. The antibody or fragment of claim 1, wherein the heavy chain constant region is a IgG1 or IgG4 heavy chain constant region.

8. The antibody or fragment of claim 1, wherein the light chain constant region is a human kappa light chain constant region.

9. An immunoconjugate having a formula of (A)-(L)-(C), wherein: (A) is the antibody or fragment of claim 1; (L) is a linker; and (C) is an agent; and wherein the linker (L) links (A) to (C).

10. A nucleic acid molecule or nucleic acid molecules encoding the antibody or fragment of claim 1.

11. A vector comprising the nucleic acid molecule(s) of claim 10.

12. A host cell comprising the vector of claim 11.

13. A method of producing an anti-tau antibody or tau-binding fragment thereof, comprising culturing the host cell of claim 12 under conditions such that the antibody or fragment is produced.

14. A pharmaceutical composition comprising the antibody or fragment of claim 1 and a pharmaceutically acceptable carrier, diluent, excipient, and/or stabilizer.

15. The composition of claim 14, further comprising a second agent.

16. The composition of claim 15, wherein the second agent and the antibody or fragment are chemically conjugated.

17. The composition of claim 15, wherein the second agent comprises one or more of a tau peptide, an N-terminal amyloid beta peptide, a mutated diphtheria toxin, another anti-tau antibody, bapineuzumab, solaneuzumab, gantenerumab, crenezumab, an IVIG immunoglobulin, another immunization therapy targeting Abeta oligomers, a compound preventing the hyperphosphorylation of tau, an active or passive immunization therapy targeting tau aggregates, an amyloid-beta aggregation inhibitor, Tramiprosate, a gamma-secretase inhibitor, semagacestat, a gamma-secretase modulator, tarenflurbil, an acetylcholinesterase inhibitor, donepezil, rivastigmine, galantamine, tacrine, a nutritive supplement, an N-Methyl-D-aspartate (NMDA) receptor antagonist, memantine, an inhibitor of DNA repair, pirenzepine or a metabolite thereof, a transition metal chelator, a growth factor, a hormone, a non-steroidal anti-inflammatory drug (NSAID), an antioxidant, a lipid lowering agent, a selective phosphodiesterase inhibitor, an inhibitor of tau aggregation, an inhibitor of protein kinases, an inhibitor of anti-mitochondrial dysfunction drugs, a neurotrophin, an inhibitor of heat shock proteins, an inhibitor of Lipoprotein-associated phospholipase A2, an anti-apoptotic compound, a metal chelator, 3-amino-1-propanesulfonic acid (3APS), 1,3-propanedisulfonate (1,3PDS), a secretase activator, a beta-secretase inhibitor, an anti-beta-amyloid antibody, a neurotransmitter, a beta-sheet breaker, an anti-inflammatory molecule, a BACE inhibitor, a muscarinic antagonist, a cholinesterase inhibitor, an HMG-CoA reductase inhibitor, an anti-amyloid antibody, vitamin E, a nicotinic acetylcholine receptor agonist, a CB1 receptor inverse agonist, a CB1 receptor antagonist, an antibiotic, a growth hormone secretagogue, a histamine H3 antagonist, an AMPA agonist, a PDE4 inhibitor, a $GABA_A$ inverse agonist, an inhibitor of amyloid aggregation, a glycogen synthase kinase beta inhibitor, a promoter of alpha secretase activity, a PDE-10 inhibitor, a cholesterol absorption inhibitor, or a pharmaceutically acceptable salt of any of the foregoing.

18. A method of treating Alzheimer's disease in a subject in need thereof, comprising administering to the subject a therapeutically effective amount of the antibody or fragment of claim 1.

19. A pharmaceutical composition comprising an anti-tau antibody or tau-binding fragment thereof and a pharmaceutically acceptable carrier, diluent, excipient, and/or stabilizer, wherein the antibody or fragment comprises a heavy chain variable region comprising SEQ ID NO: 16 and a light chain variable region comprising SEQ ID NO: 26 or SEQ ID NO: 27.

20. The composition of claim 19, wherein the antibody or fragment comprises:
a) a heavy chain comprising SEQ ID NO: 31; and
b) a light chain comprising SEQ ID NO: 57 or 58.

21. The composition of claim 19, wherein the antibody or fragment comprises:
a) a heavy chain comprising SEQ ID NO: 46; and
b) a light chain comprising SEQ ID NO: 57 or 58.

22. A method of treating Alzheimer's disease in a subject in need thereof, comprising administering to the subject a therapeutically effective amount of the composition of claim 19.

23. The composition of claim 19, further comprising a second agent.

24. The composition of claim 23, wherein the second agent and the antibody or fragment are chemically conjugated.

25. The composition of claim 23, wherein the second agent comprises one or more of a tau peptide, an N-terminal amyloid beta peptide, a mutated diphtheria toxin, another anti-tau antibody, bapineuzumab, solaneuzumab, gantenerumab, crenezumab, an IVIG immunoglobulin, another immunization therapy targeting Abeta oligomers, a compound preventing the hyperphosphorylation of tau, an active or passive immunization therapy targeting tau aggregates, an amyloid-beta aggregation inhibitor, Tramiprosate, a gamma-secretase inhibitor, semagacestat, a gamma-secretase modulator, tarenflurbil, an acetylcholinesterase inhibitor, donepezil, rivastigmine, galantamine, tacrine, a nutritive supplement, an N-Methyl-D-aspartate (NMDA) receptor antagonist, memantine, an inhibitor of DNA repair, pirenzepine or a metabolite thereof, a transition metal chelator, a growth factor, a hormone, a non-steroidal anti-inflammatory drug (NSAID), an antioxidant, a lipid lowering agent, a selective phosphodiesterase inhibitor, an inhibitor of tau aggregation, an inhibitor of protein kinases, an inhibitor of anti-mitochondrial dysfunction drugs, a neurotrophin, an inhibitor of heat shock proteins, an inhibitor of Lipoprotein-associated phospholipase A2, an anti-apoptotic compound, a metal chelator, 3-amino-1-propanesulfonic acid (3APS), 1,3-propanedisulfonate (1,3PDS), a secretase activator, a beta-secretase inhibitor, an anti-beta-amyloid antibody, a neurotransmitter, a beta-sheet breaker, an anti-inflammatory molecule, a BACE inhibitor, a muscarinic antagonist, a cholinesterase inhibitor, an HMG-CoA reductase inhibitor, an anti-amyloid antibody, vitamin E, a nicotinic acetylcholine receptor agonist, a CB1 receptor inverse agonist, a CB1 receptor antagonist, an antibiotic, a growth hormone secretagogue, a histamine H3 antagonist, an AMPA agonist, a PDE4 inhibitor, a $GABA_A$ inverse agonist, an inhibitor of amyloid aggregation, a glycogen synthase kinase beta inhibitor, a promoter of alpha secretase activity, a PDE-10 inhibitor, a cholesterol absorption inhibitor, or a pharmaceutically acceptable salt of any of the foregoing.

26. An anti-tau antibody or a tau-binding fragment thereof, wherein the antibody or fragment comprises:
   a) a heavy chain comprising SEQ ID NO: 31; and
   b) a light chain comprising SEQ ID NO: 57 or 58.

27. An anti-tau antibody or a tau-binding fragment thereof, wherein the antibody or fragment comprises:
   a) a heavy chain comprising SEQ ID NO: 46; and
   b) a light chain comprising SEQ ID NO: 57 or 58.

* * * * *

UNITED STATES PATENT AND TRADEMARK OFFICE
CERTIFICATE OF CORRECTION

PATENT NO. : 11,319,363 B2
APPLICATION NO. : 16/926062
DATED : May 3, 2022
INVENTOR(S) : Michal Novak et al.

Page 1 of 1

It is certified that error appears in the above-identified patent and that said Letters Patent is hereby corrected as shown below:

In the Claims

Claim 5, Column 325, Line 23, "and of the light chain variable region comprises" should read --and the light chain variable region comprises--.

Signed and Sealed this
Eighteenth Day of February, 2025

Coke Morgan Stewart
*Acting Director of the United States Patent and Trademark Office*